(12) United States Patent
Jandeleit et al.

(10) Patent No.: US 9,394,237 B2
(45) Date of Patent: Jul. 19, 2016

(54) β-SUBSTITUTED β-AMINO ACIDS AND ANALOGS AS CHEMOTHERAPEUTIC AGENTS

(71) Applicant: QUADRIGA BIOSCIENCES, INC., Sunnyvale, CA (US)

(72) Inventors: Bernd Jandeleit, Menlo Park, CA (US); Wolf-Nicolas Fischer, Sunnyvale, CA (US); Kerry J. Koller, San Francisco, CA (US)

(73) Assignee: Quadriga Biosciences, Inc., Sunnyvale, CA (US)

( * ) Notice: Subject to any disclaimer, the term of this patent is extended or adjusted under 35 U.S.C. 154(b) by 0 days.

(21) Appl. No.: 14/613,143

(22) Filed: Feb. 3, 2015

(65) Prior Publication Data
US 2015/0218086 A1    Aug. 6, 2015

Related U.S. Application Data

(60) Provisional application No. 61/935,246, filed on Feb. 3, 2014.

(51) Int. Cl.
| | |
|---|---|
| *C07C 229/08* | (2006.01) |
| *C07C 233/35* | (2006.01) |
| *C07C 271/46* | (2006.01) |
| *C07C 309/69* | (2006.01) |
| *C07F 9/48* | (2006.01) |
| *A61K 31/197* | (2006.01) |
| *A61K 31/662* | (2006.01) |
| *C07C 229/22* | (2006.01) |
| *C07C 229/34* | (2006.01) |
| *C07C 237/30* | (2006.01) |
| *C07C 239/20* | (2006.01) |
| *C07C 237/04* | (2006.01) |
| *C07F 9/32* | (2006.01) |

(52) U.S. Cl.
CPC ............ *C07C 229/08* (2013.01); *A61K 31/197* (2013.01); *A61K 31/662* (2013.01); *C07C 229/22* (2013.01); *C07C 229/34* (2013.01); *C07C 233/35* (2013.01); *C07C 237/04* (2013.01); *C07C 237/30* (2013.01); *C07C 239/20* (2013.01); *C07C 271/46* (2013.01); *C07C 309/69* (2013.01); *C07F 9/3264* (2013.01); *C07F 9/48* (2013.01); *C07F 9/4816* (2013.01)

(58) Field of Classification Search
CPC .. C07C 229/08; C07C 233/35; C07C 271/46; C07C 309/69; C07C 229/22; C07C 229/34; C07C 237/04; C07C 237/30; C07C 239/20; C07F 9/48; C07F 9/3264; C07F 9/4816; A61K 31/197; A61K 31/662
USPC ............ 514/114, 490, 562, 563, 564; 558/48; 560/161; 562/496; 564/15
See application file for complete search history.

(56) References Cited

U.S. PATENT DOCUMENTS

| | | | |
|---|---|---|---|
| 3,235,594 A | 2/1966 | Levi et al. | |
| 3,299,104 A | 1/1967 | Fex et al. | |
| 4,339,443 A | 7/1982 | Baillie et al. | |
| 5,015,644 A | 5/1991 | Roth et al. | |
| 5,602,278 A | 2/1997 | Kirkpatrick | |
| 5,674,906 A * | 10/1997 | Hatanaka | C07C 237/04 440/88 N |
| 5,959,113 A | 9/1999 | Harmon et al. | |
| 6,313,312 B1 | 11/2001 | Banks et al. | |
| 6,518,289 B1 | 2/2003 | Bryans et al. | |
| 6,818,787 B2 | 11/2004 | Gallop et al. | |
| 6,972,341 B2 | 12/2005 | Gallop et al. | |
| 7,109,239 B2 | 9/2006 | Gallop et al. | |
| 7,227,028 B2 | 6/2007 | Gallop et al. | |
| 7,399,785 B2 | 7/2008 | Kirkpatrick et al. | |
| 8,168,617 B2 | 5/2012 | Jandeleit et al. | |
| 8,344,028 B2 | 1/2013 | Xu et al. | |
| 8,710,256 B2 | 4/2014 | Anzalone et al. | |

(Continued)

FOREIGN PATENT DOCUMENTS

| | | |
|---|---|---|
| DE | 2731292 A1 | 1/1978 |
| EP | 731085 A1 | 9/1996 |

(Continued)

OTHER PUBLICATIONS

Pan ("V. Synthesis of Some o-Substituted-p-[Bis-(2-Chloroethyl)-amino]-phenylalanine and Test of Antitumour Action" Scientia Sinica, vol. XI, No. 4, 1962, p. 483-498).*

(Continued)

*Primary Examiner* — Jafar Parsa
*Assistant Examiner* — Amy C Bonaparte

(57) ABSTRACT

β-Substituted β-amino acids, β-substituted β-amino acid derivatives, and β-substituted β-amino acid analogs and (bio)isosteres and their use as chemotherapeutic agents are disclosed. The β-substituted β-amino acid derivatives and β-substituted β-amino acid analogs and (bio)isosteres are selective LAT1/4F2hc substrates and exhibit rapid uptake and retention in tumors expressing the LAT1/4F2hc transporter. Methods of synthesizing the β-substituted β-amino acid derivatives and β-substituted β-amino acid analogs and methods of using the compounds for treating cancer are also disclosed. The β-substituted β-amino acid derivatives and β-substituted β-amino acid analogs exhibit selective uptake in tumor cells expressing the LAT1/4F2hc transporter and accumulate in cancerous cells when administered to a subject in vivo. The β-substituted β-amino acid derivatives and β-substituted β-amino acid analogs and (bio)isosteres exhibit cytotoxicity toward several tumor types.

24 Claims, No Drawings

(56) References Cited

U.S. PATENT DOCUMENTS

| | | | |
|---|---|---|---|
| 2005/0075315 A1 | 4/2005 | Takeyama et al. | |
| 2006/0069286 A1 | 3/2006 | Allison et al. | |
| 2006/0223866 A1* | 10/2006 | Evindar | C07F 9/6561 514/365 |
| 2008/0045534 A1 | 2/2008 | Vernier et al. | |
| 2010/0144681 A1 | 6/2010 | Fuchs et al. | |

FOREIGN PATENT DOCUMENTS

| | | |
|---|---|---|
| WO | 02/066410 A1 | 8/2002 |
| WO | 2004/054566 A1 | 7/2004 |
| WO | 2005/044780 A1 | 5/2005 |
| WO | 2005/110416 A2 | 11/2005 |
| WO | 2006/124511 A2 | 11/2006 |
| WO | 2007/021937 | 2/2007 |
| WO | 2007/092190 A2 | 8/2007 |
| WO | 2008/021369 A1 | 2/2008 |
| WO | 2008/031594 A1 | 3/2008 |
| WO | 2008/088690 A2 | 7/2008 |
| WO | 2008/117175 A2 | 10/2008 |
| WO | 2010/047982 A1 | 4/2010 |
| WO | 2010/122089 A1 | 10/2010 |
| WO | 2012/011125 A1 | 1/2012 |
| WO | 2014/095739 A1 | 6/2014 |

OTHER PUBLICATIONS

Pan ("Tumor chemotherapy. V. Synthesis of some o-substituted p-[bis(2-chloroethyl)amino]phenylalanine" Hua hsüeh hsüeh pao / Huaxue Xuebao, vol. 26, No. 3, 1960, p. 131-139.*

Pan et al., "Tumor chemotherapy. V. Synthesis of some o-substituted p-[bis(2-chloroethyl)amino]phenylalanine", Acad. Sinica, 1960, 59:21475, 3 pages.

Pan et al., "Tumor chemotherapy. V. Synthesis of some o-substituted p-[bis(2-chloroethyl)amino]phenylalanines and tests", Scientia Sinica, 1962, 59:21475, 3 pages.

International Search Report and Written Opinion for PT/US2015/014299, mailed on Apr. 24, 2015, 12 pages.

International Search Report and Written Opinion for PCT/US2015/014303, mailed on May 11, 2015, 14 pages.

Abela-Medici et al., "Cytotoxic compounds. Part 21. Chloro-, methoxy-, carbonyl-derivatives of (bis-2-chloroethylamino)-phenols and -aniles", Journal of Chemical Society, Perkin Transactions 1, 1977, p. 2258-2263.

Abele et al., "Preparation of Achiral and of Enantiopure Geminally Distributed β-Amino Acids for β-Peptide Synthesis", European Journal of Organic Chemistry, Jan. 2000, Issue 1 p. 1-15.

Aldrich Technical Billetin "Diazald® and Diazomethane Generators", Black Aldrichchimica Acta, 1983, vol. 16, No. 1, p. 3-10.

Altenbach et al., "Synthesis and Structure-Activity Studies on $N$-[5-(1$H$-Imidazol-4-yl)-5, 6, 7, 8-tetrahydro-1-naphthaleny]methanesulfonamide, an Imidazole-Containing α1A-Adrenoceptor Agonist", Journal of Medicinal Chemistry, 2004, vol. 47, No. 12, p. 3220-3235.

Aoyama et al., "Chemical Manganese Dioxide (CMD), an Efficient Activated Manganese Dioxide. Application of Oxidation of Benzylic and Allylic Alcohols", Synlett, 1998, No. 1, p. 35-36.

Atwell et al., "Synthesis and Structure-Activity Relationships for 2,4-Dinitrobenzamide-5-mustards as Prodrugs for the *escherichia coli nfsB* Nitroreductase in Gene Therapy", Journal of Medicinal Chemistry, 2007, vol. 50, No. 6, p. 1197-1212.

Baggetto, "Deviant energetic metabolism of glycolytic cancer cells", Biochimie, Nov. 1992, vol. 74, Issue 11, p. 959-974.

Ballatore et al., "Carboxylic Acid (Bio)Isosteres in Drug Design", ChemMedChem, Mar. 2013, vol. 8, Issue 3, p. 385-395.

Baraldi et al., "Synthesis and Antitumor Activity of New Benzoheterocyclic Derivatives of Distamycin A", Journal of Medicinal Chemistry, 2000, vol. 43, Issue 14, p. 2675-2684.

Baratosz-Bechowski et al., "Synthesis of New N-tert-Butyloxycarbonyl-β- amino-Y-phenyl (p-substituted)-L-butyric Acid ("homo"-L-Phenylalanyl) Derivatives", Journal fuer Prakische Chemie Band, 1989, 331, 3, p. 532-536.

Baylis, "1,1-Diethoxyethylphosphinates and phosphonites. Intermediates for the synthesis of functional phosphorus acids", Tetrahedron Letters, Dec. 18, 1995, vol. 36, Issue 51, p. 9385-9388.

Beech, "2-Methyl-5-nitrobenzaldehyde", Journal of Chemical Society C: Organic, 1967, p. 2374-2375.

Black., "The Preparation and Reactions of Diazomethane", Aldrichimica Acta, Aldrich Chemical Company, Inc., 1983, vol. 16, No. 1, p. 3-22.

Blanchette et al., "Horner-Wadsworth-Emmons Reaction: Use of Lithium Chloride and an Amine for Base-Sensitive Compounds", Tetrahedron Letters, 1984, vol. 25, No. 21, p. 2183-2186.

Brown et al., "Exploiting tumor hypoxia in cancer treatment", Nature Reviews Cancer, Jun. 2004, vol. 4, p. 437-447.

Bryans et al., "Identification of Novel Ligands for the Gabapentin Binding Site on the $\alpha_2\delta$ Subunit of a Calcium Channel and Their Evaluation as Anticonvulsant Agents", Journal of Medicinal Chemistry, 1998, vol. 41, No. 11, p. 1838-1845.

Bunce et al., "Michael Reaction of Nitromethane with β,β-Distributed Acrylate Esters", Organic Preparations and Procedures International: The New Journal for Organic Synthesis, 1987, vol. 19, No. 6, p. 471-475.

Burgos-Lepley et al., "Carboxylate bioisosteres of gabapentin", Bioorganic & Medicinal Chemistry Letters, May 2006, vol. 16, Issue 9, p. 2333-2336.

Buss et al., "3,3-Difluorochlorambucil", Journal of Fluoride Chemistry, 1986, vol. 34, No. 1, p. 83-104.

Caddick et al., "A generic approach for the catalytic reduction of nitriles", Tetrahedron, Jul. 2003, vol. 59, Issue 29, p. 5417-5423.

Carruthers et al., "Synthesis and resolution of beta-(aminomethyl)-4-chlorobenzeneethanesulfinic acid a potent GABAβ receptor ligand", Bioorganic & Medicinal Chemistry Letters, 1995, vol. 5, p. 237-240.

Carruthers et al., "Synthesis of a series of sulfinic acid analogs of GABA and evaluation of their GABAβ receptor affinities", Bioorganic & Medicinal Chemistry Letters, Nov. 1998, Bvol. 8, Issue 21, p. 3059-3064.

Chandrappa et al., "An Efficient Method for Aryl Nitro Reduction and Cleavage of Azo Compounds Using Iron Powder/Calcium Chloride", Synlett, 2010, vol. 20, p. 3019-3022.

Christensen, "Role of amino acid transport and countertransport in nutrition and metabolism", Physiological Reviews, Jan. 1990, vol. 70, No. 1, p. 43-77.

Claridge et al., "Highly € -Selective Wadsworth-Emmons Reactions Promoted by Methylmagnesium Bromide", Organic Letters, 2008, vol. 10, No. 23, p. 5437-5440.

Coggiola et al., "Synthesis and biological activity of mustard derivatives of combretastatins", Bioorganic & Medicinal Chemistry Letters, 2005, vol. 15, p. 3551-3554.

Cole, "Recent stereoselective synthetic approaches to β-amino acids", Tetrahedron, 1994, vol. 50, Issue 32, p. 9517-9582.

Corey et al., "Pyridinium Chlorochromate. An Efficient Reagent for Oxidation of Primary and Secondary Alcohols to Carbonyl Compounds", Tetrahedron Letters, 1975, No. 31, p. 2647-2650.

Crosby et al., "Internediates for the synthesis of 4-substituted proline derivatives", Synlett, 2010, vol. 4, p. 539-542.

Cundy et al., "XP13512[(±)-1-([(α-Isobutanoyloxyethoxy)carbonyl]aminomethyl)-1-cyclohexane Acetic Acid], A Novel Gabapentin Prodrug: I. Design, Synthesis, Enzymatic Conversion to Gabapentin, and Transport by Intestinal Solute Transporters", The Journal of Pharmacology and Experimental Therapeutics, 2004, vol. 311, No. 1, p. 315-323.

Dagiene et al., "Carcinogenic peptides. X. Derivatives of N.alpha.-bis(2-chloroethyl)aminophenylacetyl-L-histidine", Chemical Abstract Service, 1970, 2 pages.

Davies et al., "Novel Fluorinated Prodrugs for Activation by Carboxypeptidase G2 Showing Good in Vivo Antitumor Activity in Gene-Direction Enzyme Prodrug Therapy", Journal of Medicinal Chemistry, 2005, vol. 48, No. 16, p. 5321-5328.

(56) References Cited

OTHER PUBLICATIONS

Dayal et al., "Lithium hydroxide/aqueous methanol: mild reagent for the hydrolysis of bile acid methyl esters", Steroids, May 1990, vol. 55, Issue 5, p. 233-237.
Deberardinis et al., "Beyond aerobic glycolysis: Transformed cells can engage in glutamine metabolism that exceeds the requirement for protein and nucleotide synthesis", PNAS, 2007, vol. 104, No. 49, p. 19345-19350.
Del Amo et al., "Pharmacokinetic role of L-type amino acid transporters LAT1 and LAT2", European Journal of Pharmaceutical Sciences, 2008, vol. 35, p. 161-174.
Delfourne et al., "Synthesis and in vitro antitumor activity of ring D analogues of the marine pyridoacridine ascididemin: Structure-activity relationship", Journal of Medicinal Chemistry, 2002, vol. 45, p. 3765-3771.
Delfourne et al., "Synthesis and in vitro antitumor activity of ring C and D-substituted phenanthrolin-7-one derivatives, analogues of the marine pyridoacridine alkaloids ascididemin and meridine", Bioorganic & Medicinal Chemistry, 2004, vol. 12, p. 3987-3994.
Denny et al., "Recent developments in the design of bioreductive drugs", British Journal of Cancer, 1996, vol. 74, Suppl XXVII, p. S32-S38.
Dexter et al., "Synthesis of Enantiomerically Pure β- and Y-Amino Acid Derivatives Using Functionalized Organozinc Reagents", The Journal of Organic Chemistry, 1999, vol. 64, No. 20, p. 7579-7585.
Dexter et al., "NMR Kinetic Studies on the Decomposition of β-Amidozinc Reagents: Optimization of Palladium-Catalyzed Cross-Coupling with Acid Chlorides", The Journal of Organic Chemistry, 2000, vol. 65, No. 22, p. 7417-7421.
Dheyongera et al., "Synthesis, biological evaluation, and molecular modeling of novel thioacridone derivatives related to the anticancer alkaloid acronycine", Bioorganic & Medicinal Chemistry Letters, 2005, vol. 13, p. 689-698.
Domkiene et al., "Toxicity and antineoplastic activity of alkylating compounds derived from L-histidine", Chemical Abstract Service, 1974, 128258, 1 page.
Domkiene et al., "Comparative studies of alkylating peptide like histidine derivatives", Ref. Zh., Biol., Khim., 1971, 2 pages.
Effenberger et al., "Darstellung O-geschützter ® -2-Hydroxyaldehyde und ihre Hydrocyanierung", Chemische Berichte, Jul. 1991, vol. 124, Issue 7, p. 1651-1659.
Emmons et al., "Metathetical Reactions of Silver Salts in Solution. II. The Synthesis of Alkyl Sulfonates", Journal of the American Chemical Society, 1953, vol. 75, No. 9, p. 2257.
Feau et al., "Synthesis and characterization of coumarin-based europium complexes and luminescence measurements in aqueous media", Organic & Biomolecular Chemistry, 2009, vol. 7, p. 5259-5270.
Fujikawa et al., "Design and Synthesis of Highly Sensitive Fluorogenic Substrates for Glutathione S-Transferase and Application for Activity Imaging in Living Cells", Journal of the American Chemical Society, 2008, vol. 130, No. 44, p. 14533-14543.
Felder et al., "Radioopaque contrast media. XVIII. Derivatives of 2-(3-amino-2,4,6-triiodophenyl)alkanoic acids", Journal of Medicinal Chemistry, 1970, vol. 13, No. 3, p. 559-561.
Ferlin et al., "Synthesis and antiproliferative activity of some new DNA-targeted alkylating pyrroloquinolines", Bioorganic & Medicinal Chemistry, Feb. 2004, vol. 12, No. 4, p. 771-777.
Ganapathy et al., "Nutrient transporters in cancer: relevance to Warburg hypothesis and beyond", Pharmacology & Therapeutics, Jan. 2009, vol. 121, No. 1, p. 29-40.
Gourdie et al., "DNA-directed alkylating agents. 1. Structure-activity relationships for acridine-linked aniline mustards: consequences of varying the reactivity of the mustard", Journal of Medicinal Chemistry, 1990, vol. 33, No. 4, p. 1177-1186.
Grigant et al., "The Carnitine Transporter *SLC22A5* Is Not a General Drug Transporter, but It Efficiently Translocates Mildronate", Drug Metabolism, Feb. 2009, vol. 37, No. 2, p. 330-337.
Haase et al., "L-Type Amino Acid Transporters $LAT_1$ and $LAT_4$ in Cancer: Uptake of 3-*O*-Methyl-6-$^{18}$F-Fluoro-L-Dopa in Human Adenocarcinoma and Squamous Cell Carcinoma in Vitro and In Vivo", The Journal of Nuclear Medicine, Dec. 2007, vol. 48, No. 12, p. 2063-2071.
Haines et al., "Selective cytotoxicity of a system L specific amino acid nitrogen mustard", Journal of Medicinal Chemistry, 1987, vol. 30, No. 3, p. 542-547.
Harrison et al., "β-ethoxyethyl bromide", Organic Syntheses, Coll. 1955, vol. 3, p. 370.
Hay et al., "Substituent effects on the kinetics of reductively-initiated fragmentation of nitrobenzyl carbamates designed as triggers for bioreductive prodrugs", Journal of the Chemical Society, Perkin Transactions 1, 1999, Issue 19, p. 2759-2770.
Hoekstra et al., "Chemical Development of CI-1008, an Enantiomerically Pure Anticonvulsant", Organic Process Research & Development, 1997, vol. 1, Issue 1, p. 26-38.
Hosoya et al., "Evaluation of amino acid-mustard transport as L-type amino acid transporter 1 (LAT1)-mediated alkylating agents", Biological & Pharmaceutical Bulletin, Nov. 1, 2008, vol. 31, No. 11, p. 2126-2130.
Huff et al., "Protection, metalation, and electrophilic substitution of 5-methyl tetrazole", Tetrahedron Letters, May 1996, vol. 37, Issue 21, p. 3655-3658.
Imai et al., "L-type amino acid transporter 1 expression is a prognostic marker in patients with surgically resected stage I non-small cell lung cancer", Histopathology, Jun. 2009, vol. 54, Issue 7, p. 804-813.
Jackson et al., "Synthesis of N-(*tert*-butoxycarbonyl)-β-iodoalanine methyl ester: a useful building block in the synthesis of nonnatural α-amino acids via palladium catalyzed cross coupling reactions", Organic Syntheses, 2005, vol. 81, p. 77-88.
Jager et al., "Feasibility of tumor imaging using L-3-[iodine-123]-iodo-alpha-methyl-tyrosine in extracranial tumors", Journal of Nuclear Medicine, 1998, vol. 39, No. 10, p. 1736-1743.
Ji et al., "An efficient synthesis of (R)- and (S)-baclofen via desymmetrization", Nov. 2009, vol. 50, Issue 45, p. 6166-6168.
Jordan et al., "Synthesis and Analysis of Urea and Carbamate Prodrugs as Candidates for Melanocyte-Directed Enzyme Prodrug Therapy (MDEPT)", Bioorganic & Medicinal Chemistry, 2002, vol. 10, p. 2625-2633.
Juaristi et al., "Enantioselective synthesis of β-amino acids", Aldrich Chimica Acta, 1994, vol. 27, No. 1, p. 3-11.
Kabalka et al., "Syntheses and selected reductions of conjugated mitroalkenes. A review", Organic Preparations and Procedures International, 1987, vol. 19, p. 283-328.
Kaira et al., "Fluorine-18-α-Methyltyrosine Positron Emission Tomography for Diagnosis and Staging of Lung Cancer: A Clinicopathologic Study", Clinical Cancer Research, 2007, vol. 13, p. 6369-6378.
Kaira et al., "L-type amino acid transporter 1 and CD98 expression in primary and metastatic sites of human neoplasms", Cancer Science, Dec. 2008, vol. 99, Issue 12, p. 2380-2386.
Kaira et al., "Prognostic significance of L-type amino acid transporter 1 (LAT1) and 4F2 heavy chain (CD98) expression in stage I pulmonary adenocarcinoma", Lung cancer, 2009, vol. 66, p. 120-126.
Kaji et al., "Properties of L-Type Amino Acid Transporter 1 in Epidermal Ovarian Cancer", International Journal of Gynecological Cancer, Apr. 2010, vol. 20, No. 3, p. 329336.
Kato et al., "Enhanced suppression of tumor growth by combination of angiogenesis inhibitor O-(chloroacetyl-carbamoyl)fumagillol (TNP-470) and cytotoxic agents in mice", Cancer Research, 1994, vol. 54, No. 19, p. 5143-5147.
Keller et al., "*tert*-Butoxycarbonylation of Amino Acids and their Derivatives: N-*tert*-Butoxycarbonyl-l-Phenylalanine", Organic Synthesis, 1990, vol. 7, p. 70-76.
Kim et al., "Expression of L-type amino acid transporter 1 (LAT1) and 4F2 heavy chain (4F2hc) in oral squamous cell carcinoma and its precursor lesions", Anticancer Research, 2002, vol. 24, No. 3A, p. 1671-1675.
Kim et al., "BCH, an inhibitor of system L amino acid transporters, induces apoptosis in cancer cells", Biological & Pharmaceutical Bulletin, 2008, vol. 31, No. 6, p. 1096-1100.

(56) References Cited

OTHER PUBLICATIONS

Kirkpatrick et al., "Synthesis and bioreductive potential of a Noxide derivative of the alkylating agent chlorambucil", Anti-Cancer Drugs, Aug. 1994, vol. 5, Issue 4, p. 467-472.
Kobayashi et al., "Enhanced tumor growth elicited by L-type amino acid transporter 1 in human malignant glioma cells", Neurosurgery, Feb. 2008, vol. 62, No. 2, p. 493-503.
Koh et al., "Molecular mechanisms for the activity of PX-478, an antitumor inhibitor of the hypoxia-inducible factor-1alpha", Molecular Cancer Therapeutics, Jan. 2008, vol. 7, No. 1, p. 90-100.
Krapcho et al., "Synthetic applications of dealkoxycarbonylations of malonate esters, β-keto esters, α-cyano esters and related compounds in dipolar aprotic media", Synthesis, 1982, p. 805-822 and 893-914.
Kulig et al., "Synthesis of 3,3- and 4,4-alkyl-phenyl-substituted pyrrolidin-2-one derivatives", Polish Journal of Chemistry, 2009, vol. 83, p. 1629-1636.
Kupczyk-Subotkowska et al., "Derivatives of Melphalan Designed to Enhance Drug Accumulation in Cancer Cells", Journal of Drug Targeting, 1997, vol. 4, No. 6, p. 359-370.
Laramore et al., "Fast neutron and mixed (neutron/photon) beam teletherapy for grades III and IV astrocytomas", Cancer, Jul. 1978, vol. 42, No. 1, p. 96-103.
Larden et al., "Synthesis of N-α-aminoacyl derivatives of melphalan for potential use in drug targeting", Tetrahedron Letters, Oct. 1996, vol. 37, Issue 42, p. 7581-7582.
Lebedeva et al., "Competitive Formation of β-Amino Acids, Propenoic, and Ylidenemalonic Acids by the Rodionov Reaction from Malonic Acid, Aldehydes, and Ammonium Acetate in Alcoholic Medium", Russian Journal of General Chemistry, 23005, vol. 75, Issue 7, p. 1113-1124, year is 2005.
Lelais et al., "β$^2$-amino acids-synthesis, occurrence in natural products, and components of β-peptides $^{1,2}$", Peptide Science, 2004, vol. 76, Issue 3, p. 206-243.
Li et al., "Aqueous Phosphoric Acid as a Mild Reagent for Deprotection of tert-Butyl Carbamates, Esters, and Ethers", Journal of Organic Chemistry, 2006, vol. 71, p. 9045-9050.
Limbach et al., "Synthesis of β$^3$-Homophenylalanine-Derived Amino Acids and Peptides by *Suzuki* Coupling in Solution and on Solid Support", Heveltica Chimica Acta, 2006, vol. 89, p. 1427-1442.
Lin et al., "Synthesis and structure-analgesic activity relationships of a novel series of monospirocyclopiperazinium salts (MSPZ)", Bioorganic & Medicinal Chemistry Letters, 2011, vol. 21, p. 940-943.
Liu et al., "Asymmetric synthesis of trans-3,4-distributed 2-piperidinones and pipendines", Tetrahedron: Asymmetry, 2001, vol. 12, p. 419-426.
Liu et al., "An efficient synthesis of (R)- and (S)-baclofen via desymmetrization", Tetrahedron Letters, 2009, vol. 50, p. 6166-6168.
Lombardi., "A Rapid, Safe and Convenient Procedure for the Preparation and Use of Diazomethane", Chemistry & Industry, 1990, vol. 708, 2 pages.
Loudon et al., "Conversion of Aliphatic Amides into Amines with [I,I-Bis(trifluoroacetoxy)iodo]benzene. 1. Scope of the Reaction", J. Org. Chem., 1984, vol. 49, p. 4272-4276.
Maclejewski et al., "Titanocene(III)-catalyzed conversion of N-(epoxyalkyl)anilines into indolines", Arkivoc, 2009, vi, p. 92-119.
Mann et al., "Synthesis and Biochemical Evaluation of Baclofen Analogues Locked in the Baclofen Solid-State Conformation", J. Med. Chem., 1991, vol. 34, p. 1307-1313.
Marivet et al., "Inhibition of Cyclic Adenosine-3',5'-monophosphate Phosphodiesterase from Cascular Smooth Muscle by Rolipram Analogues", J. Med. Chem., 1989, vol. 32, p. 1450-1457.
Matharu et al., "Regiospecific and conformationally restrained analogs of melphalan and DL-2-NAM-7 and their affinities for the large neutral amino acid transporter (system LAT1) of the blood-brain barrier", Bioorganic & Medicinal Chemistry, 2010, vol. 20, p. 3688-3691.
Mehta et al., "Improved Efficiency and Selectivity in Peptide Synthesis: Use of Triethylsilane as a Carbocation Scavenger in Deprotection of t-Butyl Esters and t-Butoxycarbonyl-Protected sites", Tetrahedron Letters, 1992, vol. 33, No. 37, p. 5441-5444.
Miller et al., "Alkaloids of *Vince rosea* L. (*Catharanthus roseus* G. Don). 38. 4'Dehydrated Derivatives", Journal of Medicinal Chemistry, 1977, vol. 20, No. 3, p. 409-413.
Montalbetti et al., "Amide bond formation and peptide coupling", Tetrahedron, 2005, vol. 61, p. 10827-10852.
Muller et al., "Synthesis of Fmoc-β-Homoamino Acids by Ultrasound-Promoted Wolff Rearrangement", Synthesis, Jun. 1998, p. 837-841.
Nagasawa et al., "Design of Hypoxia-Targeting Drugs as New Cancer Chemotherapeutics", Biol. Pharm. Bulletin, 2006, vol. 29, No. 12, p. 2335-2342.
Nawashiro et al., "L-type amino acid transporter 1 as a potential molecular target in human astrocytic tumors", Int. J. Cancer, 2006, vol. 119, p. 484-492.
Nejman et al., "New access to racemic β$^3$-amino acid", Tetrahedron, 2005, vol. 61, p. 8536-8541.
Nicolaou et al., "Design, Synthesis and Biological Evaluation of Nonpeptide Integrin Antagonists", Bioorganic & Medicinal Chemistry, 1998, vol. 6, p. 1185-1208.
Niculescu-Duvaz et al., "Significant Differences in Biological Parameters between Prodrugs Cleavable by Carboxypeptidase G2 That Generate 3,5-Difluoro-phenol and -aniline Nitrogen Mustards in Gene-Directed Enzyme Prodrug Therapy Systems", J. Med. Chem., 2004, vol. 47, p. 2651-2658.
Ohkame et al., "Expression of L-type Amino Acid Transporter 1 (LAT1) and 4F2 Heavy Chain (4F2hc) in Liver Tumor Lesion of Rat Models", Journal of Surgical Oncology, 2001, vol. 78, p. 265-272.
Ono et al., "Michael Addition of Secondary Nitroalkanes to β-substituted α,β-Unsaturated Compounds", Synthesis, 1984, p. 226-227.
Ordonez et al., "Stereoselective synthesis of Y-amino acids", Tetrahedron: *Asymmetry* report No. 91, 2007, vol. 18, p. 3-99.
Ordonez et al., "Stereoselective synthesis of GABOB, caritine and statine phosphonates analogues", Tetrahedron: *Asymmetry* Report No. 121, 2010, vol. 21, p. 129-147.
Osby et al., "Rapid and Efficient Reduction of Alphatic Nitro Compounds to Amines", Tetrahedron Letters, 1985, vol. 26, No. 52, p. 6413-6416.
Palacios et al., "Synthesis of β-Aminophosphonates and -Phosphinates", Chem. Rev., 2005, vol. 105, p. 899-931.
Palani et al., "Biaryl Ureas as Potent and Orally Efficacious Melanin Concentrating Hormone Receptor 1 Antagonists for the Treatment of Obesity", Journal of Medicinal Chemistry, 2005, vol. 48, p. 4746-4749.
Palmer et al., "A New Synthesis of Aromatic and Heteroaromatic Nitrogen Mustards via 3-Pyrrolines", Synthetic Communications, 1987, vol. 17, No. 5, p. 601-610.
Palmer et al., "Hypoxia-Selective Antitumor Agents. 3. Relationships between Structure and Cytotoxicity against Cultured Tumor Cells for Substituted N,N-Bis(2-chloroethyl)anilines", Journal of Medicinal Chemistry, 1990, vol. 33, p. 112-121.
Palmer et al., "Hypoxia-Selective Antitumor Agents. 5. Synthesis of Water-Soluble Nitroaniline Mustards with Selective Cytotoxicity for Hypoxia Mammalian Cells", Journal of Medicinal Chemistry, 1992, vol. 35, p. 3214-3222.
Palmer et al., "Hypoxia-Selective Antitumor Agents. 9. Structure-Activity Relationships for Hypoxia-Selective Cytotoxicity among Analogues of 5-[N,N-Bis(2-chloroethyl)amino]-2,4-dinitrobenzamide", Journal of Medicinal Chemistry, 1994, vol. 37, p. 2175-2184.
Palmer et al., V39 p. 2518 Supplemental pages, American Chemical Society, Journal of Medicinal Chemistry, 1996, vol. 39, No. 13, p. 2518-2528.
Parikh et al., "Sulfur Trioxide in the Oxidation of Alcohols by Dimethyl Sulfoxide", Journal of the American Chemical Society,1967, vol. 89, p. 5505-5507.
Peddi et al., "Structural determinants for high 5-HT2A receptor affinity of spiro[9,10-dihydroanthracene]-9,3'-pyrrolidine (SpAMDA)", Bioorganic & Medicinal Chemistry Letters, 2004, vol. 14, p. 2279-2283.

(56) References Cited

OTHER PUBLICATIONS

Podlech et al., "The Arndt-Eistert Reaction in Peptide Chemistry: A Facile Access to Homopeptides", Agnew. Chem. Int. Ed. Engl., 1995, vol. 34, No. 4, p. 471-472.
Podlech et al., "On the Preparation of β-Amino Acids from α-Amino Acids Using the Arndt-Eistert Reaction: Scope, Limitations and Stereoselectivity. Application to Carbohydrate Peptidation. Stereoselective α-Alkylations of Some β-Amino Acids", Liebigs Ann., 1995, p. 1217-1228.
Rathke et al., "The Horner-Wadsworth-Emmons Modification of the Wittig Reaction Using Triethylamine and Lithium or Magnesium Salts", Journal Org. Chem., 1985, vol. 50, No. 15, p. 2624-2626.
Reetz et al., "$CH_3Li/TiCl_4$: A Non-Basic and Highly Selective Grignard Analogue", Tetrahedron, 1986, vol. 42, No. 11, p. 2931-2935.
Remond et al., "Stereoselective Synthesis of Unsaturated and Functionalized L-NHBoc Amino Acids, Using Wittig Reaction under Mild Phase-Transfer Conditions", The Journal of Organic Chemistry, 2012, vol. 77, p. 7579-7587.
Roberts et al., "6,7-Dihydro-5H-pyrrolo[1,2-α] imidazoles as potent and selective α1A adrenoceptor partial agonists", Bioorganic & Medicinal Chemistry Letters, 2009, vol. 19, p. 3113-3117.
Ross et al., "Much Improved Conditions for the Negishi Cross-Coupling of Iodoalanine Derived Zinc Reagents with Aryl Halides", The Journal of Organic Chemistry, 2010, vol. 75, p. 245-248.
Seebach et al., "Enantioselective Preparation of $β^2$-Amino Acid Derivatives for β-Peptide Synthesis", Synthesis, 2009, No. 1, p. 1-32.
Sakata et al., "L-type amino-acid transporter 1 as a novel biomarker for high-grade malignancy in prostate cancer", Pathology International, 2009, vol. 59, p. 7-18.
Setamdideh et al., "Convenient Reduction of Nitro Compounds to their Corresponding Amines with Promotion of $NaBH_4/Ni(Oac)2.4H_2O$ System in Wet $CH_3CN$", Oriental Journal of Chemistry, 2011, vol. 27, No. 3, p. 991-996.
Sewald., "Stereoselective synthesis of β-amino acids via conjugate addition of nitrogen nucleophiles to α,β-unsaturated esters—Recent advances", Amino Acids, 1996, vol. 11, p. 397-408.
Shennan et al., "Inhibition of system L (LAT1/CD98hc) reduces the growth of cultured human breast cancer cells", Oncology Reports, 2008, vol. 20, p. 885-889.
Spreitzer et al., "Synthesis of Anticancer Compounds, I, "Dual Function" Antitumor Agents Based on Bioreduction and DNA-Alkylation", Monatshefte fur Chemie, 2007, vol. 138, p. 517-522.
Springer et al., "Novem Prodrugs Which Are Activated to Cytotoxic Alkylating Agents by Carboxypeptidase G2", Journal of Medicinal Chemistry, 1990, vol. 33, No. 2, p. 677-681.
Squires et al., "Zinc Chloride Catalysis in the Reaction of Thionyl Halides with Aliphatic Alcohols", Journal of Organic Chemistry, 1975, vol. 40, No. 1, p. 134-136.
Stowe et al., "Chirality Holds the Key for Potent Inhibition of the Botulinum Newrotoxin Serotype A Protease", Organic Letters, 2010, vol. 12, No. 4, p. 756-759.
Sulyok et al., "Solid-Phase Synthesis of a Nonpeptide RGD Mimetic Library: New Selective αvβ3 Integrin Antagonists", Journal of Medicinal Chemistry, 2001, vol. 44, p. 1938-1950.
Svenstrup et al., "New DNA Polymerase IIIC Inhibitors: 3-Substituted Anilinouracils with Potent Antibacterial Activity in vitro and in vivo", ChemMedChem, 2008, vol. 3, p. 1604-1615.
Sweeney et al., "Antitumor Activity of Deacetyl Vinblastine Amide Sulfate (Vindesine) in Rodents and Mitotic Accumulation Studies in Culture", Cancer Research, Sep. 1978, vol. 38, p. 2886-2891.
Tan et al., "A one-pot synthesis of 3-amino-3-arylpropionic acids", Tetrahedron, 2002, vol. 58, p. 7449-7461.

Taylor et al., "N-terminal bis-(2-Chloroethyl)amino and Fluorosulphonyl Analogues of Calcitonin gene-Related Peptide (8-37): Irreversible Antagonists at Calcitonin Gene-Related Paptide Receptors", Chem Biol Drug Des, 2007, vol. 70, p. 216-226.
Tercel et al., "Hypoxia-Selective Antitumor Agents. 11. Chlorambucil N-Oxide: A Reappraisal of Its Synthesis, Stability, and Selective Toxicity for Hypoxic Cells", Journal of Medicinal Chemistry, 1995, vol. 38, p. 1247-1252.
Thorn et al., "Synthesis of the Potentially Cytotoxic Compound 5-[Bis(2-chloroethyl)amino]-1,3-phenylene Biscarbamate", Journal Org. Chem., 1975, vol. 40, No. 11, p. 1556-1558.
Uchino et al., "Transport of Amino Acid-Related Compounds Mediated by L-Type Amino Acid Transporter 1 (LAT1): Insights Into the Mechanisms of Substrate Recognition", Molecular Pharmacology, 2002, vol. 61, No. 4, p. 729-737.
Urakami et al., "Evaluation of O-[$^{18}$F]fluoromethyl-D-tyrosine as a radiotracer for tumor imaging with positron emission tomography", Nuclear Medicine and Biology, 2009, vol. 36, p. 295-303.
Valeur et al., "Amide bond formation: beyond the myth of coupling reagents", Chemical Society Reviews, 2009, vol. 38, p. 606-631.
Valu et al., "DNA-Directed Alkylating Agents. 3. Structure-Activity Relationships for Acridine-Linked Aniline Mustards: Consequences of Varying the Length of the Linker Chain", Journal of Medicinal Chemistry, 1990, vol. 33, p. 3014-3019.
Van Oeveren et al., "Novel selective androgen receptor modulators: SAR studies on 6-bisalkylamino-2-quinolinones", Bioorganic & Medicinal Chemistry Letters, 2007, vol. 17, p. 1527-1531.
Vander Heiden et al., "Understanding the Warburg Effect: The Metabolic Requirements of Cell Proliferation", Science, May 2009, vol. 324, p. 1029-1033.
Verny et al., "[$^3$H]-Labeling of Hydroxyethyl Groups—Synthesis of S-@-Hydroxy [2-$^3$H] Ethyl) Glutathione and of [$^3$H]-Melphalan", Journal of Labelled Compounds and Radiopharpaceuticals, 1988, vol. 25, No. 9, p. 949-955.
Vincent et al., "Selective hydrogenolysis of benzyl ethers in the presence of benzylidene acetals with Raney nickel", Tetrahedron Letters, 2006, vol. 47, No. 24, p. 4075-4077.
Vistica., "Evidence that Melphalan in Transported by Two Leucine-Preferring Carrier Systems in the L1210 Murine Leukemia Cell", Biochimica et Biophysica Acta, 1979, vol. 550, p. 309-317.
Weisz et al., "New Synthesis of L-m-Sarcolysin and Tritiated Sarcolysin", Bioorganic & Medicinal Chemistry Letters, 1995, vol. 5, No. 24, p. 2985-2988.
Whitlock et al., "Potent and selective α1A adrenoceptor partial agonists-Novel imidazole frameworks", Bioorganic & Medicinal Chemistry Letters, 2009, vol. 19, p. 3118-3121.
Wilson et al., "Targeting hypoxia in cancer therapy", Nature Reviews Cancer, Jun. 2011, vol. 11, p. 393-410.
Xu et al., "Discovery of a novel potent GABA receptor agonist", Bioorganic & Medicinal Chemistry Letters, Aug. 2011, vol. 21, No. 21, pp. 6582-6585.
Yang et al., "Synthesis of asymmetric halomesylate mustard with aziridineethanol/alkali metal halides: application to an improved synthesis of the hypoxia prodrug PR-104", Tetrahedron, 2007, vol. 63, p. 5470-5476.
Yang et al., "Microwave-assisted expeditious synthesis of 5-fluoroalkyl-3-(aryl/alkyl)-oxazolidin-2-ones", Tetrahedron, 2013, vol. 69, p. 3331-3337.
Zheng et al., "Synthesis, biological evaluation and molecular docking studies of amide-coupled benzoic nitrogen mustard derivatives as potential antitumor agents", Bioorganic & Medicinal Chemistry, 2010, vol. 18, p. 880-886.

* cited by examiner

β-SUBSTITUTED β-AMINO ACIDS AND ANALOGS AS CHEMOTHERAPEUTIC AGENTS

This application claims the benefit under 35 U.S.C. §119 (e) of U.S. Provisional Application No. 61/935,246 filed on Feb. 3, 2014, which is incorporated by reference in its entirety.

FIELD

Disclosed herein are β-substituted β-amino acids, β-substituted β-amino acid derivatives, and β-substituted β-amino acid analogs and their use as therapeutic agents. The β-substituted β-amino acid derivatives and β-substituted β-amino acid analogs are selective substrates for LAT1/4F2hc and exhibit rapid uptake and retention in tissue such as tumors expressing the LAT1/4F2hc transporter. Pharmaceutical compositions comprising the β-substituted β-amino acid derivatives and β-substituted β-amino acid analogs and uses thereof are also disclosed.

BACKGROUND

The ability to selectively target chemotherapy has immense value in clinical practice. Cancer is a leading cause of death in the developed world, with one in every three people developing cancer during his or her lifetime. There are many treatment options for cancer including surgery, chemotherapy, radiation therapy, immunotherapy, and monoclonal antibody treatment. Unfortunately, for many patients cancer treatment options are limited and response rates remain low.

Surgery is the oldest effective form of tumor therapy and can often result in a complete cure, depending of the type and nature of the tumor. Many tumors, however, occur in locations and/or number that make surgery impossible or impractical. Also, surgical debulking is not guaranteed to remove all abnormal cells, particularly in the case of tumors located in the brain where maximum preservation of normal tissue is desired. Residual abnormal cells pose an increased risk of tumor re-growth and/or metastasis.

Radiation therapy is often used as an adjunct to surgery. Various types of radiation, both from external and implanted sources, have been used with some success. Low linear-energy-transfer (LET) sources, such as β-particles and γ-rays, require repeated treatments over extended periods of time to produce any significant reduction in tumor cells. High LET sources, such as neutrons, protons or α-particles, do not require oxygen to enhance their biological effectiveness. External beam therapy has been available for decades, however, significant radiation damage occurs to normal tissues, and patients often succumb to widespread radiation-induced necrosis (Laramore, et al., Cancer, 1978, 42(1), 96-103).

Chemotherapy is used in attempts to cure or palliate cancer. Small molecule chemotherapeutics target rapidly dividing cells, halting cell proliferation by interfering with DNA replication, cytoskeletal rearrangements and/or signaling pathways that promote cell growth. Disruption of cell division slows the growth of malignant cells and may also kill tumor cells by triggering apoptosis. Alkylating agents, such as bis (2-chloroethyl)amine derivatives, act by covalent interaction with nucleophilic heteroatoms in DNA or proteins. It is believed that these difunctional agents are able to crosslink a DNA chain within a double helix in an intrastrand or interstrand fashion, or to crosslink between DNA, proteins or other vital macromolecules. The crosslinking results in inhibitory effects on DNA replication and transcription with subsequent cell death. Since these drugs also indiscriminately kill normal populations of rapidly proliferating cells, such as those found in the immune system and in the gastrointestinal tract, side effects that limit tolerated doses, are common.

The harsh side effects and the ultimate failure of most chemotherapy regimens have motivated investigation of alternatives, including drugs that target specifically tumor cells. Normal cells and tumor cells differ markedly in nutrient and energy metabolism, a phenomenon known as the Warburg effect (Ganapathy, et al., Pharmacol Ther, 2009, 121(1), 29-40; and Vander Heiden, et al., Science, 2009, 324(5930), 1029-1033). Enhanced proliferation in tumor cells places increased demand for nutrients to serve as building blocks for the biosynthesis of macromolecules and as sources of energy. Tumor-selective nutrient accumulation is most clearly evident in imaging studies of human tumors using positron emission tomography (PET) and [$^{18}$F]-fluorodeoxyglucose (FDG). FDG accumulates at high levels in many kinds of solid tumors and is thought to be taken up into tumor cells by sugar transporters. Amino acids are the primary source of cellular nitrogen, used for nucleotide, glutathione, amino sugar, and protein synthesis. In addition, tumors often utilize the carbon skeletons of amino acids as an oxidative fuel source for ATP generation in addition to glucose and fatty acids (Baggetto, Biochimie, 1992, 74(11), 959-974; Mazurek and Eigenbrodt, 2003, Anticancer Res, 2003, 23(2A), 1149-1154; and DeBerardinis, et al., Proc Natl Acad Sci USA, 2007, 104(49), 19345-19350). Therefore, tumor cells must express select specific transporters to satisfy maintenance and growth requirements for nutritional amino acids. To compete with surrounding tissue for nutrients, tumor cells up-regulate levels of certain transporters to allow for more efficient extraction of nutrients than that of the host tissue.

Amino acid transport across the plasma membrane in mammalian cells is mediated by different transport "systems" such as the sodium-dependent systems A, ASC and N, and sodium-independent system L (Christensen, Phys Rev, 1990, 70, 43-77). System L is a ubiquitous plasma membrane amino acid transport system that is characterized by the sodium-independent uptake of bulky, hydrophobic amino acids and its high affinity interaction with 2-amino-bicyclo[2,2,1]heptane-2-carboxylic acid (BCH). System L activity is presently attributed to four sodium-independent transporters (LAT1-4). However, most cancers over-express only one member, the large amino acid transporter 1 (LAT1/4F2hc). This transporter is a heterodimer consisting of a light chain (LAT1) that constitutes the transporter and a heavy chain 4F2hc (also known as CD98, or Tumor Antigene TA1) that is required for proper targeting of the light chain to the plasma membrane. The expression and activity of LAT1/4F2hc correlates with cell proliferation and cancer growth; and up-regulation of LAT1/4F2hc has been observed, for example, in cancers of brain, colon, lung, liver, pancreas, and skin (Jager, et al., J Nucl Med, 1998, 39(10), 1736-1743; Ohkame, et al., J Surg Oncol, 2001, 78(4), 265-267; Tamai, et al., Cancer Detect Prev, 2001, 25(5), 439-445; Kim, et al., Anticancer Res, 2004, 24(3a), 1671-1675; Kobayashi, et al., Neurosurgery, 2008, 62(2), 493-503; Imai, et al., Histopathology, 2009, 54(7), 804-813; and Kaira, et al., 2009, Lung Cancer, 66(1), 120-126). Furthermore, the expression of LAT1/4F2hc has been used as an independent factor to predict poor prognoses in patients with astrocytic brain tumors, lung cancer, and prostate cancer (Nawashiro, et al., Int J Canc, 2006, 119(3), 484-492; Kaira, et al., Lung Cancer, 2009, 66(1), 120-126; Kaira, et al., Cancer Sci, 2008, 99(12), 2380-2386; and Sakata, et al., Pathol Int, 2009, 59(1), 7-18). Inhibition of LAT1/4F2hc-mediated transport with non-metabolizable amino acids such as BCH can reduce growth and induce apoptosis in cancer cells in vitro (Kim, et al., Biol Pharm Bull, 2008, 31(6), 1096-1100; Shennan and Thomson, Oncol Rep, 2008, 20(4), 885-889; and Kaji, et al., Int J Gynecol Cancer, 2010, 20(3), 329-336). Clinical studies have shown that the specificity and positive predictive value of L-[3-$^{18}$F]-α-methyltyrosine ([$^{18}$F]-FAMT) PET is superior to [$^{18}$F]-FDG PET. The uptake of [$^{18}$F]-FAMT in tumors has been closely correlated with LAT1 expression (Haase, et al., J Nucl Med, 2007, 48(12), 2063-2071; Kaira, et al., Clin Cancer Res, 2007, 13(21), 6369-6378; and Urakami, et al., Nucl Med Biol, 2009, 36(3), 295-303).

In particular, melphalan is an effective chemotherapy drug used in treating multiple myeloma, ovarian cancer, retinoblastoma, and other hematopoietic tumors. However, substrates such as gabapentin are reported to be transported much more rapidly than melphalan (Uchino, et al., Mol Pharmacol 2002, 61(4), 729-737). It is widely believed that uptake of melphalan (Alkeran®, otherwise known as L-Phenylalanine Mustard, or L-PAM) into cells is mediated by amino acid transporters. Melphalan is an alkylating agent linked to the essential amino acid phenylalanine. Because normal cells and tumor cells differ markedly in nutrient and energy metabolism (Warburg effect) (Vander Heiden, et al., Science, 2009, 324(5930), 1029-1033), melphalan was introduced into clinical practice with the expectation that it would preferentially accumulate in rapidly dividing tumor cells compared to normal cells, thereby increasing its overall therapeutic index. Surprisingly, melphalan caused many of the same side effects as other conventional alkylation agents, including myelosuppression. In a series of publications, Vistica et al. examined melphalan transport in different cell types and identified two independent transport systems for melphalan. One system, presumed to be System L, is characterized by the sodium-independent uptake of bulky, hydrophobic amino acids and its sensitivity toward inhibition with 2-amino-bicyclo[2,2,1]heptane-2-carboxylic acid (BCH) (Vistica, Biochim Biophys Acta, 1979, 550(2), 309-317). A second transport system is sodium-dependent, exhibits its highest affinity for leucine, but is insensitive to both BCH and the system A-specific inhibitor α-amino-isobutyric acid (A1B) (Vistica, Biochim Biophys Acta, 1979, 550(2), 309-317). Although LAT1 is overexpressed on the cell surface of almost all tumor cells regardless of the tissue of origin, response rates to melphalan are low for most cancer types, and the drug is only approved for the treatment of multiple myeloma and ovarian cancer. Melphalan is a poor substrate for LAT1 compared to other large amino acids such as phenylalanine or leucine (Uchino, et al., Mol Pharmacol 2002, 61(4), 729-737; and Hosoya, et al., Biol Pharm Bull, 2008, 31(11), 2126-2130). Nitrogen mustard derivatives with higher selectivity toward the LAT1/4F2hc system could reduce side effects associated with nitrogen mustard therapy, allow for an increase in dose, and extend the use into other areas of cancer treatment.

Although the potential for active transport strategies for increasing drug uptake into tumor cells is known and generally accepted, chemotherapeutics and tumor imaging agents have in general not been optimized for transporters known to be over-expressed in tumor cells. While the general concept of using LAT1/2Fhc-selective compounds to deliver therapeutic agents to tumors is appreciated, the existing art gives no guidance as to how one prepares a composition that exploits LAT1/4F2hc selective compounds. Thus, there is a need for new therapeutic agents that are more selective toward LAT1/4F2hc.

Several amino acid-related drugs that are substrates of the LAT1/4F2hc transporter are known including L-Dopa, 3-O-methyldopa, droxidopa, carbidopa, 3,3',5'-triiodothyronine, thyroxine, gabapentin, and melphalan (Uchino, et al., Mol Pharm 2002, 61(4), 729-737; and del Amo et al., Eur J Pharm Sci, 2008, 35(3), 161-174).

SUMMARY

Differentiation of malignant cancer tissue from neighboring nonmalignant tissue can be accomplished by exploiting changes in biochemical fluxes that occur in response to metabolic, genetic, and/or microstructural changes in the malignant cells. Compounds provided by the present disclosure substantially improve chemotherapy of tissue expressing the LAT1/4F2hc transporter including malignant tumors. The β-substituted β-amino acid derivatives and β-substituted β-amino acid analogs provided by the present disclosure provide greater uptake selectivity for the target tissue or cells expressing the LAT1/4F2hc transporter with low non-specific uptake for non-target tissues or cells.

Embodiments provided by the present disclosure provide novel β-substituted β-amino acid derivatives and β-substituted β-amino acid analogs, and methods of using such derivatives, for example, as chemotherapeutic agents. Certain embodiments further relate to methods of synthesizing β-substituted β-amino acid derivatives and β-substituted β-amino acid analogs and to pharmaceutical compositions comprising such derivatives. The β-substituted β-amino acid derivatives and β-substituted β-amino acid analogs the present disclosure exhibit selectivity for LAT1/4F2hc and therefore accumulate in cancerous cells when administered to a subject in vivo. Advantages provided by compounds of the present disclosure reflect the properties of LAT1/4F2hc substrates, namely, blood brain-barrier (BBB) permeability, rapid uptake, and prolonged retention in tumors expressing the LAT1/4F2hc transporter, and further serve as chemotherapeutic agents.

Compounds

In a first aspect, compounds of Formula (1) are provided:

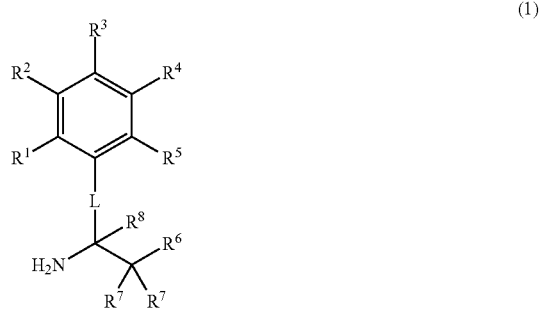

or a pharmaceutically acceptable salt thereof, wherein:
at least one of $R^1$ and $R^5$ is independently selected from halogen, —N($R^{10}$)$_2$, —N$^+$(—O$^-$)($R^{10}$)$_2$, —N(O$R^{10}$)($R^{10}$), —NO$_2$, —NO, —N($R^{10}$)(S(=O)$R^{10}$), —N($R^{10}$)(S(=O)$_2$$R^{10}$), —N($R^{10}$)(C(O)$R^{10}$), —N($R^{10}$)(C(O)O$R^{10}$), —N($R^{10}$)(C(O)N($R^{10}$)$_2$, —CN, —COO$R^{10}$, —CON($R^{10}$)$_2$, —OH, —SH, $C_{1-4}$ alkylsulfanyl, $C_{1-4}$ alkylsulfinyl, $C_{1-4}$ alkylsulfonyl, —S(O)N($R^{10}$)$_2$, —S(O)$_2$N($R^{10}$)$_2$, $C_{1-4}$ fluoroalkyl, $C_{1-4}$ fluoroalkoxy, $C_{1-6}$ alkyl, substituted $C_{1-6}$ alkyl, $C_{1-6}$ alkoxy, substituted $C_{1-6}$ alkoxy, $C_{3-6}$ cycloalkyl, substituted $C_{3-6}$ cycloalkyl, $C_{3-6}$ cycloalkyloxy, substituted $C_{3-6}$ cycloalkyloxy, $C_{4-12}$ cycloalkylalkyl, substituted $C_{4-12}$ cycloalkylalkyl, $C_{6-10}$ aryl, substituted $C_{6-10}$ aryl, $C_{7-16}$ arylalkyl, substituted $C_{7-16}$ arylalkyl, $C_{1-6}$ heteroalkyl, substituted $C_{1-6}$ heteroalkyl, $C_{1-6}$ heteroalkoxy, substituted $C_{1-6}$ heteroalkoxy, $C_{3-6}$ heterocycloalkyl, substituted $C_{3-6}$ heterocycloalkyl, $C_{4-12}$ heterocycloalkylalkyl, substituted $C_{4-12}$ heterocycloalkylalkyl, $C_{5-10}$ heteroaryl, substituted $C_{5-10}$ heteroaryl, $C_{6-16}$ heteroarylalkyl, and substituted $C_{6-16}$ heteroarylalkyl;

one of $R^1$, $R^2$, $R^3$, $R^4$, and $R^5$ comprises a chemotherapeutic moiety;

each of the other of $R^1$, $R^2$, $R^3$, $R^4$, and $R^5$ is independently selected from hydrogen, deuterio, halogen, —OH, —N($R^{10}$)$_2$, —NO$_2$, —NO, —CN, —COOR$^{10}$, —CON($R^{10}$)$_2$, $C_{1-4}$ alkylsulfanyl, $C_{1-4}$ alkylsulfinyl, $C_{1-4}$ alkylsulfonyl, $C_{1-6}$ alkyl, substituted $C_{1-6}$ alkyl, $C_{3-6}$ cycloalkyl, substituted $C_{3-6}$ cycloalkyl, $C_{1-6}$ heteroalkyl, substituted $C_{1-6}$ heteroalkyl, $C_{1-6}$ alkoxy, substituted $C_{1-6}$ alkoxy, $C_{1-6}$ heteroalkoxy, substituted $C_{1-6}$ heteroalkoxy, $C_{4-8}$ cycloalkylalkyl, and $C_{4-8}$ cycloalkylheteroalkyl;

$R^6$ is selected from a carboxylic acid (—COOH), a carboxylic acid analog, and a carboxylic acid (bio)isostere;

each $R^7$ is independently selected from hydrogen, deuterio, halogen, hydroxyl, $C_{1-6}$ alkyl, $C_{3-6}$ cycloalkyl, benzyl, and phenyl; or two $R^7$ together with the carbon to which they are bonded form a ring selected from a $C_{3-6}$ cycloalkyl ring and a $C_{3-6}$ heterocycloalkyl ring;

$R^8$ is selected from hydrogen, deuterio, halogen, $C_{1-6}$ alkyl, substituted $C_{1-6}$ alkyl, $C_{1-6}$ heteroalkyl, substituted $C_{1-6}$ heteroalkyl, $C_{1-6}$ alkoxy, substituted $C_{1-6}$ alkoxy, $C_{1-6}$ heteroalkoxy, substituted $C_{1-6}$ heteroalkoxy, $C_{3-6}$ cycloalkyl, substituted $C_{3-6}$ cycloalkyl, $C_{3-6}$ cycloalkyloxy, substituted $C_{3-6}$ cycloalkyloxy, —OH, —COOR$^{10}$, $C_{1-4}$ fluoroalkyl, $C_{1-4}$ fluoroalkoxy, $C_{3-6}$ cycloalkyl, and phenyl;

each $R^{10}$ is independently selected from hydrogen, deuterio, $C_{1-4}$ alkyl and $C_{1-4}$ alkoxy, or two geminal $R^{10}$ together with the nitrogen to which they are bonded form a 3- to 6-membered heterocyclic ring; and L is —(X)$_a$—, wherein, each X is independently selected from a bond ("—"), —C($R^{16}$)$_2$—, wherein each $R^{16}$ is independently selected from hydrogen, deuterio, halogen, hydroxyl, $C_{1-4}$ alkyl and $C_{1-4}$ alkoxy, or two $R^{16}$ together with the carbon to which they are bonded form a $C_{3-6}$ cycloalkyl ring or a $C_{3-6}$ heterocycloalkyl ring, —O—, —S—, —SO—, —SO$_2$—, —CO—, and —N($R^{17}$)—, wherein $R^{17}$ is selected from hydrogen and $C_{1-4}$ alkyl; and a is selected from 0, 1, 2, 3, and 4.

In a second aspect, chemotherapeutic moieties are provide wherein the chemotherapeutic moiety may be any suitable chemotherapeutic moiety of chemotherapeutic drugs known in the art that retains cytotoxic activity when bonded through a spacing moiety, e.g., an aryl ring and a linker L, to a β-amino acid derivative, β-amino acid analog, or β-amino acid carboxylic acid (bio)isostere as a LAT1 recognition element provided by the present disclosure. The conjugate or fusion product of the chemotherapeutic moiety with the β-amino acid derivative, β-amino acid analog, or β-amino acid carboxylic acid (bio)isostere is simultaneous a selective substrate for the LAT1/4F2hc transporter.

In a third aspect, chemotherapeutic moieties are provided, where in the chemotherapeutic moiety is selected from a nitrogen mustard —N(—CR$_2$—CR$_2$—X)$_2$, a N-monoalkyl or N,N-dialkyl triazene (—N=N—NR$_2$), a haloacetamide (—NR—CO—CH$_2$—X), an epoxide (—CROCR—R), an aziridine (—NC$_2$H$_4$), a Michael acceptor (—CR=CR-EWG-), a sulfonate or a bissulfonate ester (—OSO$_2$R or ROSO$_2$—), an N-nitrosourea (—NR—CO—N(NO)R), a bissulfonyl hydrazine (R"SO$_2$—NR—N(—)—SO$_2$R'", —SO$_2$—NR—NR'—SO$_2$R'", or R"SO$_2$—NR—NR'—SO$_2$—), a phosphoramidate (—O—P(=O)(N(R)—CH$_2$—CH$_2$—X)$_2$ or —O—P(=O)(N(—CH$_2$—CH$_2$—X)$_2$)$_2$, and a radionuclide such as, for example, 131-iodine ($^{131}$[I]—) or 211-astatine ($^{211}$[At]—).

In a fourth aspect, chemotherapeutic moieties of Formula (2) are provided:

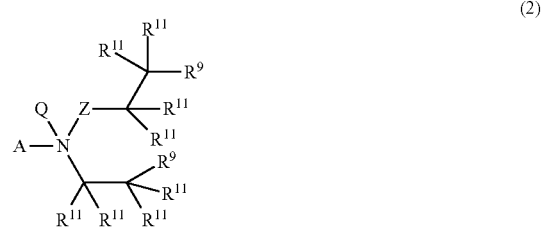

(2)

wherein,

A is selected from a bond ("—"), oxygen (—O—), sulfur (—S—), amino (—NR$^{10}$—), methylene (—CH$_2$—), methyleneoxy (—CH$_2$—O—), oxycarbonyl (—O—C(=O)—), thiocarbonyl (—S—C(=O)—), aminocarbonyl (—NR$^{10}$—C(=O)—), oxythiocarbonyl (—O—C(=S)—), thiothiocarbonyl (—S—C(=S)—), aminothiocarbonyl (—NR$^{10}$—C(=S)—), methyleneoxycarbonyl (—CH$_2$—O—C(=O)—), methylenethiocarbonyl (—CH$_2$—S—C(=O)—), methyleneaminocarbonyl (—CH$_2$—NR$^{10}$—C(=O)—), methyleneoxythiocarbonyl (—CH$_2$—O—C(=S)—), methylenethiothiocarbonyl (—CH$_2$—S—C(=S)—), methyleneaminothiocarbonyl (—CH$_2$—NR$^{10}$—C(=S)—), carbonyl (—C(=O)—), methylencarbonyl (—CH$_2$—C(=O)—), thiocarbonyl (—C(=S)—), and methylenthiocarbonyl (—CH$_2$—C(=S)—);

Z is selected from a bond ("—") and oxygen (—O—);

Q is selected from —O$^-$ (a negatively charged oxygen atom) that is bound to a positively charged nitrogen atom) and a free electron pair (:), with the proviso that when Q is —O$^-$ (a negatively charged oxygen atom that is bound to a positively charged nitrogen atom), A is selected from a bond ("—") and methylene (—CH$_2$—), Z is a bond ("—"), and the chemotherapeutic moiety of Formula (2) is an N-oxide (-A-N$^+$(—O$^-$)(—C(R$^{11}$)$_2$—C(R$^{11}$)$_2$—R$^9$)$_2$);

each $R^{11}$ is independently selected from hydrogen, deuterio, and $C_{1-3}$ alkyl; and each $R^9$ is independently selected from fluoro (—F), chloro (—Cl), bromo (—Br), iodo (—I), alkyl sulfonate (—OSO$_2$R$^{40}$, wherein $R^{40}$ is selected from $C_{1-4}$ alkyl), $C_{1-4}$ (per)fluoroalklyl sulfonate (—OSO$_2$R$^{40}$, wherein $R^{40}$ is selected from $C_{1-4}$ (per)fluoroalkyl), and (substituted) aryl sulfonate (—OSO$_2$R$^{40}$, wherein $R^{40}$ is selected from $C_{6-10}$ aryl).

In a fifth aspect, pharmaceutical compositions comprising the compound of claim 1 and a pharmaceutically acceptable vehicle are provided.

In a sixth aspect, uses of compounds of Formula (1) for treating cancer in a patient are provided, comprising administering to a patient in need of such treatment a therapeutically effective amount of the compound of claim 1.

DETAILED DESCRIPTION

Definitions

A dash ("-") that is not between two letters or symbols is used to indicate a point of attachment for a moiety or substituent. For example, —CONH$_2$ is attached through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl(allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" is specifically intended to include groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. In certain embodiments, an alkyl group is $C_{1-6}$ alkyl, $C_{1-5}$ alkyl, $C_{1-4}$ alkyl, $C_{1-3}$ alkyl, and in certain embodiments, ethyl or methyl.

"Alkylsulfanyl" also referred to as "alkylthio", refers to a radical —SR where R is alkyl or cycloalkyl as defined herein. Examples of alkylsulfanyl groups include methylsulfanyl, ethylsulfanyl, propylsulfanyl, isopropylsulfanyl, butylsulfanyl, and cyclohexylsulfanyl. In certain embodiments, an alkylsulfanyl group is $C_{1-6}$ alkylsulfanyl, in certain embodiments, $C_{1-5}$ alkylsulfanyl, in certain embodiments, $C_{1-4}$ alkylsulfanyl, in certain embodiments, $C_{1-3}$ alkylsulfanyl, in certain embodiments, ethylsulfanyl(ethylthio), and in certain embodiments, methylsulfanyl(methylthio).

"Alkylsulfinyl" refers to a radical —S(O)R where R is alkyl or cycloalkyl as defined herein. Examples of alkylsulfinyl groups include methylsulfinyl, ethylsulfinyl, propylsulfinyl, isopropylsulfinyl, butylsulfinyl, and cyclohexylsulfinyl. In certain embodiments, an alkylsulfinyl group is $C_{1-6}$ alkylsulfinyl, in certain embodiments, $C_{1-5}$ alkylsulfinyl, in certain embodiments, $C_{1-4}$ alkylsulfinyl, in certain embodiments, $C_{1-3}$ alkylsulfinyl, in certain embodiments, ethylsulfinyl, and in certain embodiments, methylsulfinyl.

"Alkylsulfonyl" refers to a radical —S(O)$_2$R where R is alkyl or cycloalkyl as defined herein. Examples of alkylsulfonyl groups include methylsulfonyl, ethylsulfonyl, propylsulfonyl, isopropylsulfonyl, butylsulfonyl, and cyclohexylsulfonyl. In certain embodiments, an alkylsulfonyl group is $C_{1-6}$ alkylsulfonyl, in certain embodiments, $C_{1-5}$ alkylsulfonyl, in certain embodiments, $C_{1-4}$ alkylsulfonyl, in certain embodiments, $C_{1-3}$ alkylsulfonyl, in certain embodiments, ethylsulfonyl, and in certain embodiments, methylsulfonyl.

"Alkoxy" refers to a radical —OR where R is alkyl as defined herein. Examples of alkoxy groups include methoxy, ethoxy, propoxy, and butoxy. In certain embodiments, an alkoxy group is $C_{1-6}$ alkoxy, in certain embodiments, $C_{1-5}$ alkoxy, in certain embodiments, $C_{1-4}$ alkoxy, in certain embodiments, $C_{1-3}$ alkoxy, and in certain embodiments, ethoxy or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group is $C_{6-10}$ aryl, $C_{6-9}$ aryl, $C_{6-8}$ aryl, and in certain embodiments, phenyl. Aryl, however, does not encompass or overlap in any way with heteroaryl, separately defined herein.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-16}$ arylalkyl, e.g., the alkanyl, alkenyl or alkynyl moiety of the arylalkyl group is $C_{1-6}$ and the aryl moiety is $C_{6-10}$, in certain embodiments, an arylalkyl group is $C_{7-16}$ arylalkyl, e.g., the alkanyl, alkenyl or alkynyl moiety of the arylalkyl group is $C_{1-6}$ and the aryl moiety is $C_{6-10}$. In certain embodiments, an arylalkyl group is $C_{7-9}$ arylalkyl, wherein the alkyl moiety is $C_{1-3}$ alkyl and the aryl moiety is phenyl. In certain embodiments, an arylalkyl group is $C_{7-16}$ arylalkyl, $C_{7-14}$ arylalkyl, $C_{7-12}$ arylalkyl, $C_{7-10}$ arylalkyl, $C_{7-8}$ arylalkyl, and in certain embodiments, benzyl.

Bioisosteres are atoms or molecules that fit the broadest definition for isosteres. The concept of bioisosterism is based on the notion that single atom, groups, moieties, or whole molecules, which have chemical and physical similarities produce similar biological effects. A bioisostere of a parent compound can still be recognized and accepted by its appropriate target, but its functions will be altered as compared to the parent molecule. Parameters affected with bioisosteric replacements include, for example, size, conformation, inductive and mesomeric effects, polarizability, capacity for electrostatic interactions, charge distribution, H-bond formation capacity, pKa (acidity), solubility, hydrophobicity, lipophilicity, hydrophilicity, polarity, potency, selectivity, reactivity, or chemical and metabolic stability, ADME (absorption, distribution, metabolism, and excretion). Although common in pharmaceuticals, carboxyl groups or carboxylic acid functional groups (—CO$_2$H) in a parent molecule may be replaced with a suitable surrogate or (bio)isostere to overcome chemical or biological shortcomings while retaining the desired attributes of the parent molecule bearing one or more carboxyl groups or carboxylic acid functional groups (—CO$_2$H). Examples of suitable surrogates or (bio)isosteres of carboxyl groups or carboxylic acid functional groups (—CO$_2$H) include hydroxamic acids (—CONR$^{12}$OH); boronic acids (—B(OH)(OR$^{12}$), phosphinic acids or derivatives thereof (—PO(OH)R$^{12}$), phosphonic acid or derivatives thereof (—PO(OH)(OR$^{12}$), sulfinic acid (—SOOH), sulfonic acid (—SO$_2$OH), sulfonamide (—SO$_2$NHR$^{12}$ or —NHSO$_2$R$^{12}$), sulfonimide or acyl sulfonimide (—SO$_2$NHCOR$^{12}$ or —CONHSO$_2$R$^{12}$), sulfonylureas (—SO$_2$NHCONHR$^{12}$ or —NHCONHSO$_2$R$^{12}$), amide (—CONHR$^{12}$ or —NHCOR$^{12}$), wherein R$^{12}$ in any of the foregoing is selected from hydrogen, C$_{1-6}$ alkyl, C$_{1-4}$ fluoroalkyl, C$_{3-6}$ cycloalkyl, and C$_{6-10}$ aryl, acylcyanamide (—CONHCN); 2,2,2-trifluoroethan-1-ols (—CH(CF$_3$)OH), 2,2,2-trifluoromethyl ketones and hydrates thereof (—COCF$_3$ and —C(OH)$_2$CF$_3$), acidic heterocycles and their annular tautomers such as, for example, tetrazole, 5-oxo-1,2,4-oxadiazole, 5-oxo-1,2,4-thiadiazole, 5-thioxo-1,2,4-oxadiazole, thiazolidinedione, oxazolidinedione, oxadiazolidinedione, 3-hydroxyisoxazole, 3-hydroxyisothiazole, 1-hydroxy-imidazole, 1-hydroxy-pyrazole, 1-hydroxy-triazole, 1H-imidazol-2-ol, tetrazole-5-thiol, 3-hydroxyquinolin-2-ones, 4-hydroxyquinolin-2-ones, tetronic acid, tetramic acid, mercaptoazoles such as sulfanyl-1H-imidazole, sulfinyl-1H-imidazole, sulfonyl-1H-imidazole, sulfanyl-1H-triazole, sulfinyl-1H-triazole, sulfonyl-1H-triazole, sulfanyl-1H-1,2,4-triazole, sulfinyl-1H-1,2,4-triazole, sulfonyl-1H-1,2,4-triazole, sulfanyl-1,4-dihydro-1,2,4-triazol-5-one, sulfinyl-1,4-dihydro-1,2,4-triazol-5-one, sulfonyl-1,4-dihydro-1,2,4-triazol-5-one, sulfanyl 1H-tetrazole, sulfanyl 2H-tetrazole, sulfinyl 1H-tetrazole, sulfinyl 2H-tetrazole, sulfonyl 1H-tetrazole, sulfonyl 2H-tetrazole, or sulfonimidamides; and; acidic oxocarbocycles or cyclic polyones and their resonance forms such as, for example, cyclopentane-1,3-diones, squaric acids, squareamides, mixed squaramates, or 2,6-difluorophenols.

"Compounds" of Formula (1) and moieties of Formula (2) disclosed herein include any specific compounds within these formulae. Compounds may be identified either by their chemical structure and/or chemical name. Compounds are named using the ChemDraw Ultra 12.0 (CambridgeSoft, Cambridge, Mass.) nomenclature program. When the chemical structure and chemical name conflict the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

Compounds of Formula (1) and moieties of Formula (2) include optical isomers of compounds of Formula (1) and moieties of Formula (2), racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds of Formula (1) include (Z)- and (E)-forms (or cis- and trans-forms) of compounds with double bonds either as single geometric isomers or mixtures thereof.

Compounds of Formula (1) and moieties of Formula (2) may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds of Formula (1) include pharmaceutically acceptable salts thereof, or pharmaceutically acceptable solvates of the free acid form of any of the foregoing, as well as crystalline forms of any of the foregoing Compounds of Formula (1) are also referred to herein as β-substituted β-amino acid derivatives and/or as β-substituted β-amino acid analogs.

"Chemotherapeutic moiety" refers to a moiety effective in treating cancer including, any of those disclosed herein. In certain embodiments, a chemotherapeutic moiety may be any suitable chemotherapeutic moiety of a chemotherapeutic drugs known in the art that retains cytotoxic activity when bonded either directly or indirectly through a suitable spacing moiety to a β-amino acid derivative, β-amino acid analog, or β-amino acid carboxylic acid (bio)isostere as a LAT1 recognition element provided by the present disclosure. The conjugate or fusion product of the chemotherapeutic moiety with the β-amino acid derivative, β-amino acid analog, or β-amino acid carboxylic acid (bio)isostere is simultaneous a selective substrate for the LAT1/4F2hc transporter.

In certain embodiments, the chemotherapeutic moiety, is selected from a nitrogen mustard (—N(—CR$_2$—CR$_2$—X)$_2$), a N-monoalkyl or N,N-dialkyl triazene (—N=N—NR$_2$), a haloacetamide (—NR—CO—CH$_2$—X), an epoxide (—CROCR—R), an aziridine (—NC$_2$H$_4$), a Michael acceptor (—CR=CR-EWG-), a sulfonate or a bissulfonate ester (—OSO$_2$R or ROSO$_2$—), an N-nitrosourea (—NR—CO—N(NO)R), a bissulfonyl hydrazine (R"SO$_2$—NR—N(—)—SO$_2$R''', —SO$_2$—NR—NR'—SO$_2$R''', or R"SO$_2$—NR—NR'—SO$_2$—), a phosphoramidate (—O—P(=O)(N(R)—CH$_2$—CH$_2$—X)$_2$ or —O—P(=O)(N(—CH$_2$—CH$_2$—X)$_2$)$_2$, and a radionuclide such as, for example, 131-iodine ($^{131}$[I]—) or 211-astatine ($^{211}$[At]—).

In certain embodiments of a compound of Formula (1), the chemotherapeutic moiety is a moiety Formula (2a):

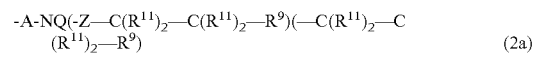

(2a)

wherein,

A is selected from a bond ("—"), oxygen (—O—), sulfur (—S—), amino (—NR$^{10}$—), methylene (—CH$_2$—), methyleneoxy (—CH$_2$—O—), oxycarbonyl (—O—C(=O)—), thiocarbonyl (—S—C(=O)—), aminocarbonyl (—NR$^{10}$—C(=O)—), oxythiocarbonyl (—O—C(=S)—), thiothiocarbonyl (—S—C(=S)—), aminothiocarbonyl (—NR$^{10}$—C(=S)—), methyleneoxycarbonyl (—CH$_2$—O—C(=O)—), methylenethiocarbonyl (—CH$_2$—S—C(=O)—), methyleneaminocarbonyl (—CH$_2$—NR$^{10}$—C(=O)—), methyleneoxythiocarbonyl (—CH$_2$—O—C(=S)—), methylenethiothiocarbonyl (—CH$_2$—S—C(=S)—), methyleneaminothiocarbonyl (—CH$_2$—NR$^{10}$—C(=S)—), carbonyl (—C(=O)—), methylencarbonyl (—CH$_2$—C(=O)—), thiocarbonyl (—C(=S)—), and methylenthiocarbonyl (—CH$_2$—C(=S)—);

Z is selected from a bond ("—") and oxygen (—O—);

Q is selected from —O$^-$ (a negatively charged oxygen atom) that is bound to a positively charged nitrogen atom) and a free electron pair (:), with the proviso that when Q is —O$^-$ (a negatively charged oxygen atom that is bound to a positively charged nitrogen atom), A is selected from a bond ("—") and methylene (—CH$_2$—), Z is a bond ("—"), and the chemotherapeutic moiety of Formula (2) is an N-oxide (-A-N$^+$(—O$^-$)(—C(R$^{11}$)$_2$—C(R$^{11}$)$_2$—R$^9$)$_2$); and each $R^{11}$ is independently selected from hydrogen, deuterio, and $C_{1-3}$ alkyl; and each $R^9$ is independently selected from fluoro (—F), chloro (—Cl), bromo (—Br), iodo (—I), alkyl sulfonate (—OSO$_2$R$^{40}$, wherein $R^{40}$ is selected from $C_{1-4}$ alkyl), $C_{1-4}$ (per)fluoroalklyl sulfonate (—OSO$_2$R$^{40}$, wherein $R^{40}$ is selected from $C_{1-4}$ (per)fluoroalkyl), and (substituted) aryl sulfonate (—OSO$_2$R$^{40}$, wherein $R^{40}$ is selected from $C_{6-10}$ aryl).

"Cycloalkyl" refers to a saturated or partially unsaturated cyclic alkyl radical. In certain embodiments, a cycloalkyl group is $C_{3-6}$ cycloalkyl, $C_{3-5}$ cycloalkyl, $C_{5-6}$ cycloalkyl, cyclopropyl, cyclopentyl, and in certain embodiments, cyclohexyl. In certain embodiments, cycloalkyl is selected from cyclopropyl, cyclobutyl, cyclopentyl, and cyclohexyl.

"Cycloalkylalkyl" refers to an acyclic alkyl radical in which one of the hydrogen atoms bonded to a carbon atom is replaced with a cycloalkyl group as defined herein. Where specific alkyl moieties are intended, the nomenclature cycloalkylalkyl, cycloalkylalkenyl, or cycloalkylalkynyl is used. In certain embodiments, a cycloalkylalkyl group is $C_{4-30}$ cycloalkylalkyl, e.g., the alkanyl, alkenyl, or alkynyl moiety of the cycloalkylalkyl group is $C_{1-10}$ and the cycloalkyl moiety of the cycloalkylalkyl moiety is $C_{3-20}$, and in certain embodiments, an cycloalkylalkyl group is $C_{4-20}$ cycloalkylalkyl, e.g., the alkanyl, alkenyl, or alkynyl moiety of the cycloalkylalkyl group is $C_{1-8}$ and the cycloalkyl moiety of the cycloalkylalkyl group is $C_{3-12}$. In certain embodiments, cycloalkylalkyl is $C_{4-9}$ cycloalkylalkyl, wherein the alkyl moiety of the cycloalkylalkyl group is $C_{1-3}$ alkyl, and the cycloalkyl moiety of the cycloalkylalkyl group is $C_{3-6}$ cycloalkyl. In certain embodiments, a cycloalkylalkyl group is $C_{4-12}$ cycloalkylalkyl, $C_{4-10}$ cycloalkylalkyl, $C_{4-8}$ cycloalkylalkyl, and $C_{4-6}$ cycloalkylalkyl. In certain embodiments a cycloalkylalkyl group is cyclopropylmethyl (—CH$_2$-cyclo-C$_3$H$_5$), cyclopentylmethyl (—CH$_2$-cyclo-C$_5$H$_9$), or cyclohexylmethyl (—CH$_2$-cyclo-C$_6$H$_{11}$). In certain embodiments a cycloalkylalkyl group is cyclopropylethenyl (—CH=CH-cyclo-C$_3$H$_5$), cyclopentylethynyl (—C≡C-cyclo-C$_5$H$_9$), or the like.

"Cycloalkylheteroalkyl" by itself or as part of another substituent refers to a heteroalkyl group in which one or more of the carbon atoms (and certain associated hydrogen atoms) of an alkyl group are independently replaced with the same or different heteroatomic group or groups and in which one of the hydrogen atoms bonded to a carbon atom is replaced with a cycloalkyl group. Where specific alkyl moieties are intended, the nomenclature cycloalkylheteroalkanyl, cycloalkylheteroalkenyl, and cycloalkylheteroalkynyl is used. In certain embodiments of cycloalkylheteroalkyl, the heteroatomic group is selected from —O—, —S—, —NH—, —N(—CH$_3$)—, —SO—, and —SO$_2$—, in certain embodiments, the heteroatomic group is selected from —O— and —NH—, and in certain embodiments the heteroatomic group is —O— or —NH—.

"Cycloalkyloxy" refers to a radical —OR where R is cycloalkyl as defined herein.

Examples of cycloalkyloxy groups include cyclopropyloxy, cyclobutyloxy, cyclopentyloxy, and cyclohexyloxy. In certain embodiments, a cycloalkyloxy group is $C_{3-6}$ cycloalkyloxy, in certain embodiments, $C_{3-5}$ cycloalkyloxy, in certain embodiments, $C_{5-6}$ cycloalkyloxy, and in certain embodiments, cyclopropyloxy, cyclobutyloxy, cyclopentyloxy, or cyclohexyloxy.

"Disease" refers to a disease, disorder, condition, or symptom of any of the foregoing.

"Fluoroalkyl" refers to an alkyl group as defined herein in which one or more of the hydrogen atoms is replaced with a fluoro. In certain embodiments, a fluoroalkyl group is $C_{1-6}$ fluoroalkyl, $C_{1-5}$ fluoroalkyl, $C_{1-4}$ fluoroalkyl, and $C_{1-3}$ fluoroalkyl. In certain embodiments, the fluoroalkyl group is pentafluoroethyl (—CF$_2$CF$_3$), and in certain embodiments, trifluoromethyl (—CF$_3$).

"Fluoroalkoxy" refers to an alkoxy group as defined herein in which one or more of the hydrogen atoms is replaced with a fluoro. In certain embodiments, a fluoroalkoxy group is $C_{1-6}$ fluoroalkoxy, $C_{1-5}$ fluoroalkoxy, $C_{1-4}$ fluoroalkoxy $C_{1-3}$, or fluoroalkoxy, and in certain embodiments, —OCF$_2$CF$_3$ or —OCF$_3$.

"β-Substituted β-amino acid derivative" refers to β-substituted β-amino acid derivatives having a carboxyl group, e.g., β-substituted β-amino acid.

"β-Substituted β-amino acid analog" refers to β-substituted β-amino acid derivatives in which the carboxyl group is replaced with a phosphinic acid group, a sulfinic acid group, or others, e.g., 3-aminopropylphosphinic acids, 3-aminopropylsulfinic acids, and others.

"Halogen" refers to a fluoro, chloro, bromo, or iodo group.

"Heteroalkoxy" refers to an alkoxy group in which one or more of the carbon atoms are replaced with a heteroatom. In certain embodiments, the heteroalkoxy group is $C_{1-6}$ heteroalkoxy, in certain embodiments, $C_{1-5}$ heteroalkoxy, in certain embodiments, $C_{1-4}$ heteroalkoxy, and in certain embodiments, $C_{1-3}$ heteroalkoxy. In certain embodiments of heteroalkoxy, the heteroatomic group is selected from —O—, —S—, —NH—, —NR—, —SO$_2$—, and —SO$_2$—, in certain embodiments, the heteroatomic group is selected from —O— and —NH—, and in certain embodiments the heteroatomic group is —O— and —NH—. In certain embodiments, a heteroalkoxy group is $C_{1-6}$ heteroalkoxy, $C_{1-5}$ heteroalkoxy, $C_{1-4}$ heteroalkoxy, and in certain embodiments $C_{1-3}$ heteroalkoxy.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —NH—, —NR—, —O—O—, —S—S—, =N—N=, —N=N—, —N=N—NR—, —PR—, —P(O)OR—, —P(O)R—, —POR—, —SO—, —SO$_2$—, —Sn(R)$_2$—, and the like, where each R is independently selected from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, and substituted $C_{7-18}$ heteroarylalkyl. In certain embodiments, each R is independently selected from hydrogen and $C_{1-3}$ alkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example, $C_{1-6}$ heteroalkyl includes groups having five carbon atoms and one heteroatom, groups having four carbon atoms and two heteroatoms, etc. In certain embodiments of heteroalkyl, the heteroatomic group is selected from —O—, —S—, —NH—, —N(—CH$_3$)—, —SO—, and —SO$_2$—, in certain embodiments, the heteroatomic group is selected from —O— and —NH—, and in certain embodiments, the heteroatomic group is —O— or —NH—. In certain embodiments, a heteroalkyl group is $C_{1-6}$ heteroalkyl, $C_{1-5}$ heteroalkyl, or $C_{1-4}$ heteroalkyl, and in certain embodiments, $C_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. In certain embodiments, when the total number of N, S, and O atoms in the heteroaryl group exceeds one, the heteroatoms may or may not be adjacent to one another. In certain embodiments, the total number of heteroatoms in the heteroaryl group is not more than two. In certain embodiments of heteroaryl, the heteroatomic group is selected from —O—, —S—, —NH—, —N(—CH$_3$)—, —SO—, and —SO$_2$—, in certain embodiments, the heteroatomic group is selected from —O— and —NH—, and in certain embodiments the heteroatomic group is —O— or —NH—. In certain embodiments, a heteroaryl group is selected from $C_{5-10}$ heteroaryl, $C_{5-9}$ heteroaryl, $C_{5-8}$ heteroaryl, $C_{5-7}$ heteroaryl, $C_{5-6}$ heteroaryl, and in certain embodiments, is $C_5$ heteroaryl and $C_6$ heteroaryl.

Examples of heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, heteroaryl groups are those derived from thiophene, pyrrole, benzothiophene, benzofuran, indole, pyridine, quinoline, imidazole, oxazole, or pyrazine. For example, in certain embodiments, heteroaryl is $C_5$ heteroaryl and is selected from furyl, thienyl, pyrrolyl, imidazolyl, pyrazolyl, isothiazolyl, or isoxazolyl. In certain embodiments, heteroaryl is $C_6$ heteroaryl, and is selected from pyridinyl, pyrazinyl, pyrimidinyl, and pyridazinyl.

"Heteroarylalkyl" refers to an arylalkyl group in which one of the carbon atoms (and certain associated hydrogen atoms) is replaced with a heteroatom. In certain embodiments, a heteroarylalkyl group is $C_{6-16}$ heteroarylalkyl, $C_{6-14}$ heteroarylalkyl, $C_{6-12}$ heteroarylalkyl, $C_{6-10}$ heteroarylalkyl, $C_{6-8}$ heteroarylalkyl, or $C_7$ heteroarylalkyl, and in certain embodiments, $C_6$ heteroarylalkyl. In certain embodiments of heteroarylalkyl, the heteroatomic group is selected from —O—, —S—, —NH—, —N(—CH$_3$)—, —SO—, and —SO$_2$—, in certain embodiments, the heteroatomic group is selected from —O— and —NH—, and in certain embodiments the heteroatomic group is —O— or —NH—.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, and Si. Examples of heterocycloalkyl groups include groups derived from epoxides, azirines, thiiranes, imidazolidine, morpholine, piperazine, piperidine, pyrazolidine, pyrrolidine, quinuclidine, and the like. In certain embodiments, heterocycloalkyl is $C_5$ heterocycloalkyl and is selected from pyrrolidinyl, tetrahydrofuranyl, tetrahydrothiophenyl, imidazolidinyl, oxazolidinyl, thiazolidinyl, doxolanyl, and dithiolanyl. In certain embodiments, heterocycloalkyl is $C_6$ heterocycloalkyl and is selected from piperidinyl, tetrahydropyranyl, piperizinyl, oxazinyl, dithianyl, and dioxanyl. In certain embodiments a heterocycloalkyl group is $C_{3-6}$ heterocycloalkyl, $C_{3-5}$ heterocycloalkyl, $C_{5-6}$ heterocycloalkyl, and in certain embodiments, $C_5$ heterocycloalkyl or $C_6$ heterocycloalkyl. In certain embodiments of heterocycloalkyl, the heteroatomic group is selected from —O—, —S—, —NH—, —N(—CH$_3$)—, —SO—, and —SO$_2$—, in certain embodiments, the heteroatomic group is selected from —O— and —NH—, and in certain embodiments the heteroatomic group is —O— or —NH—.

"Heterocycloalkylalkyl" refers to a cycloalkylalkyl group in which one or more carbon atoms (and certain associated hydrogen atoms) of the cycloalkyl ring are independently replaced with the same or different heteroatom. In certain embodiments, the heterocycloalkylalkyl is $C_{4-12}$ heterocycloalkylalkyl, $C_{4-10}$ heterocycloalkylalkyl, $C_{4-8}$ heterocycloalkylalkyl, $C_{4-6}$ heterocycloalkylalkyl, or $C_{6-7}$ heterocycloalkylalkyl, and in certain embodiments, $C_6$ heterocycloalkylalkyl or $C_7$ heterocycloalkylalkyl. In certain embodiments of heterocycloalkylalkyl, the heteroatomic group is selected from —O—, —S—, —NH—, —N(—CH$_3$)—, —SO—, and —SO$_2$—, in certain embodiments, the heteroatomic group is selected from —O— and —NH—, and in certain embodiments, the heteroatomic group is —O— or —NH—.

"Mesyl" refers to the group —OS(O)$_2$Me or —OMs.

"Parent aromatic ring system" refers to an unsaturated cyclic or polycyclic ring system having a cyclic conjugated π (pi) electron system with 4n+2 electrons (Hückel rule). Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of π-electrons corresponding to the Hückel rule (4n+2). Examples of heteroatoms to replace the carbon atoms include N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human. The term "patient" is used interchangeably with "subject."

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of inorganic acids include hydrochloric acid, hydrobromic acid, sulfuric acid, nitric acid, phosphoric acid, and the like. In certain embodiments the salts are formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. In certain embodiments, a salt is formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt. In certain embodiments wherein a compound has two or more ionizable groups, a pharmaceutically acceptable salt comprises one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art. See also: Stahl and Wermuth, C. G. (Editors), Handbook of Pharmaceutical Salts, Wiley-VCH, Weinheim, Germany, 2008.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1) or a pharmaceutically acceptable salt thereof and at least one pharmaceutically acceptable vehicle, with which the compound of Formula (1) or a pharmaceutically acceptable salt thereof is administered to a patient. Pharmaceutically acceptable vehicles are known in the art.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a solvate in which the one or more solvent molecules is water.

"Substituted" refers to a group in which one or more hydrogen atoms are independently replaced with the same or different substituent(s). In certain embodiments, each substituent is independently selected from halogen, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl. In certain embodiments, each substituent is independently selected from halogen, —NH$_2$, —OH, C$_{1-3}$ alkoxy, and C$_{1-3}$ alkyl, trifluoromethoxy, and trifluoromethyl. In certain embodiments, each substituent is independently selected from —OH, methyl, ethyl, trifluoromethyl, methoxy, ethoxy, and trifluoromethoxy. In certain embodiments, each substituent is selected from C$_{1-3}$ alkyl, =O, C$_{1-3}$ alkyl, C$_{1-3}$ alkoxy, and phenyl. In certain embodiments, each substituent is selected from —OH, —NH$_2$, C$_{1-3}$ alkyl, and C$_{1-3}$ alkoxy.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. In certain embodiments, "treating" or "treatment" refers to delaying the onset of the disease or at least one or more symptoms thereof in a patient who may be exposed to or predisposed to a disease or disorder even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient.

A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Triflyl" refers to the group —OS(O)$_2$CF$_3$ or —OTf.

Reference is now made in detail to certain embodiments of compounds, compositions, and methods. The disclosed embodiments are not intended to be limiting of the claims. To the contrary, the claims are intended to cover all alternatives, modifications, and equivalents.

LAT1/4F2hc Transporter

The GenBank accession number for human LAT1/4F2hc is NP_003477/NP_002385. Unless otherwise apparent from the context, reference to a transporter such as LAT1/4F2hc (as well as other transporters disclosed herein) includes the amino acid sequence described in or encoded by the GenBank reference number, and, allelic, cognate and induced variants and fragments thereof retaining essentially the same transporter activity. Usually such variants show at least 90% sequence identity to the exemplary Genbank nucleic acid or amino acid sequence. Allelic variants at the DNA level are the result of genetic variation between individuals of the same species. Some allelic variants at the DNA level that cause substitution, deletion or insertion of amino acids in proteins encoded by the DNA result in corresponding allelic variation at the protein level. Cognate forms of a gene refer to variation between structurally and functionally related genes between species. For example, the human gene showing the greatest sequence identity and closest functional relationship to a mouse gene is the human cognate form of the mouse gene.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. The sequence comparison algorithm enables calculation of the percent sequence identity for the test sequence(s) relative to the reference sequence, based on the designated program parameters. Optimal alignment of sequences for comparison may be conducted by methods known to those skilled in the art.

Compounds

In certain embodiments, anti-cancer agents provided by the present disclosure are compounds of Formula (1):

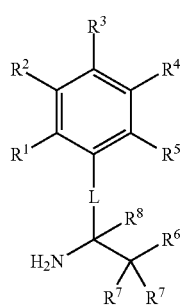

(1)

or a pharmaceutically acceptable salt thereof, wherein:

at least one of $R^1$ and $R^5$ is independently selected from halogen, —N(R$^{10}$)$_2$, —N$^+$(—O$^-$)(R$^{10}$)$_2$, —N(OR$^{10}$)(R$^{10}$), —NO$_2$, —NO, —N(R$^{10}$)(S(=O)R$^{10}$), —N(R$^{10}$)(S(=O)$_2$R$^{10}$), —N(R$^{10}$)(C(O)R$^{10}$), —N(R$^{10}$)(C(O)OR$^{10}$), —N(R$^{10}$)(C(O)N(R$^{10}$)$_2$, —CN, —COOR$^{10}$, —CON(R$^{10}$)$_2$, —OH, —SH, C$_{1-4}$ alkylsulfanyl, C$_{1-4}$ alkylsulfinyl, C$_{1-4}$ alkylsulfonyl, —S(O)N(R$^{10}$)$_2$, —S(O)$_2$N(R$^{10}$)$_2$, C$_{1-4}$ fluoroalkyl, C$_{1-4}$ fluoroalkoxy, C$_{1-6}$ alkyl, substituted C$_{1-6}$ alkyl, C$_{1-6}$ alkoxy, substituted C$_{1-6}$ alkoxy, C$_{3-6}$ cycloalkyl, substituted C$_{3-6}$ cycloalkyl, C$_{3-6}$ cycloalkyloxy, substituted C$_{3-6}$ cycloalkyloxy, C$_{4-12}$ cycloalkylalkyl, substituted C$_{4-12}$ cycloalkylalkyl, C$_{6-10}$ aryl, substituted C$_{6-10}$ aryl, C$_{7-16}$ arylalkyl, substituted C$_{7-16}$ arylalkyl, C$_{1-6}$ heteroalkyl, substituted C$_{1-6}$ heteroalkyl, C$_{1-6}$ heteroalkoxy, substituted C$_{1-6}$ heteroalkoxy, C$_{3-6}$ heterocycloalkyl, substituted C$_{3-6}$ heterocycloalkyl, C$_{4-12}$ heterocycloalkylalkyl, substituted C$_{4-12}$ heterocycloalkylalkyl, C$_{5-10}$ heteroaryl, substituted C$_{5-10}$ heteroaryl, C$_{6-16}$ heteroarylalkyl, and substituted C$_{6-16}$ heteroarylalkyl;

one of $R^1$, $R^2$, $R^3$, $R^4$, and $R^5$ comprises a chemotherapeutic moiety;

each of the other of $R^1$, $R^2$, $R^3$, $R^4$, and $R^5$ is independently selected from hydrogen, deuterio, halogen, —OH, —N(R$^{10}$)$_2$, —NO$_2$, —NO, —CN, —COOR$^{10}$, —CON(R$^{10}$)$_2$, C$_{1-4}$ alkylsulfanyl, C$_{1-4}$ alkylsulfinyl, C$_{1-4}$ alkylsulfonyl, C$_{1-6}$ alkyl, substituted C$_{1-6}$ alkyl, C$_{3-6}$ cycloalkyl, substituted C$_{3-6}$ cycloalkyl, C$_{1-6}$ heteroalkyl, substituted C$_{1-6}$ heteroalkyl, C$_{1-6}$ alkoxy, substituted C$_{1-6}$ alkoxy, C$_{1-6}$ heteroalkoxy, substituted C$_{1-6}$ heteroalkoxy, C$_{4-8}$ cycloalkylalkyl, and C$_{4-8}$ cycloalkylheteroalkyl;

$R^6$ is selected from a carboxylic acid (—COOH), a carboxylic acid analog, and a carboxylic acid (bio)isostere;

each $R^7$ is independently selected from hydrogen, deuterio, halogen, hydroxyl, C$_{1-6}$ alkyl, C$_{3-6}$ cycloalkyl, benzyl, and phenyl; or two $R^7$ together with the carbon to which they are bonded form a ring selected from a C$_{3-6}$ cycloalkyl ring and a C$_{3-6}$ heterocycloalkyl ring;

$R^8$ is selected from hydrogen, deuterio, halogen, C$_{1-6}$ alkyl, substituted C$_{1-6}$ alkyl, C$_{1-6}$ heteroalkyl, substituted C$_{1-6}$ heteroalkyl, C$_{1-6}$ alkoxy, substituted C$_{1-6}$ alkoxy, C$_{1-6}$ heteroalkoxy, substituted C$_{1-6}$ heteroalkoxy, C$_{3-6}$ cycloalkyl, substituted C$_{3-6}$ cycloalkyl, C$_{3-6}$ cycloalkyloxy, substituted C$_{3-6}$ cycloalkyloxy, —OH, —COOR$^{10}$, C$_{1-4}$ fluoroalkyl, C$_{1-4}$ fluoroalkoxy, C$_{3-6}$ cycloalkyl, and phenyl;

each $R^{10}$ is independently selected from hydrogen, C$_{1-4}$ alkyl and C$_{1-4}$ alkoxy, or two geminal $R^{10}$ together with the nitrogen to which they are bonded form a 3- to 6-membered heterocyclic ring;

L is —(X)$_a$—, wherein, each X is independently selected from a bond ("—") and —C(R$^{16}$)$_2$—, wherein each $R^{16}$ is independently selected from hydrogen, deuterio, halogen, hydroxyl, C$_{1-4}$ alkyl, and C$_{1-4}$ alkoxy, or two $R^{16}$ together with the carbon to which they are bonded form a C$_{3-6}$ cycloalkyl ring or a C$_{3-6}$ heterocycloalkyl ring, —O—, —S—, —SO—, —SO$_2$—, —CO—, and —N(R$^7$)—, wherein $R^{17}$ is selected from hydrogen, and C$_{1-4}$ alkyl; and a is selected from 0, 1, 2, 3, and 4; and each substituent is independently selected from halogen, —OH, —NH$_2$, —N(R$^{10}$)$_2$, —NO$_2$, —CF$_3$, =O (oxo), C$_{1-3}$ alkyl, C$_{1-3}$ alkoxy, and phenyl; wherein each $R^{10}$ is independently selected from hydrogen and C$_{1-3}$ alkyl.

In certain embodiments in compounds of Formula (1), $R^1$ comprises a chemotherapeutic moiety, $R^2$ comprises a chemotherapeutic moiety, $R^3$ comprises a chemotherapeutic moiety, $R^4$ comprises a chemotherapeutic moiety, and in certain embodiments, $R^5$ comprises a chemotherapeutic moiety.

In certain embodiments of a compound of Formula (1), a chemotherapeutic moiety may be any suitable chemotherapeutic moiety of a chemotherapeutic drug known in the art that retains cytotoxic activity when bonded through a spacing moiety, e.g., an aryl ring and a linker L, to a β-amino acid derivative, β-amino acid analog, or β-amino acid carboxylic acid (bio)isostere as a LAT1 recognition element provided by the present disclosure. The conjugate or fusion product of the chemotherapeutic moiety with the β-amino acid derivative, β-amino acid analog, or β-amino acid carboxylic acid (bio) isostere is simultaneous a selective substrate for the LAT1/4F2hc transporter.

In certain embodiments of a compound of Formula (1), the chemotherapeutic moiety, comprises a nitrogen mustard —N(—CR$_2$—CR$_2$—X)$_2$, a N-monoalkyl or N,N-dialkyl triazene (—N=N—NR$_2$), a haloacetamide (—NR—CO—CH$_2$—X), an epoxide (—CROCR—R), an aziridine (—NC$_2$H$_4$), a Michael acceptor (—CR=CR-EWG-), a sulfonate or a bissulfonate ester (—OSO$_2$R or ROSO$_2$—), an N-nitrosourea (—NR—CO—N(NO)R), a bissulfonyl hydrazine (R"SO$_2$—NR—N(—)—SO$_2$R''', —SO$_2$—NR—NR'—SO$_2$R''', or R"SO$_2$—NR—NR'—SO$_2$—), a phosphoramidate (—O—P(=O)(N(R)—CH$_2$—CH$_2$—X)$_2$ or —O—P(=O)(N(—CH$_2$—CH$_2$—X)$_2$)$_2$, and a radionuclide such as, for example, 131-iodine ($^{131}$[I]—) or 211-astatine ($^{211}$[At]—).

In certain embodiments of a compound of Formula (1), the chemotherapeutic moiety is a moiety Formula (2):

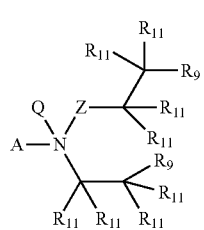

(2)

wherein,

A is selected from a bond ("—"), oxygen (—O—), sulfur (—S—), amino (—NR$^{10}$—), methylene (—CH$_2$—), methyleneoxy (—CH$_2$—O—), oxycarbonyl (—O—C(=O)—), thiocarbonyl (—S—C(=O)—), aminocarbonyl (—NR$^{10}$—C(=O)—), oxythiocarbonyl (—O—C(=S)—), thiothiocarbonyl (—S—C(=S)—), aminothiocarbonyl (—NR$^{10}$—C(=S)—), methyleneoxycarbonyl (—CH$_2$—O—C(=O)—), methylenethiocarbonyl (—CH$_2$—S—C(=O)—), methyleneaminocarbonyl (—CH$_2$—NR$^{10}$—C(=O)—), methyleneoxythiocarbonyl (—CH$_2$—O—C(=S)—), methylenethiothiocarbonyl (—CH$_2$—S—C(=S)—), methyleneaminothiocarbonyl (—CH$_2$—NR$^{10}$—C(=S)—), carbonyl (—C(=O)—), methylencarbonyl (—CH$_2$—C(=O)—), thiocarbonyl (—C(=S)—), and methylenthiocarbonyl (—CH$_2$—C(=S)—);

Z is selected from a bond ("—") and oxygen (—O—);

Q is selected from —O$^-$ (a negatively charged oxygen atom) that is bound to a positively charged nitrogen atom) and a free electron pair (:), with the proviso that when Q is —O$^-$ (a negatively charged oxygen atom that is bound to a positively charged nitrogen atom), A is selected from a bond ("—") and methylene (—CH$_2$—), Z is a bond ("—"), and the chemotherapeutic moiety of Formula (2) is an N-oxide (-A-N$^+$(—O$^-$)(—C(R$^{11}$)$_2$—C(R$^{11}$)$_2$—R$^9$)$_2$);

each R$^{11}$ is independently selected from hydrogen, deuterio, and C$_{1-3}$ alkyl; and each R$^9$ is independently selected from fluoro (—F), chloro (—Cl), bromo (—Br), iodo (—I), alkyl sulfonate (—OSO$_2$R$^{40}$, wherein R$^{40}$ is selected from C$_{1-4}$ alkyl), C$_{1-4}$ (per)fluoroalklyl sulfonate (—OSO$_2$R$^{40}$, wherein R$^{40}$ is selected from C$_{1-4}$ (per)fluoroalkyl), and (substituted) aryl sulfonate (—OSO$_2$R$^{40}$, wherein R$^{40}$ is selected from C$_{6-10}$ aryl).

In certain embodiments, a chemotherapeutic moiety of Formula (2) is selected from the structure -A-N(—Z—C(R$^{11}$)$_2$—C(R$^{11}$)$_2$—R$^9$)(—C(R$^{11}$)$_2$—C(R$^{11}$)$_2$—R$^9$ and (-A-N$^+$(—O$^-$)(—C(R$^{11}$)$_2$—C(R$^{11}$)$_2$—R$^9$)$_2$, wherein, A is selected from a bond ("—"), methylene (—CH$_2$—), oxygen (—O—), methyleneoxy (—CH$_2$—O—), oxycarbonyl (—O—C(=O)—), methyleneoxycarbonyl (—CH$_2$—O—C(=O)—), carbonyl (—C(=O)—), and methylenecarbonyl (—CH$_2$—C(=O)—);

each R$^{11}$ is independently selected from hydrogen and deuterio; and each R$^9$ is independently selected from fluoro (—F), chloro (—Cl), bromo (—Br), iodo (—I), alkyl sulfonate (—OSO$_2$R$^{40}$, wherein R$^{40}$ is selected from C$_{1-4}$ alkyl), C$_{1-4}$ (per)fluoroalklyl sulfonate (—OSO$_2$R$^{40}$, wherein R$^{40}$ is selected from C$_{1-4}$ (per)fluoroalkyl), and (substituted) aryl sulfonate (—OSO$_2$R$^{40}$, wherein R$^{40}$ is selected from C$_{6-10}$ aryl).

In certain embodiments, a chemotherapeutic moiety of Formula (2) has the structure -A-NQ(-Z—C(R$^{11}$)$_2$—C(R$^{11}$)$_2$—R$^9$)(—C(R$^{11}$)$_2$—C(R$^{11}$)$_2$—R$^9$), wherein, A is a bond ("—");

Q is a free electron pair (:);

Z is a bond ("—");

each R$^{11}$ is independently selected from hydrogen and deuterio; and each R$^9$ is independently selected from chloro (—Cl), bromo (—Br), iodo (—I), alkyl sulfonate (—OSO$_2$R$^{40}$, wherein R$^{40}$ is selected from C$_{1-4}$ alkyl), and C$_{1-4}$ (per)fluoroalklyl sulfonate (—OSO$_2$R$^{40}$, wherein R$^{40}$ is selected from C$_{1-4}$ (per)fluoroalkyl) and the chemotherapeutic moiety is —N(—CH$_{2-m}$D$_m$-CH$_{2-n}$D$_n$-R$^9$)$_2$, wherein m and n are independently selected from 0, 1, and 2.

In certain embodiments, a chemotherapeutic moiety of Formula (2) has the structure -A-NQ(-Z—C(R$^{11}$)$_2$—C(R$^{11}$)$_2$—R$^9$)(—C(R$^{11}$)$_2$—C(R$^{11}$)$_2$—R$^9$), wherein, A is methylene (—CH$_2$—);

Q is a free electron pair (:);

Z is a bond ("—");

each R$^{11}$ is independently selected from hydrogen and deuterio; and each R$^9$ is independently selected from chloro (—Cl), bromo (—Br), iodo (—I), alkyl sulfonate (—OSO$_2$R$^{40}$, wherein R$^{40}$ is selected from C$_{1-4}$ alkyl), and C$_{1-4}$ (per)fluoroalklyl sulfonate (—OSO$_2$R$^{40}$, wherein R$^{40}$ is selected from C$_{1-4}$ (per)fluoroalkyl) and the chemotherapeutic moiety is —CH$_2$—N(—CH$_{2-m}$D$_m$-CH$_{2-n}$D$_n$-R$^9$)$_2$, wherein m and n are independently selected from 0, 1, and 2.

In certain embodiments, a chemotherapeutic moiety of Formula (2) has the structure -A-NQ(-Z—C(R$^{11}$)$_2$—C(R$^{11}$)$_2$—R$^9$)(—C(R$^{11}$)$_2$—C(R$^{11}$)$_2$—R$^9$), wherein A is a bond ("—"), Q is a negatively charged oxygen (—O$^-$), Z is a bond ("—"), each R$^{11}$ is independently selected from hydrogen and deuterio; and each R$^9$ is independently selected from chloro (—Cl), bromo (—Br), iodo (—I), alkyl sulfonate (—OSO$_2$R$^{40}$, wherein R$^{40}$ is selected from C$_{1-4}$ alkyl), and C$_{1-4}$ (per)fluoroalklyl sulfonate (—OSO$_2$R$^{40}$, wherein R$^{40}$ is selected from C$_{1-4}$ (per)fluoroalkyl) and the chemotherapeutic moiety is —N$^+$(—O$^-$)(—CH$_{2-m}$D$_m$-CH$_{2-n}$D$_n$-R$^9$)$_2$, wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is methylene (—CH$_2$—), Q is a negatively charged oxygen (—O$^-$), Z is a bond ("—"), each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), and C$_{1-4}$ (per)fluoroalklyl sulfonate (—OSO$_2$$R^{40}$, wherein $R^{40}$ is selected from C$_{1-4}$ (per)fluoroalkyl) and the chemotherapeutic moiety is —CH$_2$—N$^+$(—O$^-$)(—CH$_{2-m}$D$_m$-CH$_{2-n}$D$_n$-$R^9$)$_2$, wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is a bond ("—"), Q is a free electron pair (:), Z is oxygen, each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), and C$_{1-4}$ (per)fluoroalklyl sulfonate (—OSO$_2$$R^{40}$, wherein $R^{40}$ is selected from C$_{1-4}$ (per)fluoroalkyl) and the chemotherapeutic moiety is —N(—O—CH$_{2-m}$D$_m$-CH$_{2-n}$D$_n$-$R^9$)(—CH$_{2-m}$D$_m$-CH$_{2-n}$D$_n$-$R^9$), wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is methylene (—CH$_2$—), Q is a free electron pair (:), Z is oxygen, each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), and C$_{1-4}$ (per)fluoroalklyl sulfonate (—OSO$_2$$R^{40}$, wherein $R^{40}$ is selected from C$_{1-4}$ (per)fluoroalkyl) and the chemotherapeutic moiety is —CH$_2$—N(—O—CH$_{2-m}$D$_m$-CH$_{2-n}$D$_n$-$R^9$)(—CH$_{2-m}$D$_m$-CH$_{2-n}$D$_n$-$R^9$), wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is oxygen (—O—), Q is a free electron pair (:), Z is a bond ("—"), each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), and C$_{1-4}$ (per)fluoroalklyl sulfonate (—OSO$_2$$R^{40}$, wherein $R^{40}$ is selected from C$_{1-4}$ (per)fluoroalkyl) and the chemotherapeutic moiety is —O—N(—CH$_{2-m}$D$_m$-CH$_{2-n}$D$_n$-$R^9$)$_2$, wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is methyleneoxy (—CH$_2$—O—), Q is a free electron pair (:), Z is a bond ("—"), each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), C$_{1-4}$ (per)fluoroalklyl sulfonate (—OSO$_2$$R^{40}$, wherein $R^{40}$ is selected from and C$_{1-4}$ (per)fluoroalkyl) and the chemotherapeutic moiety is —CH$_2$—O—N(—CH$_{2-m}$D$_m$-CH$_{2-n}$D$_n$-$R^9$)$_2$, wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is a carbonyl (—CO—), Q is a free electron pair (:), Z is a bond ("—"), each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), and C$_{1-4}$ (per)fluoroalklyl sulfonate (—OSO$_2$$R^{40}$, wherein $R^{40}$ is selected from C$_{1-4}$ (per)fluoroalkyl) and the chemotherapeutic moiety is —CO—N(—CH$_{2-m}$D$_m$-CH$_{2-n}$D$_n$-$R^9$)$_2$, wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is methylenecarbonyl (—CH$_2$—CO—), Q is a free electron pair (:), Z is a bond ("—"), each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), and C$_{1-4}$ (per)fluoroalklyl sulfonate (—OSO$_2$$R^{40}$, wherein $R^{40}$ is selected from C$_{1-4}$ (per)fluoroalkyl) and the chemotherapeutic moiety is —CH$_2$—CO—N(—CH$_{2-m}$D$_m$-CH$_{2-n}$D$_n$-$R^9$)$_2$, wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is oxycarbonyl (—O—CO—), Q is a free electron pair (:), Z is a bond ("—"), each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), and C$_{1-4}$ (per)fluoroalklyl sulfonate (—OSO$_2$$R^{40}$, wherein $R^{40}$ is selected from C$_{1-4}$ (per)fluoroalkyl) and the chemotherapeutic moiety is —O—CO—N(—CH$_{2-m}$D$_m$-CH$_{2-n}$D$_n$-$R^9$)$_2$, wherein m and n are independently selected from 0, 1, and 2.

In certain embodiments, a chemotherapeutic moiety of Formula (2) has the structure -A-NQ(-Z—C($R^{11}$)$_2$—C($R^{11}$)$_2$—$R^9$)(—C($R^{11}$)$_2$—C($R^{11}$)$_2$—$R^9$), wherein A is a methyleneoxycarbonyl (—CH$_2$—O—CO—), each $R^{11}$ is independently selected from hydrogen and deuterio; and each $R^9$ is independently selected from chloro (—Cl), bromo (—Br), iodo (—I), alkyl sulfonate (—OSO$_2$$R^{40}$, wherein $R^{40}$ is selected from C$_{1-4}$ alkyl), and C$_{1-4}$ (per)fluoroalklyl sulfonate (—OSO$_2$$R^{40}$, wherein $R^{40}$ is selected from C$_{1-4}$ (per)fluoroalkyl) and the chemotherapeutic moiety is —CH$_2$—O—CO—N(—CH$_{2-m}$D$_m$-CH$_{2-n}$D$_n$-$R^9$)$_2$, wherein m and n are independently selected from 0, 1, and 2.

In certain embodiments of a compound of Formula (1), the chemotherapeutic moiety comprises —N(—CH$_{2-m}$D$_m$-CH$_{2-n}$D$_n$-$R^9$)$_2$, wherein m and n are independently selected from 0, 1, and 2, and each $R^9$ is independently selected from chloro (—Cl), bromo (—Br), iodo (—I), methylsulfonyloxy (—OSO$_2$CH$_3$), and trifluoromethylsulfonyloxy (—OSO$_2$CF$_3$).

In certain embodiments of a compound of Formula (1), the chemotherapeutic moiety comprises —CH$_2$—N(—CH$_{2-m}$D$_m$-CH$_{2-n}$D$_n$-$R^9$)$_2$, wherein m and n are independently selected from 0, 1, and 2, and each $R^9$ is independently selected from chloro (—Cl), bromo (—Br), iodo (—I), methylsulfonyloxy (—OSO$_2$CH$_3$), and trifluoromethylsulfonyloxy (—OSO$_2$CF$_3$).

In certain embodiments of a compound of Formula (1), the chemotherapeutic moiety comprises —N$^+$(—O$^-$)(—CH$_{2-m}$D$_m$-CH$_{2-n}$D$_n$-$R^9$)$_2$, wherein m and n are independently selected from 0, 1, and 2, and each $R^9$ is independently selected from chloro (—Cl), bromo (—Br), iodo (—I), methylsulfonyloxy (—OSO$_2$CH$_3$), and trifluoromethylsulfonyloxy (—OSO$_2$CF$_3$).

In certain embodiments of a compound of Formula (1), the chemotherapeutic moiety comprises —$CH_2$—$N^+$(—$O^-$)(—$CH_{2-m}D_m$-$CH_{2-n}D_n$-$R^9$)$_2$, wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —N(—O—$CH_{2-m}D_m$-$CH_{2-n}D_n$-$R^9$)(—$CH_{2-m}D_m$-$CH_{2-n}D_n$-$R^9$), wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—N(—O—$CH_{2-m}D_m$-$CH_{2-n}D_n$-$R^9$)(—$CH_{2-m}D_m$-$CH_{2-n}D_n$-$R^9$), wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —O—N(—$CH_{2-m}D_m$-$CH_{2-n}D_n$-$R^9$)$_2$, wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—O—N(—$CH_{2-m}D_m$-$CH_{2-n}D_n$-$R^9$)$_2$, wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —CO—N(—$CH_{2-m}D_m$-$CH_{2-n}D_n$-$R^9$)$_2$, wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—CO—N(—$CH_{2-m}D_m$-$CH_{2-n}D_n$-$R^9$)$_2$, wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —O—CO—N(—$CH_{2-m}D_m$-$CH_{2-n}D_n$-$R^9$)$_2$, wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—O—CO—N(—$CH_{2-m}D_m$-$CH_{2-n}D_n$-$R^9$)$_2$, wherein m and n are independently selected from 0, 1, and 2, and each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —N(—$CH_2$—$CH_2$—$R^9$)$_2$, wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—N(—$CH_2$—$CH_2$—$R^9$)$_2$, wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$N^+$(—$O^-$)(—$CH_2$—$CH_2$—$R^9$)$_2$, wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—$N^+$(—$O^-$)(—$CH_2$—$CH_2$—$R^9$)$_2$, wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —N(—O—$CH_2$—$CH_2$—$R^9$)(—$CH_2$—$CH_2$—$R^9$), wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—N(—O—$CH_2$—$CH_2$—$R^9$)(—$CH_2$—$CH_2$—$R^9$), wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —O—N(—$CH_2$—$CH_2$—$R^9$)$_2$, wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—O—N(—$CH_2$—$CH_2$—$R^9$)$_2$, wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —CO—N(—$CH_2$—$CH_2$—$R^9$)$_2$, wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—CO—N(—$CH_2$—$CH_2$—$R^9$)$_2$, wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —O—CO—N(—$CH_2$—$CH_2$—$R^9$)$_2$, wherein m and n are independently selected from 0, 1, and 2, and wherein each $R^9$ is independently selected from chloro (—Cl), bromo (—Br), iodo (—I), methylsulfonyloxy (—$OSO_2CH_3$), and trifluoromethylsulfonyloxy (—$OSO_2CF_3$).

In certain embodiments of a compound of Formula (1), the chemotherapeutic moiety comprises —$CH_2$—O—CO—N(—$CH_2$—$CH_2$—$R^9$)$_2$, wherein each $R^9$ is independently selected from chloro (—Cl), bromo (—Br), iodo (—I), methylsulfonyloxy (—OSO$_2$CH$_3$), and trifluoromethylsulfonyloxy (—OSO$_2$CF$_3$).

In certain embodiments of a compound of Formula (1), R$^6$ is selected from carboxylic acid (—COOH), hydroxamic acids (—CONR$^{12}$OH), boronic acids (—B(OH)(OR$^{12}$), phosphinic acids or derivatives thereof (—PO(OH)R$^{12}$), and phosphonic acid or derivatives thereof (—PO(OH)(OR$^{12}$)), sulfinic acid (—SOOH), sulfonic acid (—SO$_2$OH), sulfonamide (—SO$_2$NHR$^{12}$ or —NHSO$_2$R$^{12}$), sulfonimide or acyl sulfonimide (—SO$_2$NHCOR$^{12}$ or —CONHSO$_2$R$^{12}$), sulfonylureas (—SO$_2$NHCONHR$^{12}$ or —NHCONHSO$_2$R$^{12}$), amide (—CONHR$^{12}$ or —NHCOR$^{12}$), acylcyanamide (—CONHCN), 2,2,2-trifluoroethan-1-ols (—CH(CF$_3$)OH), 2,2,2-trifluoromethyl ketones and hydrates thereof (—COCF$_3$ and —C(OH)$_2$CF$_3$), acidic heterocycles and annular tautomers of any of the foregoing, and acidic oxocarbocycles or cyclic polyones and resonance forms of any of the foregoing; wherein R$^{12}$ is selected from hydrogen, C$_{1-6}$ alkyl, C$_{1-4}$ fluoroalkyl, C$_{3-6}$ cycloalkyl, and C$_{6-10}$ aryl.

In certain embodiments of a compound of Formula (1), the acidic heterocycle and annular tautomers is selected from 1H-tetrazole, 5-oxo-1,2,4-oxadiazole, 5-oxo-1,2,4-thiadiazole, 5-thioxo-1,2,4-oxadiazole, thiazolidinedione, oxazolidinedione, oxadiazolidinedione, 3-hydroxyisoxazole, 3-hydroxyisothiazole, 1-hydroxy-imidazole, 1-hydroxy-pyrazole, 1-hydroxy-triazole, 1H-imidazol-2-ol, tetrazole-5-thiol, 3-hydroxyquinolin-2-one, 4-hydroxyquinolin-2-ones, tetronic acid, tetramic acid, mercaptoazoles such as sulfanyl-1H-imidazole, sulfinyl-1H-imidazole, sulfonyl-1H-imidazole, sulfanyl-1H-triazole, sulfinyl-1H-triazole, sulfonyl-1H-triazole, sulfanyl-1H-1,2,4-triazole, sulfinyl-1H-1,2,4-triazole, sulfonyl-1H-1,2,4-triazole, sulfanyl-1,4-dihydro-1,2,4-triazol-5-one, sulfinyl-1,4-dihydro-1,2,4-triazol-5-one, sulfonyl-1,4-dihydro-1,2,4-triazol-5-one, sulfanyl 1H-tetrazole, sulfanyl 2H-tetrazole, sulfinyl 1H-tetrazole, sulfinyl 2H-tetrazole, sulfonyl 1H-tetrazole, sulfonyl 2H-tetrazole, and sulfonimidamide.

In certain embodiments of a compound of Formula (1), the acidic oxocarbocycle or cyclic polyone and resonance forms is selected from cyclopentane-1,3-dione, squaric acid, squareamide, mixed squaramate, and 2,6-difluorophenol.

In certain embodiments of a compound of Formula (1), R$^6$ is selected from —COOH, —S(O)OH, —SO$_2$OH, —P(O)(OH)R$^{12}$, —P(O)(OH)(OR$^{12}$), —SO$_2$NHR$^{12}$, —NHSO$_2$R$^{12}$, —SO$_2$NHCOR$^{12}$, —CONHSO$_2$R$^{12}$, —SO$_2$NHCONHR$^{12}$, —CONHCN, 1H-tetrazol-yl, 5-oxo-1,2,4-oxadiazole, 5-oxo-1,2,4-thiadiazole, 5-thioxo-1,2,4-oxadiazole, thiazolidinedione, oxazolidinedione, oxadiazolidinedione, 3-hydroxyisoxazole, 3-hydroxyisothiazole, cyclopentane-1,3-dione, squaric acid, squareamide, and mixed squaramate; wherein R$^{12}$ is selected from hydrogen, C$_{1-4}$ alkyl, and C$_{3-5}$ cycloalkyl.

In certain embodiments of a compound of Formula (1), R$^6$ is selected from —COOH, —S(O)OH, —P(O)(OH)H, —CONHSO$_2$CH$_3$, —CONHSO$_2$CF$_3$, —SO$_2$NHCOCH$_3$, —SO$_2$NHCOCF$_3$, —NHSO$_2$CH$_3$, —NHSO$_2$CF$_3$, 1H-tetrazol-yl, 5-oxo-1,2,4-oxadiazole-yl, 5-oxo-1,2,4-thiadiazole-yl, 5-thioxo-1,2,4-oxadiazole-yl, thiazolidinedione-yl, oxazolidinedione-yl, oxadiazolidinedione-yl, 3-hydroxyisoxazole-yl, 3-hydroxyisothiazole-yl, tetronic acid-yl, tetramic acid-yl, and cyclopentane-1,3-dione-yl.

In certain embodiments of a compound of Formula (1), R$^6$ is selected from —COOH, —S(O)OH, —P(O)(OH)H, —CONHSO$_2$CH$_3$, —CONHSO$_2$CF$_3$, —SO$_2$NHCOCH$_3$, —SO$_2$NHCOCH$_3$, —SO$_2$NHCOCF$_3$, —NHSO$_2$CF$_3$, —NHSO$_2$CF$_3$, and 1H-tetrazol-5-yl.

In certain embodiments of a compound of Formula (1), R$^6$ is selected from —COOH, —S(O)OH, —P(O)(OH)H, and 1H-tetrazol-yl.

In certain embodiments of a compound of Formula (1), R$^6$ is —COOH.

In certain embodiments of a compound of Formula (1), each R$^7$ is independently selected from hydrogen, deuterio, halogen, hydroxyl, and C$_{1-4}$ alkyl, or two germinal R$^7$ together with the carbon atom to which they are bonded form a C$_{3-5}$ cycloalkyl ring.

In certain embodiments of a compound of Formula (1), each R$^7$ is independently selected from hydrogen, deuterio, fluoro, hydroxyl, methyl, ethyl, propyl, isopropyl, butyl, isobutyl, and tert-butyl, or two germinal R$^7$ together with the carbon atom to which they are bonded form a cyclopropyl ring or a cyclobutyl ring.

In certain embodiments of a compound of Formula (1), each R$^7$ is independently selected from hydrogen, deuterio, fluoro, hydroxyl, and methyl.

In certain embodiments of a compound of Formula (1), each R$^7$ is independently selected from hydrogen and deuterio.

In certain embodiments of a compound of Formula (1), each R$^7$ is hydrogen.

In certain embodiments of a compound of Formula (1), R$^8$ is selected from hydrogen, deuterio, halogen, hydroxyl, C$_{1-4}$ alkyl, C$_{1-4}$ alkoxy, C$_{1-4}$ fluoroalkyl, C$_{1-4}$ fluoroalkoxy, and cyclopropyl.

In certain embodiments of a compound of Formula (1), R$^8$ is selected from hydrogen, deuterio, halogen, hydroxyl, methyl, ethyl, propyl, isopropyl, butyl, isobutyl, tert-butyl, trifluoromethyl, methoxy, ethoxy, isopropoxy, trifluoromethoxy, and cyclopropyl.

In certain embodiments of a compound of Formula (1), R$^8$ is selected from hydrogen, methyl, ethyl, propyl, isopropyl, cyclopropyl, tert-butyl, hydroxyl, methoxy, ethoxy, isopropoxy, trifluoromethyl, and trifluoromethoxy.

In certain embodiments of a compound of Formula (1), R$^8$ is methyl.

In certain embodiments of a compound of Formula (1), R$^8$ is hydrogen.

In certain embodiments of a compound of Formula (1), each R$^{10}$ is independently selected from hydrogen and C$_{1-4}$ alkyl, or two R$^{10}$ together with the nitrogen atom to which they are bonded form a 3- to 5-membered heterocycle.

In certain embodiments of a compound of Formula (1), L is (—X—)$_a$ wherein a is selected from 0, 1, 2, 3, and 4, and X is selected from oxygen (—O—), sulfur (—S—), sulfinyl (—SO—), sulfonyl (—SO$_2$—), carbonyl (—CO—), —C(R$^{16}$)$_2$— wherein R$^{16}$ is independently selected from hydrogen, deuterio, halogen, hydroxyl, and C$_{1-4}$ alkyl, and amino (—NR$^{17}$—), wherein R$^{17}$ is selected from hydrogen, methyl, and ethyl.

In certain embodiments of a compound of Formula (1), comprises is selected from a bond ("—"), methylene (—CH$_2$—), fluoromethylene (—CFH—), difluoromethylene (—CF$_2$—), hydroxymethylene (—C(OH)H—), ethane-1,1-diyl (—CHCH$_3$—), propane-2,2-diyl (—C(CH$_3$)$_2$—), propane-1,1-diyl (—CH(CH$_2$—CH$_3$)—), oxygen (—O—), sulfur (—S—), sulfinyl (—SO—), sulfonyl (—SO$_2$—), carbonyl (—CO—), and amino (—NR$^{17}$—), wherein R$^{17}$ is selected from hydrogen, methyl, and ethyl.

In certain embodiments of a compound of Formula (1), comprises is selected from a bond ("—"), methylene (—CH$_2$—), fluoromethylene (—CFH—), difluoromethylene (—CF$_2$—), hydroxymethylene (—C(OH)H—), ethane-1,1-diyl (—CHCH$_3$—), propane-2,2-diyl (—C(CH$_3$)$_2$—), oxygen (—O—), sulfonyl (—SO$_2$—), carbonyl (—CO—), and amino (—NR$^{17}$—), wherein R$^{17}$ is selected from hydrogen and methyl.

In certain embodiments of a compound of Formula (1), a is 2 and each X is methylene (—CH$_2$—) and L is ethane-1,2-diyl (—CH$_2$—CH$_2$—); one X is methylene (—CH$_2$—) and one X is ethane-1,1-diyl (—CHCH$_3$—) and L is propane-1,2-diyl (—CH$_2$—CHCH$_3$—); one X is ethane-1,1-diyl (—CHCH$_3$—) and one X is methylene (—CH$_2$—) and L is propane-1,2-diyl (—CHCH$_3$—CH$_2$—); one X is methylene (—CH$_2$—) and one X is hydroxymethylene (—CHOH—) and L is hydroxyethane-1,2-diyl (—CH$_2$—CHOH—); one X is hydroxymethylene (—CHOH—) and one X is methylene (—CH$_2$—) and L is hydroxyethane-1,2-diyl (—CHOH—CH$_2$—); one X is methylene (—CH$_2$—) and one X is fluoromethylene (—CFH—), and L is fluoroethane-1,2-diyl (—CH$_2$—CHF—); one X is fluoromethylene (—CFH—) and one X is methylene (—CH$_2$—) and L is fluoroethane-1,2-diyl (—CHF—CH$_2$—); one X is methylene (—CH$_2$—) and one X is difluoromethylene (—CF$_2$—), and L is difluoroethane-1,2-diyl (—CH$_2$—CF$_2$—); one X is difluoromethylene (—CF$_2$—) and one X is methylene (—CH$_2$—) and L is difluoroethane-1,2-diyl (—CF$_2$—CH$_2$—); one X is carbonyl (—CO—) and one X is amino (—NR$^{17}$—) and L is carbonyl amino (—CO—NR$^{17}$—); one X is amino (—NR$^{17}$—) and one X is carbonyl (—CO—) and L is amino carbonyl (—NR$^{17}$—CO—); one X is methylene (—CH$_2$—) and one X is amino (—NR$^{17}$—) and L is methyleneamino (—CH$_2$—NR$^{17}$—); one X is amino (—NR$^{17}$—) and one X is methylene (—CH$_2$—) and L is aminomethylene (—NR$^{17}$—CH$_2$—); one X is methylene (—CH$_2$—) and one X is oxygen (—O—) and L is methyleneoxy (—CH$_2$—O—); one X is oxygen (—O—) and one X is methylene (—CH$_2$—) and L is oxymethylene (—O—CH$_2$—); one X is methylene (—CH$_2$—) and one X is sulfur (—S—) and L is methylenethiyl (—CH$_2$—S—); one X is sulfur (—S—) and one X is methylene (—CH$_2$—) and L is thiylmethylene (—S—CH$_2$—); one X is methylene (—CH$_2$—) and one X is sulfinyl (—SO—) and L is methylenesulfinyl (—CH$_2$—SO—); one X is sulfinyl (—SO—) and one X is methylene (—CH$_2$—) and L is sulfinylmethylene (—SO—CH$_2$—); one X is methylene (—CH$_2$—) and one X is sulfonyl (—SO$_2$—) and L is methylenesulfonyl (—CH$_2$—SO$_2$—); one X is sulfonyl (—SO$_2$—) and one X is methylene (—CH$_2$—) and L is sulfonylmethylene (—SO$_2$—CH$_2$—); one X is methylene (—CH$_2$—) and one X is carbonyl (—CO—) and L is methylenecarbonyl (—CH$_2$—CO—); or one X is carbonyl (—CO—) and one X is methylene (—CH$_2$—) and L is carbonylmethylene (—CO—CH$_2$—); wherein R$^{17}$ is selected from hydrogen, methyl, and ethyl.

In certain embodiments of a compound of Formula (1), a is 2 and L is selected from ethane-1,2-diyl (—CH$_2$—CH$_2$—), propane-1,2-diyl (—CH$_2$—CHCH$_3$— or —CHCH$_3$—CH$_2$—), hydroxyethane-1,2-diyl (—CH$_2$—CHOH— or —CHOH—CH$_2$—), carbonyl amino (—CO—NR$^{17}$—), amino carbonyl (—NR$^{17}$—CO—), methyleneamino (—CH$_2$—NR$^{17}$—), aminomethylene (—NR$^{17}$—CH$_2$—), methyleneoxy (—CH$_2$—O—), oxymethylen (—O—CH$_2$—), methylenethiyl (—CH$_2$—S—), thiylmethylene (—S—CH$_2$—), methylenesulfonyl (—CH$_2$—SO$_2$—), sulfonylmethylene (—SO$_2$—CH$_2$—), methylenecarbonyl (—CH$_2$—CO—), and carbonylmethylene (—CO—CH$_2$—), wherein R$^{17}$ is selected from hydrogen and methyl.

In certain embodiments of a compound of Formula (1), at least one of R$^1$ and R$^5$ is independently selected from, halogen, —N(R$^{10}$)$_2$, —N$^+$(—O$^-$)(R$^{10}$)$_2$, —N(R$^{10}$)(OR$^{10}$), —NO$_2$, —NO, —CN, —COOR$^{10}$, —CON(R$^{10}$)$_2$, —OH, C$_{1-4}$ alkyl, substituted C$_{1-4}$ alkyl, C$_{1-4}$ alkoxy, substituted C$_{1-4}$ alkoxy, C$_{1-4}$ alkylsulfanyl, C$_{1-4}$ alkylsulfinyl, C$_{1-4}$ alkylsulfonyl, C$_{1-4}$ heteroalkyl, C$_{1-4}$ heteroalkoxy, C$_{1-4}$ fluoroalkyl, C$_{1-4}$ fluoroalkoxy, C$_{3-5}$ cycloalkyl, C$_{3-5}$ cycloalkyloxy, and C$_{4-8}$ cycloalkylalkyl;

each R$^{10}$ is independently selected from hydrogen, deuterio, C$_{1-4}$ alkyl and C$_{1-4}$ alkoxy, or two geminal R$^{10}$ together with the nitrogen to which they are bonded form a 3- to 6-membered heterocyclic ring; and one of R$^1$, R$^2$, R$^3$, R$^4$, and R$^5$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$.

In certain embodiments of a compound of Formula (1), at least one of R$^1$ and R$^5$ is independently selected from halogen, —N(R$^{10}$)$_2$, —NR$^{10}$(OR$^{10}$), —NO$_2$, —NO, —OH, C$_{1-4}$ alkyl, C$_{1-4}$ alkoxy, C$_{1-4}$ alkylsulfanyl, C$_{1-4}$ alkylsulfinyl, C$_{1-4}$ fluoroalkyl, C$_{1-4}$ fluoroalkoxy, C$_{3-5}$ cycloalkyl, and C$_{3-5}$ cycloalkyloxy;

each R$^{10}$ is independently selected from hydrogen and C$_{1-3}$ alkyl, or two R$^{10}$ together with the nitrogen to which they are bonded form a 3- to 5-membered heterocyclic ring; and one of R$^1$, R$^2$, R$^3$, R$^4$, and R$^5$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N+(—O)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$.

In certain embodiments of a compound of Formula (1), each of R$^1$ and R$^5$ is independently selected from halogen, —N(R$^{10}$)$_2$, —N$^+$(—O$^-$)(R$^{10}$)$_2$, —N(R$^{10}$)(OR$^{10}$), —NO$_2$, —NO, —CN, —COOR$^{10}$, —CON(R$^{10}$)$_2$, —OH, C$_{1-4}$ alkyl, C$_{1-4}$ alkoxy, C$_{1-4}$ alkylsulfanyl, C$_{1-4}$ alkylsulfinyl, C$_{1-4}$ alkylsulfonyl, C$_{1-4}$ heteroalkyl, C$_{1-4}$ heteroalkoxy, C$_{1-4}$ fluoroalkyl, C$_{1-4}$ fluoroalkoxy, C$_{3-5}$ cycloalkyl, C$_{3-5}$ cycloalkyloxy, and C$_{4-8}$ cycloalkylalkyl;

each R$^{10}$ is independently selected from hydrogen, deuterio, C$_{1-4}$ alkyl and C$_{1-4}$ alkoxy, or two geminal R$^{10}$ together with the nitrogen to which they are bonded form a 3- to 6-membered heterocyclic ring; and one of R$^2$, R$^3$, and R$^4$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$.

In certain embodiments of a compound of Formula (1), each of R$^1$ and R$^5$ is independently selected from halogen, —N(R$^{10}$)$_2$, —NR$^{10}$(OR$^{10}$), —NO$_2$, —NO, —OH, C$_{1-4}$ alkyl, $C_{1-4}$ alkoxy, $C_{1-4}$ alkylsulfanyl, $C_{1-4}$ alkylsulfinyl, $C_{1-4}$ fluoroalkyl, $C_{1-4}$ fluoroalkoxy, $C_{3-5}$ cycloalkyl, and $C_{3-5}$ cycloalkyloxy;

each $R^{10}$ is independently selected from hydrogen and $C_{1-3}$ alkyl, or two $R^{10}$ together with the nitrogen to which they are bonded form a 3- to 5-membered heterocyclic ring; and one of $R^2$, $R^3$, and $R^4$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each $R^9$ is independently selected from —Cl, —Br, —I, —OSO$_2$CH$_3$, and —OSO$_2$CF$_3$.

In certain embodiments of a compound of Formula (1), one of $R^1$ and $R^5$ is independently selected from halogen, —N(R$^{10}$)$_2$, —N$^+$(—O$^-$)(R$^{10}$)$_2$, —N(R$^{10}$)(OR$^{10}$), —NO$_2$, —NO, —CN, —COOR$^{10}$, —CON(R$^{10}$)$_2$, —OH, $C_{1-4}$ alkyl, $C_{1-4}$ alkoxy, $C_{1-4}$ alkylsulfanyl, $C_{1-4}$ alkylsulfinyl, $C_{1-4}$ alkylsulfonyl, $C_{1-4}$ heteroalkyl, $C_{1-4}$ heteroalkoxy, $C_{1-4}$ fluoroalkyl, $C_{1-4}$ fluoroalkoxy, $C_{3-5}$ cycloalkyl, $C_{3-5}$ cycloalkyloxy, and $C_{4-8}$ cycloalkylalkyl;

each $R^{10}$ is independently selected from hydrogen, deuterio, $C_{1-4}$ alkyl and $C_{1-4}$ alkoxy, or two geminal $R^{10}$ together with the nitrogen to which they are bonded form a 3- to 6-membered heterocyclic ring; and one of $R^1$, $R^2$, $R^3$, $R^4$, and $R^5$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N+(—O)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each $R^9$ is independently selected from —Cl, —Br, —I, —OSO$_2$CH$_3$, and —OSO$_2$CF$_3$.

In certain embodiments of a compound of Formula (1), one of $R^1$ and $R^5$ is independently selected from halogen, —N(R$^{10}$)$_2$, —NR$^{10}$(OR$^{10}$), —NO$_2$, —NO, —OH, $C_{1-4}$ alkyl, $C_{1-4}$ alkoxy, $C_{1-4}$ alkylsulfanyl, $C_{1-4}$ alkylsulfinyl, $C_{1-4}$ fluoroalkyl, $C_{1-4}$ fluoroalkoxy, $C_{3-5}$ cycloalkyl, and $C_{3-5}$ cycloalkyloxy;

each $R^{10}$ is independently selected from hydrogen and $C_{1-3}$ alkyl, or two $R^{10}$ together with the nitrogen to which they are bonded form a 3- to 5-membered heterocyclic ring; and one of $R^1$, $R^2$, $R^3$, $R^4$, and $R^5$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each $R^9$ is independently selected from —Cl, —Br, —I, —OSO$_2$CH$_3$, and —OSO$_2$CF$_3$.

In certain embodiments of a compound of Formula (1), each of the other of $R^1$, $R^2$, $R^3$, $R^4$, and $R^5$ is independently is selected from hydrogen, deuterio, halogen, —N(R$^{10}$)$_2$, —N(R$^{10}$)(OR$^{10}$), —NO$_2$, —NO, —OH, —COOR$^{10}$, —CON(R$^{10}$)$_2$, —OH, $C_{1-4}$ alkylsulfanyl, $C_{1-4}$ alkylsulfinyl, $C_{1-4}$ alkylsulfonyl, $C_{1-4}$ fluoroalkyl, $C_{1-4}$ fluoroalkoxy, $C_{1-4}$ alkyl, $C_{1-4}$ alkoxy, $C_{1-4}$ heteroalkyl, $C_{1-4}$ heteroalkoxy, and $C_{4-8}$ cycloalkylalkyl; and each $R^{10}$ is independently selected from hydrogen and $C_{1-4}$ alkyl, or two $R^{10}$ together with the nitrogen to which they are bonded form a 3- to 6-membered heterocyclic ring.

In certain embodiments of a compound of Formula (1), each of the other of $R^1$, $R^2$, $R^3$, $R^4$, and $R^5$ is independently selected from hydrogen, deuterio, halogen, —NR$^{10}$$_2$, —N(R$^{10}$)(OR$^{10}$), —OH, $C_{1-4}$ alkyl, $C_{1-4}$ alkoxy, $C_{1-4}$ alkylsulfanyl, $C_{1-4}$ fluoroalkyl, and $C_{1-4}$ fluoroalkoxy, and each $R^{10}$ is independently selected from hydrogen and $C_{1-4}$ alkyl, or two $R^{10}$ together with the nitrogen to which they are bonded form a 3- to 5-membered heterocyclic ring.

In certain embodiments of a compound of Formula (1), the other of $R^1$ and $R^5$ is hydrogen.

In certain embodiments of a compound of Formula (1), each of the other of $R^1$, $R^2$, $R^3$, $R^4$, and $R^5$ is hydrogen.

In certain embodiments of a compound of Formula (1), $R^2$, $R^3$, and $R^5$ is hydrogen.

In certain embodiments of a compound of Formula (1), $R^1$ is selected from halogen, —N(R$^{10}$)$_2$, N$^+$(—O$^-$)(R$^{10}$)$_2$, —N(OR$^{10}$)(R$^{10}$), —NO$_2$, —NO, —N(R$^{10}$)(S(=O)R$^{10}$), —N(R$^{10}$)(S(=O)$_2$R$^{10}$), —N(R$^{10}$)(C(O)R$^{10}$), —N(R$^{10}$)(C(O)OR$^{10}$), —N(R$^{10}$)(C(O)N(R$^{10}$)$_2$, —CN, —COOR$^{10}$, —CON(R$^{10}$)$_2$, —OH, —SH, $C_{1-4}$ alkylsulfanyl, $C_{1-4}$ alkylsulfinyl, $C_{1-4}$ alkylsulfonyl, —S(O)N(R$^{10}$)$_2$, —S(O)$_2$N(R$^{10}$)$_2$, $C_{1-4}$ fluoroalkyl, $C_{1-4}$ fluoroalkoxy, $C_{1-6}$ alkyl, substituted $C_{1-6}$ alkyl, $C_{1-6}$ alkoxy, substituted $C_{1-6}$ alkoxy, $C_{3-6}$ cycloalkyl, substituted $C_{3-6}$ cycloalkyl, $C_{3-6}$ cycloalkyloxy, substituted $C_{3-6}$ cycloalkyloxy, $C_{4-12}$ cycloalkylalkyl, substituted $C_{4-12}$ cycloalkylalkyl, $C_{6-10}$ aryl, substituted $C_{6-10}$ aryl, $C_{7-16}$ arylalkyl, substituted $C_{7-16}$ arylalkyl, $C_{1-6}$ heteroalkyl, substituted $C_{1-6}$ heteroalkyl, $C_{1-6}$ heteroalkoxy, substituted $C_{1-6}$ heteroalkoxy, $C_{3-6}$ heterocycloalkyl, substituted $C_{3-6}$ heterocycloalkyl, $C_{4-12}$ heterocycloalkylalkyl, substituted $C_{4-12}$ heterocycloalkylalkyl, $C_{5-10}$ heteroaryl, substituted $C_{5-10}$ heteroaryl, $C_{6-16}$ heteroarylalkyl, and substituted $C_{6-16}$ heteroarylalkyl; wherein each $R^{10}$ is independently selected from hydrogen, deuterio, $C_{1-4}$ alkyl, and $C_{1-4}$ alkoxy, or two geminal $R^{10}$ together with the nitrogen to which they are bonded form a 3- to 6-membered heterocyclic ring; and $R^5$ is hydrogen.

In certain embodiments of a compound of Formula (1), $R^1$ selected from halogen, —N(R$^{10}$)$_2$, —N$^+$(—O$^-$)(R$^{10}$)$_2$, —N(R$^{10}$)(OR$^{10}$), —NO$_2$, —NO, —CN, —COOR$^{10}$, —CON(R$^{10}$)$_2$, —OH, $C_{1-4}$ alkyl, $C_{1-4}$ alkoxy, $C_{1-4}$ alkylsulfanyl, $C_{1-4}$ alkylsulfinyl, $C_{1-4}$ alkylsulfonyl, $C_{1-4}$ heteroalkyl, $C_{1-4}$ heteroalkoxy, $C_{1-4}$ fluoroalkyl, $C_{1-4}$ fluoroalkoxy, $C_{3-5}$ cycloalkyl, $C_{3-5}$ cycloalkyloxy, and $C_{4-8}$ cycloalkylalkyl; wherein each $R^{10}$ is independently selected from hydrogen, deuterio, $C_{1-4}$ alkyl, and $C_{1-4}$ alkoxy, or two geminal $R^{10}$ together with the nitrogen to which they are bonded form a 3- to 6-membered heterocyclic ring; and $R^5$ is hydrogen.

In certain embodiments of a compound of Formula (1), $R^1$ is selected from halogen, —N(R$^{10}$)$_2$, —NR$^{10}$(OR$^{10}$), —NO$_2$, —NO, —OH, $C_{1-4}$ alkyl, $C_{1-4}$ alkoxy, $C_{1-4}$ alkylsulfanyl, $C_{1-4}$ alkylsulfinyl, $C_{1-4}$ fluoroalkyl, $C_{1-4}$ fluoroalkoxy, $C_{3-5}$ cycloalkyl, and $C_{3-5}$ cycloalkyloxy; wherein each $R^{10}$ is independently selected from hydrogen and $C_{1-3}$ alkyl, or two $R^{10}$ together with the nitrogen to which they are bonded form a 3- to 5-membered heterocyclic ring; and $R^5$ is hydrogen.

In certain embodiments of a compound of Formula (1), each of $R^1$ and $R^5$ is independently selected from halogen, —N(R$^{10}$)$_2$, —N$^+$(—O$^-$)(R$^{10}$)$_2$, —N(R$^{10}$)(OR$^{10}$), —NO$_2$, —NO, —CN, —COOR$^{10}$, —CON(R$^{10}$)$_2$, —OH, C$_{1-4}$ alkyl, C$_{1-4}$ alkoxy, C$_{1-4}$ alkylsulfanyl, C$_{1-4}$ alkylsulfinyl, C$_{1-4}$ alkylsulfonyl, C$_{1-4}$ heteroalkyl, C$_{1-4}$ heteroalkoxy, C$_{1-4}$ fluoroalkyl, C$_{1-4}$ fluoroalkoxy, C$_{3-5}$ cycloalkyl, C$_{3-5}$ cycloalkyloxy, and C$_{4-8}$ cycloalkylalkyl; wherein each R$^{10}$ is independently selected from hydrogen, deuterio, C$_{1-4}$ alkyl and C$_{1-4}$ alkoxy, or two geminal R$^{10}$ together with the nitrogen to which they are bonded form a 3- to 6-membered heterocyclic ring;

one of R$^2$, R$^3$, and R$^4$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$;

each of the other of R$^2$, R$^3$, and R$^4$ is hydrogen;

R$^6$ is selected from —COOH, —S(O)OH, —P(O)(OH)H, and 1H-tetrazole;

each R$^7$ is independently selected from hydrogen, methyl, hydroxyl, and fluoro;

R$^8$ is selected from hydrogen, methyl, ethyl, propyl, isopropyl, cyclopropyl, butyl, isobutyl, cyclobutyl, tert-butyl, hydroxyl, C$_{1-4}$ alkoxy, C$_{1-4}$ fluoroalkyl, and C$_{1-4}$ fluoroalkoxy; and L is selected from a bond "—", —CH$_2$—, —C(OH)H—, —CHCH$_3$—, —C(CH$_3$)$_2$—, —CF$_2$—, —O—, —SO$_2$—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR'—CH$_2$—, —CH$_2$—O—, —O—CH$_2$—, —CH$_2$—S—, —S—CH$_2$—, —CH$_2$—SO$_2$—, —SO$_2$—CH$_2$—, —CH$_2$—CO—, and —CO—CH$_2$—, wherein R$^{17}$ is selected from hydrogen, methyl, and ethyl.

In certain embodiments of a compound of Formula (1), each of R$^1$ and R$^5$ is independently selected from halogen, —N(R$^{10}$)$_2$, —NR$^{10}$(OR$^{10}$), —NO$_2$, —NO, —OH, C$_{1-4}$ alkyl, C$_{1-4}$ alkoxy, C$_{1-4}$ alkylsulfanyl, C$_{1-4}$ alkylsulfinyl, C$_{1-4}$ fluoroalkyl, C$_{1-4}$ fluoroalkoxy, C$_{3-5}$ cycloalkyl, and C$_{3-5}$ cycloalkyloxy; wherein each R$^{10}$ is independently selected from hydrogen and C$_{1-3}$ alkyl, or two R$^{10}$ together with the nitrogen to which they are bonded form a 3- to 5-membered heterocyclic ring;

one of R$^2$, R$^3$, and R$^4$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$.

each of the other R$^2$, R$^3$, and R$^4$ is hydrogen;

R$^6$ is —COOH;

each R$^7$ is selected from hydrogen, methyl, hydroxyl, and fluoro;

R$^8$ is selected from hydrogen, methyl, ethyl, propyl, isopropyl, cyclopropyl, tert-butyl, hydroxyl, methoxy, ethoxy, isopropoxy, trifluoromethyl, and trifluoromethoxy; and L is selected from a bond "—", —CH$_2$—, —C(OH)H—, —CHCH$_3$—, —C(CH$_3$)$_2$—, —CF$_2$—, —O—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR'—CH$_2$—, —CH$_2$—O—, —O—CH$_2$—, —CH$_2$—S—, —S—CH$_2$—, —CH$_2$—SO$_2$—, —CH$_2$—CO—, and —CO—CH$_2$—, wherein R$^{17}$ is selected from hydrogen and methyl.

In certain embodiments of a compound of Formula (1),

R$^1$ is selected from halogen, —N(R$^{10}$)$_2$, —N$^+$(—O$^-$)(R$^{10}$)$_2$, —N(R$^{10}$)(OR$^{10}$), —NO$_2$, —NO, —CN, —COOR$^{10}$, —CON(R$^{10}$)$_2$, —OH, C$_{1-4}$ alkyl, C$_{1-4}$ alkoxy, C$_{1-4}$ alkylsulfanyl, C$_{1-4}$ alkylsulfinyl, C$_{1-4}$ alkylsulfonyl, C$_{1-4}$ heteroalkyl, C$_{1-4}$ heteroalkoxy, C$_{1-4}$ fluoroalkyl, C$_{1-4}$ fluoroalkoxy, C$_{3-5}$ cycloalkyl, C$_{3-5}$ cycloalkyloxy, and C$_{4-8}$ cycloalkylalkyl; wherein each R$^{10}$ is independently selected from hydrogen, deuterio, C$_{1-4}$ alkyl and C$_{1-4}$ alkoxy, or two geminal R$^{10}$ together with the nitrogen to which they are bonded form a 3- to 6-membered heterocyclic ring;

one of R$^2$, R$^3$, R$^4$, and R$^5$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N+(—O)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$;

each of the other of R$^2$, R$^3$, R$^4$, and R$^5$ is hydrogen;

R$^6$ is selected from —COOH, —S(O)OH, —P(O)(OH)H, and 1H-tetrazole;

each R$^7$ is independently selected from hydrogen, methyl, hydroxyl, and fluoro;

R$^8$ is selected from hydrogen, methyl, ethyl, propyl, isopropyl, cyclopropyl, butyl, isobutyl, cyclobutyl, tert-butyl, hydroxyl, C$_{1-4}$ alkoxy, C$_{1-4}$ fluoroalkyl, and C$_{1-4}$ fluoroalkoxy; and L is selected from a bond "—", —CH$_2$—, —C(OH)H—, —CHCH$_3$—, —C(CH$_3$)$_2$—, —CF$_2$—, —O—, —SO$_2$—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR'—CH$_2$—, —CH$_2$—O—, —O—CH$_2$—, —CH$_2$—S—, —S—CH$_2$—, —CH$_2$—SO$_2$—, —SO$_2$—CH$_2$—, —CH$_2$—CO—, and —CO—CH$_2$—, wherein R$^{17}$ is selected from hydrogen, methyl, and ethyl.

In certain embodiments of a compound of Formula (1),

R$^1$ is selected from halogen, —N(R$^{10}$)$_2$, —NR$^{10}$(OR$^{10}$), —NO$_2$, —NO, —OH, C$_{1-4}$ alkyl, C$_{1-4}$ alkoxy, C$_{1-4}$ alkylsulfanyl, C$_{1-4}$ alkylsulfinyl, C$_{1-4}$ fluoroalkyl, C$_{1-4}$ fluoroalkoxy, C$_{3-5}$ cycloalkyl, and C$_{3-5}$ cycloalkyloxy; wherein each R$^{10}$ is independently selected from hydrogen and C$_{1-3}$ alkyl, or two R$^{10}$ together with the nitrogen to which they are bonded form a 3- to 5-membered heterocyclic ring;

one of R$^2$, R$^3$, R$^4$, and R$^5$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$.

each of the other of $R^2$, $R^3$, $R^4$, and $R^5$ is hydrogen;
$R^6$ is —COOH;
each $R^7$ is selected from hydrogen, methyl, hydroxyl, and fluoro;
$R^8$ is selected from hydrogen, methyl, ethyl, propyl, isopropyl, cyclopropyl, tert-butyl, hydroxyl, methoxy, ethoxy, isopropoxy, trifluoromethyl, and trifluoromethoxy; and
L is selected from a bond "—", —CH$_2$—, —C(OH)H—, —CHCH$_3$—, —C(CH$_3$)$_2$—, —CF$_2$—, —O—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR$^{17}$—CH$_2$—, —CH$_2$—O—, —O—CH$_2$—, —CH$_2$—S—, —S—CH$_2$—, —CH$_2$—SO$_2$—, —CH$_2$—CO—, and —CO—CH$_2$—, wherein $R^{17}$ is selected from hydrogen and methyl.

In certain embodiments of a compound of Formula (1),
$R^5$ is selected from halogen, —N(R$^{10}$)$_2$, —N$^+$(—O$^-$)(R$^{10}$)$_2$, —N(R$^{10}$)(OR$^{10}$), —NO$_2$, —NO, —CN, —COOR$^{10}$, —CON(R$^{10}$)$_2$, —OH, $C_{1-4}$ alkyl, $C_{1-4}$ alkoxy, $C_{1-4}$ alkylsulfanyl, $C_{1-4}$ alkylsulfinyl, $C_{1-4}$ alkylsulfonyl, $C_{1-4}$ heteroalkyl, $C_{1-4}$ heteroalkoxy, $C_{1-4}$ fluoroalkyl, $C_{1-4}$ fluoroalkoxy, $C_{3-5}$ cycloalkyl, $C_{3-5}$ cycloalkyloxy, and $C_{4-8}$ cycloalkylalkyl; wherein each $R^{10}$ is independently selected from hydrogen, deuterio, $C_{1-4}$ alkyl and $C_{1-4}$ alkoxy, or two geminal $R^{10}$ together with the nitrogen to which they are bonded form a 3- to 6-membered heterocyclic ring;
one of $R^1$, $R^2$, $R^3$, and $R^4$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each $R^9$ is independently selected from —Cl, —Br, —I, —OSO$_2$CH$_3$, and —OSO$_2$CF$_3$;
each of the other of $R^1$, $R^2$, $R^3$, and $R^4$ is hydrogen;
$R^6$ is selected from —COOH, —S(O)OH, —P(O)(OH)H, and 1H-tetrazole;
each $R^7$ is independently selected from hydrogen, methyl, hydroxyl, and fluoro;
$R^8$ is selected from hydrogen, methyl, ethyl, propyl, isopropyl, cyclopropyl, butyl, isobutyl, cyclobutyl, tert-butyl, hydroxyl, $C_{1-4}$ alkoxy, $C_{1-4}$ fluoroalkyl, and $C_{1-4}$ fluoroalkoxy;
L is selected from a bond "—", —CH$_2$—, —C(OH)H—, —CHCH$_3$—, —C(CH$_3$)$_2$—, —CF$_2$—, —O—, —SO$_2$—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR$^{17}$—CH$_2$—, —CH$_2$—O—, —O—CH$_2$—, —CH$_2$—S—, —S—CH$_2$—, —CH$_2$—SO$_2$—, —SO$_2$—CH$_2$—, —CH$_2$—CO—, and —CO—CH$_2$—, wherein $R^{17}$ is selected from hydrogen, methyl, and ethyl.

In certain embodiments of a compound of Formula (1),
$R^5$ is selected from halogen, —N(R$^{10}$)$_2$, —NR$^{10}$(OR$^{10}$), —NO$_2$, —NO, —OH, $C_{1-4}$ alkyl, $C_{1-4}$ alkoxy, $C_{1-4}$ alkylsulfanyl, $C_{1-4}$ alkylsulfinyl, $C_{1-4}$ fluoroalkyl, $C_{1-4}$ fluoroalkoxy, $C_{3-5}$ cycloalkyl, and $C_{3-5}$ cycloalkyloxy; wherein each $R^{10}$ is independently selected from hydrogen and $C_{1-3}$ alkyl, or two $R^{10}$ together with the nitrogen to which they are bonded form a 3- to 5-membered heterocyclic ring;
one of $R^1$, $R^2$, $R^3$, and $R^4$ is selected from —N(—CH$_2$—CH$_2$—R$^9$)$_2$, —CH$_2$—N(—CH$_2$—CH$_2$—R$^9$)$_2$, —N$^+$(—O$^-$)

(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each $R^9$ is independently selected from —Cl, —Br, —I, —OSO$_2$CH$_3$, and —OSO$_2$CF$_3$;
each of the other of $R^1$, $R^2$, $R^3$, and $R^4$ is hydrogen;
$R^6$ is —COOH;
each $R^7$ is selected from hydrogen, methyl, hydroxyl, and fluoro;
$R^8$ is selected from hydrogen, methyl, ethyl, propyl, isopropyl, cyclopropyl, tert-butyl, hydroxyl, methoxy, ethoxy, isopropoxy, trifluoromethyl, and trifluoromethoxy;
L is selected from a bond "—", —CH$_2$—, —C(OH)H—, —CHCH$_3$—, —C(CH$_3$)$_2$—, —CF$_2$—, —O—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR$^{17}$—CH$_2$—, —CH$_2$—O—, —O—CH$_2$—, —CH$_2$—S—, —S—CH$_2$—, —CH$_2$—SO$_2$—, —CH$_2$—CO—, and —CO—CH$_2$—, wherein $R^{17}$ is selected from hydrogen and methyl.

In certain embodiments of a compound of Formula (1),
one of $R^1$ and $R^5$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N$^+$(—O$^-$)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each $R^9$ is independently selected from —Cl, —Br, —I, —OSO$_2$CH$_3$, and —OSO$_2$CF$_3$;
each of the other of $R^1$, $R^2$, $R^3$, $R^4$, and $R^5$ is hydrogen;
$R^6$ is selected from —COOH, —S(O)OH, —P(O)(OH)H, and 1H-tetrazole;
each $R^7$ is independently selected from hydrogen, methyl, hydroxyl, and fluoro;
$R^8$ is selected from hydrogen, methyl, ethyl, propyl, isopropyl, cyclopropyl, butyl, isobutyl, cyclobutyl, tert-butyl, hydroxyl, $C_{1-4}$ alkoxy, $C_{1-4}$ fluoroalkyl, and $C_{1-4}$ fluoroalkoxy; and
L is selected from a bond "—", —CH$_2$—, —C(OH)H—, —CHCH$_3$—, —C(CH$_3$)$_2$—, —CF$_2$—, —O—, —SO$_2$—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR$^{17}$—CH$_2$—, —CH$_2$—O—, —O—CH$_2$—, —CH$_2$—S—, —S—CH$_2$—, —CH$_2$—SO$_2$—, —SO$_2$—CH$_2$—, —CH$_2$—CO—, and —CO—CH$_2$—, wherein $R^{17}$ is selected from hydrogen, methyl, and ethyl.

In certain embodiments of a compound of Formula (1),
one of $R^1$ and $R^5$ is selected from —N(—CH$_2$—CH$_2$—R$^9$)$_2$, —CH$_2$—N(—CH$_2$—CH$_2$—R$^9$)$_2$, —N$^+$(—O$^-$)(—CH)(—CH$_2$—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—

CO—N(—CH$_2$—CH$_2$—R$^9$)$_2$, wherein each R$^9$ is independently selected from —Cl, —Br, —I, —OSO$_2$CH$_3$, and —OSO$_2$CF$_3$;

each of the other of R$^1$, R$^2$, R$^3$, R$^4$, and R$^5$ is hydrogen;

R$^6$ is —COOH;

each R$^7$ is selected from hydrogen, methyl, hydroxyl, and fluoro;

R$^8$ is selected from hydrogen, methyl, ethyl, propyl, isopropyl, cyclopropyl, tert-butyl, hydroxyl, methoxy, ethoxy, isopropoxy, trifluoromethyl, and trifluoromethoxy; and L is selected from a bond "—", —CH$_2$—, —C(OH)H—, —CHCH$_3$—, —C(CH$_3$)$_2$—, —CF$_2$—, —O—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR'—CH$_2$—, —CH$_2$—O—, —O—CH$_2$—, —CH$_2$—S—, —S—CH$_2$—, —CH$_2$—SO$_2$—, —CH$_2$—CO—, and —CO—CH$_2$—, wherein R$^{17}$ is selected from hydrogen and methyl.

In certain embodiments of a compound of Formula (1), R$^1$ is selected from halogen, —N(R$^{10}$)$_2$, —N$^+$(—O$^-$)(R$^{10}$)$_2$, —N(R$^{10}$)(OR$^{10}$), —NO$_2$, —NO, —CN, —COOR$^{10}$, —CON(R$^{10}$)$_2$, —OH, C$_{1-4}$ alkyl, C$_{1-4}$ alkoxy, C$_{1-4}$ alkylsulfanyl, C$_{1-4}$ alkylsulfinyl, C$_{1-4}$ alkylsulfonyl, C$_{1-4}$ heteroalkyl, C$_{1-4}$ heteroalkoxy, C$_{1-4}$ fluoroalkyl, C$_{1-4}$ fluoroalkoxy, C$_{3-5}$ cycloalkyl, C$_{3-5}$ cycloalkyloxy, and C$_{4-8}$ cycloalkylalkyl; wherein each R$^{10}$ is independently selected from hydrogen, deuterio, C$_{1-4}$ alkyl and C$_{1-4}$ alkoxy, or two geminal R$^{10}$ together with the nitrogen to which they are bonded form a 3- to 6-membered heterocyclic ring;

R$^4$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N(—O)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$.

each of R$^2$, R$^3$, and R$^5$ is hydrogen;

R$^6$ is selected from —COOH, —S(O)OH, —P(O)(OH)H, and 1H-tetrazole;

each R$^7$ is independently selected from hydrogen, methyl, hydroxyl, and fluoro;

R$^8$ is selected from hydrogen, methyl, ethyl, propyl, isopropyl, cyclopropyl, butyl, isobutyl, cyclobutyl, tert-butyl, hydroxyl, C$_{1-4}$ alkoxy, C$_{1-4}$ fluoroalkyl, and C$_{1-4}$ fluoroalkoxy; and L is selected from a bond "—", —CH$_2$—, —C(OH)H—, —CHCH$_3$—, —C(CH$_3$)$_2$—, —CF$_2$—, —O—, —SO$_2$—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR$^{17}$—CH$_2$—, —CH$_2$—O—, —O—CH$_2$—, —CH$_2$—S—, —S—CH$_2$—, —CH$_2$—SO$_2$—, —SO$_2$—CH$_2$—, —CH$_2$—CO—, and —CO—CH$_2$—, wherein R$^{17}$ is selected from hydrogen, methyl, and ethyl.

In certain embodiments of a compound of Formula (1), R$^1$ is selected from halogen, —N(R$^{10}$)$_2$, —NR$^{10}$(OR$^{10}$), —NO$_2$, —NO, —OH, C$_{1-4}$ alkyl, C$_{1-4}$ alkoxy, C$_{1-4}$ alkylsulfanyl, C$_{1-4}$ alkylsulfinyl, C$_{1-4}$ fluoroalkyl, C$_{1-4}$ fluoroalkoxy, C$_{3-5}$ cycloalkyl, and C$_{3-5}$ cycloalkyloxy; wherein each R$^{10}$ is independently selected from hydrogen or C$_{1-3}$ alkyl; or two R$^{10}$ together with the nitrogen to which they are bonded form a 3- to 5-membered heterocyclic ring;

R$^4$ is selected from —N(—CH$_2$—CH$_2$—R$^9$)$_2$, —CH$_2$—N(—CH$_2$—CH$_2$—R$^9$)$_2$, —N$^+$(—O$^-$)(—CH$_2$—CH$_2$—R$^9$)$_2$, —CH$_2$—N(—O)(—CH$_2$—CH$_2$—R$^9$)$_2$, —N(—O—CH$_2$—CH$_2$—R$^9$)(—CH$_2$—CH$_2$—R$^9$), —CH$_2$—N(—O—CH$_2$—CH$_2$—R$^9$)(—CH$_2$—CH$_2$—R$^9$), —O—N(—CH$_2$—CH$_2$—R$^9$)$_2$, —CH$_2$—O—N(—CH$_2$—CH$_2$—R$^9$)$_2$, —CO—N(—CH$_2$—CH$_2$—R$^9$)$_2$, —CH$_2$—CO—N(—CH$_2$—CH$_2$—R$^9$)$_2$, —O—CO—N(—CH$_2$—CH$_2$—R$^9$)$_2$, and —CH$_2$—O—CO—N(—CH$_2$—CH$_2$—R$^9$)$_2$, wherein each R$^9$ is independently selected from —Cl, —Br, —I, —OSO$_2$CH$_3$, and —OSO$_2$CF$_3$.

each of R$^2$, R$^3$, and R$^5$ is hydrogen;

R$^6$ is —COOH;

each R$^7$ is selected from hydrogen, methyl, hydroxyl, and fluoro;

R$^8$ is selected from hydrogen, methyl, ethyl, propyl, isopropyl, cyclopropyl, tert-butyl, hydroxyl, methoxy, ethoxy, isopropoxy, trifluoromethyl, and trifluoromethoxy; and L is selected from a bond "—", —CH$_2$—, —C(OH)H—, —CHCH$_3$—, —C(CH$_3$)$_2$—, —CF$_2$—, —O—, —NR$^{17}$—, —CO—, —CH$_2$—CH$_2$—, —CH$_2$—CHCH$_3$—, —CHCH$_3$—CH$_2$—, —CH$_2$—CHOH—, —CHOH—CH$_2$—, —CH$_2$—CF$_2$—, —CF$_2$—CH$_2$—, —CO—NR$^{17}$—, —NR$^{17}$—CO—, —CH$_2$—NR$^{17}$—, —NR$^{17}$—CH$_2$—, —CH$_2$—O—, —O—CH$_2$—, —CH$_2$—S—, —S—CH$_2$—, —CH$_2$—SO$_2$—, —CH$_2$—CO—, and —CO—CH$_2$—, wherein R$^{17}$ is selected from hydrogen and methyl.

In certain embodiments, R$^8$ is selected from hydrogen, deuterio, C$_{1-6}$ alkyl, substituted C$_{1-6}$ alkyl, C$_{1-6}$ heteroalkyl, substituted C$_{1-6}$ heteroalkyl, C$_{3-6}$ cycloalkyl, substituted C$_{3-6}$ cycloalkyl, —COOR$^{10}$, C$_{1-4}$ fluoroalkyl, C$_{3-6}$ cycloalkyl, and phenyl;

In certain embodiments, R$^8$ is selected from hydrogen, deuterio, C$_{1-4}$ alkyl, C$_{1-4}$ fluoroalkyl, and cyclopropyl.

In certain embodiments, R$^8$ is selected from hydrogen, deuterio, methyl, ethyl, propyl, isopropyl, butyl, isobutyl, tert-butyl, trifluoromethyl, and cyclopropyl.

In certain embodiments, L is —(X)$_a$—, wherein, each X is independently selected from a bond ("—"), —C(R$^{16}$)$_2$—, wherein each R$^{16}$ is independently selected from hydrogen, deuterio, halogen, hydroxyl, C$_{1-4}$ alkyl and C$_{1-4}$ alkoxy, or two R$^{16}$ together with the carbon to which they are bonded form a C$_{3-6}$ cycloalkyl ring or a C$_{3-6}$ heterocycloalkyl ring, —O—, —S—, —SO—, —SO$_2$—, —CO—, and —N(R$^{17}$)—, wherein R$^{17}$ is selected from hydrogen and C$_{1-4}$ alkyl; and a is selected from 0, 1, 2, 3, and 4;

In certain embodiments, L is selected from a bond ("—"), methylene (—CH$_2$—), fluoromethylene (—CFH—), difluoromethylene (—CF$_2$—), hydroxymethylene (—C(OH)H—), ethane-1,1-diyl (—CHCH$_3$—), propane-2,2-diyl (—C(CH$_3$)$_2$—), propane-1,1-diyl (—CH(CH$_2$—CH$_3$)—), sulfinyl (—SO—), sulfonyl (—SO$_2$—), and carbonyl (—CO—).

In certain embodiments, L is selected from a bond ("—"), methylene (—CH$_2$—), fluoromethylene (—CFH—), difluoromethylene (—CF$_2$—), hydroxymethylene (—C(OH)H—), ethane-1,1-diyl (—CHCH$_3$—), propane-2,2-diyl (—Ci(CH$_3$)$_2$—), sulfonyl (—SO$_2$—), and carbonyl (—CO—).

In certain embodiments, L is selected from ethane-1,2-diyl (—CH$_2$—CH$_2$—), propane-1,2-diyl (—CH$_2$—CHCH$_3$ or —CHCH$_3$—CH$_2$—), hydroxyethane-1,2-diyl (—CH$_2$—CHOH— or —CHOH—CH$_2$—), fluoroethane-1,2-diyl (—CH$_2$—CHF— or —CHF—CH$_2$—), difluoroethane-1,2-diyl (—CH$_2$—CF$_2$— or —CF$_2$—CH$_2$—), carbonyl amino (—CO—NR$^{17}$—), methyleneamino (—CH$_2$—NR$^{17}$—), methyleneoxy (—CH$_2$—O—), methylenethiyl (—CH$_2$—S—), methylenesulfinyl (—CH$_2$—SO—), sulfinylmethylene (—SO—CH$_2$—), methylenesulfonyl (—CH$_2$—SO$_2$—), sulfonylmethylene (—SO$_2$—CH$_2$—), methylenescarbonyl (—CH$_2$—CO—), and carbonylmethylene (—CO—CH$_2$—), wherein R$^{17}$ is selected from hydrogen, methyl, and ethyl.

In certain embodiments of a compound of Formula (1), the absolute stereochemistry of the beta-carbon atom is (R).

In certain embodiments of a compound of Formula (1), the absolute stereochemistry of the beta-carbon atom is (S).

In certain embodiments of a compound of Formula (1), the absolute stereochemistry of the β carbon atom is of the (R) configuration, the absolute axial stereochemistry (atropisomerism) is R$_a$, and the absolute stereochemistry of a compound of Formula (1) is (R,R$_a$).

In certain embodiments of a compound of Formula (1), the absolute stereochemistry of the β-carbon atom is of the (R) configuration, the absolute axial stereochemistry (atropisomerism) is S$_a$, and the absolute stereochemistry of a compound of Formula (1) is (R,S$_a$).

In certain embodiments of a compound of Formula (1), the absolute stereochemistry of the β-carbon atom is of the (S) configuration, the absolute axial stereochemistry (atropisomerism) is R$_a$, and the absolute stereochemistry of a compound of Formula (1) is (S,R$_a$).

In certain embodiments of a compound of Formula (1), the absolute stereochemistry of the β-carbon atom is of the (S) configuration, the absolute axial stereochemistry (atropisomerism) is S$_a$, and the absolute stereochemistry of a compound of Formula (1) is (S,S$_a$).

In certain embodiments, a compound of Formula (1) is selected from:
3-Amino-3-[5-[bis(2-chloroethyl)amino]-2-methyl-phenyl]propanoic acid (1);
3-Amino-3-[4-[bis(2-chloroethyl)amino]-2-methyl-phenyl]propanoic acid (2);
3-Amino-4-[5-[bis(2-chloroethyl)amino]-2-methyl-phenyl]butanoic acid (3);
3-Amino-4-[4-[bis(2-chloroethyl)amino]-2-methyl-phenyl]butanoic acid (4);
(3S)-3-Amino-4-[5-[bis(2-chloroethyl)amino]-2-methyl-phenyl]butanoic acid (5);
(3R)-3-Amino-4-[5-[bis(2-chloroethyl)amino]-2-methyl-phenyl]butanoic acid (6);
(3S)-3-Amino-4-[5-[bis(2-chloroethyl)amino]-2-methoxy-phenyl]butanoic acid (7);
(3S)-3-Amino-4-[3-[bis(2-chloroethyl)amino]-2,6-dimethyl-phenyl]butanoic acid (8);
(3S)-3-Amino-4-[5-[bis(2-chloroethyl)amino]-2-methyl-phenyl]-3-methyl-butanoic acid (9);
[(2R)-2-Amino-3-[5-[bis(2-chloroethyl)amino]-2-methyl-phenyl]propyl]phosphinic acid (10);
(3R)-3-Amino-4-[5-(bis(2-methylsulfonyloxyethyl)amino)-2-methyl-phenyl]butanoic acid (11);
(3R)-3-Amino-4-[5-(bis(2-bromoethyl)amino)-2-methyl-phenyl]butanoic acid (12);
(3R)-3-Amino-4-[5-(2-chloroethyl(2-methylsulfonyloxyethyl)amino)-2-methyl-phenyl]butanoic acid (13);
(3R)-3-Amino-4-[5-(2-bromoethyl(2-chloroethyl)amino)-2-methyl-phenyl]butanoic acid (14);
(3R)-3-Amino-4-[5-(2-bromoethyl(2-methylsulfonyloxyethyl)amino)-2-methyl-phenyl]butanoic acid (15);
(3S)-3-Amino-4-[[5-[bis(2-chloroethyl)amino]-2-methyl-phenyl]amino]-4-oxo-butanoic acid (16);
(3S)-3-Amino-4-[2-[bis(2-chloroethyl)amino]phenoxy]butanoic acid (17);
(3R)-3-Amino-5-[5-[bis(2-chloroethyl)amino]-2-methyl-phenyl]pentanoic acid (18);
(3R)-3-Amino-4-[5-(2-chloroethyl(chloromethyl)carbamoyl)oxy-2-methyl-phenyl]butanoic acid (19);
(3R)-3-Amino-4-[5-[bis(2-chloroethyl)carbamoyloxymethyl]-2-nitro-phenyl]butanoic acid (20);
(3R)-3-amino-4-[5-(2-chloroethoxy(2-chloroethyl)amino)-2-methyl-phenyl]butanoic acid (21);
3-[(2R)-2-Amino-4-hydroxy-4-oxo-butyl]-N,N-bis(2-chloroethyl)-4-methyl-benzeneamine oxide (22); and
(3R)-3-Amino-4-[2-[bis(2-chloroethyl)carbamoyl]phenyl]butanoic acid (23);
or a pharmaceutically acceptable salt or salts of any of the foregoing.

In certain embodiments of any of the foregoing compounds, a pharmaceutically acceptable salt is the hydrochloride salt.

In certain embodiments of any of the foregoing compounds, a pharmaceutically acceptable salt is the dihydrochloride salt.

In certain embodiments of a compound of Formula (1), a pharmaceutically acceptable salt is the hydrochloride salt.

In certain embodiments of a compound of Formula (1), a pharmaceutically acceptable salt is the dihydrochloride salt.

In certain embodiments, compounds of Formula (1) are selective substrates for the LAT1/4F2hc transporter.

In certain embodiments, compounds provided by the present disclosure exhibit a LAT1/4F2hc-dependent $V_{max}$ of at least 10% the $V_{max}$ of gabapentin. In certain embodiments, compounds provided by the present disclosure exhibit a LAT1/4F2hc-dependent $V_{max}$ of at least 20% the $V_{max}$ of gabapentin. In certain embodiments, compounds provided by the present disclosure exhibit a LAT1/4F2hc-dependent $V_{max}$ of at least 30% the $V_{max}$ of gabapentin. In certain embodiments, compounds provided by the present disclosure exhibit a LAT1/4F2hc-dependent $V_{max}$ of at least 40% the $V_{max}$ of gabapentin. In certain embodiments, compounds provided by the present disclosure exhibit a LAT1/4F2hc-dependent $V_{max}$ of at least 50% the $V_{max}$ of gabapentin. In certain embodiments, compounds provided by the present disclosure exhibit a LAT1/4F2hc-dependent $V_{max}$ of at least 60% the $V_{max}$ of gabapentin. In certain embodiments, compounds provided by the present disclosure exhibit a LAT1/4F2hc-dependent $V_{max}$ of at least 70% the $V_{max}$ of gabapentin. In certain embodiments, compounds provided by the present disclosure exhibit a LAT1/4F2hc-dependent $V_{max}$ of at least 80% the $V_{max}$ of gabapentin. In certain embodiments, compounds provided by the present disclosure exhibit a LAT1/4F2hc-dependent $V_{max}$ of at least 90% the $V_{max}$ of gabapentin. In certain embodiments, compounds provided by the present disclosure exhibit a LAT1/4F2hc-dependent $V_{max}$ of at least 100% the $V_{max}$ of gabapentin.

In certain embodiments, compounds provided by the present disclosure exhibit a LAT1/4F2hc-dependent uptake of at least 10% that of gabapentin measured at an extracellular concentration of 1 mM (1 mmol/L) and a system A-, system N-, a system ASC-, and a LAT2/4F2hc-dependent uptake of less than 50% that of L-leucine measured at an extracellular concentration of 1 mM (1 mmol/L). In certain embodiments, compounds provided by the present disclosure exhibit a LAT1/4F2hc-dependent uptake of at least 10% that of gabapentin measured at an extracellular concentration of 1 mM (1 mmol/L); and a system A-, system N-, a system ASC-, and a LAT2/4F2hc-dependent uptake of less than 40% that of L-leucine measured at an extracellular concentration of 1 mM (1 mmol/L). In certain embodiments, compounds provided by the present disclosure exhibit a LAT1/4F2hc-dependent uptake of at least 10% that of gabapentin measured at an extracellular concentration of 1 mM (1 mmol/L); and a system A-, system N-, a system ASC-, and a LAT2/4F2hc-dependent uptake of less than 30% that of L-leucine measured at an extracellular concentration of 1 mM (mmol/L). In certain embodiments, compounds provided by the present disclosure exhibit a LAT1/4F2hc-dependent uptake of at least 10% that of gabapentin measured at an extracellular concentration of 1 mM (1 mmol/L); and a system A-, system N-, a system ASC-, and a LAT2/4F2hc-dependent uptake of less than 20% that of L-leucine measured at an extracellular concentration of 1 mM (1 mmol/L). In certain embodiments, compounds provided by the present disclosure exhibit a LAT1/4F2hc-dependent uptake of at least 10% that of gabapentin measured at an extracellular concentration of 1 mM (1 mmol/L); and a system A-, system N-, a system ASC-, and a LAT2/4F2hc-dependent uptake of less than 10% that of L-leucine measured at an extracellular concentration of 1 mM (1 mmol/L). In certain embodiments, compounds provided by the present disclosure exhibit a LAT1/4F2hc-dependent uptake of at least 10% that of gabapentin measured at an extracellular concentration of 1 mM (1 mmol/L); and a system A-, system N-, a system ASC-, and a LAT2/4F2hc-dependent uptake of less than 5% that of L-leucine measured at an extracellular concentration of 1 mM (1 mmol/L). In certain embodiments, compounds provided by the present disclosure exhibit a LAT1/4F2hc-dependent uptake of at least 10% that of gabapentin measured at an extracellular concentration of 1 mM (1 mmol/L); and a system A-, system N-, a system ASC-, and a LAT2/4F2hc-dependent uptake of less than 1% that of L-leucine measured at an extracellular concentration of 1 mM (1 mmol/L).

Compounds of Formula (1) may be adapted as prodrugs to achieve desirable pharmacokinetic properties. For example, suitable prodrugs of β-substituted β-amino acid derivatives and β-substituted β-amino acid analogs are disclosed by Gallop, et al., U.S. Pat. Nos. 7,109,239, 6,972,341, 6,818,787 and 7,227,028. Prodrugs of compounds of Formula (1) include the prodrug systems disclosed by Gallop, et al., as well as others known in the art.

Synthesis of Compounds

Compounds disclosed herein may be obtained via the general synthetic methods illustrated in Schemes 1-10. General synthetic methods useful in the synthesis of compounds, precursors, and starting materials described herein are available in the art. Starting materials useful for preparing compounds and intermediates thereof, and/or practicing methods described herein, are commercially available or may be prepared by well-known synthetic methods (March's Advanced Organic Chemistry: Reactions, Mechanisms, M. B. Smith, $7^{th}$ Edition, John Wiley & Sons, Hoboken, N.J., USA, 2013; Advanced Organic Chemistry: Part B: Reaction and Synthesis, F. A. Carey and R. J. Sundberg, $5^{th}$ Edition, Springer, Germany, 2010; Comprehensive Organic Transformations, $2^{nd}$ Edition, and R. C. Larock, Wiley-VCH, Weinheim, Germany, 1999).

Additionally, as will be apparent to those skilled in the art, use of conventional protecting groups or protecting strategies may be necessary to prevent certain functional groups from undergoing undesired reactions. Suitable protecting groups for various functional groups as well as suitable conditions for protecting and deprotecting particular functional groups are well known in the art. On the other hand, many methods for selective removal of protecting groups without affecting the desired molecular architecture are also well known in the art (Wuts and Greene, Greene's Protective Groups in Organic Synthesis, $4^{th}$ Ed, 2007, Wiley-Interscience, John Wiley & Sons, Inc., Hoboken, N.J.).

It will be appreciated that where typical or preferred process conditions, e.g., reaction temperatures, reaction times, molar ratios of reactants, solvents, pressures, etc., are given other process conditions may also be used. Optimal reaction conditions may vary with the particular reactants, solvents, functional groups, and protecting groups used, but such conditions may be determined by one skilled in the art by routine optimization procedures.

Furthermore, certain compounds provided by the present disclosure may contain one or more stereogenic centers. Accordingly, and if desired, such compounds may be prepared or isolated as pure stereoisomers, e.g., as individual enantiomers, diastereomers, atropisomers, rotamers, or as stereoisomer enriched mixtures or racemates. All such stereoisomers are included within the scope of this disclosure. Pure stereoisomers (or enriched mixtures thereof) may be prepared using, for example, optically active starting materials, stereoselective reagents such as chiral catalysts and auxiliaries well known in the art. Alternatively, racemic mixtures of such compounds may be separated or partially enriched using, for example, chromatographic methods with chiral stationary phases, chiral resolving agents, and the like, also well known in the art and easily adaptable to the particular compound to be separated.

There has been an ever growing interest in the synthesis of β-amino acids with various substitution patterns. Depending on the location and the number of the substitutents, β-amino acids are categorized as (a) $\beta^2$ (mono-α-substituted), (b) $\beta^3$- (mono-β-substituted), (c) $\beta^{2,3}$-(α,β-di-substituted), (d) $\beta^{2,2}$- (α,α-di-substituted or α-geminal-disubstituted), (e) $\beta^{3,3}$-(β, β-di-substituted or β-geminal-disubstituted), (f) $\beta^{2,2,3}$-(α,α, β-tri-substituted), (g) $\beta^{2,3,3}$-(α,β,β-tri-substituted), or (h) $\beta^{2,2,3,3}$-((α,α,β,β-tetra-substituted) amino acids. Many methods for the synthesis of protected and unprotected β-amino acids with a wide variety of type and number of substituents either in racemic, enatio- or diastereomerically enriched or pure form from commercial or known starting materials are well known in the art (Enantioselective Synthesis of β-Amino Acids, $2^{nd}$ Edition, E. Juaristi and V. Soloshonok, John Wiley & Sons, 2005, Hoboken, N.J., USA, 2005; Smith, Methods of Non-α-Amino Acid Synthesis, Marcel Dekker, Inc., New York, USA, 1995; Cole, Tetrahedron, 1994, 50 (32), 9517-9582; Juaristi, et al., Aldrich Chim. Acta, 1994, 27(1), 3-11; Lelais and Seebach, Biopolymers (Peptide Science), 2004, 76, 206-243; Sewald, Amino Acids, 1996, 11, 397-408; Seebach, et al., Synthesis, 2009, (1), 1-32; and Abele and Seebach, Eur. J. Org. Chem., 2000, (1), 1-15).

In particular, many methods of preparing protected and unprotected $\beta^3$-substituted racemic or optically active β-amino acids, β-amino acids analogs, or β-amino acid carboxylic acid (bio)isosters from commercial or known starting materials are well known in the art.

In certain embodiments, such derivatives may be used as convenient starting materials for the preparation of the target compounds provided by the present disclosure. In certain embodiments, suitably functionalized protected and unprotected $\beta^3$-substituted racemic or optically active β-amino acids, β-amino acids analogs, or β-amino acid carboxylic acid (bio)isosters may be used as starting materials for the preparation of the target compounds provided by the present disclosure.

In certain embodiments, starting materials may be used in their fully protected form wherein the amino group or a synthetic equivalent or a precursor thereof and the carboxylic acid, phosphinic acid, sulfinic acid, carboxylic acid (bio) isosteres or synthetic equivalents or precursors of any of the foregoing are appropriately protected.

In certain embodiments, starting materials may be used in their hemi-protected form wherein the amino group or a synthetic equivalent or a precursor thereof is protected and the carboxylic acid group, phosphinic acid, sulfinic acid, or carboxylic acid (bio)isostere functional group or synthetic equivalents or precursors of any of the foregoing are unprotected or free.

In certain embodiments, starting materials may be used in their hemi-protected form wherein the amino group is unprotected or free and the carboxylic acid, phosphinic acid, sulfinic acid, or carboxylic acid (bio)isostere or synthetic equivalents or precursors of any of the foregoing are appropriately protected.

In certain embodiments, starting materials may be used in their full unprotected form wherein the amino group and the carboxylic acid, free phosphinic acid, free sulfinic acid, or free carboxylic acid (bio)isostere or synthetic equivalents or precursors of any of the foregoing are unprotected.

In certain embodiments, protected and unprotected $\beta^3$-substituted racemic or optically active β-amino acids, β-amino acids analogs, or β-amino acid carboxylic acid (bio)isosters bear a chemical functional group linking the $\beta^3$-carbon atom to an aromatic ring system. In certain embodiments, the aromatic ring system is functionalized with an anchoring group in order to install a chemotherapeutic moiety.

Methods of synthetic manipulations and modifications of the underlying protected or unprotected β-amino acid scaffold are well known in the art. In certain embodiments, the underlying the underlying β-amino acid scaffold may be modified to allow for regio- and/or stereoselective incorporation of auxiliary molecular functionalities. Auxiliary molecular functionalities may, for example, be incorporated to modulate interaction with LAT1 transporter proteins, e.g., efficacy of translocation through biological membranes (binding to the LAT1-transporter protein and capacity of LAT1-mediated transport), aid the modulation of physiochemical parameter, or to modulate the activity of the physiologically active N-mustard moiety, e.g., cytotoxicity.

In certain embodiments, the underlying aryl-ring may be modified to allow for regioselective incorporation of functional groups that can be converted to chemotherapeutic moieties by using reagents, methods, and protocols well known in the art.

In certain embodiments, the underlying aryl-ring may be modified to allow for regio- and/or stereoselective incorporation of auxiliary molecular functionalities into the arene scaffold. Auxiliary molecular functionalities may, for example, be incorporated to modulate interaction with LAT1 transporter proteins, e.g., efficacy of translocation through biological membranes (binding to the LAT1-transporter protein and capacity of LAT1-mediated transport), or to modulate the activity of the physiologically active chemotherapeutic moiety, e.g., cytotoxicity.

Many other methods for the preparation of appropriately functionalized or substituted, protected and unprotected $\beta^3$-substituted racemic or optically active β-amino acids, β-amino acids analogs, or β-amino acid carboxylic acid (bio) isosters, derivatives or precursors of any of the foregoing from commercial or known starting materials and employing methods and protocols are either described herein, are described in the art, or will be readily apparent to the one skilled in the art. Accordingly, the methods presented in the schemes provided by the present disclosure are illustrative rather than comprehensive.

Referring to Scheme 1, selected and representative starting materials for the preparation N-mustard functionalized β-branched β-amino acids, β-amino acid analogs, or β-amino acids carboxylic acid (bio)isosteres are compounds of Formula (A). This selection is not intended to be limiting in any way.

Referring to Scheme 1, in certain embodiments $R^1$ and/or $R^5$, and the linker L are defined as described herein; one of $R^2$, $R^3$, and $R^4$ in compounds of Formula (A) is -E-MH, wherein E is a bond ("—"), an oxygen atom (—O—), a methylene group (—CH$_2$—), a methyleneoxy group (—CH$_2$—O—), a carbonyl group (—CO—), or a methylenecarbonyl group (—CH$_2$—CO—), and wherein MH is an amino group (—NH$_2$), a hydroxyl group (—OH), or a sulfhydryl group (—SH). Each of the other remaining $R^2$, $R^3$, and $R^4$ is hydrogen; each $R^7$ and each $R^8$ is hydrogen.

Referring to Scheme 1, for example, (a) -E-MH is equivalent to a primary aromatic amino group (—NH$_2$, aniline) when E is a bond ("—") and MH is an amino group (—NH$_2$), (b) -E-MH is equivalent to a primary O-aryl hydroxylamino group (—O—NH$_2$) when E is an oxygen atom (—O—) and MH is an amino group (—NH$_2$), (c) -E-MH is equivalent to a primary aminomethyl group (—CH$_2$—NH$_2$, primary benzylic amine) when E is a methylene group (—CH$_2$—) and MH is an amino group (—NH$_2$), (d) -E-MH is equivalent to an aromatic hydroxyl group (—OH, phenol) when E is a bond ("—") and MH is a hydroxyl group (—OH), (e) -E-MH is equivalent to a hydroxymethyl group (—CH$_2$—OH, benzylic alcohol) when E is a methylene group (—CH$_2$—) and MH is a hydroxyl group (—OH), (f) -E-MH is equivalent to a primary O-benzylic hydroxylamino group (—CH$_2$—O—NH$_2$) when E is a methyleneoxy group (—CH$_2$—O—) and MH is an amino group (—NH$_2$), (g) -E-MH is equivalent to an aromatic sulhydryl group (—SH, thiophenol derivative) when E is a bond ("—") and MH is a hydroxyl group (—OH), (h) -E-MH is equivalent to a methylenesulhydryl group (—CH$_2$—SH, benzylic thiol) when E is a methylene group (—CH$_2$—) and MH is a sulfhydryl group (—SH), (i) -E-MH is equivalent to an aromatic carboxylic acid group (—CO—OH, benzoic acid) when E is a carbonyl group (—C(=O)—) and MH is a hydroxyl group (—OH), (j) -E-MH is equivalent to a carboxylic acid group (—CO—OH, benzoic acid) when E is a methylenecarbonyl group (—CH$_2$—C(=O)—) and MH is a hydroxyl group (—OH).

It will be understood by those skilled in the art that in some embodiments of the disclosure the group "-E-" in functional groups -E-MH presented in the following schemes is equivalent to the group -A- in the definition of the composition of a chemotherapeutic moiety as described herein.

Referring to Scheme 1, in certain embodiments $R^{20}$ in compounds of Formula (A) is a protected carboxyl group such as a lower alkyl ester of a carboxyl group, e.g., a methyl, ethyl, or tert-butyl ester, or a benzyl ester derivative, e.g., benzyl, pentamethylbenzyl, or (4-methoxy)benzyl. In certain embodiments, $R^{20}$ in compounds of Formula (A) is a tert-butyl ester group (CO$_2$tBu). In certain embodiments, $R^{20}$ in compounds of Formula (A) is a methyl ester group (CO$_2$Me).

Referring to Scheme 1, in certain embodiments, $R^{20}$ in compounds of Formula (A) is a protected phosphinic acid derivative, e.g., 1,1-diethyloxyethylethoxyphosphino-1-one (—P(=O)(OEt)[C(OEt)$_2$Me](U.S. Pat. No. 8,344,028; Baylis, Tetrahedron Lett, 1995, 36(51), 9385-9388; and Burgos-Lepley, et al., Bioorg. Med. Chem. Lett., 2006, 16, 2333-2336). In certain embodiments, $R^{20}$ in compounds of Formula (A) has alternatively protected phosphonates and phosphinates as described in the art (Palacios, et al., Chem. Rev., 2005, 105, 899-931; and Lejzak, et al., J. Enzyme Inhibit., 1993, 7(2), 97-103).

Referring to Scheme 1, in certain embodiments, $R^{20}$ in compounds of Formula (A) is a protected sulfinic acid precursor derivative, e.g., a 2-mercaptobenzothiazole (Carruthers, et al., Bioorg. Med. Chem. Lett, 1995, 5, 237-240; Carruthers, et al., Bioorg. Med. Chem. Lett, 1998, 5, 3059-3064; and Okawara, et al., Chem. Lett., 1984, 2015; C. E. Burgos-Lepley, et al., Bioorg. Med. Chem. Lett., 2006, 16, 2333-2336).

Referring to Scheme 1, in certain embodiments, $R^{20}$ in compounds Formula (A) is a unprotected or protected carboxylic acid (bio)isostere including a protected or unprotected 1H-tetrazole (Ballatore, et al., Chem Med Chem, 2013, 8(3), 385-395; Bryans, et al., U.S. Pat. No. 6,518,289; and Burgos-Lepley, et al., Bioorg. Med. Chem. Lett., 2006, 16, 2333-2336).

Referring to Scheme 1, in certain embodiments of compounds of Formula (A) Q is N(H)—PG where PG is a suitable nitrogen protecting group, e.g., tert-butoxycarbonyl (Boc), allyloxycarbonyl (alloc), benzyloxycarbonyl (Cbz, Z), ethoxycarbonyl, methoxycarbonyl, (R/S)-1-phenyl-ethoxycarbonyl, (R)-1-phenyl-ethoxycarbonyl, (S)-1-phenyl-ethoxycarbonyl, 1-methyl-1-phenyl-ethoxycarbonyl, formyl, acetyl, trifluoroacetyl, benzoyl, triphenylmethyl(trityl), 4-methoxyphenyl-diphenylmethyl, or di-(4-methoxyphenyl)-phenylmethyl, and the like. In certain embodiments, PG in compounds of Formula (A) is tert-butoxycarbonyl (Boc) and Q is N(H)Boc (N(H)CO$_2$tBu). In certain embodiments of compounds of Formula (A) PG is benzyloxycarbonyl (Cbz, Z), and Q is N(H)—Cbz (N(H)COOBn). In certain embodiments of compounds of Formula (A), PG is acetyl and Q is N(H)—Ac (N(H)COMe).

Referring to Scheme 1, in certain embodiments of compounds of Formula (A) Q is N(PG)$_2$, where PG is a nitrogen protecting group such as an imide-type protecting group, e.g., phthalyl or tert-butoxycarbonyl (Boc). In certain embodiments of compounds of Formula (A) PG is phthalyl and Q is N(phthalyl). In certain embodiments of compounds of Formula (A) PG is tert-butoxycarbonyl and Q is N(Boc)$_2$.

Referring to Scheme 1, in certain embodiments of compounds of Formula (A) the protected amine functionality is an imine where Q is N is CR$^{30}$R$^{31}$ and each of R$^{30}$ and R$^{31}$ is independently selected from branched C$_{1-4}$ alkyl, non-branched C$_{1-4}$ alkyl, substituted aryl, non-substituted aryl, substituted heteroaryl, and non-substituted heteroaryl.

Accordingly, the structures presented in the schemes provided by the present disclosure are illustrative rather than comprehensive.

Scheme 1

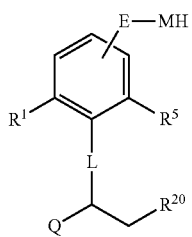

Referring to Scheme 2, in certain embodiments R$^1$ and/or R$^5$, R$^{20}$, E, the linker L, and the protecting groups PG and Q are defined as described herein; one of R$^2$, R$^3$, and R$^4$ in compounds of Formula (C) is -E-NH$_2$, wherein E is a bond ("—"), an oxygen atom (—O—), a methylene group (—CH$_2$—), or methylenoxy group (—CH$_2$—O—), and wherein MH is an amino group (—NH$_2$) so that -E-NH$_2$ is equivalent to a) a primary aromatic amino group (—NH$_2$, aniline), b) a primary O-aryl hydroxylamino group (—O—NH$_2$), c) a primary aminomethyl group (—CH$_2$—NH$_2$), or a primary O-benzyl hydroxylamino group (—CH$_2$—O—NH$_2$). Each of the other remaining R$^2$, R$^3$, and R$^4$ is hydrogen; each R$^7$ and each R$^8$ is hydrogen. X is a suitable leaving group e.g., chloro (—Cl) or bromo (—Br).

Scheme 2

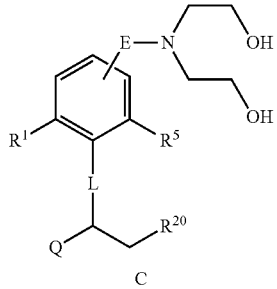

Referring to Scheme 2, conversion of the primary amino group as in compounds of Formula (B) to the N,N-bis-(2-hydroxyethyl) amino group (N,N-bis-(2-hydroxyethylation)) as in compounds of Formula (C) may be accomplished by reacting compounds of Formula (B) in suitable solvents such as about 25-75 vol.-% aqueous acetic acid (HOAc), glacial acetic acid, water, tetrahydrofuran (THF), ethanol (EtOH), 1,4-dioxane, or mixtures of any of the foregoing with an excess of ethylene oxide (oxirane) (about 4-20 equivalents) at a temperature of about −20° C. to about room temperature for about 12-48 hours. Alternatively, the reaction mixture may be heated in a sealed reaction vessel from about 80-140° C. for comparable times (Palmer, et al., J. Med. Chem. 1990, 33(1), 112-121; Jordan, et al., Bioorg. Med. Chem., 2002, 10(8), 2625-2633; Abela Medici, et al, J. Chem. Soc., Perkin Trans. 1, 1997, (20), 2258-2263; Feau, et al., Org. Biomolecular Chem., 2009, 7(24), 5259-5270; Springer, et al., J. Med. Chem., 1990, 33(2), 677-681; Taylor, et al., Chem. Biol. Drug Des., 2007, 70(3), 216-226; Buss, et al., J. Fluorine Chem., 1986, 34(1), 83-114; Larden and Cheung, Tetrahedron Lett., 1996, 37(42), 7581-7582; Spreitzer and Puschmann, Monatshefte für Chemie, 2007, 138(5), 517-522; Niculesscu-Duvaz, et al., J. Med. Chem., 2004, 47(10), 2651-2658; Weisz, et al., Bioorg. Med. Chem. Lett., 1995, 5(24), 2985-2988; Thorn, et al., J. Org. Chem, 1975, 40(11), 1556-1558; Baraldini, et al., J. Med. Chem., 2000, 53(14), 2675-2684; Zheng, et al., Bioorg., Med., Chem., 2010, 18(2), 880-886; Gourdi, et al., J., Med., Chem., 1990, 33(4), 1177-1186; Haines, et al., J. Med. Chem., 1987, 30, 542-547; Matharu, et al., Bioorg.

Med. Chem. Lett., 2010, 20, 3688-3691; and Kupczyk-Subotkowska, et al., J. Drug Targeting, 1997, 4(6), 359-370).

Referring to Scheme 2, conversion of the primary amino group as in compounds of Formula (B) to the N,N-bis-(2-hydroxyethyl) amino group (N,N-bis-(2-hydroxyethylation)) as in compounds of Formula (C) may be accomplished by reacting compounds of Formula (B) in suitable solvents such water with an excess of about 2-5 equivalents of a suitable 2-halogeno ethanol derivative, e.g., 2-chloroethanol (ClCH$_2$CH$_2$OH) or 2-bromoethanol (BrCH$_2$CH$_2$OH), and about 2.0 equivalents of a suitable inorganic base such as sodium bicarbonate (NaHCO$_3$), sodium carbonate (Na$_2$CO$_3$), or calcium carbonate (CaCO$_3$) at about reflux temperature for about 8-24 hours. Optionally, the reaction may be carried out in the presence of a catalytic amount (about 10 mol-%) of potassium iodide (KI) (Palmer, et al., J. Med. Chem. 1990, 33(1), 112-121; Coggiola, et al., Bioorg. Med. Chem. Lett., 2005, 15(15), 3551-3554; Veiny and Nicolas, J. Label. Cmpds Radiopharm., 1988, 25(9), 949-955; and Lin, Bioorg. Med. Chem. Lett., 2011, 21(3), 940-943).

Referring to Scheme 3, in certain embodiments electron-deficient aryl halides of Formula (D), activated with strongly electron withdrawing substituents for nucleophilic aromatic substitution reactions (S$_N$Ar) at the aryl ring, may be useful starting materials for incorporating N,N-bis-(2-functionalized) ethyl amino groups as in compounds of Formula (E) where the corresponding N,N-bis-(2-functionalized)ethyl amino groups are N,N-bis-(2-hydroxyethyl) amino groups. Commonly used leaving groups (—X) for S$_N$Ar-reactions include halogeno, e.g., fluoro (—F), chloro (—Cl), bromo (—Br), with accessory activating groups at the 2- or 4-position relative to the leaving group (ortho- or para-positions). Such groups decrease the electron density in the arene ring and increase the susceptibility to nucleophilic attack and displacement of the leaving group (—X). Examples of activating, strongly electron-withdrawing groups (EWG) include trifluoromethyl (—CF$_3$), cyano (—CN), nitro (—NO$_2$), amide (—CON(R$^{10}$)$_2$), and formyl (—CHO).

Useful secondary amines for the introduction of the N,N-bis-(2-hydroxyethyl) amino functionality include diethanolamine (HN(CH$_2$CH$_2$OH)$_2$), protected diethanolamine derivatives, e.g., O-benzylether protected diethanolamine (HN(CH$_2$CH$_2$OBn)$_2$), or precursors of the putative N,N-bis-(2-hydroxyethyl)amino group, e.g., 3-pyrroline. Employing O-benzylether protected diethanolamine (HN(CH$_2$CH$_2$OBn)$_2$) or 3-pyrroline necessitates conversion of the corresponding intermediate substitution products to compounds of Formula (E) bearing the target N,N-bis-(2-hydroxyethyl) amino groups using methods well known in the art.

Referring to Scheme 3, in certain embodiments R$^1$ and/or R$^5$, R$^{10}$, R$^{20}$, the linker L, the protecting group PG, and Q, the electron withdrawing group (EWG), the leaving group (—X), and the secondary amine HNR$_2$ are defined as described herein; R$^1$ and/or R$^5$ may also represent an electron withdrawing group (EWG); one or more of R$^2$, R$^3$, and R$^4$ in compounds of Formula (G) or of Formula (H) is a suitable leaving group (—X)), one or more of R$^2$, R$^3$, and R$^4$ is a electron withdrawing group (EWG) preferably in 2- or 4-position relative to the leaving group X; each of the other remaining R$^2$, R$^3$, and R$^4$ is hydrogen; each of R$^7$ and R$^8$ is hydrogen.

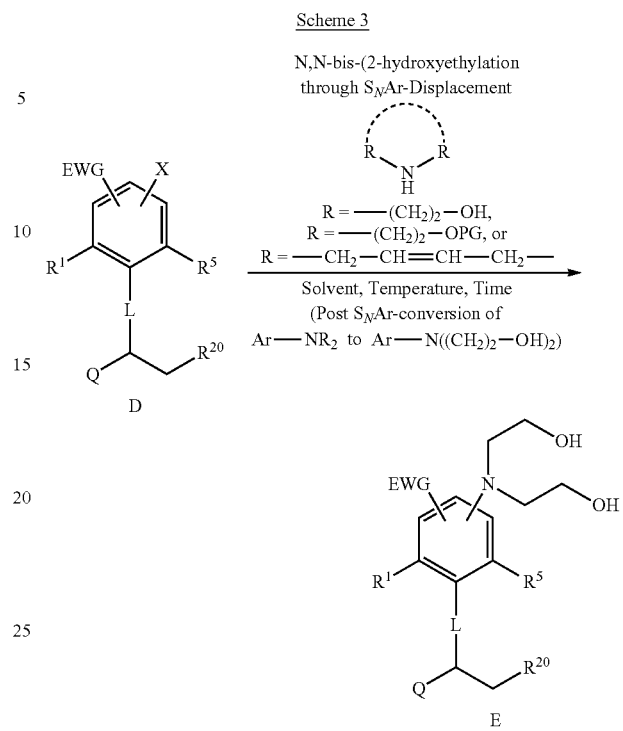

Scheme 3

Referring to Scheme 3, N,N-bis(2-hydroxyethyl)amino derivatives as in compounds of Formula (E) may be prepared through nucleophilic aromatic substitution reactions (S$_N$Ar) of aromatic halides of Formula (D) activated by electron withdrawing groups (EWGs), by reaction with an excess of about 1.5-5 equivalents of the neat amine, e.g., HN(CH$_2$CH$_2$OH)$_2$, HN(CH$_2$CH$_2$OBn)$_2$, or 3-pyrroline, (weakly basic reaction conditions) or solutions of the secondary amine in polar aprotic anhydrous solvents, e.g., anhydrous dimethylsulfoxide (DMSO), N,N-dimethylformamide (DMF), N,N-dimethylacetamide (DMAc), acetonitrile (MeCN), 1,4-dioxane, tetrahydrofuran (THF), or mixtures of the foregoing at a temperature from about 80-200° C. (sealed tube), for about 1-12 hours to provide N,N-bis(2-hydroxyethyl)amino-functionalized compounds of Formula (E). The reaction may also be carried out in the presence of a catalyst, e.g., copper powder (about 10 mol-%) (Atwell, et al., J. Med. Chem., 2007, 50(6), 1197-1212; Palmer, et al., J. Med. Chem., 1994, 37, 2175-2184; Palmer, et al., J. Med. Chem., 1992, 35(17), 3214-3222; Palmer, et al., J. Med. Chem, 1990, 33(1), 112-121; Davies, et al., J. Med. Chem. 2005, 48(16), 5321-5328; Jordan, et al., Bioorg. Med. Chem., 2002, 10(8), 2625-2633; Dheyongera, et al., Bioorg. Med. Chem., 2005, 13(3), 689-698; Lin, et al., Bioorg. Med. Chem. Lett., 2011, 21(3), 940-943; and Ferlin, et al., Bioorg. Med. Chem., 2004, 12(4), 771-777).

Referring to Scheme 3, methods to convert the N,N-bis-(2-benzyloxyethyl)amino group to a N,N-bis-(2-hydroxyethyl) amino group include, for example, catalytic hydrogenolysis of the benzyl ether groups using heterogeneous catalysts, e.g., 5-10% Pd on carbon (Pd/C) or Raney®-Nickel under standard hydrogenation reaction conditions are known in the art (Vincent and Prunet, Tetrahedron Lett, 2006, 47(24), 4075-4077).

Referring to Scheme 3, conversion the 3-pyrroline ring of the N-aryl-3-pyrroline moiety to a N,N-bis-(2-hydroxyethyl) amino group as in compounds of Formula (E) include oxidative cleavage of the C═C-double with the Lemieux-Johnson reagent (osmium tetroxide/sodium periodate, $OsO_4/NaIO_4$) or by ozonolysis with an $O_3/O_2$-gas mixture. Reductive workup, e.g., with borane-dimethylsulfide complex ($BH_3 \cdot Me_2S$), triphenylphosphine ($Ph_3P$), thiourea (C(═S)(NH$_2$)$_2$), or zinc dust, yields intermediate N,N-bis(2-oxoethyl)amino groups which may subsequently be reduced to the desired N,N-bis-(2-hydroxyethyl)amino group as in compounds of Formula (E) with suitable reducing reagents, e.g., borane-THF complex ($BH_3 \cdot THF$), or sodium borohydride ($NaBH_4$), under standard reaction conditions (Palmer and Denny, Synth. Commun., 1987, 17(5), 601-610).

In general, the biological activity of nitrogen mustards is based upon the presence of a N,N-bis(2-chloroethyl) functionality. The chemotherapeutic and cytotoxic effects are directly associated with the alkylation of DNA due to the strong electrophilic character of the N,N-bis(2-chloroethyl) functionality. Formation of covalent linkages including interstrand crosslinks (ICLs) is highly cytotoxic and involves the disruption of fundamental cellular processes including DNA replication leading to cellular death.

Many methods and reagents for converting primary alcohols to primary alkyl chlorides including conversion of N,N-bis(2-hydroxyethyl)amino groups to N,N-bis(2-chloroethyl) amino groups are known in the art. The most common methods include the use of concentrated hydrochloric acid (HCl) and various inorganic chlorides of sulfur or phosphorus which are used either in neat form or as solutions in inert solvents such as chlorinated hydrocarbons, aromatic hydrocarbons, or polar non-protic solvents, at room temperature or at elevated temperatures. Other useful chlorination methods and reagents include, for example, combinations of triphenyl phosphine and trichloroacetonitrile ($Ph_3P/Cl_3CCN$), triphenylphosphine dichloride ($Ph_3PCl_2$) (prepared from $Ph_3P$ and $Cl_2$), trimethylsilylchloride and bismuth(III) trichloride ($Me_3SiCl/BiCl_3$), mixtures of $Ph_3P$ and carbon tetrachloride ($CCl_4$), or methanesulfonyl chloride ($MeSO_2Cl$) in pyridine at elevated temperatures.

Referring to Scheme 4, it will be appreciated by one skilled in the art that the presence of particular functional or protecting group in compounds of Formula (F) and Formula (G) determines the choice a particular reagent, method, or reaction condition for the chloro-de-hydroxylation reaction.

Referring to Scheme 4, in certain embodiments $R^1$ and/or $R^5$, $R^{20}$, the linker L, E, the protecting groups PG and Q are defined as described herein; one of $R^2$, $R^3$, and $R^4$ in compounds of Formula (F) is a -E-N,N-bis(2-hydroxyethyl) amino group (-E-N(CH$_2$—CH$_2$—OH)$_2$); each of the other remaining $R^2$, $R^3$, and $R^4$ is hydrogen; and each of $R^7$ and $R^8$ is hydrogen.

Scheme 4

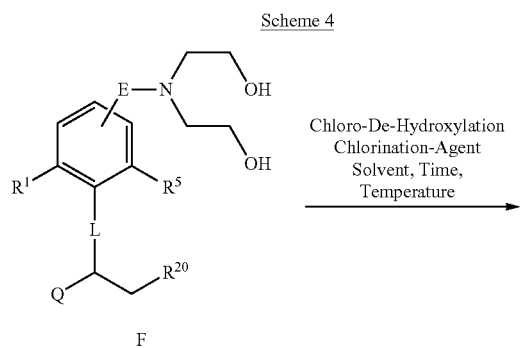

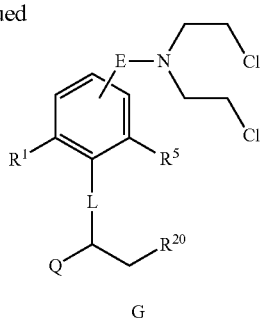

Referring to Scheme 4, in some embodiments N,N-bis(2-hydroxyethyl) compounds of Formula (F) may be reacted with an excess of about 2-15 equivalents of thionyl chloride ($SOCl_2$) either in neat form or as a solution in an anhydrous organic solvent, e.g., dichloromethane (DCM), chloroform ($CHCl_3$), 1,2-dichloroethane (DCE), benzene, or mixtures of any of the foregoing at temperatures from about 0° C. (ice bath) –40° C. or heated at reflux for about 0.5-3 hours to provide compounds of Formula (M) or of Formula (N) (Palmer, et al., J. Med. Chem. 1990, 33(1), 112-121; Jordan, et al., Bioorg. Med. Chem., 2002, 10(8), 2625-2633; Abela Medici, et al., J. Chem. Soc., Perkin Trans. 1, 1997, (20), 2258-2263; Taylor, et al., Chem. Biol. Drug Des., 2007, 70(3), 216-226; Dheyongera, Bioorg. Med. Chem. 2005, 13(3), 689-698; Zheng, Bioorg. Med. Chem. 2010, 18(2), 880-886; Gourdi, J. Med. Chem., 1990, 33(4), 1177-1186; and Lin, et al., Bioorg. Med. Chem. Lett., 2011, 21(3), 940-943). The reaction may optionally be carried out in the presence of a catalytic amount of zinc chloride ($ZnCl_2$) (10 mol-% to 40 mol-%) or in the presence of a catalytic amount of N,N-dimethylformamide (DMF) to facilitate the reaction (Squires, et al., J. Org. Chem., 1975, 40(1), 134-136; and Abela Medici, et al, J. Chem. Soc., Perkin Trans. 1, 1997, (20), 2258-2263).

Referring to Scheme 4, in some embodiments N,N-bis(2-hydroxyethyl) compounds of Formula (F) may also be reacted with an excess of about 2-10 equivalents of phosphorus(V)oxychloride (phosphoryl chloride, $POCl_3$) either in neat form or as a solution in an anhydrous organic solvent, e.g., benzene, acetonitrile, pyridine, or mixtures of any of the foregoing at a temperature from about 0° C. (ice bath) to about room temperature. The reaction mixture may also be heated from about 80° C. to about reflux temperature for about 0.5-6 hours to provide compounds of Formula (G) (Palmer, et al., J. Med. Chem. 1990, 33(1), 112-121; Feau, et al., Org. Biomolecular Chem., 2009, 7(24), 5259-5270; Valu, et al., J. Med. Chem., 1990, 33(11), 3014-3019; P. G. Baraldini, et al., J. Med., Chem., 2000, 53(14), 2675-2684; Gourdi, et al., J., Med., Chem., 1990, 33(4), 1177-1186; Haines, et al., J. Med. Chem., 1987, 30, 542-547; and Matharu, et al., Bioorg. Med. Chem. Lett., 2010, 20, 3688-3691).

Referring to Scheme 4, in some embodiments N,N-bis(2-hydroxyethyl) compounds of Formula (F) may also be reacted with an excess of carbon tetrachloride ($CCl_4$), optionally in an inert solvent, e.g., dichloromethane (DCM), in the presence of an excess of triphenylphosphine ($Ph_3P$) for about 8-24 hours at about room temperature or at reflux temperature for about 2-6 hours to provide compounds of Formula (G) (Buss, et al., J. Fluorine Chem., 1986, 34(1), 83-114; and Kupczyk-Subotkowska, et al., J. Drug Targeting, 1997, 4(6), 359-370).

Referring to Scheme 4, in some embodiments N,N-bis(2-hydroxyethyl) compounds of Formula (F) may also be reacted with methanesulfonyl chloride (MeSO$_2$Cl, MsCl) in anhydrous pyridine at about room temperature or at about 70-100° C. for about 1-3 hours to provide compounds of Formula (G) (Jordan, et al., Bioorg. Med. Chem., 2002, 10(8), 2625-2633; Abela Medici, et al, J. Chem. Soc., Perkin Trans. 1, 1997, (20), 2258-2263; Springer, et al., J. Med. Chem., 1990, 33(2), 677-681; and Larden and Cheung, Tetrahedron Lett., 1996, 37(42), 7581-7582).

Referring to Scheme 5, although halides are common leaving groups in nucleophilic substitution reactions for synthetic purposes, it is often more convenient to use the corresponding alcohols such as the ones found in N,N-bis(2-hydroxyethyl) amino groups of compounds of Formula (H). Since OH is usually considered a poor leaving group, unless protonated, conversion of a hydroxy group such as in N,N-bis(2-hydroxyethyl)amino groups of compounds of Formula (H) into reactive ester groups, most commonly sulfonic ester groups, converts the hydroxyl group into a functional group with a higher susceptibility to be displaced by an incoming nucleophile including halogenide ions. The N,N-bis(2-aryl- or (polyfluoro)alkylsulfonyloxy)amino groups of aryl- or (polyfluoro) alkylsulfonates of Formula (I) and similar sulfonic esters are most frequently prepared from N,N-bis(2-hydroxy)amino groups of diols of Formula (H) through reaction with an appropriate aryl- or (polyfluoro)alkyl-sulfonyl chloride or anhydride in the presence of a suitable base, e.g., pyridine (nucleophilic catalyst). Besides aromatic (R$^{40}$ is (substituted) aryl) sulfonic ester groups, aliphatic (R$^{40}$ is alkyl) sulfonic ester groups, and, in particular, (poly)fluorinated (R$^{40}$ is poly-F-alkyl) sulfonic ester groups as still more powerful leaving groups are frequently used for activation.

Referring to Scheme 5, in certain embodiments the R$^{40}$-group in compounds of Formula (I) or Formula (K) is for example phenyl and the leaving group is phenylsulfonyloxy (PhSO$_2$O), 4-methylphenyl(para-methylphenyl) and the leaving group is tosylate (4-methylphenylsulfonyloxy, TsO), 4-bromophenyl(para-bromophenyl) and the leaving group is brosylate (4-bromophenylsulfonyloxy, BsO), or 4-nitrophenyl(para-nitrophenyl) and the leaving group is nosylate (4-nitrophenylsulfonyloxy, NsO), methyl and the leaving group is mesylate(methanesulfonyloxy, MsO), trifluromethyl and the leaving group is triflate (trifluoromethanesulfonyloxy, TfO), nonafluoro-n-butyl and the leaving group is nonaflate (nonafluorobutanesulfonyloxy), or 2,2,2-trifluoroethyl and the leaving group is tresylate (2,2,2-trifluoroethanesulfonyloxy). In some embodiments, the R$^{40}$-group of compounds of Formula (I) and Formula (K) is methyl and the leaving group is mesylate(methansulfonyloxy, MsO). In some embodiments, the R$^{40}$-group of compounds of Formula (I) and of Formula (K) is trifluoromethyl and the leaving group is triflate (trifluoromethansulfonyloxy, TfO).

Referring to Scheme 5, N-mustard-type halides of Formula (J), Formula (K), and Formula (L) containing either (a) a N,N-bis(2-halogenoethyl)amino group (compounds of Formula (J)), (b) a N-(2-halogenoethyl)amino-, N-(2-halogeno'ethyl)amino-group (compounds of Formula (L) or mixed halogeno N-mustards), or (c) a N-(2-halogenoethyl) amino, N-(2-aryl- or (polyfluoro)alkylsulfonyloxyethyl) amino groups (compounds of Formula (K) or hybrid halogeno sulfonate N-mustards), may be prepared from the corresponding esters of sulfonic acid esters of Formula (P) through reaction with an excess or a near stoichiometric amount of an alkali metal halide (MX, MX') in suitable protic or non-protic organic solvent at elevated temperature (halode-sulfonyloxy substitution)

Referring to Scheme 5, in certain embodiments M in MX or MX' is an alkali metal cation, e.g., lithium (Li$^+$) and sodium (Na$^+$), X and X' in MX or MX' are halide anions, e.g., chloride (Cl$^-$), bromide (Br$^-$), and iodide (I$^-$). MX or MX' are alkali metal halides, e.g., lithium chloride (LiCl), lithium bromide (LiBr), sodium chloride (NaCl), sodium bromide (NaBr), or sodium iodide (NaI). In certain compounds of Formula (J), Formula (K), and Formula (L), X is a halogeno, e.g., chloro (—Cl), bromo (—Br), or iodo (—I) (Palmer, et al., J. Med. Chem. 1990, 33(1), 112-121; Palmer, et al., J. Med. Chem., 1994, 37, 2175-2184; Palmer, et al., J. Med. Chem., 1996, 39(13), 2518-2528; Davies, et al., J. Med. Chem. 2005, 48(16), 5321-5328; Niculesscu-Duvaz, et al., J. Med. Chem., 2004, 47(10), 2651-2658; Weisz, et al., Bioorg. Med. Chem. Lett., 1995, 5(24), 2985-2988; Thorn, J. Org. Chem, 1975, 40(11), 1556-1558; Lin, et al., Bioorg. Med. Chem. Lett., 2011, 21(3), 940-943; Gourdi, et al., J. Med. Chem. 1990, 33(4), 1177-1186; Yang, et al., Tetrahedron, 2007, 63(25), 5470-5476; Ferlin, et al., Bioorg. Med. Chem., 2004, 12(4), 771-777; and Coggiola, et al., Bioorg. Med. Chem. Lett., 2005, 15(15), 3551-3554).

Referring to Scheme 5, N-(2-halogenoethyl)amino, N-(2-aryl- or alkylsulfonyloxyethyl)amino groups of Formula (K) (hybrid halogeno sulfonate N-mustards) may also be prepared from primary alkyl halides of Formula (J) containing N,N-bis(2-halogenoethyl)amino groups through (a) a halode-halogenation (halide exchange reaction) or (b) a metathetical sulfonyloxy de-halogeno substitution reaction with solubilized silver sulfonates AgOSO$_2$R$^{40}$, wherein R$^{40}$ is defined as described herein under mild conditions in aprotic organic solvents (Emmons and Ferris, J Am. Chem. Soc., 1953, 75(9), 2257).

Referring to Scheme 5, for example in certain embodiments R$^1$ and/or R$^5$, R$^{20}$, R$^{40}$, X, X', E, the linker L, the protecting groups PG and Q are defined as herein; one of R$^2$, R$^3$, and R$^4$ in compounds of Formula (H) is -E-N(CH$_2$—CH$_2$—OH)$_2$ each of the other remaining R$^2$, R$^3$, and R$^4$ is hydrogen; and each of R$^7$ and R$^8$ is hydrogen.

Scheme 5

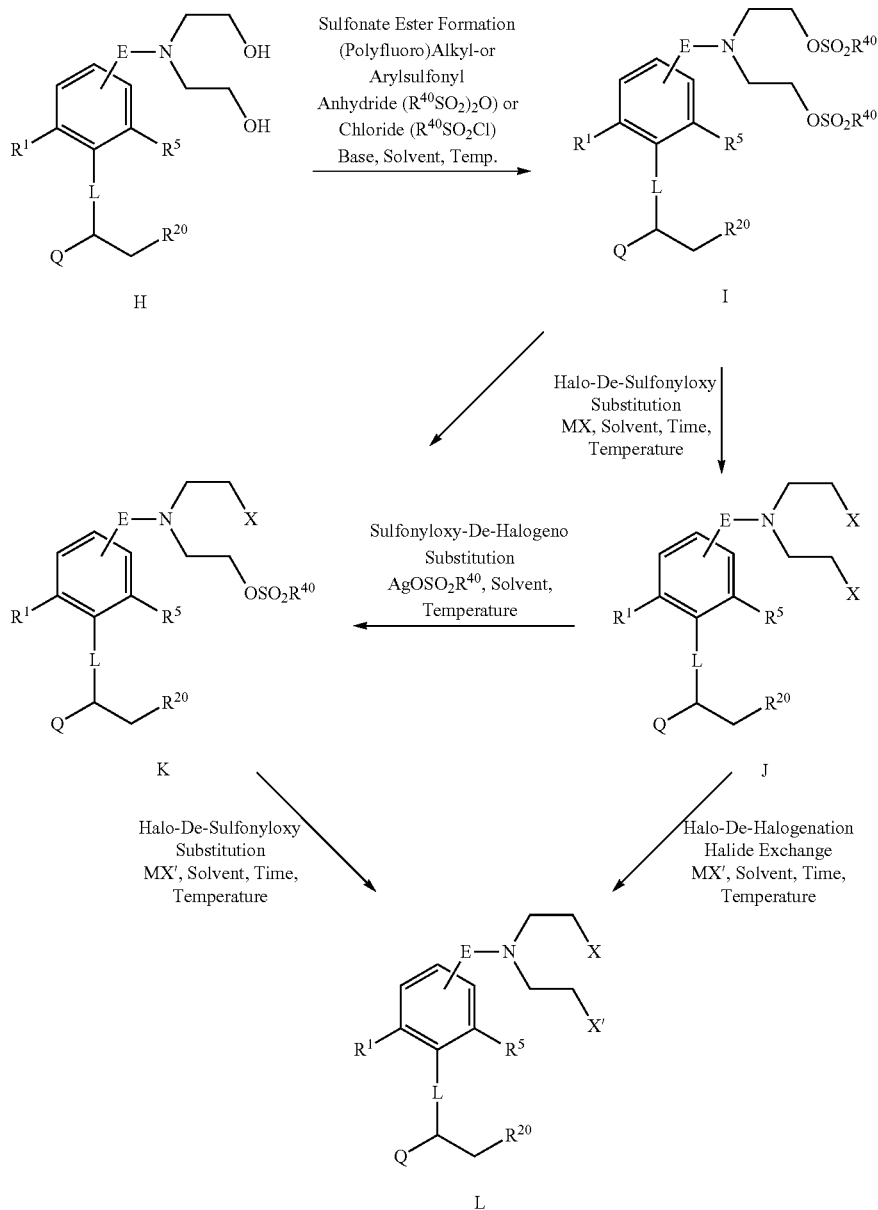

Referring to Scheme 5, in certain embodiments, the N,N-bis(2-hydroxyethyl)amino group of compounds of Formula (H) may be converted to N,N-bis(2-(polyfluoro)alkyl- or aryl-sulfonyloxyethyl)amino groups of compounds of Formula (I) (S-alkoxy-de-chlorination) by reacting diols of Formula (H) with an excess of a suitable (perfluoro)alkyl- or aryl-sulfonyl anhydride ($R^{40}SO_2)_2O$) (about 2.5-5 equivalents), e.g., methanesulfonyl anhydride ($R^{40}$ is methyl (Me), (MeSO$_2$)$_2$O)), in an inert solvent such anhydrous dichloromethane (DCM) or tetrahydrofuran (THF) or a mixture of any of the foregoing in the presence of an excess (about 2-10 equivalents) of a suitable base, e.g., anhydrous triethylamine (Et$_3$N, TEA) or anhydrous pyridine, at a temperature from about 0° C. to about room temperature for about 0.5-24 hours to afford bis-sulfonic acid esters of Formula (I). The reaction may optionally be carried out in the presence of a catalytic amount (about 20 mol-%) of 4-N,N-(dimethylamino)pyridine (DMAP).

Referring to Scheme 5, in certain embodiments, using comparable reaction conditions with respect to solvents, bases, stoichiometry of reagents, temperature, catalysts, and duration as described for the reaction of diols of Formula (H) with (ployfluoro)alkyl- or aryl-sulfonyl anhydrides, diols of Formula (H) may also be reacted with a suitable alkyl- or aryl-sulfonyl halides, e.g., methanesulfonyl chloride (mesyl chloride, MsCl) ($R^{40}$ is Me), MeSO$_2$Cl), to provide the desired bis-sulfonic acid esters of Formula (I).

Referring to Scheme 5, in certain embodiments N,N-bis(2-(polyfluoro)alkyl- or aryl-sulfonyloxyethyl)amino groups as in compounds of Formula (I) may be converted (halo-de-sulfonyloxy substitution) to N,N-bis(halogenoethyl)amino groups of compounds of Formula (J) by reacting bis-sulfonyl esters of Formula (I) with an excess of a suitable alkali metal halide salt MX, e.g., lithium chloride (LiCl), lithium bromide (LiBr), sodium chloride (NaCl), sodium bromide (NaBr), or sodium iodide (NaI) (4-16 equivalents) in a suitable organic solvent, e.g., N,N-dimethylformamide (DMF), N,N-dimethylacetamide (DMAc), acetone, 2-butanone(methyl ethyl ketone, MEK), 3-methyl-2-butanone (isopropyl methyl ketone, MIPK), acetonitrile (MeCN), methanol (MeOH), tetrahydrofuran (THF), ethyl acetate (EtOAc), or a mixture of any of the foregoing, at room temperature or heated to about 50-150° C. for about 0.5-6 hours to provide compounds of Formula (J).

Referring to Scheme 5, in certain embodiments using comparable reaction conditions with respect to solvents, temperature, and duration as described for the preparation of compounds of Formula (J), the reaction of bis-sulfonyl esters of Formula (I) may also be carried out in the presence of about one molar equivalent of a suitable alkali metal halide salt MX, as defined herein, to provide compounds of Formula (K) bearing N-(2-halogenoethyl)-, N-(2-methylsulfonyloxyethyl) amino groups (mixed halogeno/sulfonylato N-mustards).

Referring to Scheme 5, in some embodiments compounds of Formula (J) may be converted to mixed halogeno/sulfonylato N-mustards of Formula (K) by reacting N-mustard derivatives of Formula (J) where X is bromo (—Br) with about 1.0 equivalent or slightly less of a suitable soluble silver sulfonate salt, e.g., silver mesylate ($AgOSO_2Me$, AgOMs) in a polar solvent such as acetonitrile (MeCN) at about reflux temperature to provide the mixed halogeno/mesylate N-mustard of Formula (K) (methathetical reaction).

Referring to Scheme 5, in certain embodiments, using comparable reaction conditions with respect to solvents, temperature, and duration as described for the preparation of compounds of Formula (J) and of Formula (K), the reaction of bis-halogeno N-mustards of Formula (J) or of mixed halogeno/mesylate N-mustards of Formula (R) may also be carried out in the presence of about one molar equivalent of a suitable alkali metal halide salt MX', as defined herein, to provide compounds of Formula (L) bearing N-(2-halogenoethyl)-, N-(2-halogeno'ethyl) amino groups (mixed halogeno N-mustards).

Reductive N-alkylation is a form of amination/alkylation that involves the reaction of an amino group with a carbonyl group to an amine in the presence of a suitable reducing agent via an intermediate imine or protonated imine. The carbonyl group component is most commonly an aldehyde or ketone functionality, the amino group is most commonly ammonia, a primary or secondary aliphatic amino group, or a primary or secondary aromatic amino group (aniline). For indirect reductive aminations, the intermediate imine may be isolated and reduced with a suitable reducing agent. For direct reductive aminations, the reaction may be carried out simultaneously, with the imine formation and reduction occurring concurrently, typically using reducing agents that are more reactive toward protonated imines than ketones, and that are stable under moderately acidic conditions, e.g., sodium cyanoborohydride ($Na(CN)BH_3$) or sodium triacetoxyborohydride ($NaB(OAc)_3H$).

Referring to Scheme 6, the primary amino group of compounds of Formula (M) either in a suitable salt form, e.g., a hydrochloride (HCl) salt ($Ar-E-NH_2.HCl$) or as a free base ($Ar-E-NH_2$) may be subjected to a reductive N-alkylation reaction using a suitable halocarbonyl compounds (X is F, Cl or, Br) or derivatives thereof, e.g. a dimethyl acetal, and reducing agents as they are well known in the art (Palani, et al., J. Med. Chem., 2005, 48(15), 4746-4749; van Oeveren, Bioorg. Med. Chem. Lett., 2007, 17(6), 1527-1531; Delfourne, et al., Bioorg. Med. Chem., 2004, 12(15), 3987-3994; Delfourne, et al., J. Med. Chem., 2002, 47(17), 3765-3771; and M. Jordan, et al., Bioorg. Med. Chem., 2002, 10(8), 2625-2633).

Suitable halocarbonyl compounds include, for example, 2-chloroacetic acid ($ClCH_2CO_2H$, X is Cl)), 2-chloroacetaldehyde ($ClCH_2CHO$, X is Cl)), or 2-bromoacetaldehyde dimethylacetal ($(MeO)_2CHCH_2Br$, X is Br), optionally provided as solutions in suitable solvents, e.g., a 50-wt-% solution of 2-chloroacetaldehyde ($ClCH_2CHO$, X is Cl)) in water.

Referring to Scheme 6, suitable reducing agents for reductive N-alkylations of primary amino groups such as in compounds of Formula (M) using 2-chloroacetic acid include boranes, preferably borane-tetrahydrofuran complex ($H_3B.THF$), and certain alkalimetal borohydrides, e.g., lithium borohydride ($LiBH_4$) or sodium borohydride ($NaBH_4$).

Referring to Scheme 6, the reaction is generally carried out in the presence of organic solvents such as protic solvents, e.g., methanol (MeOH), acetic acid, (HOAc), trifluoroacetic acid (TFA), 85 wt-% phosphoric acid ($H_3PO_4$), glacial acetic acid (HOAC), 98 wt-% formic acid, or water, or inert organic solvents, e.g., acetonitrile (MeCN), dichloromethane (DCM), tetrahydrofuran (THF), benzene, or equivalent mixtures of any of the foregoing at a temperature from about 0° C. to about reflux temperature and for about 0.5-18 hours. In embodiments where 2-chloroacetaldehyde is used, suitable reducing agents may include, for example, sodium cyanoborohydride ($Na(CN)BH_3$), sodium triacetoxyborohydride ($NaB(OAc)_3H$, and sodium borohydride ($NaBH_4$).

Reduction via hydrogenation is can also be employed. Preferred hydrogenation conditions include catalytic hydrogenation, for example, using palladium on carbon (Pd/C) as the catalyst. As the hydrogen source, gaseous hydrogen ($H_2$-gas) at pressures ranging from about atmospheric pressure to about 150 psi, or suitable ammonium salts, e.g., ammonium hydrogencarbonate ($H_4NHCO_3$), may be employed. The hydrogenation may be carried out at ambient temperature.

Referring to Scheme 6, in certain embodiments, $R^1$ and/or $R^5$, $R^{20}$, E, the linker L, the halogeno group X, and the protecting group PG and Q are defined as herein; one of $R^2$, $R^3$, and $R^4$ in compounds of Formula (M) is -E-$NH_2$, wherein E is a bond ("—"), an oxygen atom (—O—), a methylene group (—$CH_2$—), or methylenoxy group (—$CH_2$—O—), and wherein MH is an amino group (—$NH_2$) so that -E-$NH_2$ is equivalent to a) a primary aromatic amino group (—$NH_2$, aniline), b) a primary O-aryl hydroxylamino group (—O—$NH_2$), c) a primary aminomethyl group (—$CH_2$—$NH_2$), or a primary O-benzyl hydroxylamino group (—$CH_2$—O—$NH_2$); each of the other remaining $R^2$, $R^3$, and $R^4$ is hydrogen; each of $R^7$ and $R^8$ is hydrogen.

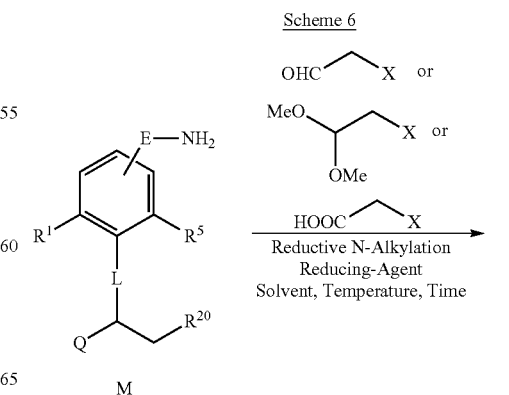

Scheme 6

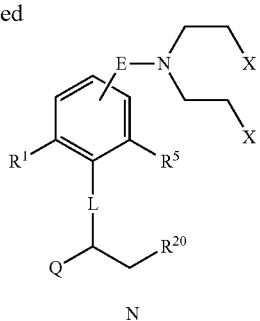

N

Referring to Scheme 6, in certain embodiments, the primary amino group of compounds of Formula (M) may be converted to N,N-bis(2-halogenoethyl)amino groups as in compounds of Formula (N) by reacting compounds of Formula (M) with an excess of about 4-10 equivalents of a 2-halogenocarbonyl compound, e.g., a 50 wt-% solution of 2-chloroacetaldehyde in water, and an excess of about 3-8 equivalents of a suitable reducing agent, e.g., sodium cyanoborohydride ($NaB(CN)H_3$). In certain embodiments, the reaction may be carried out in mixtures of methanol (MeOH) with trifluoroacetic acid (TFA), glacial acetic acid (HOAc), 98 wt-% formic acid (FA), or 85 wt-% phosphoric acid ($H_3PO_4$). For example, in certain embodiments, 1:1 (v/v), 2:1 (v/v), or 1:2 (v/v) mixtures MeOH/acid and reaction temperatures from about 0-40° C. and reaction times of about 0.5-18 hours are employed to provide protected N-mustards of Formula (N).

Estramustine (Emcyt®, Estracit®) is an antimicrotubule chemotherapy agent indicated in the US for the palliative treatment of metastatic and/or progressive prostate cancer. It is derivative of estrogen (specifically, estradiol) with a N-mustard-carbamate ester moiety.

Referring to Scheme 7, methods to functionalize alcohols or phenols with carbamoyl derivatives of secondary amines yielding carbamates as in, for example, compounds of Formula (Q) wherein M is oxygen (—O—) and G is oxygen (═O) include carbamoyl chlorides or p-nitrophenyl carbamates, and are well known in the art. Likewise, it is well known in the art that carbamates as in, for example, compounds of Formula (Q) wherein M is oxygen (—O—) and G is oxygen (═O) are also accessible through activation of alcohols or phenols with suitable formic ester derivatives including phosgene ($COCl_2$), triphosgene (bis(trichloromethyl) carbonate (BTC)), or 1,1'-carbonyldiimidazole (CDI) followed by reaction with an appropriately functionalized amine such as $HN(CH_2—CH_2—R^9)_2$ wherein $R^9$ is chloro (—Cl), bromo (—Br), iodo (—I), or (polyfluoro)alkyl- or aryl sulfonyloxy (—$OSO_2R^{40}$) or combinations thereof and $R^{40}$ is defined as described herein.

Likewise and referring to Scheme 7, many methods are known in the literature and are known by those skilled in the art to prepare compounds of Formula (Q) related to carbamates including a) S-thiocarbamates wherein M is sulfur (—S—) and G is oxygen (═O), b) O-thiocarbamates wherein M is oxygen (—O—) and G is sulfur (═S), c) dithiocarbamates wherein M is sulfur (—S—) and G is sulfur (═S), d) ureas wherein M is nitrogen (—$NR^{10}$—), and where $R^{10}$ is defined as described herein, and G is oxygen (═O), or thioureas wherein M is nitrogen (—$NR^{10}$—) and G is sulfur (═S).

Referring to Scheme 7, in certain embodiments a compound of Formula (O) is, for example, a) a phenol wherein E is a bond ("—") and MH is a hydroxyl group (—OH), b) an aniline wherein E is a bond ("—") and MH is an amino group (—$NR^{10}H$), c) a thiophenol wherein E is a bond ("—") and MH is a sulfhydryl group (—SH), d) an O-aryl hydroxylamine wherein E is oxygen (—O—) and MH is an amino group (—$NR^{10}H$), e) a benzylic alcohol wherein E is methylene (—$CH_2$—) and MH is a hydroxyl group (—OH), f) a benzylic amine wherein E is methylene (—$CH_2$—) and MH is an amino group (—$NR^{10}H$), g) a benzylic thiol wherein E is methylene (—$CH_2$—) and MH is sulfhydryl (—SH), h) an O-benzylic hydroxylamine wherein E is methyleneoxy (—$CH_2$—O—) and MH is an amino group (—$NR^{10}H$).

Referring to Scheme 7, in certain embodiments, $R^1$ and/or $R^5$, $R^{10}$, $R^{20}$, E, M, Z, the linker L, and the protecting group PG and Q are defined as described herein; one of $R^2$, $R^3$, and $R^4$ in compounds of Formula (O) is -E-MH as described herein; each of the other remaining $R^2$, $R^3$, and $R^4$ is hydrogen; each of $R^7$ and $R^8$ is hydrogen; LG is a suitable leaving group such as chloro (—Cl), 4-nitrophenyloxy ($NO_2C_6H_4O$—), or imidazole; and $R^9$ is chloro (—Cl), bromo (—Br), iodo (—I), or (polyfluoro)alkyl- or aryl sulfonyloxy (—$OSO_2R^{40}$) or combinations thereof, and $R^{40}$ is defined as described herein.

Scheme 7

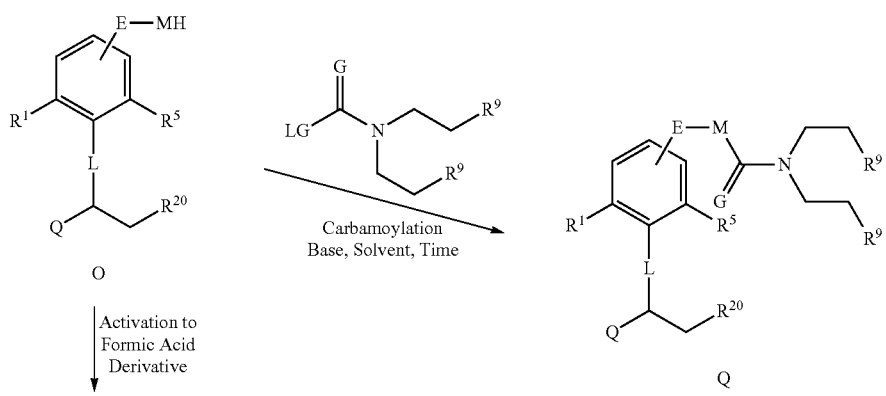

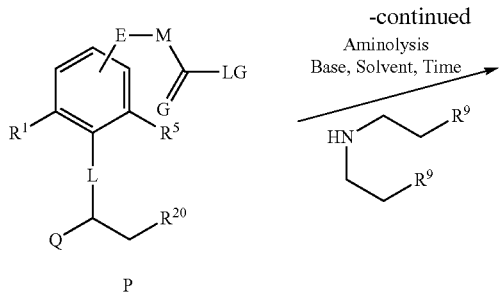

Referring to Scheme 7, in certain embodiments the alcohol, the thiol group, or the amino group of compounds of Formula (O) may be converted to the N,N-bis(2-halogeno- or 2-sulfonyloxyethyl)carbamoyl or N,N-bis(2-halogeno- or 2-sulfonyloxyethyl)thiocarbamoyl group of compounds of Formula (Q) by reacting a compound of Formula (O) with, for example, commercial N,N-bis(2-chloroethyl)carbamoyl chloride (Fex, et al., U.S. Pat. No. 3,299,104), wherein LG is chloro (—Cl), $R^9$ is chloro (—Cl), and G is oxygen (═O) or known (4-nitrophenyl) N,N-bis(2-chloroethyl)carbamate where LG is 4-nitrophenol (4-NO$_2$-Ph-O—), $R^9$ is chloro (—Cl), and G is oxygen (═O) in suitable solvents such as pyridine, or triethylamine in 1,4-dioxane/benzene mixtures and the like at temperatures of about 0-60° C. to provide carbamate, thiocarbamate, or urea derivatives of Formula (Q).

Referring to Scheme 7, in certain embodiments the MH-group of compounds of Formula (O) may be activated to their corresponding chloroformates, thiochloroformates, or carbonyl imidazoles of Formula (P) with, for example, phosgene, thiosphosgene, triphosgene, carbonyldiimidazole (CDI), thiocarbonyldiimidazole (TCDI), or the like, in the presence of a suitable base such as inorganic metal-carbonate, e.g., potassium carbonate (K$_2$CO$_3$) and bicarbonates, e.g., sodium hydrogencarbonate (NaHCO$_3$), in suitable inert solvents known in the art. The chloroformates or thiochloroformates of Formula (P) are subsequently converted to the corresponding carbamates of Formula (Q) through reaction with an appropriately functionalized amine such as HN(CH$_2$—CH$_2$—R$^9$)$_2$ wherein $R^9$ is chloro (—Cl), bromo (—Br), iodo (—I), or (polyfluoro)alkyl- or aryl sulfonyloxy (—OSO$_2$R$^{40}$) or combinations thereof, and $R^{40}$ is defined as described herein, e.g., commercial bis(2-chloroethyl)amine hydrochloride wherein $R^9$ is chloro (—Cl) or 2-bromo-N-(2-bromoethyl)ethanamine wherein $R^9$ is bromo (—Br), and in the presence of a base such as inorganic metal-carbonate, e.g., potassium carbonate (K$_2$CO$_3$) and bicarbonate, e.g., sodium hydrogencarbonate (NaHCO$_3$), ethyl acetate (EtOAc), water, or mixtures of any of the foregoing to yield carbamates of Formula (Q).

In general, the biological activity of nitrogen mustards is based upon the presence of an alkylating N,N-bis(2-chloroethyl) functionality. The chemotherapeutic and cytotoxic effects are directly associated with the alkylation of DNA due to the strong electrophilic character of the N,N-bis(2-chloroethyl) functionality. Formation of covalent linkages including interstrand crosslinks (ICLs) is highly cytotoxic and involves the disruption of fundamental cellular processes including DNA replication leading to cellular death.

Because of this property, the nitrogen mustards have been used for a number of years in laboratory investigations and in the clinical treat for malignant growth. Unfortunately, the effective dose of nitrogen mustards is in many cases close to the toxic dose and it is therefore desirable to find a nitrogen mustard or a class of nitrogen mustard type compounds possessing the high carcinolytic activity of the parent compound but having modulated toxicity.

The amide linkage masks the alkylating and toxic properties of the nitrogen mustard moiety so that the total host is not subjected to undesirable toxic effects sometime encountered with nitrogen mustard therapy: the amino acid moiety of the molecule facilitates the selective delivery of the "masked" nitrogen mustard via the amino acid transport mechanism into the tumor cells, where the higher amidase activity of the tumor cell liberates the reactivated nitrogen mustard within itself. Thus in effect it will be possible to obtain maximum effect of the nitrogen mustard on the tumor and minimum toxic effect on the host (U.S. Pat. No. 3,235,594).

Referring to Scheme 8, the amide nitrogen mustards of the present disclosure are prepared by condensing carboxylic acids of Formula (R) wherein E is a carbonyl group (—C(═O)—) or a methylenecarbonyl group (—CH$_2$—C(═O)—) with an appropriately functionalized amine such as HN(CH$_2$—CH$_2$—R$^9$)$_2$ wherein X is chloro (—Cl), bromo (—Br), iodo (—I), or (polyfluoro)alkyl- or aryl sulfonyloxy (—OSO$_2$R$^{40}$) or combinations thereof, and $R^{40}$ is defined as described herein, to provide amides of nitrogen mustards of Formula (S).

Referring to Scheme 8, a myriad of coupling methods is known in the art to facilitate the formation of amide bonds as in compounds of Formula (S) from carboxylic acids of Formula (R) (Montalbetti and Falque, Tetrahedron, 2005, 61, 10827-10852; and Valeur and Bradley, Chem. Soc. Rev., 2009, 38, 606-631).

Referring to Scheme 8, in certain embodiments, $R^1$ and/or $R^5$, $R^{20}$, E, the linker L, and the protecting group PG and Q are defined as described herein; one of $R^2$, $R^3$, and $R^4$ in compounds of Formula (R) is -E-OH as described herein; each of the other remaining $R^2$, $R^3$, and $R^4$ is hydrogen; each of $R^7$ and $R^8$ is hydrogen; and $R^9$ is a suitable functionalization providing the alkylation properties of the nitrogen mustard.

Scheme 8

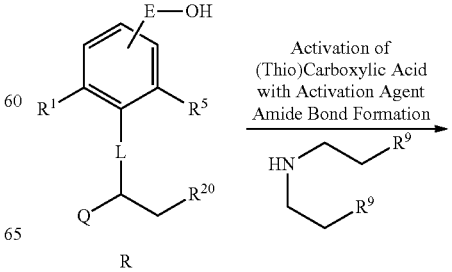

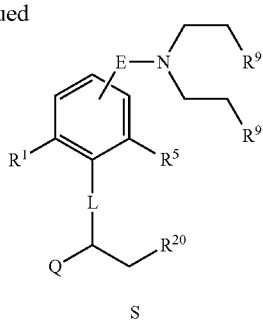

Referring to Scheme 8, in certain embodiments the (thio) carboxyl group of compounds of Formula (R) may be activated as acyl halides, acyl azides, symmetrical or unsymmetrical carboxylic, carbonic, or boronic anhydrides, acyl imidazoles, activated esters, phosphonium salts, uronium salts, or ammonium salts followed by ammonolysis of the activated intermediate either after prior isolation or in situ with an appropriately functionalized amine such as $HN(CH_2-CH_2-R^9)_2$ to provide nitrogen mustard amides of Formula (S).

Referring to Scheme 9, in certain embodiments the connector group "A" of the moiety $-A-N(CH_2-CH_2-R^9)_2$ is a bond ("—"), oxygen (—O—), sulfur (—S—), amino ($-NR^{10}-$), methylene (—$CH_2$—), methyleneoxy (—$CH_2$—O—), oxycarbonyl (—O—C(=O)—), thiocarbonyl (—S—C(=O)—), aminocarbonyl (—$NR^{10}$—C(=O)—), oxythiocarbonyl (—O—C(=S)—), thiothiocarbonyl (—S—C(=S)—), aminothiocarbonyl (—$NR^{10}$—C(=S)—), methyleneoxycarbonyl (—$CH_2$—O—C(=O)—), methylenethiocarbonyl (—$CH_2$—S—C(=O)—), methyleneaminocarbonyl (—$CH_2$—$NR^{10}$—C(=O)—), methyleneoxythiocarbonyl (—$CH_2$—O—C(=S)—), methylenethiothiocarbonyl (—$CH_2$—S—C(=S)—), methyleneaminothiocarbonyl (—$CH_2$—$NR^{10}$—C(=S)—), carbonyl (—C(=O)—), methylencarbonyl (—$CH_2$—C(=O)—), thiocarbonyl (—C(=S)—), or methylenthiocarbonyl (—$CH_2$—C(=S)—).

Referring to Scheme 9, in certain embodiments liberation of unprotected N-mustard functionalized β-substituted β-amino acid derivatives or unprotected N-mustard functionalized β-substituted β-amino acid analogs or carboxylic acid (bio)isosteres of Formula (U) from their corresponding precursors of Formula (T) may be conducted under aqueous acidic conditions (hydrolysis) (Taylor, et al., Chem. Biol. Drug Des., 2007, 70(3), 216-226; Buss, et al., J. Fluorine Chem., 1986, 34(1), 83-114; A. J. Abela, et al, J. Chem. Soc., Perkin Trans. 1, 1997, (20), 2258-2263; Weisz, et al., Bioorg. Med. Chem. Lett., 1995, 5(24), 2985-2988; Zheng, Bioorg., Med., Chem., 2010, 18(2), 880-886; Haines, et al., J. Med. Chem., 1987, 30, 542-547; and Matharu, et al., Bioorg., Med., Chem., Lett., 2010, 20, 3688-3691).

Referring to Scheme 9, in certain embodiments liberation of unprotected N-mustard functionalized β-substituted β-amino acid derivatives or unprotected N-mustard functionalized β-substituted β-amino acid analogs or carboxylic acid (bio)isosteres of Formula (U) from their corresponding precursors of Formula (T) may also be conducted under anhydrous acidic conditions (Springer, et al., J. Med. Chem., 1990, 33(2), 677-681; Davies, et al., J. Med. Chem. 2005, 48(16), 5321-5328; Niculesscu-Duvaz, et al., J. Med. Chem., 2004, 47(10), 2651-2658; Verny and Nicolas, J. Label. Cmpds. Radiopharm., 1988, 25(9), 949-955; Thorn, et al., J. Org. Chem, 1975, 40(11), 1556-1558; Baraldini, et al., J. Med. Chem., 2000, 53(14), 2675-2684; Gourdi, et al., J. Med. Chem., 1990, 33(4), 1177-1186; and Kupczyk-Subotkowska, et al., J. Drug Targeting, 1997, 4(6), 359-370).

Referring to Scheme 9, it will be understood by those skilled in the art that protected N-mustard functionalized β-substituted β-amino acid precursors of Formula (T) or protected N-mustard β-substituted β-amino acid analog or carboxylic acid (bio)isosteres precursors of Formula (T) bearing different combinations of suitable protecting groups may also be prepared. Different combinations of protecting groups may require specific reactants and reaction conditions for effective removal of specific set of different protection groups to provide unprotected N-mustard β-substituted β-amino acid derivatives or unprotected N-mustard functionalized β-substituted β-amino acid derivatives, analogs, or carboxylic acid (bio)isosteres of Formula (U).

Referring to Scheme 9, in certain embodiments of compounds of Formula (T) and of Formula (U) $R^1$ and/or $R^5$, $R^9$, the connector group A, the protecting groups PG and Q, and the linker L are defined as described herein; $R^6$ is an unprotected carboxylic acid, a carboxylic acid analog or a carboxylic acid (bio)isostere as defined herein; $R^{20}$ is a protected carboxylic acid, a carboxylic acid analog or a carboxylic acid (bio)isostere as defined herein; one of $R^2$, $R^3$, and $R^4$ is a N,N-bis-(2-functionalized)ethylamino group (nitrogen mustard group) linked to a connector A ($-A-N(CH_2-CH_2-R^9)_2$); each of the remaining $R^2$, $R^3$, and $R^4$ is hydrogen; each of $R^7$ and $R^8$ is hydrogen.

Scheme 9

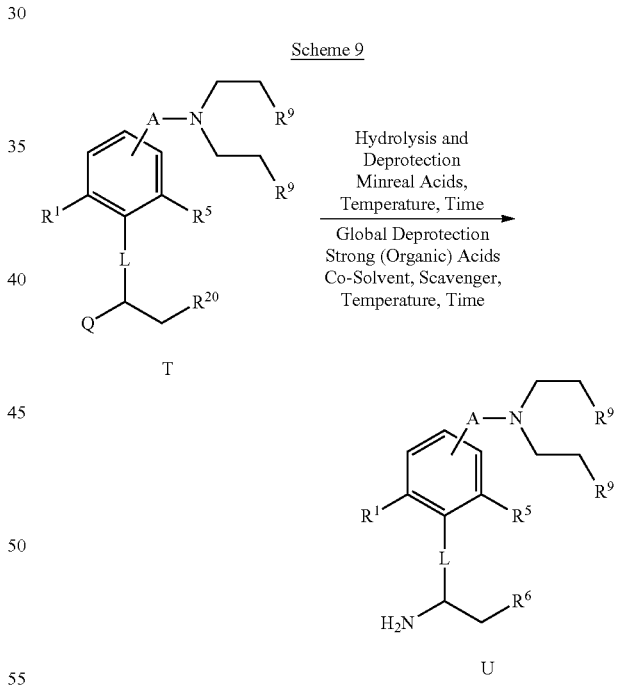

Referring to Scheme 9, hydrolytic acidic global deprotection of compounds of Formula (T) to provide N-mustard functionalized β-substituted β-amino acid derivatives or N-mustard functionalized β-substituted β-amino acid analogs or carboxylic acid (bio)isosteres of Formula (U) may be accomplished by treating protected precursors of Formula (T) at elevated temperatures from about 40-150° C. with aqueous mineral acids, e.g., 2 M to ~12 M hydrochloric acid (HCl) for about 6-24 hours. In certain embodiments, mixtures of the mineral acid with organic solvents may be used. A useful aqueous mineral acid reaction mixture to facilitate global deprotection is, e.g., a 1:1 (v/v) mixture of concentrated hydrochloric acid (~12 M or ~37 wt-% HCl) with 1,4-dioxane.

Referring to Scheme 9, other aqueous mineral acids with a non-nucleophilic anion known in the art can be used to facilitate hydrolytic acidic global deprotection of compounds of Formula (T) bearing acid-labile or hydrolysis sensitive protecting groups of the protected carboxylic moiety, of the protected carboxylic acid (bio)isostere, or of the amino functionality of compounds of Formula (T) to provide N-mustard functionalized β-substituted β-amino acid derivatives or N-mustard functionalized β-substituted β-amino acid analogs or carboxylic acid (bio)isosteres of Formula (U).

Referring to Scheme 9, suitable mineral acids may for example include diluted or concentrated aqueous solutions of hydrobromic acid (HBr), hydroiodic acid (HI), sulfuric acid ($H_2SO_4$), perchloric acid ($HClO_4$), and phosphoric acid ($H_3PO_4$), mixtures of any of the foregoing or mixtures with suitable organic solvents, e.g., 1,4-dioxane, with any of the foregoing.

It is within the ability of one skilled in the art to select specific and suitable aqueous mineral acids and reaction conditions for hydrolytic acidic hydrolytic acidic global deprotection of compounds of Formula (T) to provide N-mustard functionalized β-substituted β-amino acid derivatives or N-mustard functionalized β-substituted β-amino acid analogs or carboxylic acid (bio)isosteres of Formula (U).

Referring to Scheme 9, simultaneous global deprotection of compounds of Formula (T) where $R^{20}$ is an acid labile moiety derived from a carboxylic acid, e.g., $CO_2tBu$, $CO_2$-pentamethylbenzyl, $CO_2$-(4-methoxyl)benzyl, or $CO_2$-trityl, and Q is a protected amino group derived from an acid-labile N-protecting group, e.g., N(H)Boc, N(H)trityl, N(H)(4-methoxy)phenyl-diphenylmethyl, or N(H)di-((4-methoxy)phenyl)-phenylmethyl, may also be accomplished by reaction with strong organic acids under anhydrous conditions to liberate free (unprotected)N-mustard functionalized β-substituted β-amino acid derivatives or N-mustard functionalized β-substituted β-amino acid analogs or carboxylic acid (bio)isosteres of Formula (U).

In certain embodiments, strong (organic) acids useful for global deprotection under anhydrous conditions include trifluoroacetic acid (TFA), 98 wt-% formic acid (FA), methanesulfonic acid ($MeSO_3H$), 85 wt-% phosphoric acid ($H_3PO_4$), 2 M hydrogen chloride (HCl) in diethyl ether ($Et_2O$), 4 M hydrogen chloride (HCl) in 1,4-dioxane, or a saturated solution of HCl in ethyl acetate (EtOAc) (Li, et al., J. Org. Chem., 2006, 71, 9045-9050).

Depending of the overall sensitivity to strong (organic) acids), compounds of Formula (T) may be reacted with neat either neat strong (organic) acid or with solutions of the strong organic acid in suitable inert solvents such as dichloromethane (DCM), dichloroethane (DCE), 1,4-dioxane, diethylether ($Et_2O$), tetrahydrofuran (THF), or toluene typically in ratios ranging from neat (organic) acid to about 10 vol-% (organic) acid in said inert solvent, and reaction temperatures ranging from about 0-50° C. for about 1-24 hours to provide unprotected N-mustard functionalized β-substituted β-amino acid derivatives or unprotected N-mustard functionalized β-substituted β-amino acid analogs or carboxylic acid (bio)isosteres of Formula (U).

Optionally, 2-5 equivalents of a suitable scavenging agent such as triethysilane ($Et_3SiH$) (TES), triisopropylsilane ($iPr_3SiH$), thioanisole, or 1,2-dithioethane ($HSCH_2CH_2HS$) may be added to the reaction mixture to suppress formation of unwanted side reactions and byproducts originating, for example, from alkylation of electron-rich aromatic scaffolds or sulfide groups under global deprotection conditions disclosed herein to provide unprotected N-mustard functionalized β-substituted β-amino acid derivatives or unprotected N-mustard functionalized β-substituted β-amino acid analogs or carboxylic acid (bio)isosteres of Formula (U).

Separation of unprotected N-mustard functionalized β-substituted β-amino acid derivatives or unprotected N-mustard functionalized β-substituted β-amino acid analogs or carboxylic acid (bio)isosteres of Formula (U) from unreacted starting materials, unwanted byproducts, and impurities may be accomplished using, for example, solid-phase extraction (SPE) techniques, e.g., with QMA® cartridges (Waters, USA), LiChrolut® cartridges (EMD Chemicals, USA), or Whatman SAX cartridges (Whatman, USA), preparative normal or reverse phase TLC, reverse phase (RP) semi-preparative or preparative HPLC, crystallization, precipitation, or any other suitable method known in the art.

Purified unprotected N-mustard functionalized β-substituted β amino acid derivatives or unprotected N-mustard functionalized β-substituted β-amino acid analogs or carboxylic acid (bio)isosteres of Formula (U) may be isolated using any of the methods known in the art. For example, such methods include removal of HPLC solvents (mobile phase) of the combined fractions containing the N-mustard functionalized β-substituted β-amino acid derivatives or N-mustard functionalized β-substituted β-amino acid analogs or carboxylic acid (bioisosteres) of Formula (U) under reduced pressure with a rotary evaporator, or removal of (aqueous) solvent mixtures by primary lyophilization.

Any method known in the art may be used to produce acid addition salts or salts including pharmaceutically acceptable acid addition salts or salts of compounds of Formula (U) (Handbook of Pharmaceutical Salts—Properties, Selection, and Use, Stahl and Wermuth, Wiley-VCH, Weinheim, Germany, 2008).

The lyophilization may optionally be conducted in the presence of one or more equivalents of a mineral acid, optionally with a pharmaceutically acceptable counterion, to form (pharmaceutically acceptable) acid addition salts of compounds of Formula (U). For example, one or more equivalents of hydrochloric acid (HCl) may be added prior to lyophiliation to form mono-, di-, or polyhydrochloride salts of compounds of Formula (U) or mixtures thereof.

The lyophilization may optionally be conducted in the presence of one or more equivalents of a base, optionally with a pharmaceutically acceptable counterion, to form (pharmaceutically acceptable) salts of compounds of Formula (U). For example, one or more equivalents of sodium hydrogen carbonate ($NaHCO_3$) may be added prior to lyophiliation to form mono-, di-, or poly sodium salts of compounds of Formula (U) or mixtures thereof.

A characteristic feature of solid tumours is the presence of cells at very low oxygen concentrations (hypoxia; partial pressure of oxygen in tumorous tissue of 0.05-5.0%) often surrounding areas of necrosis. There are clear links between hypoxia and the lack of response to radiotherapy and intrinsic resistance to cytotoxic therapy. It has also been demonstrated that hypoxia in tumours tends to select for a more malignant phenotype (Wilson and Hay, Nat. Rev. Canc., 2011, 11, 393-410; and Brown and Wilson, Nat. Rev. Canc., 2004, 4, 437-447).

Reductive metabolic processes are more prevalent in the hypoxic environment of solid tumors. Reductive enzyme systems have the ability to reduce certain functional groups. For example, aromatic and aliphatic N-oxides ($—N^+(O^-)R_2$) are known to be reducible to the corresponding amines ($—NR_2$), and nitro groups ($—NO_2$) can be either reduced to the corresponding amines (—NH$_2$) or to hydroxylamines (—NH(OH)) depending on the oxygen saturation of the tissue (Denny, et al., Br. J. Canc., 1996, 74, Suppl. XXVII, S32-S38; and Nagasawa, et al., Biol. Pharm. Bull., 2006, 29(12), 2335-2342).

One promising approach for the design of cancer-cell-selective mustards exploits selective enzymatic reduction of nitroaryl compounds in the oxygen-starved (hypoxic) cells found in solid tumors. N-Oxide derivatives of nitrogen mustards including N-oxides of melphalan (PX-478; Kirkpatrick, et al., U.S. Pat. No. 7,399,785; Koh, et al., Mol. Canc. Ther., 2008, 7(1), 90-100; www.medkoo.com) and chlorambucil (Kirkatrick, et al., Anti-Cancer Drugs, 1994, 5, 467-472; Tercel, et al., J. Med. Chem., 1995, 38, 1247-1252; and Kirckpatrick, U.S. Pat. No. 5,602,273) have been investigated as bioreductive prodrugs with reduced systemic toxicity in comparison to the parent drugs. Those drugs take advantage of a) the hypoxic nature, and b) the reductive nature, of certain tumorous cells. The N-oxide functional group deactivates the extremely reactive alkylating agent through capture of the lone electron pair of the parent nitrogen mustard moiety thus diminishing the alkylating properties and the off-target toxicities associated with that. Bioreductive activation within the hypoxic tumor environment or milieu by hypoxic cells and their reductive enzyme systems is believed to restore the cytotoxicity of the free nitrogen mustards. The overall effect is an enhanced therapeutic index of the N-oxides of nitrogen mustards relative to their parent nitrogen mustards.

Depending on the pH and the nature of the solvent, particularly aprotic organic solvents, N-oxides of nitrogen mustards are known to intramolecularly rearrange to the corresponding more stable hydroxylamines with markedly less intrinsic cytotoxic potential (Tercel, et al., J. Med. Chem., 1995, 38, 1247-1252; and Kirckpatrick, U.S. Pat. No. 5,602, 273). However, it is also known that said hydroxylamines are able to convert back to the parent N-oxides in vivo where the latter can be reduced in the hypoxic and reductive environment of tumorous cells where the underlying nitrogen mustards exerts their cytotoxicity.

Referring to Scheme 10, in certain embodiments of compounds of Formula (V), Formula (W), and of Formula (X) $R^1$ and/or $R^5$, $R^6$, $R^9$, and the linker L are defined as described herein; one of $R^2$, $R^3$, and $R^4$ is a N,N-bis-(2-functionalized) ethylamino group (nitrogen mustard group) linked to a connector group "A" (-A-N(CH$_2$—CH$_2$—R$^9$)$_2$) wherein the connector group "A" is a bond ("—") or a methylene group (—CH$_2$—); each of the remaining $R^2$, $R^3$, and $R^4$ is hydrogen; each of $R^7$ and $R^8$ is hydrogen.

Scheme 10

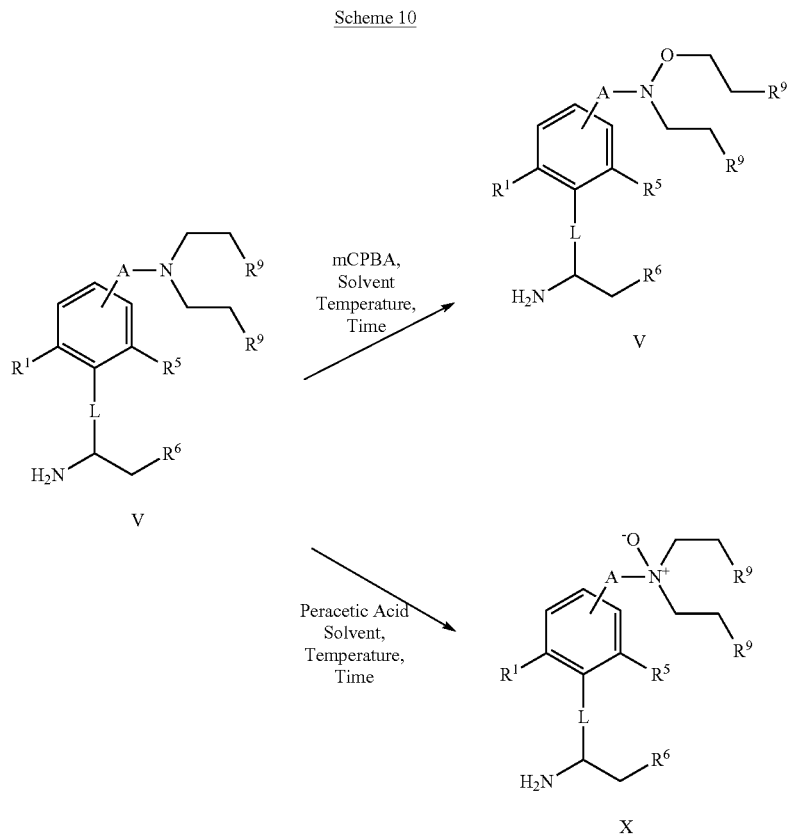

Referring to Scheme 10, N-oxidation of the N-mustard group of compounds of Formula (V) with a slight excess of 3-chloroperbezoic acid (meta-chloroperbenzoic acid, mCPBA) in a solvent such as dichloromethane (DCM) at about room temperature followed by work-up with aqueous sodium hydrogencarbonate furnishes the more stable hydroxylamine (through putative re-arrangement via a cyclic oxazetidinium species) of Formula (W).

Referring to Scheme 10, N-oxidation of the N-mustard group of compounds of Formula (V) with 3-5 equivalents of peracetic acid (MeCO(O$_2$H)), prepared from 35 wt-% aqueous hydrogen peroxide (H$_2$O$_2$) in glacial acetic acid (HOAc), in a solvent such as dichloromethane (DCM) at about room temperature followed by acid extraction furnishes the corresponding N-oxide of Formula (X).

Characterization

To determine the extent to which compounds provided by the present disclosure enter cells via the LAT1/4F2hc transporter, amino acid uptake assays into cells that are transfected with DNA encoding the LAT1 and 4F2hc subunits may be performed using, for example, HEK (human embryonic kidney) or CHO (Chinese hamster ovary) cells. Oocytes may also be injected with cRNA LAT1 and 4F2hc to express LAT1/4F2hc transporter. Compounds may be screened either for specificity for the LAT1/4F2hc transporter or for transport into cells endogenously expressing a plurality of transporters. The results of a screening method (e.g., a competition uptake, exchange or direct uptake assay) using a cell expressing the LAT1/4F2hc transporter may be compared with the results of a control cell(s) lacking the LAT1/4F2hc transporter or in the presence of a specific inhibitor of the LAT1/4F2hc transporter.

In competition experiments, the ability of a compound to specifically bind to the LAT1/4F2hc transporter is determined. A known substrate (reference substrate) for the LAT1/4F2hc transporter and a test compound are added to cells expressing the LAT1/4F2hc transporter. For example, gabapentin may be used as a reference because it demonstrates high selectivity for LAT1/4F2hc. Gabapentin is not a substrate for the intestinal amino acid transporters $B^{0,+}$, $ATB^{0,+}$, and LAT2, whereas gabapentin may be a substrate for the organic cation transporter OCTN2 (Cundy, et al., J Pharm Exp Ther, 2004, 311(1), 315-323; and Grigat, et al., Drug Metabol Disp, 2009, 37(2), 330-337). The amount or rate of transport of the reference substrate in the presence of the test compound is compared to the amount or rate of transport of the reference substrate in the absence of the test compound. If the amount or rate of transport of the reference substrate is decreased by the presence of the test compound, the test compound binds to the LAT1/4F2hc transporter.

Compounds that bind the LAT1/4F2hc transporter can be further analyzed to determine if they are transported by the LAT1/4F2hc transporter or only compete for binding to the transporter. Transport of a compound into a cell can be determined by detecting a signal from within a cell from any of a variety of reporters. The reporter can be as simple as a label such as a fluorophore, a chromophore, a radionuclide, or a reporter can be an agent that is detected utilizing liquid chromatography-mass spectroscopy (LC/MS/MS). The same methods of detection can be used to determine if a reporter is transported from the intracellular space to the medium by administering the test compound to the outside of the cell and sampling the media for the presence of the intracellular reporter after a predetermined period of time (exchange assays).

Having determined that a compound is a substrate for LAT1/4F2hc, a further screen may be performed to determine the selectivity of the compound toward other membrane transporters. Selectivity refers to the affinities with which a compound is transported by different transporters. In order to demonstrate selectivity for LAT1/4F2hc, a compound may be tested in uptake and/or competition assays for other transporters. Transporters that could potentially transport LAT1/4F2hc substrates include SLC1A4 (ASCT1; NP_003029), SLC1A5 (ASCT2; NP_005619), SLC6A1 (GAT1; NP_003033), SLC6A5 (GlyT2; NP_004202), SLC6A6 (TauT; NP_003034), SLC6A8 (CT1; NP_005620), SLC6A9 (GlyT1; NM_008865), SLC6A11 (GAT3; NP_55044), SLC6A12 (BGT1; NP_003035), SLC6A13 (GAT2; NP_057699), SLC6A14 ($ATB^{0,+}$; NP_009162), SLC6A15 ($B^0AT2$; NP_001139807), SLC6A17 (XT1; NP_001010898), SLC6A18 ($B^0AT3$; NP_872438), SLC6A19 ($B^0AT1$; NP_001003841), SLC7A6 ($y^+LAT2$; NP_001070253), SLC7A7 ($y^+LAT1$; NP_001119577), SLC7A8 (LAT2; NP_036376), SLC7A9 ($b^{0,+}AT$; NP_055085), SCL7A10 (ASC-1; NP_062823), SLC15A1 (PepT1; NP_005064), SLC15A2 (PepT2; NP_066568), SLC16A1 (MCT1; NP_003042), SLC16A2 (MCT8; NP_006508), SLC16A10 (TAT1; NP_061063), SLCO1B1 (OATP1B1; NP_006437), SLCO1B3 (OATP1B3; NP_062818), SLC22A1 (OCT1; NP_003048), SLC22A2 (OCT2; NP_003049), SLC22A4 (OCTN1; NP_003050), SLC22A5 (OCTN2; NP_003051), SLC22A8 (OAT3; NP_004245), SLC36A1 (PAT1; NP_510968), SLC36A1 (PAT1; NP_510968), SLC36A2 (PAT2; NP_861441), SLC38A1 (SNAT1; NP_109599), SLC38A2 (SNAT2; NP_061849), SLC38A3 (SNAT3; NP_006832), SLC38A4 (SNAT4; NP_060488), SLC38A5 (SNAT5; NP_0277053), SLC43A1 (LAT3; NP_003618), and SLC43A2 (LAT4; NP_689559).

Human genes required for functional expression of a transporter of interest may be cloned using PCR, fully sequenced, and subcloned into plasmids that can be used for expression in mammalian cells or *Xenopus laevis* oocytes. Unless otherwise noted, all subunits of a transporter of interest are co-expressed in each heterologous system described in the examples. Because many mammalian cell lines exhibit high levels of amino acid transport activity, expression in *Xenopus laevis* oocytes can be advantageous due to the low levels of endogenous amino acid transport. To assess transport function of a specific transporter protein, it can be desirable to clone the cDNA and express the protein in cells that have low endogenous transport activity. Competition assays may be performed with labeled compounds that are optimal substrates (reference substrates) for the transporter of interest. Typically, uptake levels of a test compound are compared to uptake of a reference substrate for the transporter of interest.

Compounds of Formula (1) are substrates for LAT1/4F2hc and have a $V_{max}$ of at least 10%, 20%, and in certain embodiments, at least 50% that of gabapentin. Concomitantly, the compounds have a low affinity toward amino acid transporters of system A, system N, system ASC, and the system L transporter LAT2/4F2hc.

Biodistribution studies with normal and tumor-bearing rats may be used to determine the disposition of actively transported compounds and the selectivity of substrate accumulation in tissue that expresses the LAT1/4F2hc transporter compared with other tissue. Imaging techniques can qualitatively and quantitatively elucidate the role of transport proteins in drug disposition, for example, whole body autoradiography (WBA). WBA allows both the visualization and the quantification of radionuclide-labeled compound levels in a thin section of the whole animal. Information obtained using WBA is analogous to data obtained from diagnostic imaging, albeit at a single point in time.

Pharmaceutical Compositions

Compounds of Formula (1) or pharmaceutically acceptable salts thereof may be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. In certain embodiments, pharmaceutical compositions provided by the present disclosure are injectable formulations. In certain embodiments, pharmaceutical compositions provided by the present disclosure are injectable intravenous formulations. In certain embodiments, pharmaceutical compositions provided by the present disclosure are oral formulations. Oral formulations may be oral dosage forms.

Pharmaceutical compositions provided by the present disclosure may comprise a therapeutically-effective amount of a compound of Formula (1) or a pharmaceutically acceptable salt thereof together with a suitable amount of one or more pharmaceutically acceptable vehicles so as to provide a composition for proper administration to a patient. Suitable pharmaceutical vehicles and methods of preparing pharmaceutical compositions are described in the art.

In certain embodiments, a compound of Formula (1) or a pharmaceutically acceptable salt thereof may be administered by intravenous injection. Suitable forms for injection include sterile aqueous solutions or dispersions of a compound of Formula (1). In certain embodiments, a compound may be formulated in a physiological buffer solution. Prior to administration, a compound of Formula (1) or a pharmaceutically acceptable salt thereof may be sterilized by any art recognized the technique, including addition of antibacterial or antifungal agents, for example, paraben, chlorobutanol, phenol, sorbic acid, thimersol, and the like. In certain embodiments, a compound of Formula (1) or a pharmaceutically acceptable salt thereof may be sterilized by filtration before administration to a subject thereby minimizing or eliminating the need for additional sterilization agents. An injectable dosage of a compound of Formula (1) may include from about 0.01 mL to about 10 mL, from about 0.1 mL to about 10 mL, from about 0.1 mL to about 5 mL, and in certain embodiments, from about 1 mL to about 5 mL.

Pharmaceutical compositions may comprise a therapeutically effective amount of one or more compounds of Formula (1), preferably in purified form, together with a suitable amount of a pharmaceutically acceptable vehicle, so as to provide a form for proper administration to a patient. When administered to a patient, the compounds and pharmaceutically acceptable vehicles are preferably sterile. Water is a preferred vehicle when the compound is administered intravenously. Saline solutions and aqueous dextrose and glycerol solutions may also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Pharmaceutical compositions may also contain minor amounts of wetting or emulsifying agents, or pH buffering agents. In addition, auxiliary, stabilizing, thickening, lubricating and coloring agents may be used.

Pharmaceutical compositions comprising a compound may be manufactured by means of conventional mixing, dissolving, granulating, levitating, emulsifying, encapsulating, entrapping or lyophilizing processes. Pharmaceutical compositions may be formulated in a conventional manner using one or more physiologically acceptable carriers, diluents; excipients or auxiliaries, which facilitate processing of compounds into preparations which can be used pharmaceutically. Proper formulation is dependent upon the route of administration chosen.

Pharmaceutical compositions provided by the present disclosure may take the form of solutions, suspensions, emulsion, or any other form suitable for use. Examples of suitable pharmaceutical vehicles are described in the art.

For parenteral administration, compounds of Formula (1) may be incorporated into a solution or suspension. Parenteral administration refers to the administration by injection, for instance by intravenous, intracapsular, intrathecal, intrapleural, intratumoral, or intraperitoneal injection or intravesically. In certain embodiments, a compound of Formula (1) is administered intravenously.

A solution or suspension may also comprise at least one of the following adjuvants: sterile diluents such as water for injection, saline, fixed oils, polyethylene glycols, glycerol, propylene glycol or other synthetic solvents, antioxidants such as ascorbic acid or sodium bisulfite, buffers such as acetates, citrates or phosphates, and agents for adjustment of the tonicity such as sodium chloride or dextrose. A parenteral preparation may be enclosed into ampoules, disposable syringes or multiple dosage vessels made of glass or plastic.

For topical administration, a compound of Formula (1) may be formulated as a solution, gel, ointment, cream, suspension, etc. For transmucosal administration, penetrants appropriate to the barrier to be permeated may be used in the formulation. Such penetrants are generally known in the art. Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, for example, sodium channel blockers, antibiotics, N-acetyl cysteine, homocysteine, sodium 2-mercaptoethane sulfonate (MESNA), and phospholipids.

When a compound is acidic or basic it may be included in any of the above-described formulations as the free acid or free base, a pharmaceutically acceptable salt, a solvate of any of the foregoing, or a hydrate of any of the foregoing. Pharmaceutically acceptable salts substantially retain the activity of the free acid or base, may be prepared by reaction with bases or acids, and tend to be more soluble in aqueous and other protic solvents than the corresponding free acid or base form.

Assessing single patient response to therapy and qualifying a patient for optimal therapy are among the greatest challenges of modern healthcare and relate to trends in personalized medicine. The novel β-substituted β-amino acid derivatives and β-substituted β-amino acid analogs provided by the present disclosure have a high selectivity for LAT1/4F2hc. Radio-labeled compounds for positron emission tomography (PET) or Single Photon Emission Computed Tomography (SPECT) with the same selectivity toward LAT1/4F2hc may be used to predict the efficacy of the treatment based on a single-study, case-by-case patient analysis thus excluding subjects that are expected not to benefit from treatment. PET/SPECT scans using radiolabeled LAT1/4F2hc selective substrates, once correlated to the concentration β-substituted β-amino acid derivatives or β-substituted β-amino acid analogs of Formula (1) can provide a three-dimensional distribution map, which can then be used for macroscopic dose calculations.

Accordingly, it is within the capability of those of skill in the art to assay and use the compounds of Formula (1) and/or pharmaceutical compositions thereof for therapy.

Therapeutic Dose

A compound of Formula (1) and/or pharmaceutical composition thereof can generally be used in an amount effective to achieve the intended purpose. For use to treat a disease such as cancer, a compound of Formula (1) and/or pharmaceutical compositions thereof, may be administered or applied in a therapeutically effective amount.

The amount of a compound of Formula (1) and/or pharmaceutical composition thereof that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of a compound of Formula (1) and/or pharmaceutical composition thereof administered will depend on, among other factors, the subject being treated, the weight of the subject, the severity of the affliction, the manner of administration and the judgment of the prescribing physician.

A compound of Formula (1) may be assayed in vitro and in vivo, for the desired therapeutic activity, prior to use in humans. For example, in vitro assays may be used to determine whether administration of a specific compound or a combination of compounds is preferred. The compounds may also be demonstrated to be effective and safe using animal model systems.

In certain embodiments, a therapeutically effective dose of a compound of Formula (1) and/or pharmaceutical composition thereof will provide therapeutic benefit without causing substantial toxicity. Toxicity of compounds of Formula (1) and/or pharmaceutical compositions thereof may be determined using standard pharmaceutical procedures and may be readily ascertained by the skilled artisan. The dose ratio between toxic and therapeutic effect is the therapeutic index. In certain embodiments, a compound of Formula (1) and/or pharmaceutical composition thereof exhibits a particularly high therapeutic index in treating disease and disorders. In certain embodiments, a dose of a compound of Formula (1) and/or pharmaceutical composition thereof will be within a range of circulating concentrations that include an effective dose with minimal toxicity.

Kits

A compound of Formula (1), a pharmaceutically acceptable salt thereof, or a pharmaceutical composition of any of the foregoing may be included in a kit that may be used to administer the compound to a patient for therapeutic purposes. A kit may include a pharmaceutical composition comprising a compound of Formula (1) suitable for administration to a patient and instructions for administering the pharmaceutical composition to the patient. In certain embodiments, a kit for use in treating cancer in a patient comprises a compound of Formula (1) or a pharmaceutically acceptable salt thereof, a pharmaceutically acceptable vehicle for administering the compound, and instructions for administering the compound to a patient.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Therapeutic Uses

Compounds of Formula (1) may be used for treating cancer in a patient, wherein the cancerous tissue expresses the LAT1/4F2hc. In certain embodiments, the cancerous tissue expressing the LAT1/4F2hc transporter is in the brain of the patient.

Compounds of Formula (1) may be used in the treatment of a wide variety of neoplasms where elevated LAT1/4F2hc mediated uptake occurs. Compounds of Formula (1) are particularly useful for treating brain tumors, including metastases of other solid tumors, such as lung or breast cancer, in the brain.

In certain embodiments, a compound of Formula (1) or a pharmaceutical composition comprising a compound of Formula (1) may be administered to treat a cancer known to be treated by an alkylating agent, such as, for example, melphalan.

In certain embodiments, a compound of Formula (1) or a pharmaceutical composition comprising a compound of Formula (1) may be used to treat, for example, one or more of the following cancers: adult acute lymphoblastic leukemia (all), childhood acute lymphoblastic leukemia (all), childhood acute myeloid leukemia (aml), adult acute myeloid leukemia (aml), childhood adrenocortical carcinoma, a IDs-related cancers, a IDs-related lymphoma, anal cancer, appendix cancer, astrocytoma, childhood atypical teratoid/rhabdoid tumor, basal cell carcinoma (nonmelanoma), extrahepatic bile duct cancer, childhood bladder cancer, bone cancer, osteosarcoma, malignant fibrous histiocytoma, childhood craniopharyngioma, childhood brain stem glioma, adult brain tumor, childhood brain tumor, childhood brain stem glioma, childhood central nervous system embryonal tumors, childhood cerebellar astrocytoma, brain tumor, cerebral astrocytoma/malignant glioma, ductal carcinoma in situ, childhood ependymoblastoma, childhood ependymoma, childhood esthesioneuroblastoma, childhood medulloblastoma, childhood medulloepithelioma, childhood pineal parenchymal tumors of intermediate differentiation, supratentorial primitive neuroectodermal tumors and pineoblastoma, childhood visual pathway and hypothalamic glioma, childhood brain and spinal cord tumors, breast cancer, childhood breast cancer, male breast cancer, childhood bronchial tumors, hematopoetic tumors of the lymphoid lineage, hematopoetic tumors of the myeloid lineage, burkitt lymphoma, childhood carcinoid tumor, gastrointestinal carcinoid tumor, carcinoma of head and neck, childhood central nervous system embryonal tumors, primary central nervous system lymphoma, childhood cerebellar astrocytoma, cerebral astrocytoma/malignant glioma, childhood cervical cancer, childhood cancers, childhood chordoma, chronic lymphocytic leukemia (cll), chronic myeloproliferative disorders, colorectal cancer, cutaneous t-cell lymphoma, childhood central nervous system embryonal tumors, desmoplastic small round cell tumor, endometrial cancer, childhood ependymoblastoma, childhood ependymoma, esophageal cancer, childhood esophageal cancer, ewing family of tumors, childhood extracranial germ cell tumor, extragonadal germ cell tumor, extrahepatic bile duct cancer, dye cancer, Intraocular melanoma, retinoblastoma, gallbladder cancer, gastric (stomach) cancer, childhood gastric (stomach) cancer, gastrointestinal carcinoid tumor, gastrointestinal stromal tumor (gIst), childhood gastrointestinal stromal cell tumor, childhood extracranial germ cell tumor, extragonadal germ cell tumor, ovarian germ cell tumor, gestational trophoblastic tumor/disease, adult glioma, glioblastoma, childhood brain stem, childhood cerebral astrocytoma, childhood visual pathway and hypothalamic glioma, hairy cell leukemia, childhood heart cancer, head and neck cancer, childhood head and neck cancer, adult (primary) hepatocellular (liver) cancer, childhood (primary) hepatocellular (liver) cancer, adult Hodgkin lymphoma, childhood Hodgkin lymphoma, hypopharyngeal cancer, childhood hypothalamic and visual pathway glioma, intraocular melanoma, pancreatic neuroendocrine tumors (islet cell tumors), endocrine pancreas tumors (islet cell tumors), Kaposi sarcoma, kidney (renal cell) cancer, kidney cancer, laryngeal cancer, childhood laryngeal cancer, adult acute lymphoblastic leukemia, childhood acute lymphoblastic leukemia, adult acute myeloid leukemia, childhood acute myeloid leukemia, chronic myelogenous leukemia (cml), hairy cell leukemia, lip and oral cavity cancer, adult primary liver cancer, childhood primary liver cancer, non-small cell lung cancer, small cell lung cancer, a IDs-related lymphoma, Burkitt lymphoma, t-cell lymphoma, b-cell lymphoma, cutaneous t-cell lymphoma, adult Hodgkin lymphoma, childhood Hodgkin lymphoma, adult non-Hodgkin lymphoma, childhood non-Hodgkin lymphoma, primary central nervous system lymphoma, langerhans cell histiocytosis, Waldenstrom macroglobulinemia, malignant fibrous histiocytoma of bone and osteosarcoma, childhood medulloblastoma, childhood medulloepithelioma, melanoma, intraocular (dye) melanoma, Merkel cell carcinoma, adult malignant mesothelioma, childhood mesothelioma, primary metastatic squamous neck cancer with occult, mouth cancer, myelodysplastic/myeloproliferative neoplasms, midline tract carcinoma involving nUt gene, childhood multiple endocrine neoplasia syndrome, multiple myeloma/plasma cell neoplasm, mycosis fungoides, myelodysplastic syndromes myelodysplastic/myeloproliferative diseases, chronic myelogenous leukemia, adult acute myeloid leukemia, childhood acute myeloid leukemia, multiple myeloma, chronic myeloproliferative disorders, malignant germ cell tumors, nasal cavity and paranasal sinus cancer, nasopharyngeal cancer, childhood nasopharyngeal cancer, neuroblastoma, adult non-Hodgkin lymphoma, childhood non-Hodgkin lymphoma, non-small cell lung cancer, childhood oral cancer, lip and oral cavity cancer, oropharyngeal cancer, osteosarcoma and malignant fibrous histiocytoma of bone, childhood ovarian cancer, ovarian epithelial cancer, ovarian germ cell tumor, ovarian low malignant potential tumor, pancreatic cancer, childhood pancreatic cancer, islet cell tumors, childhood papillomatosis, paranasal sinus and nasal cavity cancer, parathyroid cancer, penile cancer, pharyngeal cancer, pheochromocytoma, childhood pineal parenchymal tumors of intermediate differentiation, childhood pineoblastoma and supratentorial primitive neuroectodermal tumors, pituitary tumor, paraganglioma, plasma cell neoplasm/multiple myeloma, pleuropulmonary blastoma, childhood pleuropulmonary blastoma, primary central nervous system (cns) lymphoma, pregnancy and breast cancer, primary central nervous system lymphoma, prostate cancer, rectal cancer, renal cell (kidney) cancer, childhood renal cell (kidney) cancer, renal pelvis and ureter, transitional cell cancer, respiratory tract carcinoma involving the nUt gene on chromosome 15, retinoblastoma, childhood rhabdomyosarcoma, salivary gland cancer, childhood salivary gland cancer, sarcoma (dwing family of tumors), Kaposi sarcoma, adult soft tissue sarcoma, childhood soft tissue sarcoma, uterine sarcoma, sézary syndrome, skin cancer (nonmelanoma), childhood skin cancer, melanoma, Merkel cell skin carcinoma, small cell lung cancer, small intestine cancer, adult soft tissue sarcoma, childhood soft tissue sarcoma, squamous cell carcinoma (nonmelanoma), primary and metastatic squamous neck cancer with occult, stomach (gastric) cancer, childhood stomach (gastric) cancer, childhood supratentorial primitive neuroectodermal tumors, cutaneous t-cell lymphoma, testicular cancer, throat cancer, thymoma and thymic carcinoma, childhood thymoma and thymic carcinoma, thyroid cancer, childhood thyroid cancer, gestational trophoblastic tumor, adult unknown primary site, carcinoma of, childhood cancer of unknown primary site, unusual cancers of childhood, transitional cell cancer of ureter and renal pelvis, urethral cancer, endometrial uterine cancer, uterine sarcoma, vaginal cancer, childhood vaginal cancer, childhood visual pathway and hypothalamic glioma, vulvar cancer, Waldenstrom macroglobulinemia, Wilms tumor, women's cancers, and systemic and central metastases of any of the foregoing.

In certain embodiments, a compound of Formula (1) or a pharmaceutical composition comprising a compound of Formula (1) may be used to treat, for example, one or more of the following cancers wherein the cancer is selected from any of the primary adult and childhood brain and CNS cancers including glioblastoma (GBM) and astrocystoma, skin cancers including melanoma, lung cancers including small cell lung cancers, non-small cell lung cancers (NSCLC), and large cell lung cancers, breasts cancers including triple negative breast cancer (TNBC), blood cancers including myelodysplastic syndrome (MDS), multiple myeloma (MM), and acute myeloid leukemia (AML), prostate cancer including castrate resistant prostate cancer (CRPC), liver cancers including hepatocellular carcinoma (HCC), esophageal and gastric cancers, and any systemic and central metastases of any of the foregoing.

Compounds of Formula (1) maybe used to treat a cancer in which there is differential LAT1/4F2hc transport activity relative to surrounding tissue and/or tissue in other body organs. Patients having a tumor exhibiting a greater LAT1/4F2hc transport activity than non-diseased tissue are expected to respond more favorably to treatment with a therapeutic agent that is a substrate for the LAT1/4F2hc transporter and to experience fewer adverse effects associated with the effects of the therapeutic agent on non-diseased tissue. Compounds of Formula (1) are therapeutic agents, are substrates for the LAT1/4F2hc transporter, and exhibit cytotoxicity.

The amount of a compound of Formula (1) that will be effective in the treatment of a cancer will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of compound of Formula (1) administered may depend on, among other factors, the subject being treated, the weight of the subject, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound of Formula (1) and appropriate dosing intervals may be selected to maintain a sustained therapeutically effective concentration of the compound of Formula (1) in the blood of a patient, and in certain embodiments, without exceeding a minimum adverse concentration.

In certain embodiments, pharmaceutical compositions comprising a compound of Formula (1) may be administered once per day, twice per day, and in certain embodiments at intervals of more than once per day. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of compound of Formula (1) contained within each of the multiple dosage forms may be the same or different.

Suitable daily dosage ranges for administration may range from about 2 mg to about 50 mg of a compound of Formula (1) per kilogram body weight.

Suitable daily dosage ranges for administration may range from about 1 mg to about 100 mg of a compound of Formula (1) per square meter ($m^2$) of body surface.

In certain embodiments, a compound of Formula (1) may be administered to treat cancer in a subject in an amount from about 50 mg to about 2,000 mg per day, from about 100 mg to about 1,500 mg per day, from about 200 mg to about 1,000 mg per day, or in any other appropriate daily dose.

In certain embodiments, pharmaceutical compositions comprising a compound of Formula (1) may be administered to treat cancer in a subject so as to provide a therapeutically effective concentration of a compound of Formula (1) in the blood or plasma of the subject. In certain embodiments, a therapeutically effective concentration of a compound of Formula (1) in the blood or plasma of a subject is from about 1 µg/mL to about 60 µg/mL, from about 2 µg/mL to about 50 µg/mL, from about 5 µg/mL to about 40 µg/mL, from about 5 µg/mL to about 20 µg/mL, and in certain embodiments, from about 5 µg/mL to about 10 µg/mL. In certain embodiments, a therapeutically effective concentration of a compound of Formula (1) in the blood or plasma of a subject is at least about 2 µg/mL, at least about 5 µg/mL, at least about 10 µg/mL, at least about 15 µg/mL, at least about 25 µg/mL, and in certain embodiments, at least about 30 µg/mL. In certain embodiments, a therapeutically effective concentration of a compound of Formula (1) in the blood or plasma of a subject is less than an amount that causes unacceptable adverse effects including adverse effects to homeostasis. In certain embodiments, a therapeutically effective concentration of a compound of Formula (1) in the blood or plasma of a subject is an amount sufficient to restore and/or maintain homeostasis in the subject.

In certain embodiments, pharmaceutical compositions comprising a compound of Formula (1) may be administered to treat cancer in a subject so as to provide a therapeutically effective concentration of a compound of Formula (1) in the blood or plasma of a subject for an extended period of time such as, for example, for at least about 4 hours, for at least about 6 hours, for at least about 8 hours, for at least about 10 hours, and in certain embodiments, for at least about 12 hours.

The amount of a compound of Formula (1) administered may vary during a treatment regimen.

Pharmaceutical compositions provided by the present disclosure may further comprise one or more pharmaceutically active compounds in addition to a compound of Formula (1). Such compounds may be provided to treat the cancer being treated with the compound of Formula (1) or to treat a disease, disorder, or condition other than the cancer being treated with the compound of Formula (1).

In certain embodiments, a compound of Formula (1) may be used in combination with at least one other therapeutic agent. In certain embodiments, a compound of Formula (1) may be administered to a patient together with another compound for treating cancer in the subject. In certain embodiments, the at least one other therapeutic agent may be a different compound of Formula (1). A compound of Formula (1) and the at least one other therapeutic agent may act additively or, and in certain embodiments, synergistically. The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating cancer or a different disease, disorder or condition than cancer. Methods provided by the present disclosure include administration of a compound of Formula (1) and one or more other therapeutic agents provided that the combined administration does not inhibit the therapeutic efficacy of a compound of Formula (1) and/or does not produce adverse combination effects.

In certain embodiments, pharmaceutical compositions comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain embodiments of combination therapy, the combination therapy may comprise alternating between administering a compound of Formula (1) and a composition comprising another therapeutic agent, e.g., to minimize adverse drug effects associated with a particular drug. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

In certain embodiments, pharmaceutical compositions comprising a compound of Formula (1) may be administered with one or more substances to enhance, modulate and/or control release, bioavailability, therapeutic efficacy, therapeutic potency, stability, and the like of a compound of Formula (1). For example, to enhance the therapeutic efficacy of a compound of Formula (1), a compound of Formula (1) or a pharmaceutical composition comprising a compound of Formula (1) may be co-administered with one or more active agents to increase the absorption or diffusion of the compound of Formula (1) from the gastrointestinal tract to the systemic circulation, or to inhibit degradation of the compound of Formula (1) in the blood of a subject. In certain embodiments, a pharmaceutical composition comprising a compound of Formula (1) may be co-administered with an active agent having pharmacological effects that enhance the therapeutic efficacy of the compound of Formula (1).

In certain embodiments, a compound of Formula (1) or a pharmaceutical composition comprising a compound of Formula (1) may be administered in conjunction with an agent known or believed to be effective in treating cancer in a patient.

For example, in certain embodiments, a compound of Formula (1) or a pharmaceutical composition comprising a compound of Formula (1) may be administered in conjunction with another chemotherapeutic agents, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing. In certain embodiments, a compound of Formula (1) and/or pharmaceutical compositions thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxurubicin, bleomycin, mithamycin, mitomycin C, L-asparaginase, and interferon alpha; platinum coordination complexes such as cis-platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; and radiation therapy.

In certain embodiments, a compound of Formula (1) may be coadministered with a compound that inhibits DNA repair such as, for example, O6-benzylguanine (O6-BG).

In certain embodiments, a compound of Formula (1) may be coadministered with a compound that blocks and/or inhibits transporters other than LAT1 such as, for example, amino acids. In certain embodiments, compounds of Formula (1) may be administered to a patient together with one or more amino acids such as, for example, arginine (Arg), serine (Ser), lysine (Lys), asparagine (Asn), glutamine (Gln), threonine (Thr), or mixtures of any of the foregoing. In certain embodiments, co-administration of amino acids is intended to saturate amino acid transporters that interact with compounds of Formula (1) and thereby increase the selectivity for LAT1.

The efficacy of administering a compound of Formula (1) for treating cancer may be assessed using in vitro and animal studies and in clinical trials.

The suitability of compounds of Formula (1) and/or pharmaceutical compositions thereof in treating cancers listed above may be determined by methods described in the art. For example, screens developed to demonstrate the anti-tumor activity of oncolytic agents are known (Miller, et al., J Med Chem, 1977, 20(3), 409-413; Sweeney, et al., Cancer Res, 1978, 38(9), 2886-2891; and Weiss and Von Hoff, Semin Oncol, 1985, 12(3 Suppl 4), 69-74). Accordingly, it is well with the capability of those of skill in the art to assay and use the compounds and/or pharmaceutical compositions thereof to treat the above diseases or disorders.

Methods provided by the present disclosure have use in animals, including mammals, such as in humans.

EXAMPLES

The following examples describe in detail the synthesis of compounds of Formula (1), characterization of compounds of Formula (1), and uses of compounds of Formula (1). It will be apparent to those skilled in the art that many modifications, both to materials and methods, may be practiced without departing from the scope of the disclosure.

General Experimental Protocols

All reagents and solvents were purchased from commercial suppliers and used without further purification or manipulation.

Proton NMR spectra were recorded on a Varian Mercury Plus300 MHz Spectrometer equipped with an Oxford magnet, a Sun Sunblade 150 host computer, a Solaris operating system, VNMR data processing software, and a HP LaserJet printer. Where specifically noted, a Varian VNMRS 400 Spectrometer was used (400 MHz). $CDCl_3$ (99.8% D), MeOH-$d^4$ ($CD_3OD$, 99.8+% D), deuteroxide ($D_2O$) (99.8+% D) were used as recording solvents unless otherwise noted. The $CHCl_3$, MeOH-$d^3$, HDO solvent signals or tetramethylsilane (TMS) were used for calibration of the individual spectra.

Analytical thin layer chromatography (TLC) was performed using EMD Millipore aluminum-backed TLC sheets (EMD5554-7) pre-coated with silica gel 60 F254 (200 μm thickness, 60 Å pore size) where F254 is a fluorescent indicator with a 254 nm excitation wavelength. An ENF-240C Spectroline® UV-lamp (Spectronics Corporation, USA) was used for TLC detection and visualization. Dyeing or staining reagents for TLC detection and visualization, e.g., an ethanolic ninhydrin solution or a 0.2 wt-% aqueous potassium permanganate ($KMnO_4$) solution, were prepared according methods known in the art.

Analytical LC/MS was performed on a Shimadzu LC/MS-2020 Prominence Series system equipped with CBM-20A communication bus module (Shimadzu 228-45012-32), a SPD-20AV UV/VIS detector (Shimadzu 228-45004-32), a SIL-20AC autosampler (Shimadzu 228-45136-32), DGU-20A5 degasser (Shimadzu 228-45019-32), two LC-20AD XP HPLC pumps (Shimadzu 228-45137-32), an Agilent Zorbax 5 μm XDB-C18 2.1×50 mm column (Agilent 960 967-902), and a commercial desktop computer and printer for data computation. Gradients of water (solvent A) (Arrowhead, Nestle North America, Inc.) and acetonitrile (MeCN; solvent B) (EMD AX0145-1 or Aldrich CHROMASOLV® 439134) containing 0.075 vol-% of formic acid (EMD FX0440-7) were used in analytical LC/MS analyses.

Analytical LC/UV was performed on an Agilent 1100 Series system equipped with an Agilent 1100 Series degasser (Agilent G1379A), an Agilent 1100 Series quad pump (Agilent G1311A), an Agilent 1100 Series autosampler (ALS) (Agilent G1329A), an Agilent 1100 Series COLCOM (Agilent G1316A), a Phenomenex Gemini C18 5 μm 110 Å pore size 150×4.6 mm HPLC column (Phenomenex 00F-4435-E0), a Compaq Presario personal computer, and a HP LaserJet P2015 printer for data computation. Gradients of water (solvent A) (Arrowhead, Nestle North America, Inc.) and acetonitrile (MeCN; solvent B) (EMD AX0145-1 or Aldrich CHROMASOLV® 439134) containing 0.075 vol-% of formic acid (EMD FX0440-7) were used in analytical LC/UV analyses.

Preparative HPLC was conducted with a Varian ProStar Series system equipped with a Model 340 UV-C UV-VIS detector, a Model 210 solvent delivery module, a Hamilton PRP-112-20 μm 100 Å 21.2×250 mm preparative HPLC column (Hamilton 79428), and a commercial desktop personal computer for data computation. Gradients of water (solvent A) (Arrowhead, Nestle North America, Inc.) and acetonitrile (MeCN; solvent B) (EMD AX0145-1 or Aldrich CHROMASOLV® 439134) containing 0.1 vol-% of formic acid (EMD FX0440-7) were used for preparative HPLC purifications.

Compound isolation from aqueous solvent mixtures, e.g., acetonitrile/water/0.1 vol-% formic acid, was accomplished by primary lyophilization of pooled and frozen (after freeze drying) fractions under reduced pressure at room temperature using manifold freeze dryers such as Heto Drywinner DW 6-85-1, Heto FD4, or VIRTIS Freezemobile 25 ES equipped with a high vacuum pump. Optionally, and if the isolated compound had ionizable functional groups such as an amino group or a carboxylic acid, the lyophilization process was conducted in the presence of an excess (about 1.1 to 5.0 equivalents) of 1.0 M hydrochloric acid (HCl) to yield the purified compound(s) as the corresponding hydrochloride salt (HCl-salt), dihydrochloride salts, and/or the corresponding protonated free carboxylic acid. Melting points were determined in duplicate with a SRS OptiMelt MPA-100 automated melting point system with digital imaging processing technology and are uncorrected (Stanford Research Systems, USA).

Filtrations were conducted using commercial Celite® 545 (EMD CX0574-1) which was compressed in to glass Büchner-funnels to create a plug of 2-5 cm thickness. Reaction mixtures containing precipitated reaction side products or heterogenous catalyst residues were filtered off using standard techniques. Care must be taken filtering off activated catalysts or finely dispersed metals (ignition!).

Unless otherwise noted, aqueous work-up typically constitutes dilution of a crude reaction product, with or without residual reaction solvent, with 1.0 M hydrochloric acid (HCl) or a saturated aqueous solution of ammonium chloride ($NH_4Cl$), multiple extraction with an organic solvent, e.g., ethyl acetate (EtOAc), diethyl ether ($Et_2O$), or dichloromethane (DCM), washing with water, a saturated aqueous solution of sodium hydrogencarbonate ($NaHCO_3$), and brine (saturated aqueous solution of sodium chloride (NaCl)), drying of the organic phase (combined organic extracts) over anhydrous magnesium sulfate ($MgSO_4$) (EMD MX0075-1) or sodium sulfate ($Na_2SO_4$) (EMD SX0760E-3), filtration, washing of the filter residue, and evaporation of the combined filtrates under reduced pressure using a rotary evaporator at room or elevated temperature followed by compound purification e.g., silica gel column chromatography, crystallization or titruation.

Silica gel column chromatography was conducted with silica gel (about 100-200 mL silica gel per gram of compound) 600.04-0.063 mm (40-63 μm, 230-400 mesh) (EMD Millipore EM1.09385.9026/EM1.09385.1033/EM1.09385.2503) using single solvents or mixtures of suitable solvents, e.g., ethyl acetate (EtOAc) and hexane or dichloromethane (DCM) and methanol (MeOH), as determined by TLC. Samples/fractions containing desired product detected by analytical TLC and/or analytical LC/MS, or LC/UV were pooled and the solvents were removed under reduced pressure using a Heidolph Laborota 4001 Efficient rotary evaporator (Heidolph, Germany) (Heidolph 519-10000-01-5) equipped with a HB digit heating bath (Heidolph 517-01002-01-4), and a Rotavac valve control vacuum pump (Heidolph 591-00130-01-0).

Chemical names were generated using the ChemDraw Ultra 12.0 (CambridgeSoft, Cambridge, Mass., USA) nomenclature program.

Description 1

General Procedure for the Reduction of Benzoic Acids to Benzylic Alcohols

Adapting literature known protocols (Hay, et al., J. Chem. Soc., Perkin Trans. 1, 1999, 2759-2770; Fujikawa, et al., J. Am. Chem. Soc., 2008, 130, 14533-14543; Allen, et al., International Publication No. WO 2010/122089; and Gerspacher, et al., International Publication No. WO2008/031594), commercial borane dimethylsulfide ($BH_3.DMS$, $BH_3.SMe_2$) (2.0 M in THF) (50 mL, 100 mmol) or borane tetrahydrofurane complex ($BH_3.THF$) (1.0 M in THF) (100 mL, 100 mmol) is added dropwise at room temperature to a stirred solution of the nitrobenzoic acid (50 mmol) in anhydrous THF (250 mL). Optionally, the reaction is performed in the presence of trimethyl borate ($B(OMe)_3$) (200 mmol). The solution is heated at reflux for 4-6 hours (~75° C. oil bath temperature). The reaction is monitored by TLC and/or LCMS to completion. After cooling to about 5° C. (ice bath), the reaction is carefully quenched with a 1:1 (v/v) mixture of methanol (MeOH)/water (25 mL) followed by 5 N hydrochloric acid (HCl) (50 mL). The mixture is heated at about 50° C. for about 30-60 min and the majority of the volatile solvents are removed under reduced pressure. Water is added and the aqueous phase is extracted with ethyl acetate (3×). The combined organic extracts are successively washed with a saturated aqueous sodium hydrogencarbonate ($NaHCO_3$) solution (1×) and with brine (1×), dried over anhydrous magnesium sulfate ($MgSO_4$), filtered, and the solvents are evaporated to dryness under reduced pressure. If needed, the crude material is purified by silica gel column chromatography or is re-crystallized.

Description 2

General Procedure for the Oxidation of Benzylic Alcohols to Aromatic Aldehydes

Variant A: Adapting literature known protocols (Parikh, et al., J. Am. Chem. Soc. 1967, 89, 5505-5507; and Jandeleit, et al., U.S. Pat. No. 8,168,617), to a solution of the alcohol (50 mmol), dimethylsulfoxide (DMSO) (28.5 mL, 400 mmol), triethylamine ($Et_3N$, TEA) (34.8 mL, 250 mmol) in anhydrous dichloromethane (DCM) (300 mL) is added at 0° C. (ice bath) in small portions commercial sulfur trioxide-pyridine complex ($Pyr.SO_3$) (23.9 g, 150 mmol). The reaction mixture is stirred with gradual warming to room temperature for about 4-12 hours. The reaction is monitored by TLC and/or LCMS to completion. The majority of volatile is evaporated under reduced pressure and the residue is diluted with 2 M hydrochloric acid until acidic. The aqueous phase is extracted with ethyl acetate (EtOAc) (3×). The combined organic extracts are successively washed with a saturated aqueous sodium hydrogencarbonate ($NaHCO_3$) solution (1×) and with brine (1×), dried over anhydrous magnesium sulfate (MgSO4), filtered, and the solvents are evaporated to dryness under reduced pressure. If needed, the crude material is purified by silica gel column chromatography or is re-crystallized.

Variant B: Adapting literature known protocol (Aoyama, et al., Synlett, 1998, 35-36), commercial activated manganese (IV) oxide ($MnO_2$) (250-275 mmol) is added at room temperature to a solution of the benzylic alcohol (25 mmol) in dichloromethane (DCM) (100 mL). The reaction mixture is stirred for 12-24 h. The reaction is monitored by TLC and/or LCMS to completion. The reaction mixture is filtered over a short path of Celite® 545 and the filtrate is concentrated under reduced pressure. The material is often of sufficient purity to be used directly in the next step without further isolation and purification. If needed, the crude material is purified by silica gel column chromatography or is re-crystallized.

Variant C: Adapting a literature known protocol (Corey and Suggs, Tetrahedron Lett., 1975, 16(31), 2647-2650; and Fujikawa, et al., J. Am. Chem. Soc., 2008, 130, 14533-14543), to a solution of the benzylic alcohol (20 mmol) in dichloromethane (DCM) (100 mL) is added commercial pyridinium chlorochromate ($Pyr^+CrO_3Cl^-$, PCC) (28-40 mmol). The reaction mixture is heated to reflux (55° C. oil bath temperature) for 1-4 hours. The reaction is monitored by TLC and/or LCMS to completion. The reaction is cooled to room temperature. Work-up and product isolation and purification are conducted as described for Variant B.

Description 3

General Procedure for 3-Amino-3-Arylpropionic Acids Via Rodionov Reaction

Adapting literature known protocols (Tran and Weaver, Tetrahedron, 2002, 58, 7449-7461; and Lebedev, et al., Russian J. Gen. Chem, 2005, 75(7), 1113-1124), 3-amino-3-arylpropionic acids are prepared in one-pot according to Rodionov by heating a mixture of the aromatic aldehyde (30 mmol, malonic acid (30 mmol), and ammonium acetate ($NH_4OAc$) (4.7 g, 60.7 mmol) in ethanol (about 50-100 mL) at reflux for about 12-48 hours (oil bath). The reaction is followed by LC/MS to completion. The reaction mixture is cooled to room temperature upon the target compound precipitates generally out. The precipitate is filtered off using a Büchner-funnel and the filter residue is washed with additional EtOH (2×). The collected product is dried under reduced pressure to afford of the target compound generally as a colorless solids which are often of sufficient purity to be used directly in the next step without further purification and isolation procedures.

Description 4

General Procedure for the Preparation of Amino Acid Methyl Esters

Adapting literature protocols (Fuchs, et al., U.S. Publication No. 2010/144681; and Allison, et al., U.S. Publication No. 2006/069286), the free (unprotected) or N-(tert-butoxycarbonyl)-protected amino acids (10 mmol) is suspended in anhydrous methanol (MeOH) (about 30-80 mL) and cooled to about 0° C. (ice bath). Neat thionyl chloride ($SOCl_2$) (40-50 mmol) is added carefully, and the reaction mixture is heated at reflux for about 1-6 h before cooling down to room temperature. The reaction was followed by LC/MS to completion. The solvents are evaporated under reduced pressure using a rotary evaporator. The residue is co-evaporated with additional MeOH (2×50) to remove residual volatiles and solvent. Residual solvents are removed under reduced pressure to afford the amino acid methyl esters generally as colorless solids, which are generally of sufficient purity to be used directly in the next step without further purification and isolation procedures.

Description 5

General Procedure for the Amino Acid N-Protection with Alkyl Chloroformates

Adapting literature protocols well known in the art, the unprotected amino acid derivative or a salt thereof, e.g. a hydrochloride salt, (10 mmol) is suspended in anhydrous dichloromethane (DCM) (about 30-50 mL) and the mixture is cooled to about 0° C. (ice bath). Neat diisopropylethylamine (DIPEA, Hünigs-base) (20-50 mmol) is added followed by the appropriate alkyl chloroformate (15 mmol), e.g., benzylchloroformate (ZCl or CbzCl) or ethylchloroformate, is added dropwise and the reaction mixture is stirred with gradual warming to room temperature for overnight. The reaction is monitored by TLC and/or LC/MS to completion. The solvents are removed under reduced pressure using a rotary evaporator. The residue is diluted with 1.0 molar hydrochloric acid (HCl) and the aqueous phase is extracted with ethyl acetate (EtOAc) (3×). The combined organic extracts are dried over anhydrous sodium sulfate ($Na_2SO_4$) or anhydrous magnesium sulfate ($MgSO_4$), and filtered using a Büchner funnel. The filter residue is washed with additional EtOAc, and the combined organic filtrates are evaporated under reduced pressure using a rotary evaporator. The crude material is purified by silica gel column chromatography or is re-crystallized to afford the target compounds.

Description 6

General Procedure for the Reduction of Nitro-Aromates to Anilines

Variant A: Adapting a literature known protocol (Chandrappa, et al., Synlett, 2010, (20), 3019-3022), to a suspension of the nitro aromatic derivative (10 mmol) in a mixture of ethanol (EtOH) or methanol (MeOH) with water (10-20 mL alcohol:0.5-3 mL water), iron powder (Fe) (30-100 mmol), and calcium chloride dihydrate ($CaCl_2.2H_2O$) (5-10 mmol) are added. The resulting reaction mixture is heated from about 50° C. to about reflux (oil bath) for about 0.5-3 h. The reaction is followed by TLC (nihydrin stain) and/or analytical LC/MS to completion. The reaction mixture is cooled to room temperature and filtered through a short path of Celite® 545 to remove iron residues. The filter aid is washed with additional alcohol/water mixture or ethyl acetate (EtOAc) (3×). The combined organic filtrates are dried over anhydrous sodium sulfate ($Na_2SO_4$) or anhydrous magnesium sulfate ($MgSO_4$), the drying agent is filtered off, the filter residue is washed with additional MeOH or EtOAc, filtered over a Büchner funnel, and the combined filtrates are evaporated under reduced pressure using a rotary evaporator. The crude material may be purified by silica gel column chromatography preferentially using dichloromethane (DCM) and methanol mixtures optionally containing 1-5 vol-% of triethylamine or is re-crystallized.

Variant B: Adapting literature protocols well known in the art, the nitro aromatic derivative (10 mmol) is dissolved in methanol (MeOH), ethanol (EtOH), ethyl acetate (EtOAc), or mixtures of any of the foregoing (25-50 mL). The heterogeneous catalyst (5 or 10 wt-% palladium on charcoal containing ~50 wt-% water) (about 25-50 wt-% with respect to the nitro aromatic derivative) is added. Optionally, a small amount of acidic additives, e.g. few drops of HOAc or 1.0 M hydrochloric acid (HCl) are added to activate the catalyst. The atmosphere is exchanged to hydrogen (3× evacuation/refill technique) and the reaction mixture is stirred at room temperature under about 15 psi ($H_2$-balloon) for 1-12 h. Optionally, the reaction is carried out in a stainless steel reactor or a Parr-hydrogenation apparatus if higher pressures of $H_2$ are required. The reaction is monitored by TLC and/or LCMS to completion. The reaction mixture is filtered over a short plug of Celite® 545, the filtration aid is washed with MeOH, and the combined filtrates are evaporated under reduced pressure. The crude material is purified as described under Variant A.

Description 7

General Procedure for the Reductive N-Alkylation

Adapting literature known protocols (Palani, et al., J. Med. Chem., 2005, 48(15), 4746-4749; van Oeveren, Bioorg. Med. Chem. Lett., 2007, 17(6), 1527-1531; Delfourne, et al., Bioorg. Med. Chem., 2004, 12(15), 3987-3994; Delfourne, et al., J. Med. Chem., 2002, 47(17), 3765-3771; and Jordan, et al., Bioorg. Med. Chem., 2002, 10(8), 2625-2633), to a solution of the aniline (or a suspension of an aniline addition salt, e.g., a hydrochloride salt) (10 mmol) in methanol (MeOH) (30 mL) at about 5-15° C. (water bath with some ice) is added trifluoroacetic acid (TFA) (15 mL) (Variant A), acetic acid (15-20 mL) (HOAc) (Variant B), or 85 wt-% phosphoric acid ($H_3PO_4$) (Variant C). To the cooled solution, is added commercial 2-chloroacetaldehyde ($ClCH_2CHO$) (~50 wt-% in water, ~7.87 M) (~6.5 mL, ~50 mmol). The reaction mixture is stirred for about 15-30 min at this temperature when sodium cyanoborohydride ($NaBH_3CN$) (2.51 g, 40 mmol) was added in small portions (exothermic hydrogen evolution!). The reaction mixture is stirred for 15-120 min with gradual warming to room temperature. In some case copious amounts of a precipitate are generated during the reaction. The reaction is monitored by TLC and/or LC/MS to completion. The majority of the volatiles (Variants A and B) are evaporated under reduced pressure (rotary evaporator; ambient to 35° C. bath temperature). The residue is dissolved in ethyl acetate (EtOAc) and the organic phase is successively washed with a saturated aqueous solution of sodium hydrogencarbonate ($NaHCO_3$) (2×) and brine (1×). The organic solution is dried over anhydrous magnesium sulfate ($MgSO_4$), filtered, and the organic solvents were evaporated to dryness under reduced pressure. If non non-volatile acids are used (Variant C), the reaction mixture is diluted with water and neutralized (pH 5-7) with solid sodium hydrogencarbonate ($NaHCO_3$). The aqueous phase is extracted with ethyl acetate (EtOAc) (3×) and the combined organic extracts are treated as described for Variants A and B. The crude material is purified by silica gel column chromatography or is re-crystallized.

Description 8

General Procedure for Deprotection by Acid Hydrolysis with Strong Aqueous Acids

Adapting literature known protocols (Taylor, et al., Chem. Biol. Drug Des., 2007, 70(3), 216-226; Buss, et al., J. Fluorine Chem., 1986, 34(1), 83-114; Abela, et al, J. Chem. Soc., Perkin Trans. 1, 1997, (20), 2258-2263; Weisz, et al., Bioorg. Med. Chem. Lett., 1995, 5(24), 2985-2988; Zheng, Bioorg., Med., Chem., 2010, 18(2), 880-886; Haines, et al., J. Med. Chem., 1987, 30, 542-547; and Matharu, et al., Bioorg., Med., Chem., Lett., 2010, 20, 3688-3691), hydrolytic removal of protecting groups is conducted through heating a suspension or solution of the corresponding protected N-mustard (1 mmol) in 2-12 M of an aqueous hydrohalogenic acid (5-10 mL/mmol) or a 20-80 vol-% mixture of a 2-12 M of an aqueous hydrohalogenic acid with 1,4-dioxane (5-10 mL/mmol) at an elevated temperature from about 30° C. to about 150° C. (sealed tube) for 1-24 h. The reaction e is be followed by TLC and/or LC/MS to completion. Organic side products, e.g., phthalic acid or benzoic acid, may be extracted with an organic solvent, e.g., ethyl acetate (EtOAc) or chloroform ($CHCl_3$). The aqueous solution or organic volatile solvents are evaporated using a rotary evaporator (40° C. to 60 OC water bath temperature) to yield the crude target product which may be dissolved in a ~50 vol-% aqueous acetonitrile (MeCN) followed by lyophilization. Where applicable, the crude target compound is further purified by RP-HPLC purification using acetonitrile/water mixtures containing 0.05-0.1 vol-% formic acid (FA) or trifluoroacetic acid (TFA) followed by primary lyophilization, optionally in the presence of 1.0 or an excess of an acid capable of forming pharmaceutically acceptable salt addition products. Where applicable, the crude material is purified by re-crystallization, titruation, or repeated precipitation.

Description 9

Global Deprotection of Under Anhydrous Conditions with Strong Acids

Variant A: Adapting literature known protocols (Springer, et al., J. Med. Chem., 1990, 33(2), 677-681; Davies, et al., J. Med. Chem. 2005, 48(16), 5321-5328; Niculesscu-Duvaz, et al., J. Med. Chem., 2004, 47(10), 2651-2658; Verny and Nicolas, J. Label. Cmpds, Radiopharm., 1988, 25(9), 949-955; Thorn, et al., J. Org. Chem, 1975, 40(11), 1556-1558; Baraldini, et al., J. Med. Chem., 2000, 53(14), 2675-2684; Gourdi, et al., J. Med. Chem., 1990, 33(4), 1177-1186; and Kupczyk-Subotkowska, et al., J. Drug Targeting, 1997, 4(6), 359-370), a solution of the corresponding protected N,N-bis(2-chloroethyl)aryl-substituted β-substituted β-amino acid precursor (1.0 mmol) in neat trifluoroacetic acid (TFA), a mixture of TFA and dichloromethane (DCM) or 1,2-dichloroethane (DCE) (90 vol.-% TFA to 90 vol.-% organic solvent), or 98% formic acid ($HCO_2H$) (10-25 mL/mmol) is stirred at about room temperature for about 1-24 h. Optionally, scavengers (2-5 mmol) such as triethylsilane ($Et_3SiH$), triisopropylsilane ($iPr_3SiH$), thioanisole (PhSMe), or 1,2-dithioethane ($HSCH_2CH_2HS$) are added to the reaction mixture to suppress unwanted side reactions (Metha, Tetrahedron Lett., 1992, 33(37), 5411-5444). The reaction is be followed by TLC and/or analytical LC/MS to completion. The solvent is removed under reduced pressure using a rotary evaporator (water bath temperature at about 30° C.). Optionally, residual acid traces are azeotropically removed through repeated co-evaporation (5-10×) under reduced pressure using a suitable co-solvent, e.g., ethyl acetate (EtOAc), toluene, or DCM to yield the crude target compound, which may be used directly in in vitro or in vivo experiments. Further purification is conducted as described for Description 8.

Variant B: Adapting literature known protocols, a solution of the corresponding protected N,N-bis(2-chloroethyl)aryl-substituted β-substituted γ-amino acid precursor (1.0 mmol) in 2 M hydrogen chloride in diethyl ether (2.0 M HCl in $Et_2O$) or 4 M hydrogen chloride in 1,4-dioxane (4.0 M HCl in 1,4-dioxane) is stirred at about room temperature for about 1-36 h. Optionally scavengers are the same as in Variant A. The reaction is be followed by TLC and/or analytical LC/MS to completion. The reaction mixture is centrifuged for about 10 min at 3000 rpm, the supernatant decanted or pipetted off, and the precipitate is suspended in anhydrous $Et_2O$ repeating the centrifugation/washing sequence (2-3×). The crude target compound may be used directly in in vitro or in vivo experiments. Further purification is conducted as described for Description 8.

Description 10

General Procedure for the Bromination of Benzylic Alcohols to Benzylic Bromides

Adapting literature known protocols (Harrison and Diehl, Org. Synth., 1955, Coll. Vol. 3, 370), the benzylic alcohol (50 mmol) is dissolved in unhydrous dichloromethane (DCM) (about 100-150 mL) and the solution is cooled to about 00 (ice bath). To the solution is dropwise added a commercial 1.0 M solution of phosphorus tribromide ($PBr_3$) (50 mmol) and the resulting mixture is stirred for about 1-2 h at this temperature.

The reaction is followed by TLC to completion. The reaction mixture is poured onto a mixture of crushed ice and a saturated sodium hydrogencarbonate solution. After phase separation, the aqueous phase is extracted with DCM or ethyl acetate (EtOAc) and the combined organic extracts are washed with a saturated aqueous solution of sodium hydrogencarbonate ($NaHCO_3$) (1×) and brine (1×), dried over anhydrous magnesium sulfate ($MgSO_4$), filtered, the filter residue is washed with DCM, and the combined organic filters are evaporated under reduced pressure. If needed, the crude material is purified by silica gel column chromatography or is re-crystallized.

Description 11

General Procedure for the Arndt-Eistert Homologation of Amino Acids

Part A: Adapting literature protocols (Aldrich Technical Bulletin: Diazald® and Diazomethane Generators; Black, Aldrichchimica Acta, 1983, 16(1), 3-10; and Lombardy, Chem. Ind., 1990, 708), a solution of diazomethane ($CH_2N_2$) in diethyl ether ($Et_2O$) is freshly prepared prior to use in an Aldrich Diazald® apparatus through addition of a solution of commercial N-methyl-N-nitrosotoluene-4-sulphonamide (Diazald®) (15 g, 70.0 mmol) in $Et_2O$ (150 mL) to a reaction mixture containing potassium hydroxide (KOH) (15 g, 267 mmol) in $Et_2O$ (25 mL), water (30 mL), and 2-(2-ethoxyethoxyl)ethanol (50 mL) at about 65° C. (oil bath). The reaction is completed when the yellow color subsided. The $CH_2N_2$ is trapped in $Et_2O$.

Part B: Adapting literature protocols (Podlech and Seebach, Liebigs Ann., 1995, 1217-1228; Limbach, et al., Liebigs Ann., 2006, 89(7), 1427-1441; Podlech and Seebach, Angew. Chem. Int. Ed. Engl., 1995, 34(4), 471-472; Müller, et al., Synthesis, 1998, (6), 837-841); and Bartosz-Bechowski and Konopinska, J. Prakt. Chem., 1989, 331(3), 532-536), an N-protected amino acid derivative (10 mmol) is dissolved under a nitrogen atmosphere in anhydrous tetrahydrofuran (THF) and the solution is cooled to about −20° C. (dry ice/acetone bath). To the solution is added N-methylmorpholine (NMM) (13 mmol), followed by neat isobutyl chloroformate (12 mmol). The reaction mixture is stirred at about −20° C. for about 2 h, when an excess of (5-10 equivalents) of the freshly prepared ethereal solution of diazomethane is added. Optionally, the precipitated NMM hydrochloride (NMM.HCl) is filtered off under a nitrogen atmosphere prior to diazotation. The reaction mixture is gradually warmed to room temperature and stirred for an additional 2 h. Excess diazomethane is quenched with a few drops of acetic acid (HOAc). The solvents are removed under reduced pressure using a rotary evaporator. The residue is dissolved in a mixture of $Et_2O$ and ethyl acetate (EtOAc). Basic aqueous work-up with a saturated aqueous solution of sodium hydrogencarbonate ($NaHCO_3$) and silica gel column chromatography furnish the diazoketonmes typically as light yellow solids.

Part C: Adapting literature protocols (see Part B), an N-protected diazoketone (10 mmol) is dissolved under a nitrogen atmosphere in anhydrous methanol (MeOH) (about 2-4 mL) and anhydrous tetrahydrofuran (THF) (about 20-25 mL) and the solution is degassed and placed under a nitrogen atmosphere (3 times evacuation/refill cycling) and under exclusion from (sun)light. A mixture of silver benzoate (AgBz) (5.0 mmol) in THF (about 5-10 mL) and triethylamine (TEA) (20 mmol) is added slowly at room temperature. Gas evolution! The reaction mixture is stirred for about 1-4 hours at room temperature and concentrated under reduced pressure using a rotary evaporator. The residue is purified by silica gel column chromatography using (EtOAc) and hexane mixtures.

Description 12

General Procedures for the Preparation of Succinimidyl Esters

Adapting a literature protocol (Dexter and Jackson, J. Org. Chem., 1999, 64, 7579-7585), to a stirred solution of the N-protected aspartic acid β-alkyl ester (25 mmol) in ethyl acetate (EtOAc) or acetonitrile (MeCN) (about 25-75 mL) is added solid N-hydroxysuccinimide (NHS, HOSu) (26-28 mmol) at about 00 (ice bath). A solution of dicyclohexylcarbodimide (DCC) (25-26 mmol) in EtOAc or MeCN (about 25 mL) is added slowly. Optionally, solid DCC is added in small portions. Optionally, any of the common carboxylic acid activation agents can be used for this reaction (Montalbetti and Falque, Tetrahedron, 2005, 61, 10827-10852; and Valeur and M Bradley, Chem. Soc. Rev., 2009, 38, 606-631). The reaction is stirred with gradual warming to room temperature for about 6-24 hours. The reaction is monitored by TLC to completion. The precipitated dicyclohexylurea (DCU) is filtered off using a Büchner-funnel, and the filtrate is washed with a saturated aqueous solution of sodium hydrogencarbonate ($NaHCO_3$) (3×), brine (1×), dried over anhydrous magnesium sulfate ($MgSO_4$), filtered, and evaporated under reduced pressure using a rotary evaporator. The OSu-esters are usually obtained in quantitative yield and may be of sufficient purity to be used directly in the next steps without further isolation and purification.

Description 13

General Procedures for the Reduction of Succinimidyl Esters to Alcohols

Adapting a literature protocol (Dexter and Jackson, J. Org. Chem., 1999, 64, 7579-7585), sodium borohydride ($NaBH_4$) (15-20 mmol) is dissolved in water (about 3-6 mL) and tetrahydrofuran (about 25-50 mL) at about 0° C. (ice bath). A solution of the succimidyl-ester (10.0 mmol) in THF (about 5-10 mL) is added dropwise over about 1 minute. The reaction is monitored by TLC to completion (<30 min). The reaction is quenched through addition of 1.0 M hydrochloric acid (pH ~1-2) or a saturated aqueous solution of ammonium chloride ($NH_4Cl$). Volatiles (THF) is partially removed underreduced pressure using a rotary evaporator. The aqueous phase is extracted with ethyl acetate (EtOAc) (3×). The combined organic extracts are washed with a saturated aqueous solution of sodium hydrogencarbonate ($NaHCO_3$) (1×), brine (1×), dried over anhydrous magnesium sulfate ($MgSO_4$), filtered, and evaporated under reduced pressure using a rotary evaporator. The residue is purified by silica gel column chromatography using EtOAc and hexane mixtures.

Description 14

General Procedures for the Preparation of Iodides from Alcohols

Adapting a literature protocol (Dexter and Jackson, J. Org. Chem., 1999, 64, 7579-7585), triphenylphosphine (40 mmol), imidazole (40 mmol), and iodine (40 mmol) are added to anhydrous dichloromethane (DCM) (about 100-120 mL). A solution of the alcohol (40 mmol) in DCM (about 40 mL) is added at room temperature. The reaction is monitored by TLC to completion (about 1-2 h). The reaction mixture is filtered (Büchner-funnel) to remove precipitated triphenylphosphine oxide ($Ph_3PO$) and the filtrate is washed with a 1.0 M aqueous solution of sodium thiosulfate ($Na_2S_2O_3$) (2×), brine (1×), dried over anhydrous magnesium sulfate (MgSO4), filtered, and evaporated under reduced pressure using a rotary evaporator. The residue is first slurried in diethyl ether (removal of additional $Ph_3PO$), filtered through over a short bed of silica gel or purified by silica gel column chromatography.

Description 15

General Procedure for the Negishi-Coupling with Aromatic Halides

Part A: Adapting literature protocols (Dexter and Jackson, J. Org. Chem., 1999, 64, 7579-7585; Dexter, et al., J. Org. Chem., 2000, 65, 7417-7421; Jackson and M. Perez-Gonzales, Org. Synth., 2005, 81, 77-88; Ross, J. Org. Chem., 2010, 75, 245-248; Anzalone, et al., U.S. Pat. No. 8,710,256; Hoepping, et al., Internatinoal Publication No. WO 2014/095739; and Jackson and Perez-Gonzales, Org. Synth., 2005, 81, 77-88), zinc dust (Zn) (30 mmol, 3-6 equivalents) is suspended under an atmosphere of inert gas (nitrogen or argon) in anhydrous degassed N,N-dimethylformamide (DMF), N,N-dimethyl acetamide (DMAc or DMA), tetrahydrofuran (THF), or 2-methyl-tetrahydrofuran (2-Me-THF) (about 5-10 mL). The zinc metal is activated by addition of elemental iodine ($I_2$) (about 1.5-3.0 mmol, 15-30 mol-%) and trimethyl silylchloride (MeSiCl, TMSCl) (about 1.5-3.0 mmol, 15-30 mol-%). After subsiding of the exotherm, the appropriate iodo-compound (5-10 mmol) is added, optionally as a solution in a small amount of the same anhydrous an degassed solvent, followed by addition of the same amounts of $I_2$ and TMSCl. Optionally, a combination of 1,2-dibromoethane (3 mmol, 30 mol-%) and TMSCl (6 mol %) may be used to activate the zinc dust. After subsiding of the exotherm to room temperature and settling of the zinc dust, the supernatend containing the appropriate zinc organic compound is ready to use in the subsequent Negishi cross-coupling reaction.

Part B: Adapting literature protocols (see Part A), the supernatand containing the appropriate zinc organic compound is transferred to a solution of the aryl halide (6.5-13 mmol, 1.3 equivalents), tris(benzylideneacetone)dipalladium ($Pd_2(dba)_3$) (0.125-0.25 mmol, 2.5 mol-%) and tris(o-tolyl)phosphine (P(o-tol)$_3$) (0.5-1 mmol, 10 mol-%) or SPhos (2-dicyclohexylphosphino-2',6'-dimethoxybiphenyl) (0.25-0.5 mmol, 5 mol-%) in anhydrous dry degassed N,N-dimethylformamide (DMF), N,N-dimethyl acetamide (DMAc or DMA), tetrahydrofuran (THF), or 2-methyl-tetrahydrofuran (2-Me-THF) (about 5-10 mL). The reaction mixture is stirred at room temperature for 1-12 hours or heated under an inert gas atmosphere to about 40-60° C. for about 1-12 hours. Heating is required to cross-couple aryl bromides. He reaction is followed by TLC and/or LCMS to completion. Dilution with water is followed by extraction of the aqueous phase with ethyl acetate (EtOAc) (3×). The combined organic extracts are washed with a saturated aqueous solution of sodium hydrogencarbonate ($NaHCO_3$) (1×), brine (1×), dried over anhydrous magnesium sulfate ($MgSO_4$), filtered, and evaporated under reduced pressure using a rotary evaporator. The residue is purified by silica gel column chromatography using EtOAc and hexane mixtures.

Description 16

General Procedure for the N,N-Bis-(2-Hydroxyethylation) of Anilines with Ethylene Oxide Adapting literature known protocols (Palmer, et al., J. Med. Chem. 1990, 33(1), 112-121; Jordan, et al., Bioorg. Med. Chem., 2002, 10(8), 2625-2633; Abela Medici, et al, J. Chem. Soc., Perkin Trans. 1, 1997, (20), 2258-2263; Feau, et al., Org. Biomolecular Chem., 2009, 7(24), 5259-5270; Springer, et al., J. Med. Chem., 1990, 33(2), 677-681; Taylor, et al., Chem. Biol. Drug Des., 2007, 70(3), 216-226; Buss, et al., J. Fluorine Chem., 1986, 34(1), 83-114; Larden and Cheung, Tetrahedron Lett., 1996, 37(42), 7581-7582; Spreitzer and Puschmann, Monatshefte für Chemie, 2007, 138(5), 517-522; Niculesscu-Duvaz, et al., J. Med. Chem., 2004, 47(10), 2651-2658; Weisz, et al., Bioorg. Med. Chem. Lett., 1995, 5(24), 2985-2988; Thorn, et al., J. Org. Chem, 1975, 40(11), 1556-1558; Baraldini, et al., J. Med., Chem., 2000, 53(14), 2675-2684; Zheng, et al., Bioorg., Med., Chem., 2010, 18(2), 880-886; Gourdi, et al., J., Med., Chem., 1990, 33(4), 1177-1186; Haines, et al., J. Med. Chem., 1987, 30, 542-547; Matharu, et al., Bioorg. Med. Chem. Lett., 2010, 20, 3688-3691; and Kupczyk-Subotkowska, et al., J. Drug Targeting, 1997, 4(6), 359-370), a mixture of the corresponding aniline (25.0 mmol) in aqueous acetic acid (HOAc) (25-75 vol-%) (25-100 mL) is cooled to about −20° C. (ice/sodium chloride bath) to about 0° C. (ice bath). Optionally, the solvent may also glacial acetic acid (HOAc), water, tetrahydrofuran (THF), ethanol (EtOH), 1,4-dioxane (for higher temperature reactions), or mixtures of any of the foregoing. An excess of ethylene oxide (oxirane) (100-400 mmol) is added to the reaction mixture either neat in pre-cooled form or dissolved in any of the foregoing solvents or mixtures thereof. The reaction mixture is stirred at about room temperature for about 12-48 h. Alternatively, the reaction mixture may be heated in a sealed reaction vessel at 80-140° C. for a similar time. The reaction is followed by TLC and/or LC/MS and is usually complete when the reaction mixture turns clear. The solvents are removed under reduced pressure using a rotary evaporator (40-60° C. water bath temperature). The residue is diluted with ethyl acetate (EtOAc), washed with brine, dried over anhydrous magnesium sulfate ($MgSO_4$) or sodium sulfate ($Na_2SO_4$), filtered, and the solvents removed under reduced pressure using a rotary evaporator to yield the target compound, which may be used directly in the next step. The crude material may be further purified by silica gel column chromatography using EtOAc, methanol (MeOH), dichloromethane and hexanes, or mixtures of any of the foregoing to furnish the purified target compound. Alternatively, the crude target compound may be further purified by re-crystallization.

Description 17

General Procedures for Chlorination of N,N-Bis(2-Hydroxyethyl)-Groups

Variant A: Chlorination with Thionyl Chloride ($SOCl_2$)
Adapting literature known protocols (Palmer, et al., J. Med. Chem. 1990, 33(1), 112-121; Jordan, et al., Bioorg. Med. Chem., 2002, 10(8), 2625-2633; Abela Medici, et al., J. Chem. Soc., Perkin Trans. 1, 1997, (20), 2258-2263; Taylor, et al., Chem. Biol. Drug Des., 2007, 70(3), 216-226; Dheyongera, Bioorg. Med. Chem. 2005, 13(3), 689-698; Zheng, Bioorg. Med. Chem. 2010, 18(2), 880-886; Gourdi, J.

Med. Chem., 1990, 33(4), 1177-1186; and Lin, et al., Bioorg. Med. Chem. Lett., 2011, 21(3), 940-943), to a solution of thionyl chloride (SOCl$_2$) (10-75 mmol) in an anhydrous organic solvent, e.g., dichloromethane (DCM), chloroform (CHCl$_3$), 1,2-dichloroethane (DCE), benzene, or mixtures of any of the foregoing (25-100 mL) is added at a temperature from about 0° C. (ice bath) to about room temperature the corresponding N,N-bis(2-hydroxyethyl) derivative (5.0 mmol), either in neat form (portions) or as a solution in a small volume in any of the foregoing solvents. The reaction mixture is stirred at about room temperature to about 40° C. or heated to reflux for about 10 minutes to about 3 h. Optionally, the reaction is carried out using neat SOCl$_2$ directly as the solvent. Optionally, the reaction is carried out in the presence of a catalytic amount of zinc chloride (ZnCl$_2$) (10 mol-% to 40 mol-%) or N,N-dimethylformamide (about 1 to 3 drops) to facilitate the reaction (Squires, et al., J. Org. Chem., 1975, 40(1), 134-136; and Abela Medici, et al, J. Chem. Soc., Perkin Trans. 1, 1997, (20), 2258-2263). The reaction is followed by TLC and/or LC/MS to completion. Volatiles (solvents and excess of SOCl$_2$) are removed under reduced pressure using a rotary evaporator. Optionally, a small amount of co-solvent, e.g., of benzene, is added to assist in azeotropic co-evaporation and removal of residual excess chlorination agent. The residue is diluted with 1.0 M hydrochloric acid (HCl). The aqueous phase is extracted with ethyl acetate (EtOAc) (3×), and the combined organic extracts are washed with a saturated aqueous solution of sodium hydrogen carbonate (NaHCO$_3$) (2×) and brine (1×). The organic layer is dried over anhydrous magnesium sulfate (MgSO$_4$) or sodium sulfate (Na$_2$SO$_4$), filtered, and the solvents removed under reduced pressure using a rotary evaporator. The residue is purified by silica gel column chromatography using EtOAc and hexanes mixtures.

Variant B: Chlorination with Phosphoryl Chloride (POCl$_3$)

Adapting literature known protocols (Palmer, et al., J. Med. Chem. 1990, 33(1), 112-121; Feau, et al., Org. Biomolecular Chem., 2009, 7(24), 5259-5270; Valu, et al., J. Med. Chem., 1990, 33(11), 3014-3019; Baraldini, et al., J. Med., Chem., 2000, 53(14), 2675-2684; Gourdi, et al., J., Med., Chem., 1990, 33(4), 1177-1186; Haines, et al., J. Med. Chem., 1987, 30, 542-547; and Matharu, et al., Bioorg. Med. Chem. Lett., 2010, 20, 3688-3691), to a solution of phosphorus(V) oxychloride (phosphoryl chloride, POCl$_3$) (10-50 mmol) in an anhydrous organic solvent, e.g., benzene, acetonitrile, pyridine, or mixtures of any of the foregoing (25-100 mL) is added at a temperature from about 0° C. (ice bath) to about room temperature the corresponding N,N-bis(2-hydroxyethyl) derivative (5.0 mmol) either in neat form (portions) or as a solution in a small volume in any of the foregoing solvents. The remainder of the reaction, work-up, and product isolation are essentially conducted as described in Variant A.

Variant C: Chlorination with Methanesulfonyl Chloride/Pyridine

Adapting literature known protocols (Jordan, et al., Bioorg. Med. Chem., 2002, 10(8), 2625-2633; Abela Medici, et al, J. Chem. Soc., Perkin Trans. 1, 1997, (20), 2258-2263; Springer, et al., J. Med. Chem., 1990, 33(2), 677-681; Larden and Cheung, Tetrahedron Lett., 1996, 37(42), 7581-7582), a solution of methanesulfonyl chloride (MsCl) (20.0 mmol) in anhydrous pyridine (about 10 mL) is drop-wise added with stirring and at a temperature of about 0° C. (ice bath) to a solution of the corresponding N,N-bis(2-hydroxyethyl) derivative (5 mmol) in anhydrous pyridine (about 10 mL). After about 30 minutes, the reaction mixture is heated at 50-100° C. for about 1-3 h. After cooling to room temperature, potential precipitates, if any, e.g., pyridinium methansulfonate, are filtered off before the solvents are partially removed under reduced pressure using a rotary evaporator. The remainder of the reaction, work-up, and product isolation are essentially conducted as described in Variant A.

Variant D: Chlorination with Triphenylphosphine/Tetrachlorocarbon (PPh$_3$/CCl$_4$)

Adapting literature known protocols (Buss, et al., J. Fluorine Chem., 1986, 34(1), 83-114; and Kupczyk-Subotkowska, et al., J. Drug Targeting, 1997, 4(6), 359-370), a solution of the corresponding N,N-bis(2-hydroxyethyl) derivative (5 mmol) in anhydrous dichloromethane (DCM) (about 25 mL) containing carbon tetrachloride (CCl$_4$) (15-25 mmol) is cooled to about 0° C. (ice bath). Alternatively, neat carbon tetrachloride (CCl$_4$) (25 mL) is used as a reaction solvent. The reaction mixture is stirred, and triphenylphosphine (Ph$_3$P) (10-15 mmol) is added in portions. The reaction mixture is stirred for about 8-14 h with gradual warming to room temperature. Alternatively, the reaction mixture is heated at reflux for about 2-6 h. The reaction is followed by TLC and/or LC/MS to completion. The reaction mixture is cooled to room temperature and the solvents are removed under reduced pressure using a rotary evaporator. The residue is triturated with diethyl ether (Et$_2$O) (3×) to remove some of the triphenylphosphine oxide (Ph$_3$PO). The organic phase is evaporated under reduced pressure using a rotary evaporator. The remainder of the reaction, work-up, and product isolation are essentially conducted as described in Variant A.

Description 18

General Procedure for the Mesylation of N,N-Bis(2-Hydroxyethyl)-Groups

Variant A: Adapting literature protocols (Davies, et al., J. Med. Chem. 2005, 48(16), 5321-5328; Springer, et al., J. Med. Chem., 1990, 33(2), 677-681; Niculesscu-Duvaz, et al., J. Med. Chem., 2004, 47(10), 2651-2658; and Yang, et al., Tetrahedron, 2007, 63(25), 5470-5476), to a cooled solution (about 0° C. (ice bath)) of the corresponding N,N-bis(2-hydroxyethyl) derivative (5.0 mmol) in anhydrous dichloromethane (DCM) (25-50 mL) are added triethylamine (Et$_3$N, TEA) (25.0 mmol) or anhydrous pyridine (25.0 mmol), and a catalytic amount of 4-N,N-(dimethylamino) pyridine (DMAP) (1.0 mmol, 20 mol-%). Methanesulfonyl anhydride (Ms$_2$O) (20.0 mmol) is added portion-wise or as a solution in DCM (5-10 mL). The reaction mixture is stirred with gradual warming to room temperature for about 8-24 h. The reaction is be followed by TLC and/or LC/MS. Solvents are removed under reduced pressure using a rotary evaporator. The residue is diluted with 1.0 M hydrochloric acid (HCl), and the aqueous phase is extracted with ethyl acetate (EtOAc) (3×). The combined organic extracts are washed with a saturated aqueous solution of sodium hydrogen carbonate (NaHCO$_3$), and brine, dried over anhydrous magnesium sulfate (MgSO$_4$) or sodium sulfate (Na$_2$SO$_4$), filtered, and the solvents are removed under reduced pressure using a rotary evaporator to yield the target compound, which may be used directly in the next step. Alternatively, the crude residue may be further purified by silica gel column chromatography using EtOAc, methanol (MeOH), dichloromethane (DCM), and hexanes, or mixtures of any of the foregoing to furnish the purified target compound. Alternatively, the crude target compound may be further purified by re-crystallization.

Variant B: Adapting literature known protocols (Palmer, et al., J. Med. Chem. 1990, 33(1), 112-121; B. D. Palmer, et al., J. Med. Chem., 1994, 37, 2175-2184; Palmer, et al., J. Med. Chem, 1996, 39(13), 2518-2528; Spreitzer and Puschmann, Monatshefte für Chemie, 2007, 138(5), 517-522; Lin, et al., Bioorg. Med. Chem. Lett., 2011, 21(3), 940-943; Gourdi, et al., J. Med. Chem., 1990, 33(4), 1177-1186; Ferlin, et al., Bioorg. Med. Chem., 2004, 12(4), 771-777; Thorn, et al., J. Org. Chem, 1975, 40(11), 1556-1558; Coggiola, et al., Bioorg. Med. Chem. Lett., 2005, 15(15), 3551-3554), to a cooled solution (about 0° C. (ice bath)) of the corresponding N,N-bis(2-hydroxyethyl) derivative (5.0 mmol) in anhydrous dichloromethane (DCM), tetrahydrofuran (THF), ethyl acetate (EtOAc), or a mixture thereof (20-40 mL) are added triethylamine ($Et_3N$, TEA) (15.0 mmol) or anhydrous pyridine (25.0 mmol). Methanesulfonyl chloride (MsCl) (12.5 mmol) is added drop-wise to the reaction mixture. The reaction mixture is stirred for about 1-2 h at this temperature. The reaction may be followed by TLC and/or LC/MS. Aqueous work-up and purification by silica gel chromatography are performed as described for Variant A.

Description 19

General Procedure for the Finkelstein Conversion to N,N-Bis(2-Halogenoethyl)-Groups Adapting literature known protocols (Palmer, et al., J. Med. Chem. 1990, 33(1), 112-121; Palmer, et al., J. Med. Chem., 1994, 37, 2175-2184; Palmer, et al., J. Med. Chem., 1996, 39(13), 2518-2528; Davies, et al., J. Med. Chem. 2005, 48(16), 5321-5328; Niculesscu-Duvaz, et al., J. Med. Chem., 2004, 47(10), 2651-2658; Weisz, et al., Bioorg. Med. Chem. Lett., 1995, 5(24), 2985-2988; Thorn, J. Org. Chem, 1975, 40(11), 1556-1558; Lin, et al., Bioorg. Med. Chem. Lett., 2011, 21(3), 940-943; Gourdi, et al., J. Med. Chem. 1990, 33(4), 1177-1186; Yang, et al., Tetrahedron, 2007, 63(25), 5470-5476; Ferlin, et al., Bioorg. Med. Chem., 2004, 12(4), 771-777; and Coggiola, et al., Bioorg. Med. Chem. Lett., 2005, 15(15), 3551-3554), a slurry of the corresponding N,N-bis(2-methylsulfonyloxyethyl) derivative (5.0 mmol) and an alkali metal halide, e.g., lithium chloride (LiCl), lithium bromide (LiBr), sodium chloride (NaCl), sodium bromide (NaBr), or sodium iodide (NaI) (20-80 mmol) in an anhydrous organic solvent, e.g., N,N-dimethylformamide (DMF), N,N-dimethylacetamide (DMAc), acetone, 2-butanone(methyl ethyl ketone, MEK), 3-methyl-2-butanone (isopropyl methyl ketone, MIPK), acetonitrile (MeCN), methanol (MeOH), tetrahydrofuran (THF), ethyl acetate (EtOAc) or a mixture of any of the foregoing (10-30 mL), is stirred at room temperature or heated at 50-150° C. for about 1-12 h. The reaction is followed by TLC and/or LC/MS to completion. Solvents are partially or completely removed under reduced pressure using a rotary evaporator. The residue is diluted with 1.0 M hydrochloric acid (HCl), and the aqueous phase is extracted with ethyl acetate (EtOAc) (3×). The combined organic extracts are washed with a saturated aqueous solution of sodium hydrogen carbonate ($NaHCO_3$), and brine, dried over anhydrous magnesium sulfate ($MgSO_4$) or sodium sulfate ($Na_2SO_4$), filtered, and the solvents are removed under reduced pressure using a rotary evaporator to yield the target compound, which may be used directly in the next step. Alternatively, the crude residue may be further purified by silica gel column chromatography using EtOAc, methanol (MeOH), dichloromethane (DCM), and hexanes, or mixtures of any of the foregoing to furnish the purified target compound. Alternatively, the crude target compound may be further purified by re-crystallization.

Example 1

3-Amino-3-[5-[bis(2-chloroethyl)amino]-2-methylphenyl]propanoic acid (1)

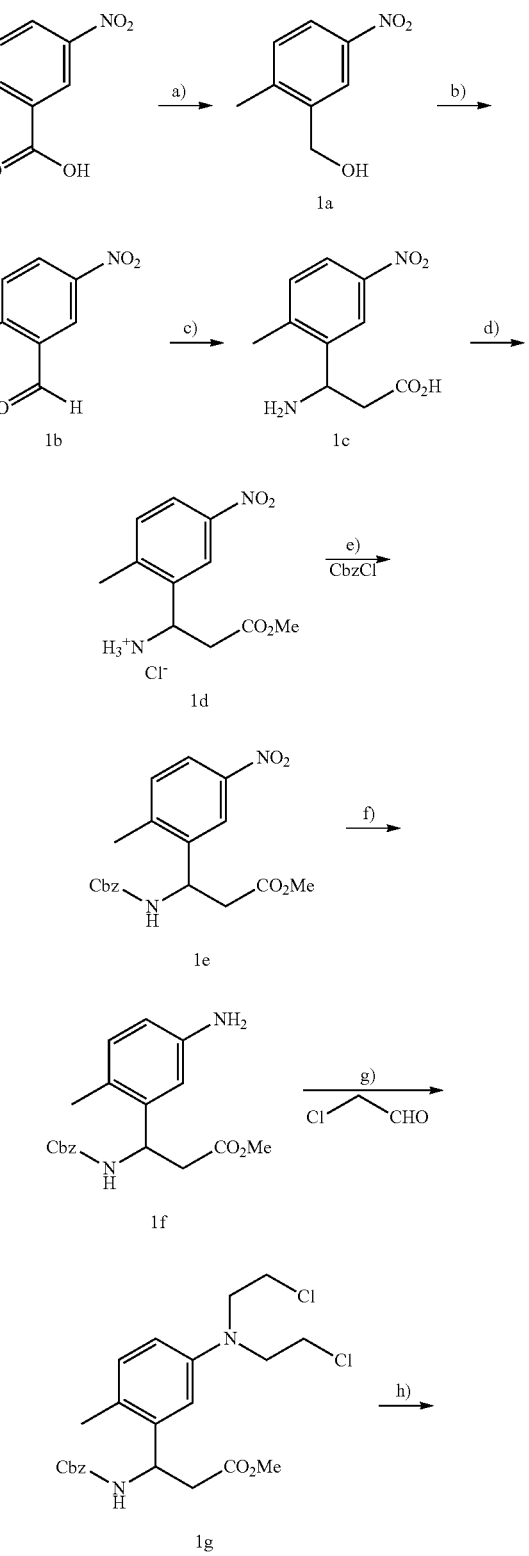

-continued

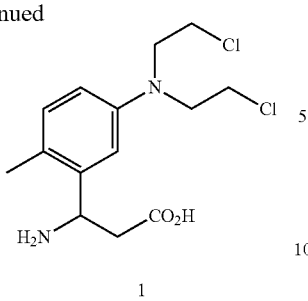

1

Step A: (2-Methyl-5-nitro-phenyl)methanol (1a)

Following the General Procedure of Description 1, 2-methyl-5-nitro-phenyl)methanol (1a) was prepared from commercial 2-methyl-5-nitro benzoic acid (50.0 g, 276 mmol) with borane dimethylsulfide complex (2.0 M $BH_3.SMe_2$ in THF) (166 mL, 332 mmol) in anhydrous tetrahydrofuran (400 mL) to yield 44.0 g (~quantitative yield) of the target compound (1a) as a pale yellow solid which was of sufficient purity to be used directly in the next step without further isolation and purification. $R_f$: ~0.50 (EtOAc/Hxn=1:1 v/v). $^1$H NMR (300 MHz, $CDCl_3$): δ 8.30 (d, J=2.4 Hz, 1H), 8.05 (dd, J=8.4, 2.4 Hz, 1H), 7.31 (d, J=8.1 Hz, 1H), 4.78 (d, J=5.1 Hz, 2H), 2.41 (s, 3H), 1.87 (br. t, J=5.1 Hz, 1H) ppm. The compound is also commercially available.

Step B: 2-Methyl-5-nitro-benzaldehyde (1b)

Following the General Procedure of Description 2 (Variant A), 2-methyl-5-nitro-benzaldehyde (1b) (Beech, J. Chem. Soc. (C), 1967, 2374-2375) was prepared from 2-methyl-5-nitro-phenyl)methanol (1a) (16.3 g, 97.3 mmol) in the presence of dimethylsulfoxide (DMSO) (56.8 mL, 62.6 g, 0.80 mol), triethylamine (TEA, $Et_3N$) (69.5 mL, 50.6 g, 0.50 mmol), and sulfur trioxide pyridine complex ($SO_3$.pyridine) (47.8 g, 0.30 mol) in dichloromethane (600 mL). Purification by silica gel column chromatography using a mixture of ethyl acetate (EtOAc) and hexane (EtOAc/hexane=1:4 v/v) afforded 12.6 g (78% yield) of the target compound (1b) as a yellow-beige solid.

Following the General Procedure of Description 2 (Variant B), 2-methyl-5-nitro-benzaldehyde (1b) (Beech, J. Chem. Soc. (C), 1967, 2374-2375) was prepared from 2-methyl-5-nitro-phenyl)methanol (1a) (4.03 g, 24.1 mmol) in the presence of manganese dioxide ($MnO_2$) (22 g, 254 mmol) in dichloromethane (DCM) (100 mL). Work-up afforded 3.56 g (89% yield) of the target compound (1b) as a pale yellow to beige solid. The material was of sufficient purity to be used directly in the next step without further isolation and purification.

Following the General Procedure of Description 2 (Variant C), 2-methyl-5-nitro-benzaldehyde (1b) (Beech, J. Chem. Soc. (C), 1967, 2374-2375) was prepared from 2-methyl-5-nitro-phenyl)methanol (1a) (5.00 g, 29.9 mmol) in the presence of pyridinium chlorochromate (PCC) (9.02 g, 41.9 mmol) in dichloromethane (DCM) (150 mL). Purification by silica gel column chromatography using mixtures of ethyl acetate (EtOAc) and hexane (EtOAc/hexane=1:4 v/v→EtOAc/hexane=1:4 v/v) afforded 4.67 g (94% yield) of the target compound (1b) as a yellow-beige solid. $R_f$: ~0.76 (EtOAc/Hxn=1:2 v/v). $^1$H NMR (300 MHz, $CDCl_3$): δ 10.32 (s, 1H), 8.65 (dd, J=2.7 Hz, 1H), 8.31 (dd, J=8.4, 2.4 Hz, 1H), 7.47 (d, J=8.4 Hz, 1H), 2.79 (s, 3H) ppm. The compound is also commercially available.

Step C: 3-Amino-3-(2-methyl-5-nitro-phenyl)propanoic acid (1c)

Following the General Procedure of Description 3, 3-amino-3-(2-methyl-5-nitro-phenyl)propanoic acid (1c) was prepared from 2-methyl-5-nitro-benzaldehyde (1b) (5.0 g, 30.3 mmol), malonic acid (3.2 g, 30.3 mmol), and ammonium acetate ($NH_4OAc$) (4.7 g, 60.7 mmol) in ethanol (EtOH) (70 mL) at reflux for 48 hours (oil bath). The reaction was followed by LC/MS to completion. Filtrative work-up afforded 2.2 g (32% yield) of the target compound (1c) as a colorless solid which was of sufficient purity to be used directly in the next step without further purification and isolation procedures. $^1$H NMR (300 MHz, $D_2O$): δ 8.20 (d, J=2.4 Hz, 1H), 8.01 (dd, J=8.1, 2.1 Hz, 1H), 7.38 (d, J=8.7 Hz, 1H), 4.84 (t, J=6.9 Hz, 1H), 2.80-2.60 (m, 2H), 2.37 (s, 3H) ppm. LC/MS: $R_t$=0.480 min; ESI (pos.) m/z=225.1 $(M+H+)^+$, ESI (neg.) m/z=223.0 $(M–H^+)^–$, 447.1 $(2M–H^+)^–$.

Step D: Methyl 3-amino-3-(2-methyl-4-nitro-phenyl)propanoate Hydrochloride (1d)

Following the General Procedure of Description 4, methyl 3-amino-3-(2-methyl-4-nitro-phenyl)propanoate hydrochloride (1d) was prepared in a suspension in anhydrous methanol (MeOH) (40 mL) from 3-amino-3-(2-methyl-5-nitro-phenyl)propanoic acid (1c) (2.2 g, 9.81 mmol) with neat thionyl chloride ($SOCl_2$) (3.54 mL, 5.8 g, 49.1 mmol). Evaporative work-up afforded 2.73 g (about quantitative yield) of the target compound (1d) as a colorless solid, which was of sufficient purity to be used directly in the next step without further purification and isolation procedures. $^1$H NMR (300 MHz, DMSO-$d^6$): δ 8.86 (br. s, 3H), 8.60 (d, J=2.1 Hz, 1H), 8.11 (dd, J=8.4, 2.1 Hz, 1H), 7.53 (d, J=8.4 Hz, 1H), 4.86 (br. m, 1H), 3.53 (s, 3H), 3.29 (dd, J=16.8, 6.0 Hz, 1H), 3.13 (dd, J=16.8, 8.7 Hz, 1H) ppm. LC/MS: $R_t$=0.492 min; ESI (pos.) m/z=239.1 $(M+H^+)^+$.

Step E: Methyl 3-benzyloxycarbonylamino-3-(2-methyl-5-nitro-phenyl)propanoate (1e)

Following the General Procedure of Description 5, methyl 3-benzyloxycarbonylamino-3-(2-methyl-5-nitro-phenyl)propanoate (1e) was prepared from crude methyl 3-amino-3-(2-methyl-4-nitro-phenyl)propanoate hydrochloride (1d) (2.7 g, 9.81 mmol), benzyl chloroformate (ZCl, CbzCl) (2.20 mL, 2.63 g of 95% purity=2.5 g, 14.7 mmol), and diisopropylethylamine (DIPEA, Hünigs-base) (6.87 mL, 5.1 g, 39.2 mmol) in anhydrous dichloromethane (DCM) (50 mL). Acidic aqueous work-up and purification by silica gel column chromatography afforded 3.4 g (92% yield) of the target compound (1e) as a colorless solid. $R_f$=0.44 (EtOAc/Hxn=1:2 v/v). $^1$H NMR (300 MHz, $CDCl_3$): δ 8.16 (d, J=2.7 Hz, 1H), 8.24 (dd, J=8.4, 2.4 Hz, 1H), 7.38-7.26 (m, 6H), 5.86 (br. d, 1H), 5.42-5.36 (br. m, 1H), 5.09 (d, J=12.0 Hz, 1H), 5.04 (d, J=12.0 Hz, 1H), 3.64 (s, 3H), 2.84-2.78 (br. m, 2H) ppm. LC/MS: $R_t$=1.790 min; ESI (pos.) m/z=373.2 $(M+H^+)^+$, 767.6 $(2M+Na^+)^+$, ESI (neg.) m/z=743.2 $(2M–H^+)^–$.

Step F: Methyl 3-(5-amino-2-methyl-phenyl)-3-benzyloxycarbonylamino-propanoate (1f)

Following the General Procedure for of Description 6 (Variant A), methyl 3-(5-amino-2-methyl-phenyl)-3-benzyloxycarbonylamino-propanoate (1f) was prepared from methyl 3-benzyloxycarbonylamino-3-(2-methyl-5-nitrophenyl)propanoate (1e) (3.35 g, 8.99 mmol), iron powder (Fe) (4.5 g, 81.1 mmol), and calcium chloride dihydrate ($CaCl_2 \cdot 2H_2O$) (0.6 g, 4.05 mmol) in a mixture of methanol (MeOH)/water (68 mL:12 mL v/v). The reaction mixture was heated at reflux for 2 hours (oil bath). Removal of the iron residues by filtration and compound isolation procedures yielded 3.1 g (about quantitative yield) of the target compound (1f) as a light yellow solid which was of sufficient purity to be used directly in the nest step without further isolation and purification. $^1$H NMR (300 MHz, DMSO-d$^6$): δ 7.85 (d, J=8.1 Hz, 1H), 7.36-7.24 (m, 5H), 6.74 (d, J=7.8 Hz, 1H), 6.51 (d, J=2.1 Hz, 1H), 6.33 (dd, J=8.4, 2.4 Hz, 1H), 5.10-5.00 (m, 1H), 4.98 (d, J=12.3 Hz, 1H), 4.92 (d, J=12.9 Hz, 1H), 4.79 (br. s, 2H), 3.54 (s, 3H) ppm. LC/MS: $R_t$=1.072 min; ESI (pos.) m/z=365.1 (M+Na$^+$)$^+$, 685.2 (2M+Na$^+$)$^+$, 702.2 (2M+Na$^+$)$^+$.

Step G: Methyl 3-benzyloxycarbonylamino-3-[5-[bis (2-chloroethyl)amino]-2-methyl-phenyl]propanoate (1g)

Following the General Procedure for of Description 7 (Variant A), methyl 3-benzyloxycarbonylamino-3-[5-[bis(2-chloroethyl)amino]-2-methyl-phenyl]propanoate (1g) was prepared from methyl 3-(5-amino-2-methyl-phenyl)-3-benzyloxycarbonylamino-propanoate (1f) (3.1 g, 9.0 mmol), 2-chloroacetaldehyde (~50 wt-% in water, ~7.87 M) (5.8 mL, 45.6 mmol), and sodium cyanoborohydride (NaBH$_3$CN) (2.4 g of 95% purity=2.3 g, 36.6 mmol) in a mixture of methanol (MeOH) (60 mL) and trifluoroacetic acid (TFA) (30 mL). Aqueous work-up and purification by silica gel column chromatography with an ethyl acetate (EtOAc) hexane mixture (EtOAc/hexane=1:2, v/v) afforded 2.90 g (69% yield) of the title compound (1g) as a colorless solid. $R_f$=0.55 (EtOAc/hexane=1:2, v/v, ninhydrine negative). $^1$H NMR (300 MHz, CDCl$_3$): δ 7.40-7.32, (br. m, 5H), 7.03 (d, J=8.4 Hz, 1H), 6.58 (d, J=2.4 Hz, 1H), 6.52 (dd, J=8.4, 2.7 Hz, 1H), 5.78-5.62 (br. m, 1H), 5.34-5.26 (m, 1H), 5.09 (d, J=12.6 Hz, 1H), 5.07 (d, J=12.6 Hz, 1H), 3.78-3.54 (m, 11H), 2.84-2.78 (m, 2H) ppm. LC/MS: $R_t$=2.271 min; ESI (pos.) m/z=467.1 (M+H$^+$)$^+$, 489.1 (M+Na$^+$)$^+$. LC/UV: $R_t$=12.939 min, 100.0% AUC at λ=254 nm.

Step H: 3-Amino-3-[5-[bis(2-chloroethyl)amino]-2-methyl-phenyl]propanoic acid (1)

Following the General Procedure of Description 8, 3-amino-3-[5-[bis(2-chloroethyl)amino]-2-methyl-phenyl] propanoic acid (1) was prepared through hydrolytic deprotection of methyl 3-benzyloxycarbonylamino-3-[5-[bis(2-chloroethyl)amino]-2-methyl-phenyl]propanoate (1g) (2.9 g, 6.2 mmol) in a mixture of concentrated hydrochloric acid (HCl) (20 mL) and 1,4-dioxane (20 mL) at about 100° C. (oil bath) in 48 hours. The residue was purified by preparative HPLC, immediately frozen after collection, followed by primary lyophilization to afford 728 mg (33% yield) of the target compound (1) as a colorless solid. $^1$H NMR (300 MHz, DMSO-d$^6$): δ 6.98 (d, J=8.4 Hz, 1H), 6.85 (d, J=2.4 Hz, 1H), 6.56 (dd, J=8.4, 2.4 Hz, 1H), 4.36 (dd, J=9.9, 4.5 Hz, 1H), 3.56-3.53 (br. m, 8H), 2.48-2.44 (m, 2H) ppm. LC/MS: $R_t$=1.226 min; ESI (pos.) m/z=319.2 (M+H$^+$)$^+$, ESI (neg.) m/z=316.9 (M−H$^+$)$^−$, 635.1 (2M−H$^+$)$^−$. LC/UV: $R_t$=6.723 min, 99.3% AUC at λ=254 nm. Various batches of mono- or dihydrochloride salts of (1) were prepared by primary lyophilization of solutions of (5) in aqueous acetonitrile (MeCN) containing either 1.0 eq. of 1.0 N hydrochloric acid (HCl) or an excess of 1.0 N or higher concentrated hydrochloric acid (HCl).

Example 2

3-Amino-3-[4-[bis(2-chloroethyl)amino]-2-methyl-phenyl]propanoic acid (2)

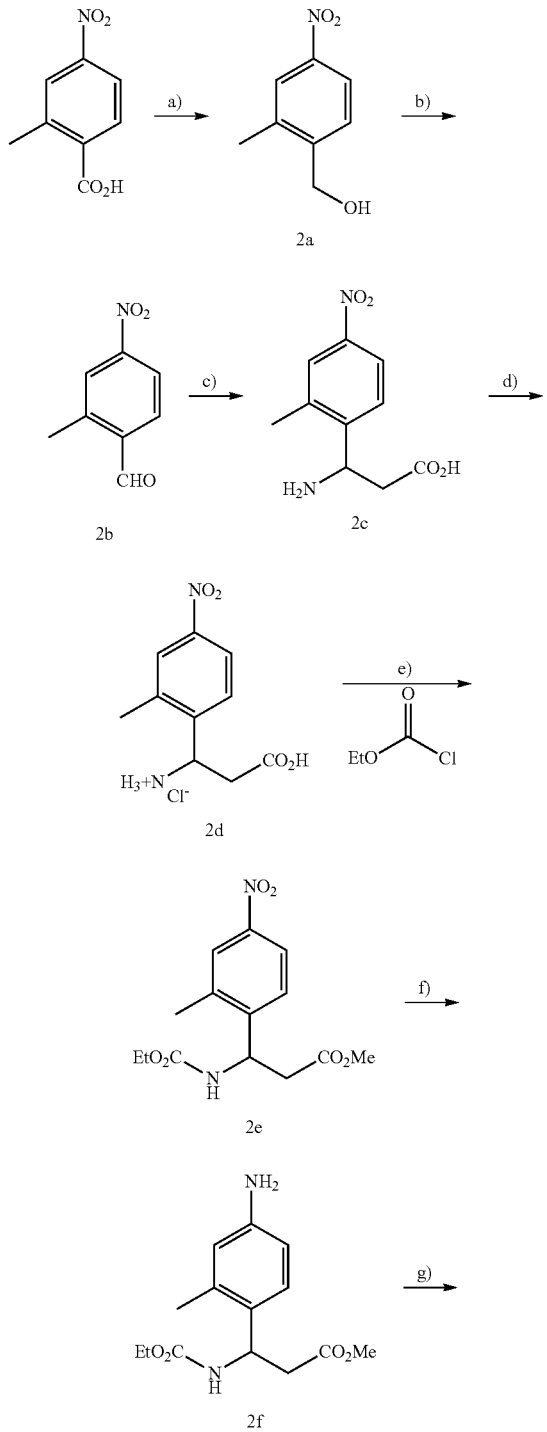

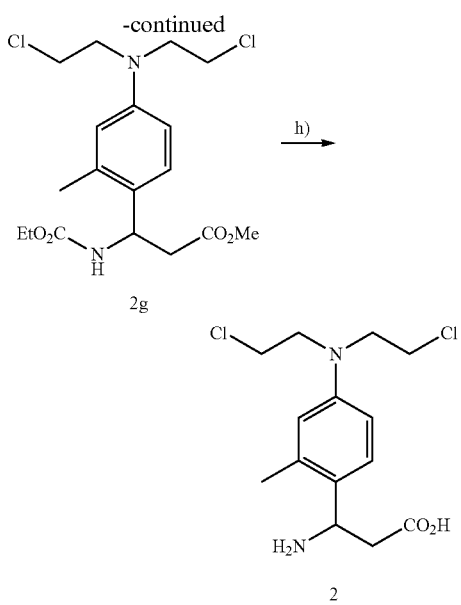

Step A: (2-Methyl-4-nitro-phenyl)methanol (2a)

Following the General Procedure of 1, 2-methyl-4-nitro-phenyl)methanol (2a) was prepared from commercial 2-methyl-4-nitro benzoic acid (5.0 g, 27.6 mmol) with borane dimethylsulfide complex (2.0 M $BH_3.SMe_2$ in THF) (27.6 mL, 55.2 mmol) in anhydrous tetrahydrofuran (100 mL) to yield 4.62 g (quantitative yield) of the target compound (7a) as a pale yellow solid which was of sufficient purity to be used directly in the next step without further isolation and purification. $R_f$: ~0.50 (EtOAc/Hxn=1:1 v/v). $^1$H NMR (300 MHz, $CDCl_3$): δ 8.07 (dd, J=8.4, 2.1 Hz, 1H), 8.02 (d, J=2.1 Hz, 1H), 7.62 (d, J=8.1 Hz, 1H), 4.79 (s, 2H), 2.38 (s, 3H), 1.87 (br. s, 1H) ppm. The spectroscopic data correspond to the data provided in the literature. The compound is also commercially available.

Step B: 2-Methyl-4-nitro-benzaldehyde (2b)

Following the General Procedure of Description 2 (Variant B), 2-methyl-4-nitro-benzaldehyde (2b) was prepared from 2-methyl-4-nitro-phenyl)methanol (1a) (8.4 g, 50.3 mmol) in the presence of manganese dioxide ($MnO_2$) (48.1 g, 553 mmol). Work-up afforded 7.5 g (90% yield) of the target compound (7b) as a yellow solid. The material was of sufficient purity to be used directly in the next step without further isolation and purification. $R_f$: ~0.58 (EtOAc/Hxn=1:2 v/v). $^1$H NMR (300 MHz, $CDCl_3$): δ 10.39 (s, 1H), 8.20 (dd, J=8.4, 2.1 Hz, 1H), 8.14 (br. s, 1H), 7.98 (d, J=8.1 Hz, 1H), 2.79 (s, 3H) ppm. The spectroscopic data correspond to the data provided in the literature. The compound is also commercially available.

Step C: 3-Amino-3-(2-methyl-4-nitro-phenyl)propanoic acid (2c)

Following the General Procedure of Description 3, 3-amino-3-(2-methyl-4-nitro-phenyl)propanoic acid (2c) was prepared from 2-methyl-4-nitro-benzaldehyde (2b) (800 mg, 5.0 mmol), malonic acid (520 mg, 5.0 mmol), and ammonium acetate ($NH_4OAc$) (578 mg, 7.5 mmol) in ethanol (EtOH) (10 mL) at reflux for 48 h (oil bath). The reaction was followed by LC/MS to completion. Filtrative work-up afforded 510 mg (45% yield) of the target compound (1c) as a near colorless solid which was of sufficient purity to be used directly in the next step without further purification and isolation. $^1$H NMR (300 MHz, $D_2O$): δ 8.01-7.97 (m, 2H), 7.46 (d, J=8.4 Hz, 1H), 4.83 (t, J=7.2 Hz, 1H), 2.70-2.65 (m, 2H), 2.33 (s, 3H) ppm. LC/MS: $R_t$=1.274 min; ESI (pos.) m/z=225.1 $(M+H^+)^+$.

Step D: Methyl 3-amino-3-(2-methyl-4-nitro-phenyl) propanoate Hydrochloride (2d)

Following the General Procedure of Description 4, methyl 3-amino-3-(2-methyl-4-nitro-phenyl)propanoate hydrochloride (2d) was prepared in a suspension in anhydrous methanol (MeOH) (10 mL) from 3-amino-3-(2-methyl-4-nitro-phenyl) propanoic acid (2c) (510 mg, 2.27 mmol) with neat thionyl chloride ($SOCl_2$) (2.0 mL, 3.28 g, 27.5 mmol). Evaporative work-up afforded 2.73 g (about quantitative yield) of the target compound (1d) as a colorless solid, which was of sufficient purity to be used directly in the next step without further purification and isolation. LC/MS: $R_t$=0.508 min; ESI (pos.) m/z=239.1 $(M+H^+)^+$.

Step E: Methyl 3-(ethoxycarbonylamino)-3-(2-methyl-4-nitro-phenyl)propanoate (2e)

Following the General Procedure of Description 5, methyl 3-(ethoxycarbonylamino)-3-(2-methyl-4-nitro-phenyl)propanoate (2e) was prepared from crude methyl 3-amino-3-(2-methyl-4-nitro-phenyl)propanoate hydrochloride (2e) (624 mg, 2.27 mmol), ethyl chloroformate (EtOCOCl) (327 μL, 371 mg 3.42 mmol), and diisopropylethylamine (DIPEA, Hünigs-base) (1.12 mL, 885 mg, 6.84 mmol) in anhydrous dichloromethane (DCM) (10 mL). Silica gel column chromatography afforded 701 mg (about quantitative yield) of the target compound (2e) as a colorless solid. $R_f$=0.42 (EtOAc/Hxn=1:1 v/v).

Step F: Methyl 3-(4-amino-2-methyl-phenyl)-3-(ethoxycarbonylamino)propanoate (2f)

Following the General Procedure of Description 6 (Variant B), methyl 3-(4-amino-2-methyl-phenyl)-3-(ethoxycarbonylamino)propanoate (2f) is prepared from methyl 3-(ethoxycarbonylamino)-3-(2-methyl-4-nitro-phenyl)propanoate (2e) (701 mg, 2.26 mmol) through hydrogenation (about 15 psi; $H_2$-filled balloon) in the presence 10 wt-% Pd/C containing 50-wt-% water (~70 mg) and at room temperature for about 12 hours to afford 632 mg (about quantitative yield) of the target compound (2f) as a brownish oil, which was of sufficient purity to be used in the next step without additional purification and isolation. LC/MS: $R_t$=0.533 min; ESI (pos.) m/z=303.1 $(M+H^+)^+$.

Step G: Methyl 3-[4-[bis(2-chloroethyl)amino]-2-methyl-phenyl]-3-(ethoxycarbonylamino)-propanoate (2g)

Following the General Procedure for of Description 7 (Variant A), methyl 3-[4-[bis(2-chloroethyl)amino]-2-methyl-phenyl]-3-(ethoxycarbonylamino)-propanoate (2g) was prepared from methyl 3-(4-amino-2-methyl-phenyl)-3-(ethoxycarbonylamino)propanoate (2f) (632 mg, 2.26 mmol), 2-chloroacetaldehyde (~50 wt-% in water, ~7.87 M) (1.44 mL, 11.3 mmol), and sodium cyanoborohydride ($NaBH_3CN$) (598 mg of 95% purity=568 g, 9.04 mmol) in a mixture of methanol (MeOH) (20 mL) and trifluoroacetic acid (TFA) (10 mL). Purification by silica gel column chromatography with an ethyl acetate (EtOAc)/hexane mixture (EtOAc/hexane=1:1, v/v) afforded 714 mg (78% yield) of the title compound (2g) as a colorless solid. $R_f$=0.54 (EtOAc/Hxn=1:2 v/v, ninhydrine negative). $^1$H NMR (300 MHz, CDCl$_3$): δ 7.11 (d, J=8.4 Hz, 1H), 6.49 (dd, J=8.7, 2.7 Hz, 1H), 6.44 (d, J=2.4 Hz, 1H), 5.36-5.22 (m, 2H), 4.08 (q, J=7.2 Hz, 2H), 3.76-3.54 (m, 11H), 2.90-2.70 (m, 2H), 2.39 (s, 3H), 1.21 (t, J=7.2 Hz, 3H) ppm. LC/MS: $R_t$=2.174 min; ESI (pos.) m/z=405.1 (M+H$^+$)$^+$.

Step H: 3-Amino-3-[4-[bis(2-chloroethyl)amino]-2-methyl-phenyl]propanoic acid (2)

Following the General Procedure of Description 8, 3-amino-3-[4-[bis(2-chloroethyl)amino]-2-methyl-phenyl]propanoic acid (2) was prepared through hydrolytic deprotection of methyl 3-[4-[bis(2-chloroethyl)amino]-2-methyl-phenyl]-3-(ethoxycarbonylamino)-propanoate (2g) (150 mg, 0.37 mmol) in concentrated hydrochloric acid (HCl) (5 mL) at about 100° C. (oil bath) in 48 h. The residue was partially purified by preparative HPLC, immediately frozen after collection, followed by primary lyophilization to afford 40 mg of the target compound (1) as a colorless solid. $^1$H NMR (300 MHz, DMSO-d$^6$): δ 7.30 (d, J=6.3 Hz, 1H), 6.63 (dd, J=6.6, 2.1 Hz, 1H), 6.56 (d, J=1.8 Hz, 1H), 4.55 (t, J=5.7 Hz, 1H), 3.76-3.62 (br. m, 8H), 2.84 (dd, J=12.3, 5.1 Hz, 1H), 2.71 (dd, J=12.0, 5.7 Hz, 1H), 2.29 (s, 3H) ppm. LC/MS: $R_t$=1.094 min; ESI (neg.) m/z=317.0 (M−H$^+$)$^-$. LC/UV: $R_t$=7.393 min, 98.6% AUC at λ=254 nm.

Example 3

3-Amino-4-[5-[bis(2-chloroethyl)amino]-2-methyl-phenyl]butanoic acid (3)

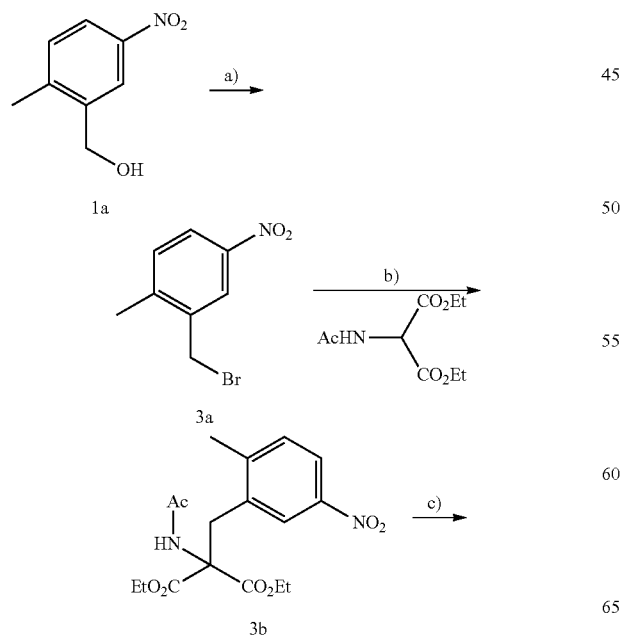

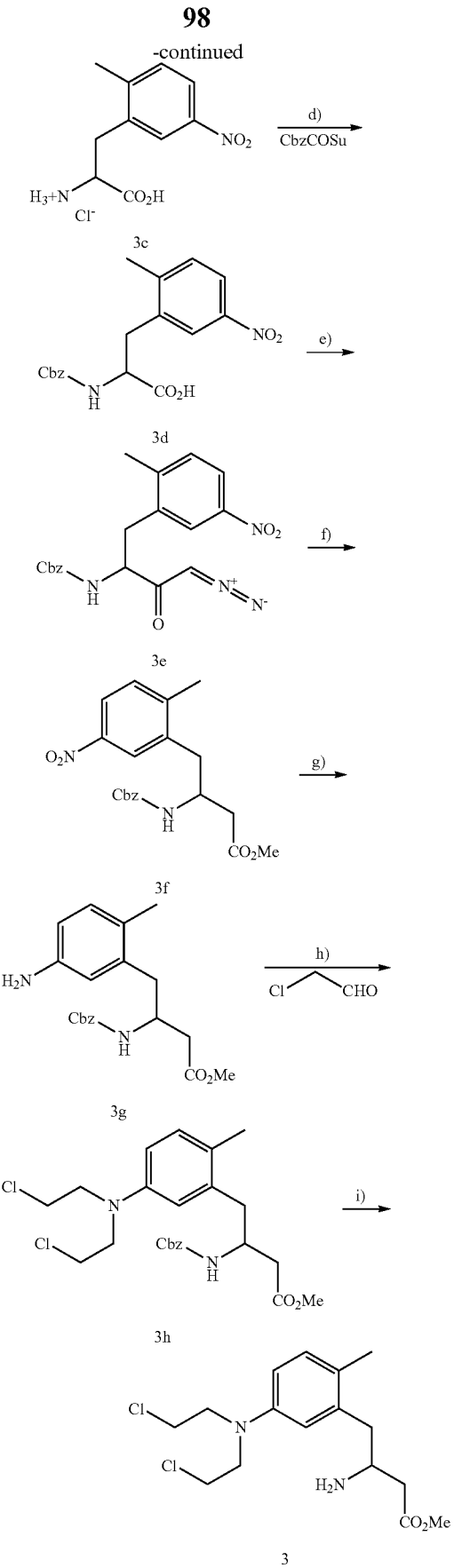

Step A: 2-(Bromomethyl)-1-methyl-4-nitro-benzene (3a)

Following the General Procedure of Description 10, 2-(bromomethyl)-1-methyl-4-nitro-benzene (3a) was prepared through bromination of (2-methyl-5-nitro-phenyl)methanol (1a) (11.0 g, 65.8 mmol) (prepared as described in Example 1) dissolved in dichloromethane (DCM) (110 mL) with a solution of phosphorus tribromide ($PBr_3$) in (1.0 M $PBr_3$ in DCM) (65.8 mL). Aqueous work-up yielded 11.3 g (75% yield) of a light yellow solid which was of sufficient purity to be used directly and without further isolation and purification in the next step. $R_f$=0.56 (EtOAc/Hxn=1:5 v/v). $^1$H NMR (300 MHz, $CDCl_3$): δ 8.19 (d, J=2.4 Hz, 1H), 8.07 (dd, J=8.4, 2.7 Hz, 1H), 7.36 (d, J=8.7 Hz, 1H), 4.53 (s, 2H), 2.52 (s, 2H) ppm. The spectroscopic data correspond to the data provided in the literature. The compound is also commercially available.

Step B: Diethyl 2-acetamido-2-[(2-methyl-5-nitro-phenyl)methyl]propanedioate (3b)

Adapting a literature protocol (Haudegond, et al., J. Org. Chem., 1979, 44(17), 3063-3065), an ethanolic solution of sodium ethanolate (NaOEt) (35.6 mmol) was freshly prepared from elemental sodium (Na) (819 mg, 35.6 mmol) in anhydrous ethanol (EtOH) (80 mL) under an atmosphere of nitrogen at room temperature. When the $H_2$-evolution was ceased, commercial diethyl 2-acetamidopropanedioate (7.9 g, 36.4 mmol) was added in small portions. The reaction mixture was heated at about 75° C. (oil bath) for about 30 min before 2-(bromomethyl)-1-methyl-4-nitro-benzene (3a) (8.2 g, 35.6 mmol) was added, and the reaction mixture was heated at reflux (oil bath) for about 10 h. The reaction was followed by LC/MS to completion. The solid was collected by filtration using a Büchner-funnel and the residue was washed successively with EtOH (2×) and ethyl acetate (EtOAc) (1×), and dried under reduced pressure to afford 8.4 g (64% yield) of the target compound diethyl 2-acetamido-2-[(2-methyl-5-nitro-phenyl)methyl]propanedioate (3b) as a colorless solid. $^1$H NMR (300 MHz, DMSO-$d^6$): δ 8.29 (s, 1H), 8.00 (dd, J=8.1, 2.4 Hz, 1H), 7.72 (d, J=2.4 Hz, 1H), 7.45 (d, J=8.7 Hz, 1H), 4.15 (q, J=7.2 Hz, 4H), 3.58 (s, 2H), 2.26 (s, 3H), 1.90 (s, 3H), 1.17 (t, J=7.2 Hz, 6H) ppm. LC/MS: $R_f$=1.818 min; ESI (pos.) m/z=367.1 $(M+H^+)^+$, 755.3 $(2M+Na^+)^+$.

Step C: 2-Amino-3-(2-methyl-5-nitro-phenyl)propanoic acid hydrochloride (3c)

Following the General Procedure of Description 8, 2-amino-3-(2-methyl-5-nitro-phenyl)propanoic acid hydrochloride (3c) was prepared by acid hydrolysis of diethyl 2-acetamido-2-[(2-methyl-5-nitro-phenyl)methyl]propanedioate (3b) (8.4 g, 22.9 mmol) with concentrated (~37 wt-%) hydrochloric acid (HCl) (150 mL). The suspension was heated at reflux (oil bath) for about 6 h. The reaction was followed by LC/MS to completion. The cooled clear solution was evaporated under reduced pressure using a rotary evaporator to yield 6.7 g (about quantitative yield) of the target compound (3c) as a colorless solid. $^1$H NMR (300 MHz, DMSO-$d^6$): δ 8.58 (br. s, 3H), 8.12 (d, J=2.1 Hz, 1H), 8.03 (dd, J=8.4, 2.4 Hz, 1H), 7.47 (d, J=8.7 Hz, 1H), 4.20-4.10 (m, 1H), 3.25 (d, J=7.2 Hz, 2H), 2.42 (s, 3H) ppm. LC/MS: $R_f$=0.705 min; ESI (pos.) m/z=225.1 $(M+H^+)^+$, 449.1 $(2M+H^+)^+$; ESI (neg.) m/z=223.0 $(M-H^+)^-$, 447.1 $(2M-H^+)^-$.

Step D: 2-Benzyloxycarbonylamino-3-(2-methyl-5-nitro-phenyl)propanoic acid (3d)

Adapting a literature protocol, 2-benzyloxycarbonylamino-3-(2-methyl-5-nitro-phenyl)propanoic acid (3d) was prepared from 2-amino-3-(2-methyl-5-nitro-phenyl)propanoic acid hydrochloride (3c) (6.7 g, 25.7 mmol) in 1,4-dioxane (50 mL) and a 10 wt-% aq. solution of sodium hydroxide (NaOH) (~3.75 M, 13.7 mL, 51.4 mmol) at about 0° C. (ice bath). Water (32 mL) was added followed by solid sodium hydrogencarbonate ($NaHCO_3$) (2.15 g, 25.7 mmol), and commercial benzyl(2,5-dioxopyrrolidin-1-yl) carbonate (CbzOSu) (6.4 g, 25.7 mmol). The reaction mixture was stirred overnight at room temperature. The volatiles were removed under reduced pressure using a rotary evaporator. Acid work up at a pH of about 3 and trituration of the crude product with ethyl acetate (EtOAc) and hexane (Hxn) (EtOAc/Hxn=3:7) at about 50° C. (oil bath), the solid was collected by filtration (Büchner-funnel) to afford 6.1 g (65% yield) of the target compound (3d) as a colorless solid. $^1$H NMR (300 MHz, $CDCl_3$): δ 8.02-7.98 (m, 2H), 7.40-7.21 (m, 6H), 5.33 (d, J=8.4 Hz, 1H), 5.06 (d, J=12.0 Hz, 1H), 5.03 (d, J=12.0 Hz, 1H), 4.74-4.70 (m, 1H), 3.57 (dd, J=14.7, 5.4 Hz, 1H), 3.08 (dd, J=14.4, 7.8 Hz, 1H), 2.45 (s, 3H) ppm. LC/MS: $R_f$=1.812 min; ESI (neg.) m/z=357.1 $(M-H^+)^-$, 715.1 $(2M-H^+)^-$.

Step E: Benzyl N-[3-diazo-1-[(2-methyl-5-nitro-phenyl)methyl]-2-oxo-propyl]carbamate (3e)

Following the general procedure of Description 11 (Part A), a solution of diazomethane ($CH_2N_2$) in diethyl ether ($Et_2O$) was freshly prepared prior to use in an Aldrich Diazald® apparatus from commercial N-methyl-N-nitrosotoluene-4-sulphonamide (Diazald®) (15 g, 70.0 mmol), potassium hydroxide (KOH) (15 g, 267 mmol) in a mixture of $Et_2O$ (25 mL), water (30 mL), and 2-(2-ethoxyethoxyl)ethanol (50 mL) at about 65° C. (oil bath). The etheral distillate was trapped in $Et_2O$ (150 mL) in $Et_2O$ (150 mL).

Following the general procedure of Description 11 (Part B), the mixed anhydride of (3d) is prepared from 2-benzyloxycarbonylamino-3-(2-methyl-5-nitro-phenyl)propanoic acid (3d) (3.0 g, 8.38 mmol), N-methylmorpholine (NMM) (1.20 mL, 1.1 g, 10.9 mmol), neat isobutyl chloroformate (1.34 mL, 1.4 g, 10.1 mmol) at about –20° C. (dry ice/acetone bath) under a nitrogen atmosphere. After the 2 hours –20° C., an excess of (~6 equivalents) of the freshly prepared ethereal solution of diazomethane was added (~100 mL). Aqueous work and purification by silica gel column chromatography (EtOAc/Hxn=2:3 v/v) afforded 2.5 g (85% yield of the target compound benzyl N-[3-diazo-1-[(2-methyl-5-nitro-phenyl)methyl]-2-oxo-propyl]carbamate (3e) as a light yellow solid. $R_f$=0.25 (EtOAc/Hxn=2:3 v/v). $^1$H NMR (300 MHz, $CDCl_3$): δ 8.02-7.98 (m, 2H), 7.40-7.24 (m, 6H), 5.46 (d, J=8.4 Hz, 1H), 5.29 (s, 1H), 5.05 (d, J=12.0 Hz, 1H), 5.02 (d, J=12.6 Hz, 1H), 4.52-4.46 (m, 1H), 3.23 (dd, J=14.1, 6.6 Hz, 1H), 2.97 (dd, J=13.8, 7.8 Hz, 1H), 2.44 (s, 3H) ppm.

Step F: Methyl 3-benzyloxycarbonylamino-4-(2-methyl-5-nitro-phenyl)butanoate (3f)

Following the general procedure of Description 11 (Part C), methyl 3-benzyloxycarbonylamino-4-(2-methyl-5-nitro-phenyl)butanoate (3f) is prepared from benzyl N-[3-diazo-1-[(2-methyl-5-nitro-phenyl)methyl]-2-oxo-propyl]carbamate (3e) (2.5 g, 6.55 mmol) and a mixture of silver benzoate (AgBz) (0.75 g, 3.3 mmol) in THF (5 mL) and triethylamine (TEA) (1.93 mL, 1.4 g, 13.1 mmol) in a mixture of degassed anhydrous methanol (MeOH) (2.1 mL) and degassed anhydrous tetrahydrofuran (THF) (15 mL) at room temperature and under a nitrogen atmosphere. Evaporative work-up followed by silica gel column chromatography purification (EtOAc/Hxn=2:3, v/v) afforded 2.1 g (82% yield) of the target compound (3f) as a colorless solid. $R_f$=0.33 (EtOAc/Hxn=2:3 v/v). $^1$H NMR (300 MHz, CDCl$_3$): δ 8.00-87.95 (m, 2H), 7.38-7.24 (m, 6H), 5.48 (d, J=9.3 Hz, 1H), 5.02 (s, 2H), 4.30-4.21 (m, 1H), 3.72 (s, 3H), 3.06-3.01 (m, 1H), 2.97-2.54 (m, 1H), 2.64-2.50 (m, 2H), 2.48 (s, 3H) ppm.

Step G: Methyl 4-(5-amino-2-methyl-phenyl)-3-benzyloxycarbonylamino-butanoate (3g)

Following the General Procedure for of Description 6 (Variant A), methyl 4-(5-amino-2-methyl-phenyl)-3-benzyloxycarbonylamino-butanoate (3g) was prepared from methyl 3-benzyloxycarbonylamino-4-(2-methyl-5-nitrophenyl)butanoate (3f) (2.1 g, 5.4 mmol), iron powder (Fe) (2.7 g, 48.9 mmol), and calcium chloride dihydrate (CaCl$_2$.2H$_2$O) (0.35 g, 2.4 mmol) in a mixture of methanol (MeOH)/water (41 mL:7.5 mL, v/v). The reaction mixture was heated at reflux for about 2 hours (oil bath). Removal of the iron residues by filtration and compound isolation procedures yielded 1.9 g (~quantitative yield) of the target compound (3g) as a light yellow solid which was of sufficient purity to be used directly in the nest step without further isolation and purification. $^1$H NMR (300 MHz, DMSO-d$^6$): δ 7.38-7.24 (m, 5H), 6.75 (d, J=7.5 Hz, 1H), 6.36-6.30 (m, 2H), 4.97 (s, 2H), 4.72 (br. s, 2H), 4.15-3.85 (m, 1H), 3.50 (s, 3H), 3.18-3.14 (m, 2H), 2.68-2.64 (m, 1H), 2.50-2.35 (m, 1H, superimposed with solvent), 2.09 (s, 3H) ppm. LC/MS: $R_t$=1.158 min; ESI (pos.) m/z=379.1 (M+H$^+$)$^+$, 713.4 (2M+H$^+$)$^+$.

Step H: Methyl 3-benzyloxycarbonylamino-4-[5-[bis(2-chloroethyl)amino]-2-methyl-phenyl]butanoate (3h)

Following the General Procedure for of Description 7 (Variant A), methyl 3-benzyloxycarbonylamino-4-[5-[bis(2-chloroethyl)amino]-2-methyl-phenyl]butanoate (3i) was prepared from methyl 4-(5-amino-2-methyl-phenyl)-3-benzyloxycarbonylamino-butanoate (3h) (1.9 g, 5.3 mmol), 2-chloroacetaldehyde (~50 wt-% in water, ~7.87 M) (3.4 mL, 26.5 mmol), and sodium cyanoborohydride (NaBH$_3$CN) (1.41 g of 95% purity=1.34 g, 21.3 mmol) in a mixture of methanol (MeOH) (34 mL) and trifluoroacetic acid (TFA) (17 mL). Purification by silica gel column chromatography with an ethyl acetate (EtOAc)/hexane mixture (EtOAc/hexane=1:2, v/v) afforded 2.16 g (85% yield) of the title compound (3h) as a colorless solid. $R_f$=0.37 (EtOAc/hexane=1:2, v/v, ninhydrine negative). $^1$H NMR (300 MHz, CDCl$_3$): δ 7.36-7.24 (m, 5H), 7.03 (d, J=8.4 Hz, 1H), 6.50 (dd, J=8.4, 2.7 Hz, 1H), 6.44-6.41 (br. m, 1H), 5.50 (d, J=8.7 Hz, 1H), 5.08 (s, 2H), 4.26-418 (br. m, 1H), 3.70 (s, 3H), 3.70-3.54 (m, 8H), 2.96 (dd, J=13.8, 6.3 Hz, 1H), 2.76 (dd, J=13.8, 8.4 Hz, 1H), 2.55 (br. d, J=4.8 Hz, 2H), 2.26 (s, 3H) ppm. LC/MS: $R_t$=2.526 min; ESI (pos.) m/z=503.1 (M+H$^+$)$^+$. LC/UV: $R_t$=6.552 min, 100.0% AUC at λ=254 nm.

Step I: 3-Amino-4-[5-[bis(2-chloroethyl)amino]-2-methyl-phenyl]butanoic acid (3)

Following the General Procedure for of Description 8, 3-amino-4-[5-[bis(2-chloroethyl)amino]-2-methyl-phenyl]butanoic acid (3) was prepared through acidic hydrolysis of methyl 3-benzyloxycarbonylamino-4-[5-[bis(2-chloroethyl)amino]-2-methyl-phenyl]butanoate (3i) (2.16 g, 4.15 mmol) in a mixture of concentrated hydrochloric acid (HCl) (30 mL) and 1,4-dioxane (30 mL). The residue was purified by preparative HPLC, immediately frozen after collection, followed by primary lyophilization to afford 722 mg of the target compound (3) as a colorless powder. $^1$H NMR (300 MHz, DMSO-d$^6$): δ 7.30 (d, J=9.0 Hz, 1H), 6.56-6.50 (m, 2H), 3.76-3.60 (br. m, 10 H), 3.65-3.36 (br. m, 1H), 2.75 (dd, J=13.5, 6.6 Hz, 1H), 2.65 (dd, J=13.2, 7.8 Hz, 1H), 2.13 (s, 3H), 2.06 (d, J=3.9 Hz, 1H), 2.00 (dd, J=16.2, 9.3 Hz, 1H) ppm. LC/MS: $R_t$=1.094 min; ESI (pos.) m/z=333.1 (M+H+)+; ESI (neg.) m/z=330.9.0 (M–H$^+$)$^-$. LC/UV: $R_t$=7.134 min, 95.5% AUC at λ=254 nm. The analytical data correspond to the analytical data of the (S)-isomer (5) and the (R)-isomer (6). Various batches of mono- or dihydrochloride salts of (3) can be prepared by primary lyophilization of solutions of (3) in aqueous acetonitrile (MeCN) containing either 1.0 eq. of 1.0 N hydrochloric acid (HCl) or an excess of 1.0 N or higher concentrated hydrochloric acid (HCl).

Example 4

3-Amino-4-[4-[bis(2-chloroethyl)amino]-2-methyl-phenyl]butanoic acid (4)

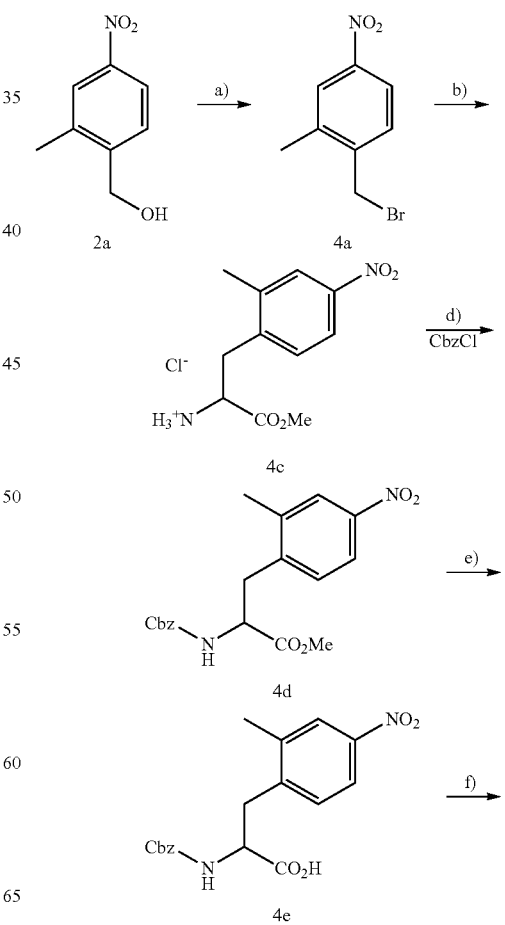

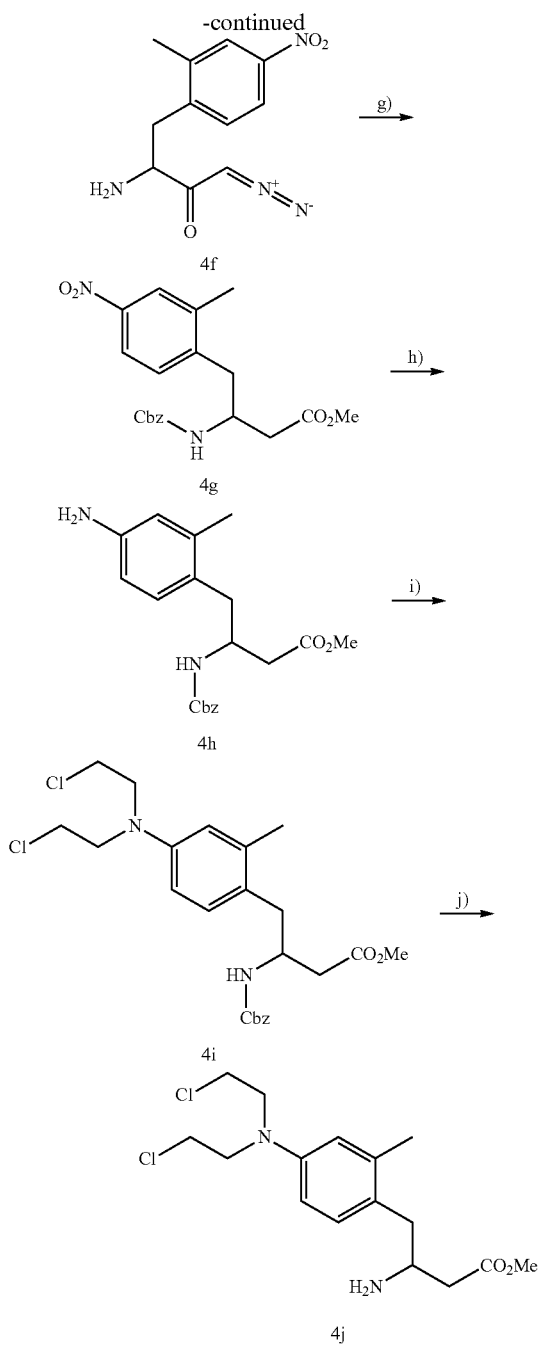

Step C: Methyl 2-amino-3-(2-methyl-4-nitro-phenyl) propanoate Hydrochloride (4c)

Adapting literature protocols (, methyl 2-amino-3-(2-methyl-4-nitro-phenyl)propanoate Hydrochloride (4c) was prepared through alkylation commercial methyl[(phenylmethylidene)amino]acetate (1.84 g, 10.4 mmol), with 1-(bromomethyl)-4-nitro-benzene (4b) (2.86 g, 12.5 mmol), potassium carbonate ($K_2CO_3$) (4.31 g, 31.2 mmol), benzyltriethylammonium chloride (BTEAC) (237 mg, 1.04 mmol) in acetonitrile (MeCN) (30 mL). The reaction mixture was stirred for about 6 hours at room temperature, filtered, and concentrated under reduced pressure using a rotary evaporator. The residue was diluted with diethyl ether ($Et_2O$) and the organic layer was washed with brine. The phases were separated and the organic layer was concentrated to a total volume of about 20 mL. 1.0 M Hydrochloric acid (HCl) (50 mL) was added, and the reaction mixture was kept overnight at room temperature. The reaction mixture was further diluted with diethyl ether ($Et_2O$) and the phases were separated. The aqueous phase was concentrated under reduced pressure using a rotary evaporator.

Following the General Synthesis of Description 4, the crude material was diluted with anhydrous methanol (MeOH) (20 mL) and treated with excess thionyl chloride ($SOCl_2$) at about 0° C. (ice bath). The reaction mixture was subsequently heated to about 80° C. (oil bath) for about 1 h before solvents and volatiles were removed under reduced pressure using a rotary evaporator to afford 2.18 g (76% yield) of the target compound (4c) as a colorless solid. LC/MS: $R_t$=0.687 min; ESI (pos.) m/z=239.1 $(M+H^+)^+$.

Step D: Methyl 2-benzyloxycarbonylamino-3-(2-methyl-4-nitro-phenyl)propanoate (4d)

Following the General Procedure of Description 5, methyl 2-benzyloxycarbonylamino-3-(2-methyl-4-nitro-phenyl) propanoate (4d) was prepared from methyl 2-amino-3-(2-methyl-4-nitro-phenyl)propanoate hydrochloride (4c) (2.18 g, 7.94 mmol), benzyl chloroformate (CbzCl, ZCl) (1.65 mL, 1.97 g, 11.9 mmol), and diisopropylethylamine (DIPEA, Hünigs-base) (3.92 mL, 3.07 g, 23.7 mmol) in dichloromethane (DCM) (50.0 mL). Aqueous work-up and purification by silica gel colunchromatography (EtOAc/Hxn=1:2 v/v) afforded 1.94 g (40% yield) of the target compound (4d) as a colorless solid. $R_f$=0.44 (EtOAc/Hxn=1:2 v/v). $^1$H NMR (400 MHz, $CDCl_3$): δ 8.06-8.00 (m, 1H), 7.94-7.86 (m, 1H), 7.40-7.20 (m, 6H), 5.36 (d, 1H), 5.06 (d, 1H), 5.00 (d, 1H), 4.70-4.60 (m, 1H), 3.68 (s, 3H), 3.26 (dd, 1H), 3.04 (dd, 1H), 2.40 (s, 3H) ppm. LC/MS: $R_t$=2.085 min; ESI (pos.) m/z=373.3 (M+H+)+; ESI (neg.) m/z=371.1 $(M-H^+)^-$.

Step E: 2-Benzyloxycarbonylamino-3-(2-methyl-4-nitro-phenyl)propanoic acid (4e)

Adapting a literature protocol (Dayal, et al., Steroids, 1990, 55(5), 233-237), a reaction mixture of methyl 2-benzyloxycarbonylamino-3-(2-methyl-4-nitro-phenyl)propanoate (4d) (1.94 g, 5.20 mmol) and commercial lithium hydroxide monohydrate ($LiOH.H_2O$) (436 mg, 10.4 mmol) in a mixture of tetrahydrofuran (THF)/methanol (MeOH)/water (20:10: 10 mL v/v/v) was stirred at room temperature. The reaction was followed by TLC and LC/MS to completion. Acidic aqueous work-up at about pH 4 and subsequent crystallization from ethyl acetate (EtOAc) furnished 900 mg (48% yield) of the target compound (4e) as a colorless solid. $^1$H NMR (400 MHz, $CDCl_3$): δ 7.96-7.92 (m, 1H), 7.90-7.80 (m,

Step A: 1-(Bromomethyl)-4-nitro-benzene (4a)

Following the General Procedure of Description 10, 1-(bromomethyl)-4-nitro-benzene (4a) was prepared through bromination of (2-methyl-4-nitro-phenyl)methanol (2a) (18.0 g, 108 mmol) (prepared as described in Example 2) dissolved in dichloromethane (DCM) (200 mL) with a solution of phosphorus tribromide ($PBr_3$) in (1.0 M $PBr_3$ in DCM) (108 mL). Aqueous work-up yielded 16.0 g (64% yield) of a light yellow solid which was of sufficient purity to be used directly and without further isolation and purification in the next step. $R_f$=0.51 (EtOAc/Hxn=1:5 v/v). The spectroscopic data correspond to the data provided in the literature.

1H), 7.36-7.18 (m, 6H), 5.62 (d, 1H), 5.00 (d, 1H), 4.93 (d, 1H), 4.60-4.50 (m, 1H), 3.26 (dd, 1H), 2.98 (dd, 1H), 2.38 (s, 3H) ppm. LC/MS: $R_t$=1.818 min; ESI (pos.) m/z=359.1 (M+H+)+; ESI (neg.) m/z=357.0 (M–H+)⁻.

Step F: Benzyl N-[3-diazo-1-[(2-methyl-4-nitro-cyclohexa-2,4-dien-1-yl)methyl]-2-oxo-propyl]carbamate (4f)

Following the General Procedure of Description 12 (Parts A-B), benzyl N-[3-diazo-1-[(2-methyl-4-nitro-cyclohexa-2,4-dien-1-yl)methyl]-2-oxo-propyl]carbamate (4f) was prepared from 2-benzyloxycarbonylamino-3-(2-methyl-4-nitrophenyl)propanoic acid (4e) (700 mg, 1.97 mmol), N-methylmorpholine (NMM) (433 µL, 398 mg, 3.94 mmol), isobutyl chloroformate (515 µL, 538 mg, 3.94 mmol) in anhydrous tetrahydrofuran (THF) (10 mL) and about 16 mmol of freshly prepared diazomethane in $Et_2O$. Silica gel column chromatography (EtOAc/Hxn=1:2 v/v) afforded 350 mg (46% yield) of the target compound (4f) as a colorless solid. $R_f$=0.24 (EtOAc/Hxn=1:2, v/v). $^1$H NMR (400 MHz, $CDCl_3$): δ 8.02-7.98 (m, 1H), 7.96-7.88 (m, 1H), 7.38-7.20 (m, 6H), 5.40 (d, 1H), 5.20 (s, 1H), 5.08 (d, 1H), 5.02 (d, 1H), 4.50-4.40 (m, 1H), 3.18 (dd, 1H), 2.96 (dd, 1H), 2.42 (s, 3H) ppm. LC/MS: $R_t$=1.991 min; ESI (pos.) m/z=405.0 (M+Na+)+.

Step G: Methyl 3-benzyloxycarbonylamino-4-(2-methyl-4-nitro-phenyl)butanoate (4g)

Following the General Procedure of Description 12 (Part C), methyl 3-benzyloxycarbonylamino-4-(2-methyl-4-nitrophenyl)butanoate (4g) was prepared from benzyl N-[3-diazo-1-[(2-methyl-4-nitro-cyclohexa-2,4-dien-1-yl)methyl]-2-oxo-propyl]carbamate (4f) (350 mg, 0.916 mmol) in Methanol (MeOH) (10 mL) and silver benzoate (AgBz) (0.75 g, 3.3 mmol) dissolved in triethylamine (TEA) (3.0 mL, 2.29 g, 4.32 mmol). Silica gel column chromatography (EtOAc/Hxn=2:3 v/v) afforded 220 mg (62% yield) of the target compound (4g) as pale yellow solid. $^1$H NMR (400 MHz, $CDCl_3$): δ 8.02-7.98 (m, 1H), 7.92-7.86 (m, 1H), 7.40-7.18 (m, 6H), 5.46 (d, 1H), 5.04-4.96 (m, 2H), 4.28-4.18 (m, 1H), 3.69 (s, 3H), 3.08 (dd, 1H), 2.90 (dd, 1H), 2.60 (dd, 1H), 2.54 (dd, 1H), 2.44 (s, 3H) ppm. LC/MS: $R_t$=2.082 min; ESI (pos.) m/z=387.2 (M+H+)+; ESI (neg.) m/z=384.9 (M–H+)⁻.

Step H: Methyl 4-(4-amino-2-methyl-phenyl)-3-benzyloxycarbonylamino-butanoate (4h)

Following the General Procedure for of Description 6 (Variant A), methyl 4-(4-amino-2-methyl-phenyl)-3-benzyloxycarbonylamino-butanoate (4h) was prepared from methyl 3-benzyloxycarbonylamino-4-(2-methyl-4-nitrophenyl)butanoate (4g) (220 mg, 0.570 mmol), iron powder (Fe) (286 mg, 5.13 mmol), and anhydrous calcium chloride ($CaCl_2$) (28 mg, 0.257 mmol) in 85 vol-% aqueous methanol (MeOH) (20 mL). The reaction mixture was heated at reflux for about 2 hours (oil bath). Removal of the iron residues by filtration and compound isolation procedures yielded 200 mg (about quantitative yield) of the target compound (4h) as a light yellow oil which was of sufficient purity to be used directly in the nest step without further isolation and purification. LC/MS: $R_t$=1.034 min; ESI (pos.) m/z=357.1 (M+H+)+, 379.1 (M+Na+)+.

Step I: Methyl 3-benzyloxycarbonylamino-4-[4-[bis(2-chloroethyl)amino]-2-methyl-phenyl]butanoate (4i)

Following the General Procedure for of Description 7 (Variant A), methyl 3-benzyloxycarbonylamino-4-[4-[bis(2-chloroethyl)amino]-2-methyl-phenyl]butanoate (4i) was prepared from methyl 4-(4-amino-2-methyl-phenyl)-3-benzyloxycarbonylamino-butanoate (4h) (200 mg, 0.561 mmol), 2-chloroacetaldehyde (~50 wt-% in water, ~7.87 M) (357 µL, 2.87 mmol), and sodium cyanoborohydride ($NaBH_3CN$) (148 mg of 95% purity=141 mg, 2.24 mmol) in a mixture of methanol (MeOH) (20 mL) and trifluoroacetic acid (TFA) (10 mL). Aqueous work-up and purification by silica gel column chromatography with an ethyl acetate (EtOAc)/hexane mixture (EtOAc/hexane=2:3, v/v) afforded 260 mg (96% yield) of the title compound (4i) as a colorless oil. $R_f$=0.41 (EtOAc/Hxn=1:2, v/v). $^1$H NMR (400 MHz, $CDCl_3$): δ 7.40-7.28 (m, 5H), 6.92-6.88 (d, 1H), 6.46-6.38 (m, 2H), 5.38 (d, 1H), 5.10-5.00 (m, 2H), 4.10-4.00 (m, 1H), 3.70-3.56 (m, 11H), 2.84 (dd, 1H), 2.70 (dd, 1H), 2.58-2.42 (m, 2H), 2.30 (s, 3H) ppm. LC/MS: $R_t$=2.470 min; ESI (pos.) m/z=481.2 (M+H+)+.

Step J: 3-Amino-4-[4-[bis(2-chloroethyl)amino]-2-methyl-phenyl]butanoic acid (4)

Following the General Procedure for of Description 8, 3-amino-4-[4-[bis(2-chloroethyl)amino]-2-methyl-phenyl]butanoic acid (4) was prepared through hydrolysis of methyl 3-benzyloxycarbonylamino-4-[4-[bis(2-chloroethyl)amino]-2-methyl-phenyl]butanoate (4i) (260 mg, 0.54 mmol) in a mixture of concentrated hydrochloric acid (HCl) (1 mL) and 1,4-dioxane (1 mL). Purification by preparative HPLC afforded 82 mg (46% recovery) of the target compound (4) after primary lyophilization as a colorless solid. $^1$H NMR (400 MHz, DMSO-$d^6$): δ 6.96-6.90 (d, 1H), 6.56-6.46 (m, 2H), 3.70-3.56 (br. m, 9H), 3.30 (br. s, superimposed with water signal, 3H), 2.70 (dd, 1H), 2.56 (dd, 1H), 2.18 (s, 3H), 2.10-1.98 (m, 2H) ppm. LC/MS: $R_t$=1.195 min; ESI (pos.) m/z=333.1 (M+H+)+; ESI (neg.) m/z=331.0 (M–H+)⁻. LC/UV: $R_t$=7.896 min, 96.5% AUC at λ=254 nm. Various batches of mono- or dihydrochloride salts of (4) can be prepared by primary lyophilization of solutions of (4) in aqueous acetonitrile (MeCN) containing either 1.0 eq. of 1.0 N hydrochloric acid (HCl) or an excess of 1.0 N or higher concentrated hydrochloric acid (HCl).

Example 5

(3S)-3-Amino-4-[5-[bis(2-chloroethyl)amino]-2-methyl-phenyl]butanoic acid (5)

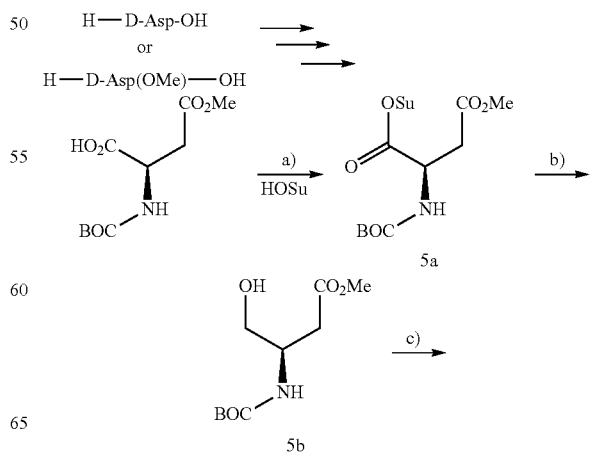

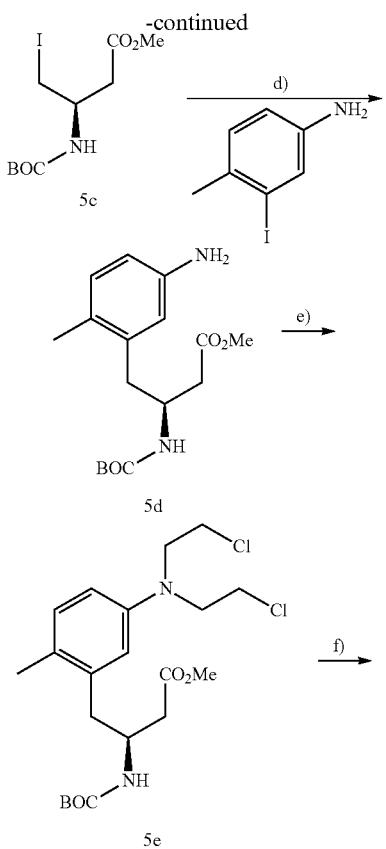

Step A: O¹-(2,5-Dioxopyrrolidin-1-yl)O⁴-methyl
(2R)-2-(tert-butoxycarbonylamino)-butanedioate
(5a)

Following the General Procedure of Description 12, O-(2, 5-Dioxopyrrolidin-1-yl) O⁴-methyl(2R)-2-(tert-butoxycarbonylamino)-butanedioate (5a) was prepared from (2R)-2-(tert-butoxycarbonylamino)-4-methoxy-4-oxo-butanoic acid (9.46 g, 38.3 mmol) (commercially available or prepared from commercial H-D-Asp(OMe)-OHHCl (10.5 g, 57.3 mmol) (preparable following the General Procedure of Description 4) and Boc₂O (12.5 g, 57.3 mmol) in a mixture of 1,4-dioxane (100 mL) and a freshly prepared 1.0 N aqueous sodium hydroxide (NaOH) solution (126 mL, 126 mmol) (9.46 g (67% yield) (Keller, et al., Org. Synth., 1985, 63, 160)), N-hydroxysuccinimide(1-hydroxypyrrolidine-2,5-dione, HOSu, NHS) (4.69 g, 40.8 mmol), and dicyclohexylcarbodiimide (DCC) (8.02 g, 38.9 mmol in ethyl acetate (EtoAc) (120 mL) at room temperature. Filtration and aqueous work-up furnished 13.2 g (quantitative yield) of the title compound (5a) as a colorless solid which was of sufficient purity to be used directly and without further isolation and purification in the next step. $R_f$=0.45 (EtOAc/hexane=1:1, v/v). ¹H NMR (300 MHz, CDCl₃): δ 5.64 (br. d, J=9.3 Hz, 1H), 5.03-4.96 (m, 1H), 3.75 (s, 3H), 3.12 (dd, J=17.4, 4.5 Hz, 1H), 3.12 (dd, J=17.7, 4.5 Hz, 1H), 2.83 (br. s, 4H), 1.45 (s, 9H) ppm. LC/MS: $R_t$=1.463 min; ESI (pos.) m/z=367.15 (M+Na⁺)⁺.

Step B: Methyl(3R)-3-(tert-butoxycarbonylamino)-
4-hydroxy-butanoate (5b)

Following the General Procedure of Description 13, methyl(3R)-3-(tert-butoxycarbonylamino)-4-hydroxy-butanoate (5b) was prepared through reduction of O¹-(2,5-dioxopyrrolidin-1-yl) O⁴-methyl(2R)-2-(tert-butoxycarbonylamino)-butanedioate (5a) (13.2 g, 38.3 mmol) with sodium borohydride (NaBH₄) (2.41 g, 63.7 mmol) in tetrahydrofuran (THF)/water (133 mL/17 mL). Aqueous work-up and purification by silica gel column chromatography with an ethyl acetate (EtOAc)/hexane mixture (EtOAc/hexane=4:3, v/v) furnished 5.73 g (43% yield over 3 steps) of the title compound (5b) as a colorless oil. $R_f$=0.34 (EtOAc/hexane=1:1, v/v). ¹H NMR (400 MHz, CDCl₃): δ 5.30 (br. d, 1H), 4.06-3.92 (m, 1H), 3.70-3.68 (m, superimposed, 5H), 2.63 (d, J=5.7 Hz, 2H), 1.43 (s, 9H) ppm. LC/MS: $R_t$=1.027 min; ESI (pos.) m/z=489.25 (2M+Na⁺)⁺. The analytical data correspond with the analytical data for the (S)-enatiomer in the literature (Dexter and Jackson, J. Org. Chem., 1999, 64, 7579-7585).

Step C: Methyl(3R)-3-(tert-butoxycarbonylamino)-
4-iodo-butanoate (5c)

Following the General Procedure of Description 14, methyl(3R)-3-(tert-butoxycarbonylamino)-4-iodo-butanoate (5c) was prepared from methyl(3R)-3-(tert-butoxycarbonylamino)-4-hydroxy-butanoate (5b) (5.73 g, 24.6 mmol), iodine (I₂) (6.23 g, 24.6 mmol), triphenylphosphine (PPh₃) (6.45 g, 24.6 mmol), and imidazole (1.67 g, 24.6 mmol) in anhydrous dichloromethane (DCM) (100 mL). Aqueous reductive work-up and purification by silica gel column chromatography with an ethyl acetate (EtOAc)/hexane mixture (EtOAc/hexane=7:3, v/v) furnished 4.30 g (51% yield) of the title compound (5c) as a colorless to beige solid. $R_f$=0.79 (EtOAc/hexane=7:3, v/v). ¹H NMR (400 MHz, CDCl₃): δ 5.10 (br. d, J=7.2 Hz, 1H), 4.00-3.80 (m, 1H), 3.69 (s, 3H), 3.50-3.36 (m, 2H), 2.76 (dd, J=16.5, 5.4 Hz, 1H), 2.62 (dd, J=16.5, 6.3 Hz, 1H), 1.43 (s, 9H) ppm. The analytical data correspond with the analytical data for the (S)-enatiomer in the literature (Dexter and Jackson, J. Org. Chem., 1999, 64, 7579-7585).

Step D: Methyl(3S)-4-(5-amino-2-methyl-phenyl)-3-
(tert-butoxycarbonylamino)butanoate (5d)

Following the General Procedure of Description 15 (Part A), zinc dust (Zn) (1.96 g, 30.0 mmol) was activated with elemental iodine (I₂) (190 mg, 0.75 mmol, 15 mol-%) and trimethyl silylchloride (MeSiCl, TMSCl) (95 μL, 81 mg, 0.75 mmol, 15 mol-%) in degassed anhydrous N,N-dimethylformamide (DMF) (6 mL). The zinc insertion product was prepared from methyl(3R)-3-(tert-butoxycarbonylamino)-4-iodo-butanoate (5c) (1.72 g, 5.0 mmol) in the presence of additional I₂ (190 mg, 0.75 mmol, 15 mol-%) and TMSCl (95 μL, 81 mg, 0.75 mmol, 15 mol-%).

Following the General Procedure of Description 15 (Part B), the zinc insertion product of (5c) was used in situ to cross couple with commercial 3-iodo-4-methyl-aniline (583 mg, 2.5 mmol) in the presence of tris(benzylideneacetone)dipalladium ($Pd_2(dba)_3$) (57 mg, 0.03 mmol, 2.5 mol-%) and tris (o-tolyl)phosphine (P(o-tol)$_3$) (76 mg, 0.25 mmol, 10 mol-%) in anhydrous degassed DMF (6 mL). Filtration, aqueous work-up, and purification by silica gel column chromatography with ethyl acetate (EtOAc)/hexane mixtures (EtOAc/hexane=7:3→1:1, v/v) furnished 1.04 g (65% yield) of the title compound (5d) as a yellow viscous oil. $R_f$~0.28 (EtOAc/hexane=1:1, v/v). $^1$H NMR (400 MHz, $CDCl_3$): δ 6.89 (d, J=8.4 Hz, 1H), 6.48-6.44 (m, 2H), 5.10-5.02 (br. m, 1H), 4.18-4.08 (m, 1H), 3.65 (s, 3H), 3.30 (br. s, 2H), 2.82-2.78 (br. dd, 1H), 2.70 (dd, J=10.2, 6.0 Hz, 1H), 2.51 (dd, J=16.0, 5.2 Hz, 1H), 2.45 (dd, J=16.0, 5.6 Hz, 1H), 2.19 (s, 3H), 1.38 (s, 9H) ppm. LC/MS: $R_t$=1.320 min. LC/MS: m/z=323.20 $(M+H^+)^+$, 345.15 $(M+Na^+)^+$.

Step E: Methyl(3S)-4-[5-[bis(2-chloroethyl)amino]-2-methyl-phenyl]-3-(tert-butoxycarbonylamino)butanoate (5e)

Following the General Procedure of Description 7 (Variant C), methyl(3S)-4-[5-[bis(2-chloroethyl)amino]-2-methyl-phenyl]-3-(tert-butoxycarbonylamino)butanoate (5e) was prepared from methyl(3S)-4-(5-amino-2-methyl-phenyl)-3-(tert-butoxycarbonylamino)-butanoate (5d) (967 mg, 3.0 mmol), 2-chloroacetaldehyde (~50 wt-% in water, ~7.87 M) (3.05 mL, 24.0 mmol), and sodium cyanoborohydride ($NaBH_3CN$) (624 mg of 95% purity=593 mg, 9.43 mmol) in a mixture of methanol (MeOH) (18 mL) and 85 wt-% phosphoric acid ($H_3PO_4$) (8.1 mL). Aqueous work-up and purification by silica gel column chromatography with an ethyl acetate (EtOAc)/hexane mixture (EtOAc/hexane=1:4, v/v) afforded 1.4 g (97% yield) of the title compound (5e) as a colorless oil. $R_f$~0.32 (EtOAc/Hxn=4:1, v/v). $^1$H NMR (400 MHz, $CDCl_3$): δ 7.00 (d, J=8.5 Hz, 1H), 6.49 (d, J=2.4 Hz, 1H), 6.42 (s, 1H), 5.10-5.04 (br. m, 1H), 3.69 (s, 3H), 3.67-3.59 (m, 8H), 2.90-2.80 (m, 1H), 2.78-2.70 (m, 1H), 2.60-2.40 (m, 2H), 2.23 (s, 3H), 1.37 (s, 9H) ppm. LC/MS: $R_t$=2.533 min; ESI (pos.) m/z=447.15 $(M+H^+)^+$, 469.15 $(M+Na^+)^+$.

Step F: (3S)-3-Amino-4-[5-[bis(2-chloroethyl)amino]-2-methyl-phenyl]butanoic acid (5)

Following the General Procedure of Description 8, (3S)-3-amino-4-[5-[bis(2-chloroethyl)amino]-2-methyl-phenyl]butanoic acid (5) was prepared through hydrolytic deprotection of methyl(3S)-4-[5-[bis(2-chloroethyl)amino]-2-methyl-phenyl]-3-(tert-butoxycarbonylamino)butanoate (5e) (~1.4 g, 3.13 mmol) in a mixture of concentrated hydrochloric acid (HCl) (7.5 mL) and 1,4-dioxane (7.5 mL). Part of the crude material obtained after work-up was purified by preparative HPLC to afford ~20 mg of the target compound (5) as a colorless solid after primary lyophilization. $^1$H NMR (400 MHz, MeOH-d$^4$): δ 7.04 (d, J=8.4 Hz, 1H), 6.59 (d, J=8.4 Hz, 1H), 6.54 (s, 1H), 3.74-3.68 (br. m, 4H), 3.67-3.62 (br. m, 4H), 3.58-3.50 (m, 1H), 2.92-2.86 (m, 2H), 2.44 (dd, J=16.8, 4.0 Hz, 1H), 2.31 (dd, J=16.8, 8.4 Hz, 1H), 2.22 (s, 3H) ppm. The analytical data correspond to the analytical data obtained for racemic compound (3). Various batches of mono- or dihydrochloride salts of (6) can be prepared by primary lyophilization of solutions of (5) in aqueous acetonitrile (MeCN) containing either 1.0 eq. of 1.0 N hydrochloric acid (HCl) or an excess of 1.0 N or higher concentrated hydrochloric acid (HCl).

Example 6

(3R)-3-Amino-4-[5-[bis(2-chloroethyl)amino]-2-methyl-phenyl]butanoic acid (6)

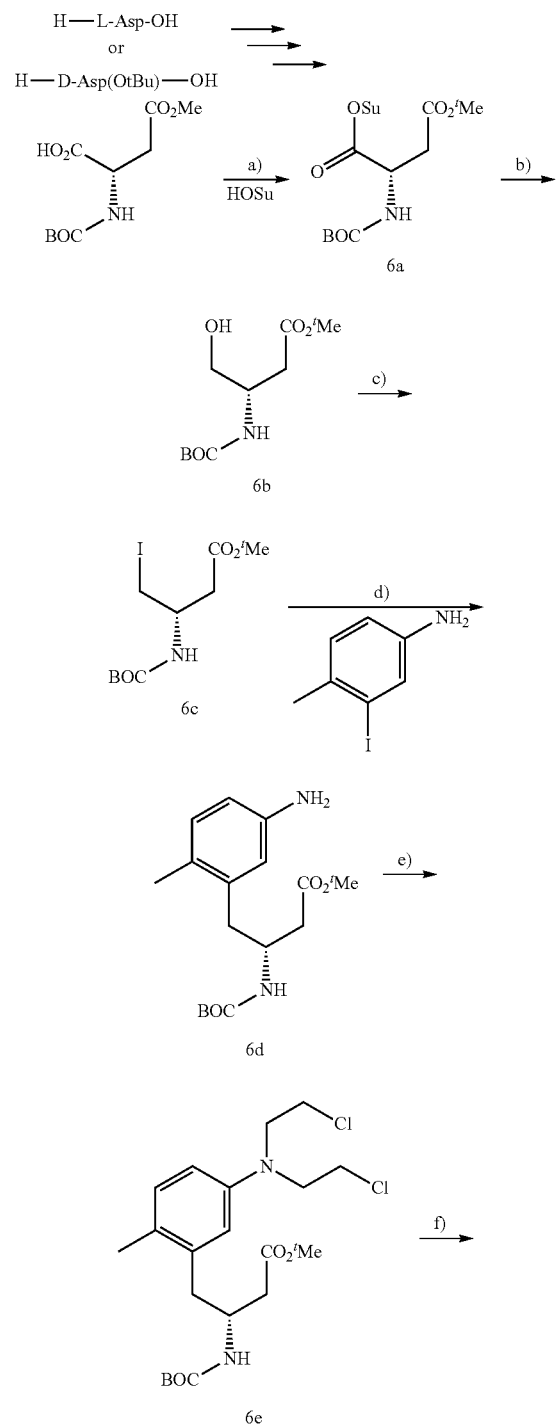

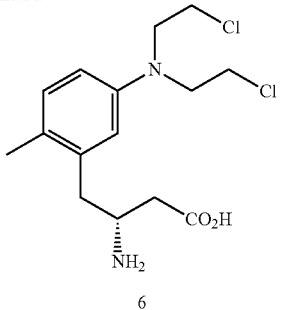 [SMILES: Cc1ccc(N(CCCl)CCCl)cc1C[C@@H](N)CC(=O)O]

Step A: O¹-(2,5-Dioxopyrrolidin-1-yl)O⁴-tert-butyl (2S)-2-(tert-butoxycarbonylamino)-butanedioate (6a)

Following the General Procedure of Description 12, O¹-(2,5-Dioxopyrrolidin-1-yl) O⁴-tert-butyl(2S)-2-(tert-butoxycarbonylamino)-butanedioate (6a) was prepared from (2S)-2-(tert-butoxycarbonylamino)-4-tert-butoxy-4-oxo-butanoic acid (8.32 g, 28.8 mmol) (commercially available or prepared following the General Procedure of Description 4 from commercial H-L-Asp(OtBu)-OH (5.68 g, 30.0 mmol) and Boc$_2$O (6.55 g, 30.0 mmol) in a mixture of 1,4-dioxane (25 mL) and a freshly prepared 1.0 N aqueous sodium hydroxide (NaOH) solution (33 mL, 33 mmol) (8.33 g, 96% yield) (Keller, et al., Org. Synth., 1985, 63, 160)), N-hydroxysuccinimide(1-hydroxypyrrolidine-2,5-dione, HOSu, NHS) (3.53 g, 30.7 mmol), and dicyclohexylcarbodiimide (DCC) (6.03 g, 29.2 mmol in ethyl acetate (EtoAc) (100 mL) at room temperature. Filtration and aqueous work-up furnished 11.8 g (quantitative yield) of the title compound (6a) as a colorless solid which was of sufficient purity to be used directly and without further isolation and purification in the next step. $R_f$~0.56 (EtOAc/hexane=1:1, v/v); $R_f$~0.34 (EtOAc/hexane=1:2, v/v). $^1$H NMR (300 MHz, CDCl$_3$): δ 5.63 (d, J=9.3 Hz, 1H), 5.00-4.92 (m, 1H), 3.01 (dd, J=17.4, 5.1 Hz, 1H), 2.84 (dd, superimposed, J=17.4, 4.8 Hz, 1H), 2.84 (s, superimposed, 4H), 1.47 (s, 9H), 1.45 (s, 9H) ppm. LC/MS: $R_t$=2.567 min; ESI (pos.) m/z=409.15 (M+Na$^+$)$^+$, 795.35 (2M+Na$^+$)$^+$; ESI (neg.) m/z=384.90.

Step B: tert-Butyl(3S)-3-(tert-butoxycarbonylamino)-4-hydroxy-butanoate (6b)

Following the General Procedure of Description 13, tert-butyl(3S)-3-(tert-butoxycarbonylamino)-4-hydroxy-butanoate (6b) was prepared through reduction of O¹-(2,5-dioxopyrrolidin-1-yl) O⁴-tert-butyl(2S)-2-(tert-butoxycarbonylamino)-butanedioate (6a) (11.8 g, 30.5 mmol) with sodium borohydride (NaBH$_4$) (2.31 g, 61.0 mmol) in tetrahydrofuran (THF)/water (110 mL/16 mL). Aqueous work-up and purification by silica gel column chromatography with an ethyl acetate (EtOAc)/hexane mixture (EtOAc/hexane=11:9, v/v) furnished 7.30 g (87% yield) of the title compound (6b) as a colorless viscous oil. $R_f$~0.52 (EtOAc/hexane=1:1, v/v). $^1$H NMR (400 MHz, CDCl$_3$): δ 5.23 (br. d, J=5.1 Hz, 1H), 4.02-3.90 (m, 1H), 3.67 (d, J=4.8 Hz, 2H), 2.55 (dd, superimposed, J=15.3, 6.0 Hz, 1H), 2.48 (dd, superimposed, J=15.3, 6.3 Hz, 1H), 1.44 (s, 9H), 1.43 (s, 9H) ppm. LC/MS: $R_t$=1.887 min; ESI (pos.) m/z=298.10 (M+Na$^+$)$^+$; m/z=573.35 (2M+Na$^+$)$^+$.

Step C: tert-Butyl(3S)-3-(tert-butoxycarbonylamino)-4-iodo-butanoate (6c)

Following the General Procedure of Description 14, tert-butyl(3S)-3-(tert-butoxycarbonylamino)-4-iodo-butanoate (6c) was prepared from tert-butyl(3S)-3-(tert-butoxycarbonylamino)-4-hydroxy-butanoate (6b) (4.46 g, 16.2 mmol), iodine (I$_2$) (4.10 g, 16.2 mmol), triphenylphosphine (PPh$_3$) (4.25 g, 16.2 mmol), and imidazole (1.10 g, 16.2 mmol) in anhydrous dichloromethane (DCM) (70 mL). Aqueous reductive work-up and purification by silica gel column chromatography with ethyl acetate (EtOAc)/hexane mixtures (EtOAc/hexane=7:3→1:1, v/v) furnished 4.20 g (67% yield) of the title compound (6c) as a colorless to beige solid. $R_f$~0.79 (EtOAc/hexane=7:3, v/v). $^1$H NMR (400 MHz, CDCl$_3$): δ 5.09 (br. d, J=8.4 Hz, 1H), 3.90-3.80 (m, 1H), 3.44-3.30 (m, 2H), 2.60 (dd, J=15.9, 6.0 Hz, 1H), 2.51 (dd, J=15.9, 6.0 Hz, 1H), 1.45 (s, 9H), 1.43 (s, 9H) ppm. LC/MS: $R_t$=2.332 min; ESI (neg.) m/z=384.80 (M−H$^+$)$^−$.

Step D: tert-Butyl(3R)-4-(5-amino-2-methyl-phenyl)-3-(tert-butoxycarbonylamino)-butanoate (6d)

Following the General Procedure of Description 15 (Part A), zinc dust (Zn) (4.07 g, 62.3 mmol) is activated with elemental iodine (I$_2$) (396 mg, 1.56 mmol, 15 mol-%) and trimethyl silylchloride (MeSiCl, TMSCl) (197 μL, 169 mg, 0.75 mmol, 15 mol-%) in degassed anhydrous N,N-dimethylformamide (DMF) (6 mL). The zinc insertion product was prepared from tert-butyl(3S)-3-(tert-butoxycarbonylamino)-4-iodo-butanoate (6c) (4.01 g, 10.4 mmol) in the presence of additional elemental I$_2$ (396 mg, 1.56 mmol, 15 mol-%) and TMSCl (197 μL, 169 mg, 0.75 mmol, 15 mol-%).

Following the General Procedure of Description 15 (Part B), The zinc insertion product of (6c) was used in situ to cross couple with commercial 3-iodo-4-methyl-aniline (1.21 g, 5.2 mmol) in the presence of tris(benzylideneacetone)dipalladium (Pd$_2$(dba)$_3$) (119 mg, 0.13 mmol, 2.5 mol-%) and tris(o-tolyl)phosphine (P(o-tol)$_3$) (158 mg, 0.52 mmol, 10 mol-%) in anhydrous degassed DMF (6 mL). Filtration, aqueous work-up, and purification by silica gel column chromatography with an ethyl acetate (EtOAc)/hexane mixture (EtOAc/hexane=7:3, v/v) furnished 1.15 g (61% yield) of the title compound (6d) as a yellow viscous oil. $R_f$~0.28 (EtOAc/hexane=1:1, v/v). $^1$H NMR (300 MHz, CDCl$_3$): δ 6.91 (d, J=8.1 Hz, 1H), 6.50-6.46 (m, 2H), 5.20-5.10 (br. m, 1H), 4.18-4.00 (m, 1H), 3.24 (br. s, 2H), 2.88-2.78 (br. dd, 1H), 2.70 (dd, 1H), 2.44 (dd, J=15.4 Hz, 5.4 Hz, 1H), 2.36 (dd, J=15.4 Hz, 5.4 Hz, 1H), 2.22 (s, 3H), 1.45 (s, 9H), 1.40 (s, 9H) ppm. LC/MS: $R_t$=1.433 min; ESI (pos.) m/z=365.20 (M+H$^+$)$^+$.

Step E: tert-Butyl(3R)-4-[5-[bis(2-chloroethyl)amino]-2-methyl-phenyl]-3-(tert-butoxycarbonylamino)butanoate (6e)

Following the General Procedure of Description 7 (Variant C), tert-butyl(3R)-4-[5-[bis(2-chloroethyl)amino]-2-methyl-phenyl]-3-(tert-butoxycarbonylamino)butanoate (6e) was prepared from tert-butyl(3R)-4-(5-amino-2-methyl-phenyl)-3-(tert-butoxycarbonylamino)-butanoate (6d) (1.07 g, 2.92 mmol), 2-chloroacetaldehyde (~50 wt-% in water, ~7.87 M) (3.0 mL, 23.6 mmol), and sodium cyanoborohydride (NaBH$_3$CN) (1.25 g of 95% purity=1.19 g, 18.9 mmol) in a mixture of methanol (MeOH) (18 mL) and 85 wt-% phosphoric acid (H$_3$PO$_4$) (9 mL). Aqueous work-up and purification by silica gel column chromatography with an ethyl acetate (EtOAc)/hexane mixture (EtOAc/hexane=1:6, v/v) afforded 1.06 g (74% yield) of the title compound (6e) as a colorless oil. $R_f$~0.55 (EtOAc/hexane=1:4, v/v). $^1$H NMR (400 MHz, CDCl$_3$): δ 6.98 (d, J=8.4 Hz, 1H), 6.45 (d, J=8.4 Hz, 1H), 6.42 (s, 1H), 5.00 (br. d, 1H), 4.18-4.00 (m, 1H), 3.70-3.50 (m, 8H), 2.80-2.60 (m, 2H), 2.41 (dd, J=16.0, 5.6 Hz, 1H), 2.32 (dd, J=16.0, 6.0 Hz, 1H), 2.21 (s, 3H), 1.42 (s, 9H), 1.32 (s, 9H) ppm. LC/MS: $R_t$=2.944 min; ESI (pos.) m/z=489.20 (M+H$^+$)$^+$.

Step F: (3R)-3-Amino-4-[5-[bis(2-chloroethyl) amino]-2-methyl-phenyl]butanoic acid (6)

Following the General Procedure of Description 8, (3R)-3-amino-4-[5-[bis(2-chloroethyl)amino]-2-methyl-phenyl] butanoic acid (6) was prepared through hydrolytic deprotection of tert-butyl(3R)-4-[5-[bis(2-chloroethyl)amino]-2-methyl-phenyl]-3-(tert-butoxycarbonylamino)butanoate (6e) (160 mg, 0.33 mmol) in a mixture of concentrated hydrochloric acid (HCl) (1 mL) and 1,4-dioxane (1 mL). The crude material obtained after work-up was purified by preparative HPLC to afford ~86 mg (79% recovery) of the target compound (6) as a colorless solid after primary lyophilization. $^1$H NMR (400 MHz, MeOH-d$^4$): δ 7.04 (d, J=8.4 Hz, 1H), 6.59 (d, J=8.4 Hz, 1H), 6.54 (s, 1H), 3.74-3.68 (br. m, 4H), 3.67-3.62 (br. m, 4H), 3.60-3.52 (m, 1H), 2.92-2.86 (m, 2H), 2.46 (dd, J=16.8, 4.0 Hz, 1H), 2.34 (dd, J=16.8, 8.4 Hz, 1H), 2.22 (s, 3H) ppm. LC/MS: $R_t$=1.317 min; 100% AUC at λ=254 nm; ESI (pos.) m/z=333.05 (M+H$^+$)$^+$. LC/UV: $R_t$=8.489 min, 99.1% AUC at λ=254 nm. The analytical data correspond to the analytical data obtained for racemic compound (3).

Various batches of mono- or dihydrochloride salts of (6) can be prepared by primary lyophilization of solutions of (6) in aqueous acetonitrile (MeCN) containing either 1.0 eq. of 1.0 N hydrochloric acid (HCl) or an excess of 1.0 N or higher concentrated hydrochloric acid (HCl). Following the General Procedure of Description 9 (Variant B), dihydrochloride salts of (6) can also be prepared through deprotection with 2 N HCl in diethyl ether (2 N HCl in Et$_2$O) to yield the target compound (6) as a solid dihydrochloride salt after evaporation of the solvents and lyophilization from an aqueous solution. The material is generally of sufficient purity to be used directly and without further isolation and purification in in vitro and/or in vivo evaluation.

Example 7

(3S)-3-Amino-4-[5-[bis(2-chloroethyl)amino]-2-methoxy-phenyl]butanoic acid (7)

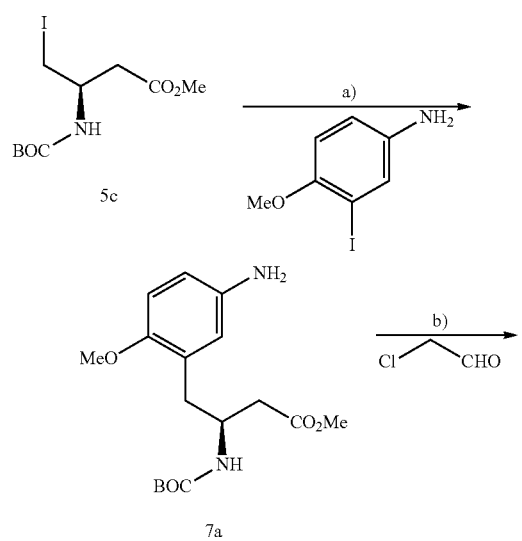

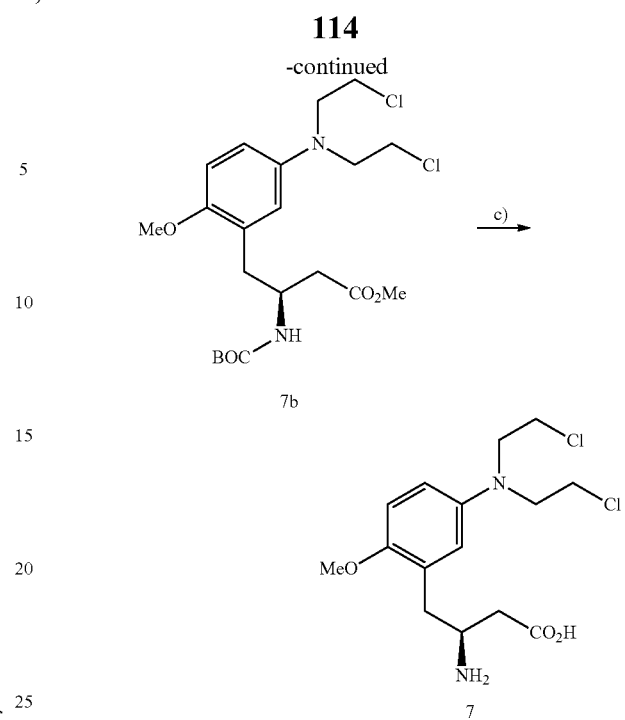

Step A: Methyl(3S)-4-(5-amino-2-methoxy-phenyl)-3-(tert-butoxycarbonylamino)-butanoate (7a)

Following the General Procedure of Description 15 (Part A), zinc dust (Zn) (392 mg, 6.0 mmol) was activated with elemental iodine (I$_2$) (38 mg, 0.15 mmol, 15 mol-%) and trimethyl silylchloride (MeSiCl, TMSCl) (19 μL, 16 mg, 0.15 mmol, 15 mol-%) in degassed anhydrous N,N-dimethylformamide (DMF) (2 mL). The zinc insertion product was prepared from methyl(3R)-3-(tert-butoxycarbonylamino)-4-iodo-butanoate (5c) (343 mg, 1.0 mmol) in the presence of additional I$_2$ (38 mg, 0.15 mmol, 15 mol-%) and TMSCl (19 μL, 16 mg, 0.15 mmol, 15 mol-%).

Following the General Procedure of Description 15 (Part A), the zinc insertion product of (5c) was used in situ to cross couple with commercial 3-iodo-4-methoxy-aniline (249 mg, 1.0 mmol) in the presence of tris(benzylideneacetone)dipalladium (Pd$_2$(dba)$_3$) (23 mg, 0.025 mmol, 2.5 mol-%) and tris(o-tolyl)phosphine (P(o-tol)$_3$) (30 mg, 0.10 mmol, 10 mol-%) in anhydrous degassed DMF (3 mL). Filtration, aqueous work-up, and purification by silica gel column chromatography with ethyl acetate (EtOAc)/hexane and dichloromethane(DCM)/EtOAc mixtures (EtOAc/hexane=1:1, v/v→DCM/EtOAc=1:1, v/v) furnished ~280 mg (66% yield; ~80% purity by AUC) of the title compound (7a) as a yellow viscous oil. $R_f$~0.23 (EtOAc/hexane=1:1, v/v). $^1$H NMR (300 MHz, CDCl$_3$): δ 6.90 (br s, 1H), 6.78 (br. d, J=8.1 Hz, 1H), 6.70 (d, J=8.7 Hz, 1H), 5.28 (br. d, J=8.1 Hz, 1H), 4.40-4.10 (m, 1H), 3.37 (s, 3H), 2.90-2.80 (br. m, 1H), 2.75 (dd, J=12.6, 6.3 Hz, 1H), 2.50 (d, J=5.1 Hz, 2H), 1.35 (s, 9H) ppm. LC/MS: $R_t$=0.908 min; ESI (pos.) m/z=339.15 (M+H$^+$)$^+$, 677.40 (2M+H$^+$)$^+$, 699.35 (2M+Na$^+$)$^+$.

Step B: Methyl(3S)-4-[5-[bis(2-chloroethyl)amino]-2-methoxy-phenyl]-3-(tert-butoxycarbonylamino) butanoate (7b)

Following the General Procedure of Description 7 (Variant C), methyl(3S)-4-[5-[bis(2-chloroethyl)amino]-2-methoxyphenyl]-3-(tert-butoxycarbonylamino)butanoate (7b) was prepared from methyl(3S)-4-(5-amino-2-methoxy-phenyl)-3-(tert-butoxycarbonylamino)-butanoate (7a) (280 mg, 0.83 mmol, ~80% purity), 2-chloroacetaldehyde (~50 wt-% in water, ~7.87 M) (842 μL, 6.63 mmol), and sodium cyanoborohydride (NaBH$_3$CN) (105 mg of 95% purity=100 mg, 1.59 mmol) in a mixture of methanol (MeOH) (5 mL) and 85 wt-% phosphoric acid (H$_3$PO$_4$) (2.5 mL). Aqueous work-up and purification by silica gel column chromatography with an ethyl acetate (EtOAc)/hexane mixture (EtOAc/hexane=1:4, v/v) afforded 104 mg (27% yield) of the title compound (7b) as a colorless oil. R$_f$~0.30 (EtOAc/hexane=1:4); LC/MS: R$_t$=2.493 min; ESI (pos.) m/z=463.20 (M+H$^+$)$^+$.

Step C: (3S)-3-Amino-4-[5-[bis(2-chloroethyl)amino]-2-methoxy-phenyl]butanoic acid (7)

Following the General Procedure of Description 8, (3S)-3-amino-4-[5-[bis(2-chloroethyl)amino]-2-methoxy-phenyl]butanoic acid (7) was prepared from methyl(3S)-4-[5-[bis(2-chloroethyl)amino]-2-methoxy-phenyl]-3-(tert-butoxycarbonylamino)butanoate (7b) (104 mg, 0.224 mmol) by hydrolysis in a mixture of concentrated hydrochloric acid (HCl) (3 mL) and 1,4-dioxane (3 mL) at about 60° C. (oil bath) for about 6 hours to afford ~90 mg (~95% yield) the title compound (7) as a dihydrochloride salt after evaporation of the solvents under reduced pressure. LC/MS: R$_t$=1.207 min; ~100% purity by AUC at λ=254 nm. ESI (pos.) m/z=349.05 (M+H$^+$)$^+$.

Example 8

(3S)-3-Amino-4-[3-[bis(2-chloroethyl)amino]-2,6-dimethyl-phenyl]butanoic acid (8)

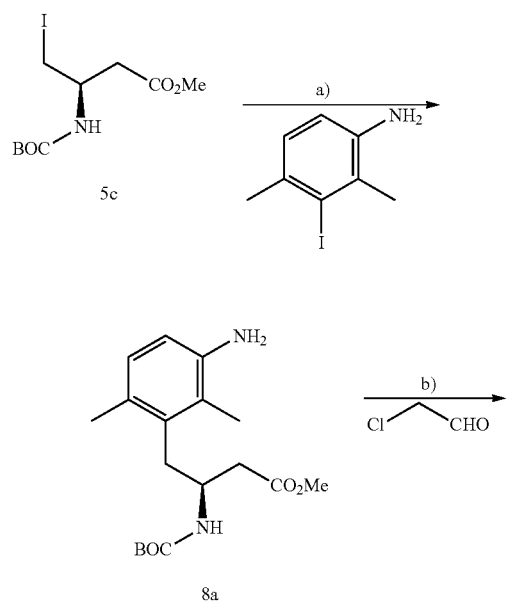

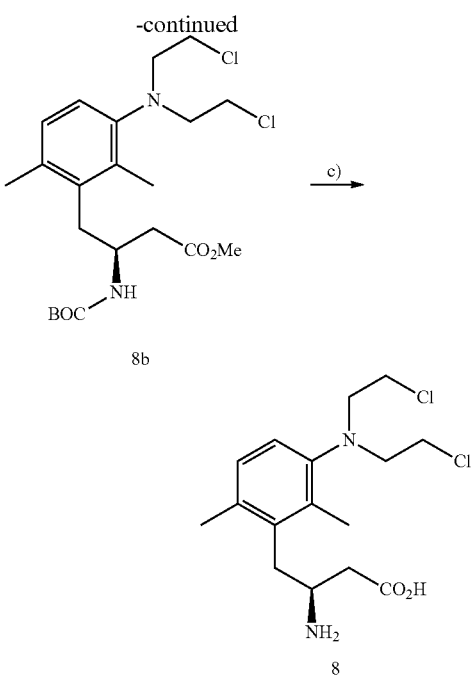

Step A: Methyl(3S)-4-β-amino-2,6-dimethyl-phenyl)-3-(tert-butoxycarbonylamino)-butanoate (8a)

Following the General Procedure of Description 15 (Part A), zinc dust (Zn) (392 mg, 6.0 mmol) is activated with elemental iodine (I$_2$) (38 mg, 0.15 mmol, 15 mol-%) and trimethyl silylchloride (MeSiCl, TMSCl) (19 μL, 16 mg, 0.15 mmol, 15 mol-%) in degassed anhydrous N,N-dimethylformamide (DMF) (3 mL). The zinc insertion product is prepared from methyl(3R)-3-(tert-butoxycarbonylamino)-4-iodo-butanoate (5c) (343 mg, 1.0 mmol) in the presence of additional I$_2$ (38 mg, 0.15 mmol, 15 mol-%) and TMSCl (19 μL, 16 mg, 0.15 mmol, 15 mol-%).

Following the General Procedure of Description 15 (Part B), the zinc insertion product of (5c) is used in situ to cross couple with 3-iodo-2,4-dimethyl-aniline (247 mg, 1.0 mmol; preparable following Description 6 from commercial 2-iodo-1,3-dimethyl-4-nitro-benzene (2.78 g, 10.0 mmol), 5.6 g iron powder (Fe), and calcium chloride dehydrate (CaCl$_2$.2H$_2$O) (1.47 g, 10.0 mmol) in a mixture of ethanol (EtOH) (20 mL) and water (1 mL)) in the presence of tris(benzylideneacetone) dipalladium (Pd$_2$(dba)$_3$) (23 mg, 0.025 mmol, 2.5 mol-%) and tris(o-tolyl)phosphine (P(o-tol)$_3$) (30 mg, 0.10 mmol, 10 mol-%) in anhydrous degassed DMF (3 mL). Filtration, aqueous work-up, and purification by silica gel column chromatography furnish the title compound (8a).

Step B: Methyl(3S)-4-[3-[bis(2-chloroethyl)amino]-2,6-dimethyl-phenyl]-3-(tert-butoxycarbonylamino)butanoate (8b)

Following the General Procedure of Description 7 (Variant C), methyl(3S)-4-[3-[bis(2-chloroethyl)amino]-2,6-dimethyl-phenyl]-3-(tert-butoxycarbonylamino)butanoate (8b) is prepared from methyl(3S)-4-(3-amino-2,6-dimethyl-phenyl)-3-(tert-butoxycarbonylamino)-butanoate (8a) (336 mg, 1.0 mmol), 2-chloroacetaldehyde (~50 wt-% in water, ~7.87 M) (700 μL, 5.51 mmol), and sodium cyanoborohydride (NaBH$_3$CN) (264 mg of 95% purity=251 mg, 4.0 mmol) in a mixture of methanol (MeOH) (6 mL) and 85 wt-% phosphoric acid (H$_3$PO$_4$) (3 mL). Aqueous work-up and purification by silica gel column chromatography furnish the title compound (8b).

Step C: (3S)-3-Amino-4-[3-[bis(2-chloroethyl)amino]-2,6-dimethyl-phenyl]butanoic acid (8)

Following the General Procedure of Description 8, (3S)-3-amino-4-[3-[bis(2-chloroethyl)amino]-2,6-dimethyl-phenyl]butanoic acid (8) is prepared from methyl(3S)-4-[3-[bis(2-chloroethyl)amino]-2,6-dimethyl-phenyl]-3-(tert-butoxycarbonylamino)butanoate (8b) (461 mg, 1.0 mmol) by hydrolysis in a mixture of concentrated hydrochloric acid (HCl) (about 5 mL) and 1,4-dioxane (about 5 mL) at about 60° C. for about 15 hours to afford the title compound (8) as a solid dihydrochloride salt after isolation using evaporation and lyophilization. The material thus obtained is purified by preparative RP-HPLC using a water/acetonitrile/0.1 vol-% formic acid gradient to afford the title compound (8) as a dihydrochloride salt after final lyophilization of the solvents in the presence of an excess of 1.0 M hydrochloric acid (HCl).

Example 9

(3S)-3-Amino-4-[5-[bis(2-chloroethyl)amino]-2-methyl-phenyl]-3-methyl-butanoic acid (9)

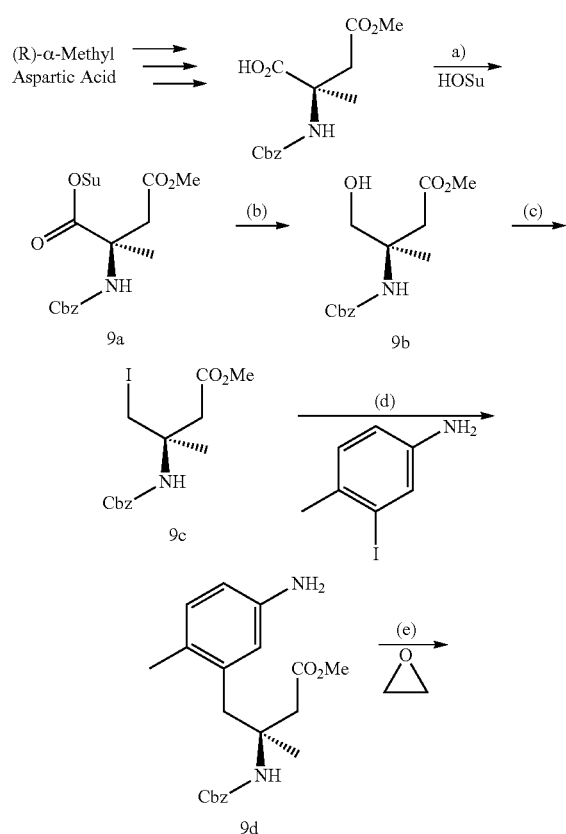

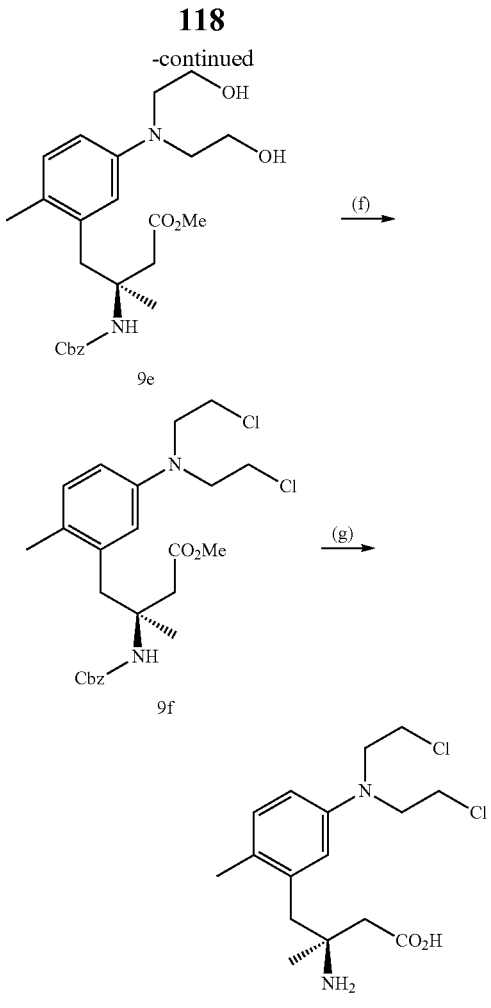

Step A: O$^1$-(2,5-Dioxopyrrolidin-1-yl)O$^4$-methyl (2R)-2-benzyloxycarbonylamino-2-methyl-butanedioate (9a)

Following the General Procedure of Description 12, O$^1$-(2,5-Dioxopyrrolidin-1-yl) O$^4$-methyl(2R)-2-benzyloxycarbonylamino-2-methyl-butanedioate (9a) is prepared from (2R)-2-benzyloxycarbonylamino-4-methoxy-2-methyl-4-oxo-butanoic acid (2.95 g, 10.0 mmol) (preparable in two steps from commercial (R)-α-methyl aspartic acid: i) SOCl$_2$, MeOH, 0° C.→room temperature, 3 h; ii) Cbz-OSu (N-(benzyloxycarbonyloxy)succinimide), aq. K$_3$PO$_4$/toluene, 0° C.→room temperature, 14 h) following a literature known protocol (Gauvreau, et al., International Publication No. WO 2008/088690)), N-hydroxysuccinimide(1-hydroxypyrrolidine-2,5-dione, HOSu, NHS) (1.21 g, 10.5 mmol), and dicyclohexylcarbodiimide (DCC) (2.06 g, 10.0 mmol in ethyl acetate (EtoAc) (40 mL) at room temperature. Filtration and aqueous work-up furnish the title compound (9a) which may be of sufficient purity to be used directly in the next step without further isolation and purification.

Step B: Methyl(3R)-3-benzyloxycarbonylamino-4-hydroxy-3-methyl-butanoate (9b)

Following the General Procedure of Description 13, methyl(3R)-3-benzyloxycarbonylamino-4-hydroxy-3-methyl-butanoate (9b) is prepared through reduction of $O^1$-(2,5-Dioxopyrrolidin-1-yl)$O^4$-methyl(2R)-2-benzyloxycarbonylamino-2-methyl-butanedioate (9a) (3.92 g, 10.0 mmol) with sodium borohydride (NaBH$_4$) (757 mg, 20.0 mmol) in tetrahydrofuran (THF)/water (40 mL/5 mL). Aqueous work-up and purification by silica gel column chromatography furnish the title compound (9b).

Step C: Methyl(3R)-3-benzyloxycarbonylamino-4-iodo-3-methyl-butanoate (9c)

Following the General Procedure of Description 14, methyl(3R)-3-benzyloxycarbonylamino-4-iodo-3-methyl-butanoate (9c) is prepared from methyl(3R)-3-benzyloxycarbonylamino-4-hydroxy-3-methyl-butanoate (9b) (2.81 g, 10.0 mmol), iodine (I$_2$) (2.54 g, 10.0 mmol), triphenylphosphine (PPh$_3$) (2.62 g, 10.0 mmol), and imidazole (681 mg, 10.0 mmol) in anhydrous dichloromethane (DCM) (50 mL). Aqueous reductive work-up and purification by silica gel column chromatography furnish the title compound (9c).

Step D: Methyl(3S)-4-(5-amino-2-methyl-phenyl)-3-benzyloxycarbonylamino-3-methyl-butanoate (9d)

Following the General Procedure of Description 15 (Part A), zinc dust (Zn) (784 mg, 12.0 mmol) is activated with elemental iodine (I$_2$) (76 mg, 0.30 mmol, 15 mol-%) and trimethyl silylchloride (MeSiCl, TMSCl) (38 µL, 32 mg, 0.30 mmol, 15 mol-%) in degassed anhydrous N,N-dimethylformamide (DMF) (6 mL). The zinc insertion product is prepared from methyl(3R)-3-benzyloxycarbonylamino-4-iodo-3-methyl-butanoate (9c) (782 mg, 2.0 mmol) in the presence of additional I$_2$ (76 mg, 0.30 mmol, 15 mol-%) and TMSCl (38 µL, 32 mg, 0.30 mmol, 15 mol-%).

Following the General Procedure of Description 15 (Part B), the zinc insertion product of (9c) is used in situ to cross couple with commercial 3-iodo-4-methyl-aniline (466 mg, 2.0 mmol) in the presence of tris(benzylideneacetone)dipalladium (Pd$_2$(dba)$_3$) (46 mg, 0.05 mmol, 2.5 mol-%) and tris (o-tolyl)phosphine (P(o-tol)$_3$) (60 mg, 0.20 mmol, 10 mol-%) in anhydrous degassed DMF (6 mL). Filtration, aqueous work-up, and purification by silica gel column chromatography furnish the title compound (9d).

Step E: Methyl(3S)-3-benzyloxycarbonylamino-4-[5-(bis(2-hydroxyethyl)amino)-2-methyl-phenyl]-3-methyl-butanoate (9e)

Following General Procedure of Description 16, methyl (3S)-3-benzyloxycarbonylamino-4-[5-(bis(2-hydroxyethyl)amino)-2-methyl-phenyl]-3-methyl-butanoate (9e) is prepared from methyl(3S)-4-(5-amino-2-methyl-phenyl)-3-benzyloxycarbonylamino-3-methyl-butanoate (9d) (3.70 g, 10.0 mmol) through reaction with ethylene oxide (12.5 mL, 11.0 g, 100.0 mmol) in 15 mL of 50 vol.-% aqueous acetic acid (HOAc) for 24 hours at room temperature to yield the title compound (9e) after aqueous work-up and purification by silica gel chromatography.

Step F: Methyl(3S)-3-benzyloxycarbonylamino-4-[5-[bis(2-chloroethyl)amino]-2-methyl-phenyl]-3-methyl-butanoate (9f)

Following the General Procedure of Description 17, methyl(3S)-3-benzyloxycarbonylamino-4-[5-[bis(2-chloroethyl)amino]-2-methyl-phenyl]-3-methyl-butanoate (9f) is prepared from methyl(3S)-4-(5-amino-2-methyl-phenyl)-3-benzyloxycarbonylamino-3-methyl-butanoate (9d) (1.85 g, 5.0 mmol) through reaction with i) thionyl chloride (SOCl$_2$) (3.63 mL, 5.93 g, 50 mmol) in 25 mL of anhydrous chloroform (CHCl$_3$) for 2 hours at reflux temperature (Variant A), ii) phosphoryl chloride (POCl$_3$) (2.34 mL, 3.83 g, 25.0 mmol) in anhydrous benzene (20 mL) for about 5 h at a temperature of about 80° C. (Variant B), iii) methanesulfonyl chloride (MsCl) (1.94 mL, 2.86 g, 25.0 mmol) in anhydrous pyridine (20 mL) for 2 hours at 90° C. (Variant C), or iv) triphenylphosphine (Ph$_3$P) (2.62 g, 10.0 mmol) and carbon tetrachloride (CCl$_4$) (1.45 mL, 2.31 g, 15.0 mmol) in anhydrous dichloromethane (DCM) (20 mL) at room temperature for 8 hours (Variant D) to yield the target compound (9f) after work-up and purification by silica gel column chromatography.

Step G: (3S)-3-Amino-4-[5-[bis(2-chloroethyl) amino]-2-methyl-phenyl]-3-methyl-butanoic acid (9)

Following the General Procedure of Description 8, (3S)-3-amino-4-[5-[bis(2-chloroethyl)amino]-2-methyl-phenyl]-3-methyl-butanoic acid (9) is prepared through hydrolytic deprotection of methyl(3S)-3-benzyloxycarbonylamino-4-[5-[bis(2-chloroethyl)amino]-2-methyl-phenyl]-3-methyl-butanoate (9f) (495 mg, 1.0 mmol) in a mixture of concentrated hydrochloric acid (HCl) (5 mL) and 1,4-dioxane (5 mL) and obtained as a solid dihydrochloride salt after isolation using evaporation and lyophilization. The material thus obtained is purified by preparative RP-HPLC using a water/acetonitrile/0.1 vol-% formic acid gradient to afford the title compound (9) as a dihydrochloride salt after final lyophilization of the solvents in the presence of an excess of 1.0 M hydrochloric acid (HCl).

Example 10

[(2R)-2-amino-3-[5-[bis(2-chloroethyl)amino]-2-methyl-phenyl]propyl]phosphinic acid (10)

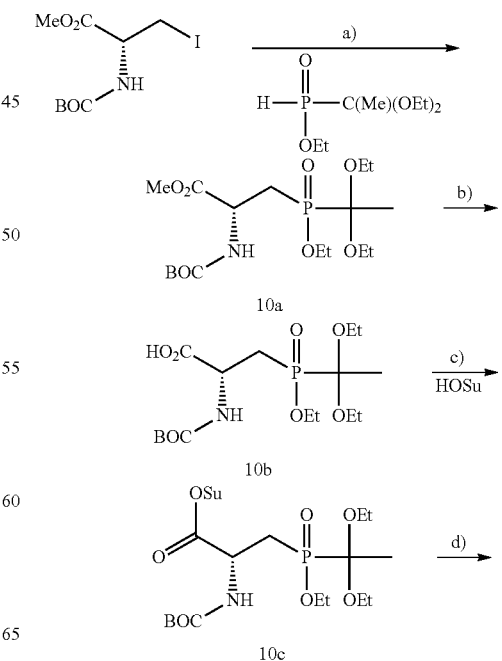

-continued

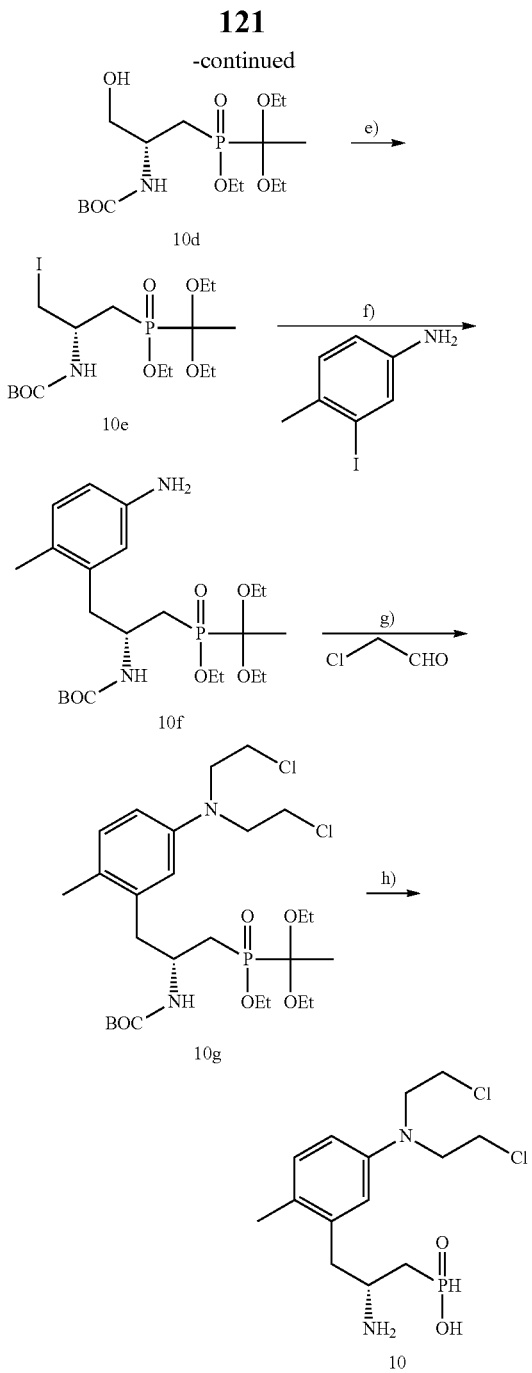

Step A: Methyl(2R)-2-(tert-butoxycarbonylamino)-
3-(1,1-diethoxyethyl(ethoxy)-phosphoryl)propanoate
(10a)

Adapting literature protocols, methyl(2R)-2-(tert-butoxycarbonylamino)-3-(1,1-diethoxyethyl(ethoxy)-phosphoryl) propanoate (10a) is prepared form commercial methyl(2R)-2-(tert-butoxycarbonylamino)-3-iodo-propanoate (Jackson and Perez-Gonzalez, Org. Synth., 2005, 81, 77-88) (3.29 g, 10.0 mmol) and 1-(1-ethoxy-1-ethoxyphosphonoyl-ethoxy)ethane (2.10 g, 10.0 mmol) (preparable from 80-90 wt-% aqueous hypophosphorous acid ($H_3PO_2$), triethylorthoacetate and $BF_3$-etherate ($BF_3.OEt_2$) catalyst; (Baylis, Tetrahedron Lett., 1995, 36(51), 9385-9388) in the presence of sodium hydride (NaH) (60 wt-% suspension in mineral oil) (400 mg, 10.0 mmol) in anhydrous toluene (50 mL). The reaction if followed by TLC and/or LC/MS to completion. Aqueous work-up and purification by silica gel column chromatography furnish the title compound (10a).

Step B: (2R)-2-(tert-Butoxycarbonylamino)-3-(1,1-diethoxyethyl(ethoxy)-phosphoryl)propanoic acid
(10b)

Adapting a literature known protocol (Dayal, et al., Steroids, 1990, 55(5), 233-237), a reaction mixture of methyl (2R)-2-(tert-butoxycarbonylamino)-3-(1,1-diethoxyethyl (ethoxy)-phosphoryl)propanoate (10a) (4.11 g, 10.0 mmol) and commercial lithium hydroxide monohydrate ($LiOH.H_2O$) (839 mg, 20.0 mmol) in a mixture of water (20 mL) and methanol (MeOH) (5 mL) is stirred at room temperature. The reaction is monitored by TLC and/or LC/MS to completion. Acidic aqueous work-up and purification by silica gel column chromatography furnish the title compound (2R)-2-(tert-butoxycarbonylamino)-3-(1,1-diethoxyethyl (ethoxy)phosphoryl)propanoic acid (10b) which may be used directly in the next step without further isolation and purification.

Step C: (2,5-Dioxopyrrolidin-1-yl) (2R)-2-(tert-butoxycarbonylamino)-3-(1,1-diethoxyethyl(ethoxy) phosphoryl)propanoate (10c)

Following the General Procedure of Description 12, (2,5-dioxopyrrolidin-1-yl) (2R)-2-(tert-butoxycarbonylamino)-3-(1,1-diethoxyethyl(ethoxy)phosphoryl)propanoate (10c) is prepared from (2R)-2-(tert-butoxycarbonylamino)-3-(1,1-diethoxyethyl(ethoxy)-phosphoryl)propanoic acid (10b) (3.97 g, 10.0 mmol), N-hydroxysuccinimide(1-hydroxypyrrolidine-2,5-dione, HOSu, NHS) (1.21 g, 10.5 mmol), and dicyclohexylcarbodiimide (DCC) (2.06 g, 10.0 mmol in ethyl acetate (EtoAc) (40 mL) at room temperature. Filtration and aqueous work-up furnish the title compound (10c) which may be of sufficient purity to be used directly in the next step without further isolation and purification.

Step D: tert-Butyl N-[(1R)-1-[(1,1-diethoxyethyl (ethoxy)phosphoryl)methyl]-2-hydroxy-ethyl]carbamate (10d)

Following the General Procedure of Description 13, tert-butyl N-[(1R)-1-[(1,1-diethoxyethyl(ethoxy)phosphoryl) methyl]-2-hydroxy-ethyl]carbamate (10d) is prepared through reduction of (2,5-dioxopyrrolidin-1-yl) (2R)-2-(tert-butoxycarbonylamino)-3-(1,1-diethoxyethyl(ethoxy)phosphoryl)propanoate (10c) (4.95 g, 10.0 mmol) with sodium borohydride ($NaBH_4$) (757 mg, 20.0 mmol) in tetrahydrofuran (THF)/water (40 mL/5 mL). Aqueous work-up and purification by silica gel column chromatography furnish the title compound (10d).

Step E: tert-Butyl N-[(1S)-1-[(1,1-diethoxyethyl (ethoxy)phosphoryl)methyl]-2-iodo-ethyl]carbamate (10e)

Following the General Procedure of Description 14, tert-butyl N-[(1S)-1-[(1,1-diethoxyethyl(ethoxy)phosphoryl)methyl]-2-iodo-ethyl]carbamate (10e) is prepared from tert-butyl N-[(1R)-1-[(1,1-diethoxyethyl(ethoxy)phosphoryl) methyl]-2-hydroxy-ethyl]carbamate (10d) (3.83 g, 10.0 mmol), iodine ($I_2$) (2.54 g, 10.0 mmol), triphenylphosphine (PPh₃) (2.62 g, 10.0 mmol), and imidazole (681 mg, 10.0 mmol) in anhydrous dichloromethane (DCM) (50 mL). Aqueous reductive work-up and purification by silica gel column chromatography furnish the title compound (10e).

Step F: tert-Butyl N-[(1R)-1-[(5-amino-2-methyl-phenyl)methyl]-2-(1,1-diethoxyethyl(ethoxy)phosphoryl)ethyl]carbamate (10f)

Following the General Procedure of Description 15 (Part A), zinc dust (Zn) (784 mg, 12.0 mmol) is activated with elemental iodine (I₂) (76 mg, 0.30 mmol, 15 mol-%) and trimethylsilylchloride (MeSiCl, TMSCl) (38 µL, 32 mg, 0.30 mmol, 15 mol-%) in degassed anhydrous N,N-dimethylformamide (DMF) (6 mL). The zinc insertion product is prepared from tert-butyl N-[(1S)-1-[(1,1-diethoxyethyl(ethoxy)phosphoryl)methyl]-2-iodo-ethyl]carbamate (10e) (987 mg, 2.0 mmol) in the presence of additional I₂ (76 mg, 0.30 mmol, 15 mol-%) and TMSCl (38 µL, 32 mg, 0.30 mmol, 15 mol-%).

Following the General Procedure of Description 15 (Part B), which is used in situ to cross couple with commercial 3-iodo-4-methyl-aniline (466 mg, 2.0 mmol) in the presence of tris(benzylideneacetone)dipalladium (Pd₂(dba)₃) (46 mg, 0.05 mmol, 2.5 mol-%) and tris(o-tolyl)phosphine (P(o-tol)₃) (60 mg, 0.20 mmol, 10 mol-%) in anhydrous degassed DMF (6 mL). Filtration, aqueous work-up, and purification by silica gel column chromatography furnish the title compound (10f).

Step G: tert-Butyl N-[(1R)-1-[[5-[bis(2-chloroethyl)amino]-2-methyl-phenyl]methyl]-2-(1,1-diethoxyethyl(ethoxy)phosphoryl)ethyl]carbamate (10g)

Following the General Procedure of Description 7 (Variant C), tert-butyl N-[(1R)-1-[[5-[bis(2-chloroethyl)amino]-2-methyl-phenyl]methyl]-2-(1,1-diethoxyethyl(ethoxy)phosphoryl)ethyl]carbamate (10g) is prepared from tert-butyl N-[(1R)-1-[(5-amino-2-methyl-phenyl)methyl]-2-(1,1-diethoxyethyl(ethoxy)phosphoryl)ethyl]carbamate (10f) (472 mg, 1.0 mmol), 2-chloroacetaldehyde (~50 wt-% in water, ~7.87 M) (700 µL, 5.51 mmol), and sodium cyanoborohydride (NaBH₃CN) (264 mg of 95% purity=251 mg, 4.0 mmol) in a mixture of methanol (MeOH) (6 mL) and 85 wt-% phosphoric acid (H₃PO₄) (3 mL). Aqueous work-up and purification by silica gel column chromatography furnish the title compound (10g).

Step H: [(2R)-2-Amino-3-[5-[bis(2-chloroethyl)amino]-2-methyl-phenyl]propyl]phosphinic acid (10)

Following the General Procedure of Description 8, [(2R)-2-amino-3-[5-[bis(2-chloroethyl)amino]-2-methyl-phenyl]propyl]phosphinic acid (10) is prepared through hydrolytic deprotection of tert-butyl N-[(1R)-1-[[5-[bis(2-chloroethyl)amino]-2-methyl-phenyl]methyl]-2-(1,1-diethoxyethyl(ethoxy)phosphoryl)ethyl]carbamate (10g) (598 mg, 1.0 mmol) in a mixture of concentrated hydrochloric acid (HCl) (5 mL) and 1,4-dioxane (5 mL) and obtained as a solid dihydrochloride salt after isolation using evaporation and lyophilization. The material thus obtained is purified by preparative RP-HPLC using a water/acetonitrile/0.1 vol-% formic acid gradient to afford the title compound (9) as a dihydrochloride salt after final lyophilization of the solvents in the presence of an excess of 1.0 M hydrochloric acid (HCl).

Example 11

(3R)-3-Amino-4-[5-(2-methylsulfonyloxyethyl(propyl)amino)-2-methyl-phenyl]butanoic acid (11)

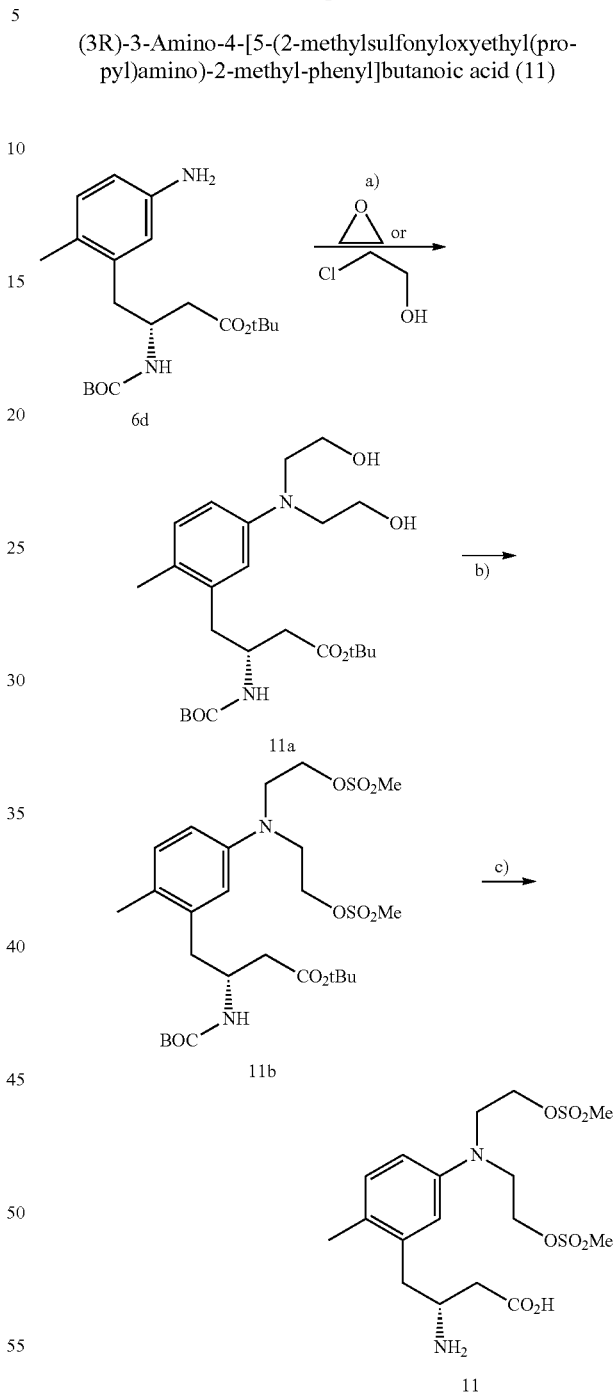

Step A: tert-Butyl(3R)-4-[5-(bis(2-hydroxyethyl)amino)-2-methyl-phenyl]-3-(tert-butoxycarbonylamino)butanoate (11a)

Variant A: Following General Procedure of Description 16, tert-butyl(3R)-4-[5-(bis(2-hydroxyethyl)amino)-2-methyl-phenyl]-3-(tert-butoxycarbonylamino)butanoate (11a) is prepared from tert-butyl(3R)-4-(5-amino-2-methyl-phenyl)-3-

(tert-butoxycarbonylamino)-butanoate (6d) (3.64 g, 10.0 mmol) through reaction with ethylene oxide (12.5 mL, 11.0 g, 100.0 mmol) in 15 mL of 50 vol.-% aqueous acetic acid (HOAc) for 24 hours at room temperature to yield the title compound (11) after aqueous work-up and purification by silica gel chromatography.

Variant B: Adapting literature known protocols (Palmer, et al., J. Med. Chem. 1990, 33(1), 112-121; Coggiola, et al., Bioorg. Med. Chem. Lett., 2005, 15(15), 3551-3554; Verny and Nicolas, J. Label. Cmpds Radiopharm., 1988, 25(9), 949-955; and Lin, Bioorg. Med. Chem. Lett., 2011, 21(3), 940-943), a reaction mixture of tert-butyl(3R)-4-(5-amino-2-methyl-phenyl)-3-(tert-butoxycarbonylamino)-butanoate (6d) (3.64 g, 10.0 mmol) and commercial 2-chloroethanol (2.68 mL, 3.22 g, 40.0 mmol), calcium carbonate ($CaCO_3$) (2.0 g, 20.0 mmol, 2.0 equivalents) in water (about 35 mL), and a catalytic amount of potassium iodide (KI) (166 mg, 1.0 mmol, 10 mol-%) is heated at reflux for about 12-24 hours. The reaction is followed by TLC and/or LC/MS to completion. The pH of the reaction mixture is adjusted to ~7 with a 2.5 M (10 wt-%) aqueous solution of sodium hydroxide (NaOH). Aqueous work-up and purification by silica gel column chromatography furnish the target compound (11a).

Step B: tert-Butyl(3R)-4-[5-(bis(2-methylsulfonyloxyethyl)amino)-2-methyl-phenyl]-3-(tert-butoxycarbonylamino)butanoate (11b)

Following the General Procedures of Description 18, tert-butyl(3R)-4-[5-(bis(2-methylsulfonyloxyethyl)amino)-2-methyl-phenyl]-3-(tert-butoxycarbonylamino)butanoate (1 b) is prepared from tert-butyl(3R)-4-[5-(bis(2-hydroxyethyl) amino)-2-methyl-phenyl]-3-(tert-butoxycarbonylamino)butanoate (11a) (2.26 g, 5.0 mmol) and either methanesulfonyl anhydride ($Ms_2O$) (3.48 g, 20.0 mmol) in the presence of triethylamine (TEA, $Et_3N$) (3.48 mL, 2.54 g, 25.0 mmol) and 4-N,N-(dimethylamino)pyridine (DMAP) (122 mg, 1.0 mmol, 20 mol-%) in anhydrous dichloromethane (DCM) (30 mL) (Variant A) or methanesulfonyl chloride (MsCl) (0.96 mL, 1.44 g, 12.5 mmol) in the presence of triethylamine (TEA, $Et_3N$) (2.10 mL, 1.52 g, 15.0 mmol) or pyridine (4.0 mL, 3.96 g, 50.0 mmol) in anhydrous dichloromethane (DCM) (30 mL) (Variant B) to yield the target compound (11b) after aqueous work-up and purification by silica gel column chromatography.

Step C: (3R)-3-Amino-4-[5-(bis(2-methylsulfonyloxyethyl)amino)-2-methyl-phenyl]butanoic acid (11)

Following the General Procedure of Description 9 (Variant B), (3R)-3-amino-4-[5-(bis(2-methylsulfonyloxyethyl) amino)-2-methyl-phenyl]butanoic acid (11) is prepared from tert-butyl(3R)-4-[5-(bis(2-methylsulfonyloxyethyl)amino)-2-methyl-phenyl]-3-(tert-butoxycarbonylamino)butanoate (11b) (609 mg, 1.0 mmol) in 2 N HCl in diethyl ether (2 N HCl in $Et_2O$) (10 mL, 20 mmol) to yield the target compound (11) as an solid dihydrochloride salt after evaporation of the solvents and lyophilization from an aqueous solution. The material may be further purified by preparative HPLC followed by lyophilization. Optionally, the lyophilization is conducted in the presence of 1 equivalent or an excess of 1.0 M hydrochloric acid (HCl).

Example 12

(3R)-3-Amino-4-[5-(bis(2-bromoethyl)amino)-2-methyl-phenyl]butanoic acid (12)

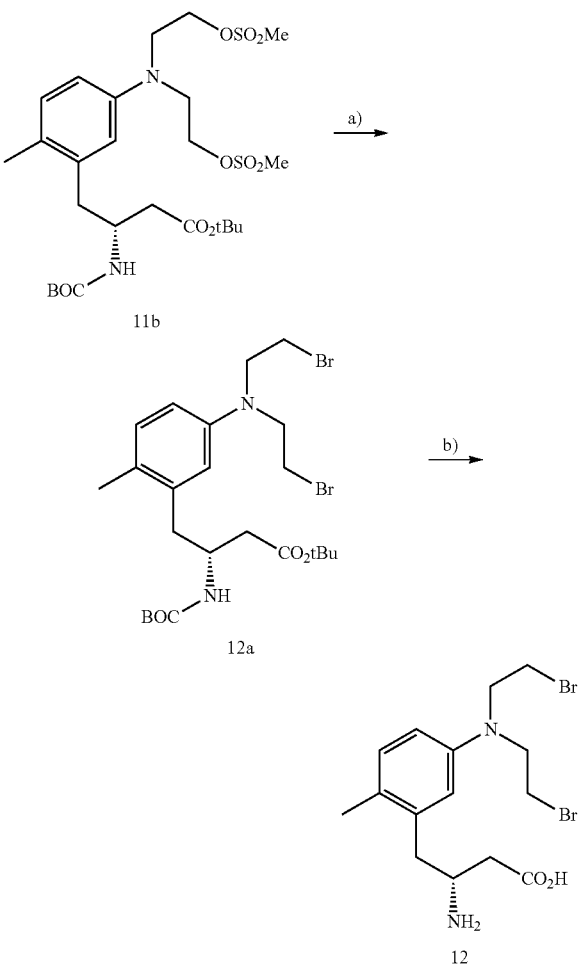

Step A: tert-Butyl(3R)-4-[5-(bis(2-bromoethyl) amino)-2-methyl-phenyl]-3-(tert-butoxycarbonylamino)butanoate (12a)

Following the General Procedure of Description 19, tert-butyl(3R)-4-[5-(bis(2-bromoethyl)amino)-2-methyl-phenyl]-3-(tert-butoxycarbonylamino)butanoate (12a) is prepared from tert-butyl(3R)-4-[5-(bis(2-methylsulfonyloxyethyl)amino)-2-methyl-phenyl]-3-(tert-butoxycarbonylamino)butanoate (11b) (1.22 g, 2.0 mmol) through reaction with lithium bromide (LiBr) (1.74 g, 20.0 mmol) in tetrahydrofuran (THF) (10 mL) at reflux temperature for about 6 h to yield the title compound (12a) after aqueous work-up and purification by silica gel column chromatography with ethyl acetate (EtOAc) and hexane mixtures.

Step B: (3R)-3-Amino-4-[5-(bis(2-bromoethyl) amino)-2-methyl-phenyl]butanoic acid (12)

Following the General Procedure of Description 9 (Variant A), (3R)-3-amino-4-[5-(bis(2-bromoethyl)amino)-2-methylphenyl]butanoic acid (12) is prepared from tert-butyl(3R)-4-[5-(bis(2-bromoethyl)amino)-2-methyl-phenyl]-3-(tert-butoxycarbonylamino)butanoate (12a) (578 mg, 1.0 mmol) through deprotection in a trifluoroacetic acid (TFA)/dichloromethane (DCM) mixture (TFA/DCM=1:1 v/v, 10 mL) at room temperature for about 6 h to yield the target compound (12) as a ditrifluoroacetate salt after evaporation and lyophilization from an aqueous acetonitrile solution. The material may be further purified by preparative RP-HPLC using a water/acetonitrile/0.1 vol-% formic acid gradient followed by lyophilization in the presence of 1.0 equivalent or an excess of 1.0 M hydrobromic acid (HBr).

Example 13

(3R)-3-Amino-4-[5-(2-chloroethyl(2-methylsulfonyloxyethyl)amino)-2-methyl-phenyl]butanoic acid (13)

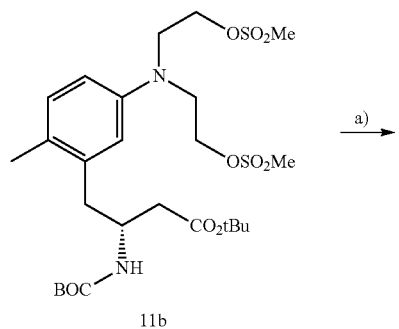

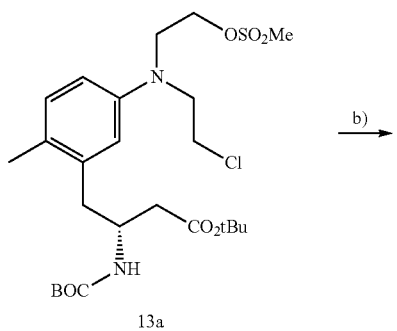

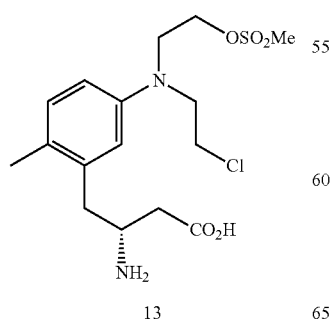

Step A: tert-Butyl(3R)-3-(tert-butoxycarbonylamino)-4-[5-(2-chloroethyl(2-methylsulfonyloxyethyl)amino)-2-methyl-phenyl]butanoate (13a)

Following the General Procedure of Description 19, tert-butyl(3R)-3-(tert-butoxycarbonylamino)-4-[5-(2-chloroethyl(2-methylsulfonyloxyethyl)amino)-2-methyl-phenyl]butanoate (13a) is prepared from tert-butyl(3R)-4-[5-(bis(2-methylsulfonyloxyethyl)amino)-2-methyl-phenyl]-3-(tert-butoxycarbonylamino)butanoate (1 b) (2.44 g, 4.0 mmol) through reaction with lithium chloride (LiCl) (186 mg, 2.2 mmol) in anhydrous acetonitrile (MeCN) (20 mL) at reflux temperature for 1.5 h to yield the title compound (13a) after aqueous work-up and purification by silica gel column chromatography.

Step B: (3R)-3-Amino-4-[5-(2-chloroethyl(2-methylsulfonyloxyethyl)amino)-2-methyl-phenyl]butanoic acid (13)

Following the General Procedure of Description 9 (Variant A), (3R)-3-amino-4-[5-(2-chloroethyl(2-methylsulfonyloxyethyl)amino)-2-methyl-phenyl]butanoic acid (13) is prepared from tert-butyl(3R)-3-(tert-butoxycarbonylamino)-4-[5-(2-chloroethyl(2-methylsulfonyloxyethyl)amino)-2-methyl-phenyl]butanoate (13a) (549 mg, 1.0 mmol) through deprotection in a trifluoroacetic acid (TFA)/dichloromethane (DCM) mixture (TFA/DCM=1:1 v/v, 10 mL) at room temperature for about 6 h to yield the target compound (13) as a ditrifluoroacetate salt after evaporation and lyophilization from an aqueous acetonitrile solution.

Example 14

(3R)-3-Amino-4-[5-(2-bromoethyl(2-chloroethyl)amino)-2-methyl-phenyl]butanoic acid (14)

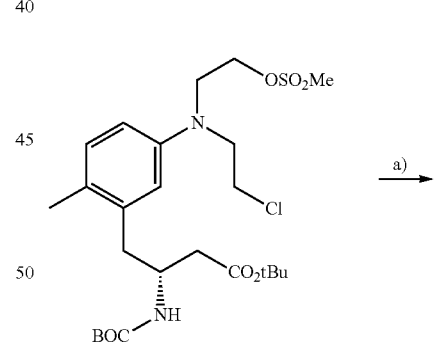

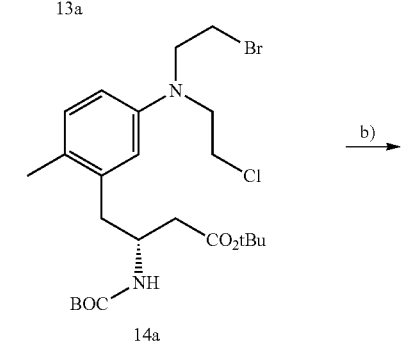

-continued

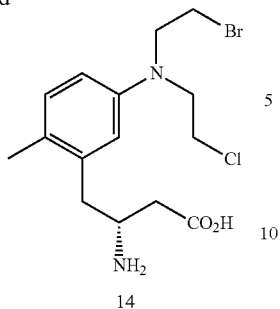

14

Step A: tert-Butyl(3R)-4-[5-(2-bromoethyl(2-chloro-ethyl)amino)-2-methyl-phenyl]-3-(tert-butoxycarbonylamino)butanoate (14a)

Following the General Procedure of Description 19, tert-butyl(3R)-4-[5-(2-bromoethyl(2-chloroethyl)amino)-2-methyl-phenyl]-3-(tert-butoxycarbonylamino)butanoate (14a) is prepared from tert-Butyl(3R)-3-(tert-butoxycarbonylamino)-4-[5-(2-chloroethyl(2-methylsulfonyloxyethyl)amino)-2-methyl-phenyl]butanoate (13a) (1.10 g, 2.0 mmol) through reaction with lithium chloride (LiBr) (191 mg, 2.2 mmol) in anhydrous acetonitrile (MeCN) (10 mL) at reflux temperature for about 2 h to yield the title compound (14a) after aqueous work-up and purification by silica gel column chromatography.

Step B: (3R)-3-Amino-4-[5-(2-bromoethyl(2-chloroethyl)amino)-2-methyl-phenyl]butanoic acid (14)

Following the General Procedure of Description 9 (Variant A), (3R)-3-amino-4-[5-(2-bromoethyl(2-chloroethyl)amino)-2-methyl-phenyl]butanoic acid (14) is prepared from tert-butyl(3R)-4-[5-(2-bromoethyl(2-chloroethyl)amino)-2-methyl-phenyl]-3-(tert-butoxycarbonylamino)butanoate (14a) (533 mg, 1.0 mmol) through deprotection in a trifluoroacetic acid (TFA)/dichloromethane (DCM) mixture (TFA/DCM=1:1 v/v, 10 mL) at room temperature for about 6 h to yield the target compound (14) as a ditrifluoroacetate salt after evaporation and lyophilization from an aqueous acetonitrile solution. The material may be further purified by preparative RP-HPLC followed using a water/acetonitrile/0.1 vol-% formic acid gradient followed by lyophilization.

Example 15

(3R)-3-Amino-4-[5-(2-bromoethyl(2-methylsulfonyloxyethyl)amino)-2-methyl-phenyl]butanoic acid (15)

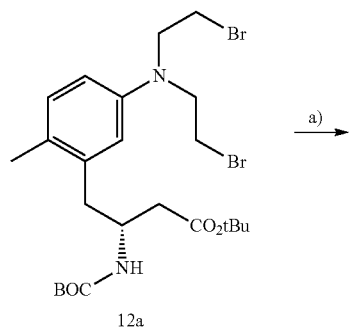

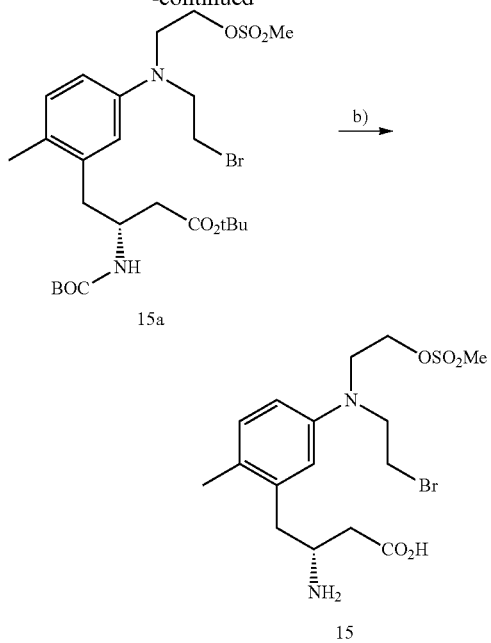

Step A: tert-Butyl(3R)-4-[5-(2-bromoethyl(2-methylsulfonyloxyethyl)amino)-2-methyl-phenyl]-3-(tert-butoxycarbonylamino)butanoate (15a)

Adapting literature known protocols (Emmons and A. F. Ferris, J. Am Chem. Soc. 1953, 75(9), 2257-2257), tert-butyl (3R)-4-[5-(2-bromoethyl(2-methylsulfonyloxyethyl)amino)-2-methyl-phenyl]-3-(tert-butoxycarbonylamino)butanoate (15a) is prepared from tert-butyl(3R)-4-[5-(bis(2-bromoethyl)amino)-2-methyl-phenyl]-3-(tert-butoxycarbonylamino)butanoate (12a) (1.16 g, 2.0 mmol) with silver methanesulfonate (silver mesylate, AgOMs) (365 mg, 1.8 mmol) in anhydrous acetonitrile (MeCN) (8 mL) at reflux temperature for about 1 h under exclusion of light. Aqueous work-up and purification by silica gel column chromatography afford the title compound (15a).

Step B: (3R)-3-Amino-4-[5-(2-bromoethyl(2-methylsulfonyloxyethyl)amino)-2-methyl-phenyl]butanoic acid (15)

Following the General Procedure of Description 9 (Variant A), (3R)-3-amino-4-[5-(2-bromoethyl(2-methylsulfonyloxyethyl)amino)-2-methyl-phenyl]butanoic acid (15) is prepared from tert-butyl(3R)-4-[5-(2-bromoethyl(2-methylsulfonyloxyethyl)amino)-2-methyl-phenyl]-3-(tert-butoxycarbonylamino)butanoate (15a) (594 mg, 1.0 mmol) through deprotection in a trifluoroacetic acid (TFA)/dichloromethane (DCM) mixture (TFA/DCM=1:1 v/v, 10 mL) at room temperature for about 6 h to yield the target compound (15) as a ditrifluoroacetate salt after evaporation and lyophilization from an aqueous acetonitrile solution. The material may be further purified by preparative RP-HPLC followed using a water/acetonitrile/0.1 vol-% formic acid gradient followed by lyophilization.

Example 16

(3S)-3-Amino-4-[[5-[bis(2-chloroethyl)amino]-2-methyl-phenyl]amino]-4-oxo-butanoic acid (16)

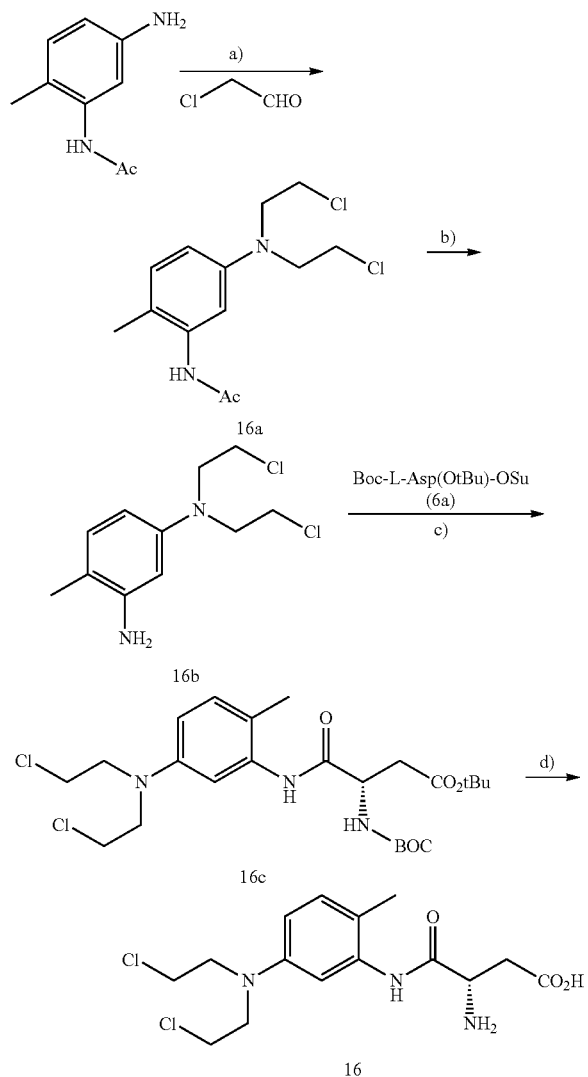

Step A: N-[5-[Bis(2-chloroethyl)amino]-2-methyl-phenyl]acetamide (16a)

Following the General Procedure of Description 7 (Variant A), N-[5-[bis(2-chloroethyl)amino]-2-methyl-phenyl]acetamide (16a) is prepared from commercial N-(5-amino-2-methylphenyl)acetamide (161 mg, 1.0 mmol), 2-chloroacetaldehyde (~50 wt-% in water, ~7.87 M) (700 μL, 5.51 mmol), and sodium cyanoborohydride (NaBH$_3$CN) (264 mg of 95% purity=251 mg, 4.0 mmol) in a mixture of methanol (MeOH) (6 mL) and trifluoroacaetic acid (3 mL). Aqueous work-up and purification by silica gel column chromatography furnish the title compound (16a).

Step B: N$^1$,N$^1$-Bis(2-chloroethyl)-4-methyl-benzene-1,3-diamine (16b)

Following the General Procedure of Description 8, N$^1$,N$^1$-bis(2-chloroethyl)-4-methyl-benzene-1,3-diamine (16b) is prepared from methyl N-[5-[bis(2-chloroethyl)amino]-2-methyl-phenyl]acetamide (16a) (289 mg, 1.0 mmol) by hydrolysis in concentrated hydrochloric acid (HCl) (about 5 mL) at reflux for about 2 hours to afford the title compound (16b) as a solid dihydrochloride salt after isolation using evaporation and lyophilization. The material thus obtained can be used directly in the nest step without further isolation and purification in the next step.

Step C: tert-Butyl(3S)-4-[[5-[bis(2-chloroethyl)amino]-2-methyl-phenyl]amino]-3-(tert-butoxycarbonylamino)-4-oxo-butanoate (16c)

Adapting a literature known protocol (Levi and Weed, U.S. Pat. No. 3,235,594 (1966)), to a solution of O$^1$-(2,5-Dioxopyrrolidin-1-yl)O$^4$-tert-butyl(2S)-2-(tert-butoxycarbonylamino)-butanedioate (Boc-L-Asp(Osu)-OtBu) (6a) (386 mg, 1.0 mmol) in anhydrous acetonitrile (MeCN) (10 mL) is added N,N-bis(2-chloroethyl)-4-methyl-benzene-1,3-diamine (16b) as a bis hydrochloride salt (320 mg, 1.0 mmol) followed by neat triethylamine (Et$_3$N, TEA) (321 μL, 233 mg, 2.3 mmol). The reaction mixture is stirred for about 12 h at room temperature. The reaction is followed by TLC and/or LC/MS to completion. The volatile solvents are removed under reduced pressure using a rotary evaporator. Aqueous work-up and purification by silica gel column chromatography furnish the target compound (16c).

Step D: (3S)-3-Amino-4-[[5-[bis(2-chloroethyl)amino]-2-methyl-phenyl]amino]-4-oxo-butanoic acid (16)

Following the General Procedure of Description 9 (Variant B), (3S)-3-amino-4-[[5-[bis(2-chloroethyl)amino]-2-methyl-phenyl]amino]-4-oxo-butanoic acid (16) is prepared from tert-butyl(3S)-4-[[5-[bis(2-chloroethyl)amino]-2-methyl-phenyl]amino]-3-(tert-butoxycarbonylamino)-4-oxo-butanoate (16c) (518 mg, 1.0 mmol) in 2.0 N HCl in diethyl ether (2.0 N HCl in Et$_2$O) (10 mL, 20 mmol) to yield the target compound (15) as an solid dihydrochloride salt after evaporation of the solvents and lyophilization from an aqueous solution. The material may be further purified by preparative HPLC followed by lyophilization. Optionally, the lyophilization is conducted in the presence of 1 equivalent of 1.0 M hydrochloric acid (HCl).

Example 17

(3S)-3-Amino-4-[2-[bis(2-chloroethyl)amino]phenoxy]butanoic acid (17)

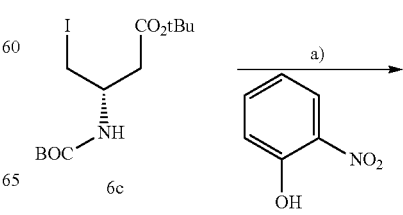

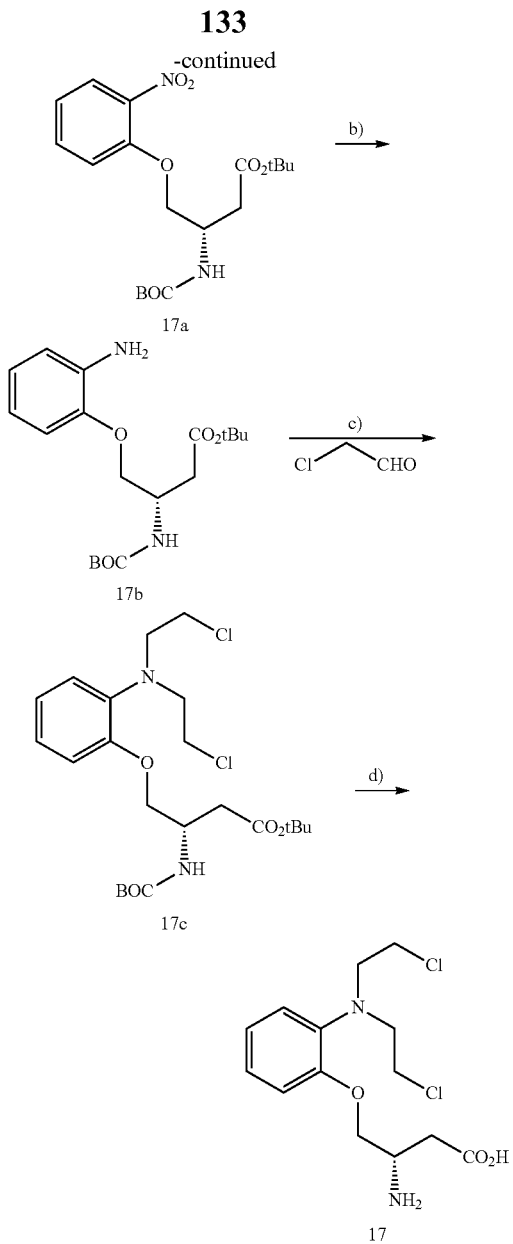

nylamino)butanoate (17b) is prepared by catalytic reduction of tert-butyl(3S)-3-(tert-butoxycarbonylamino)-4-(2-nitrophenoxyl)butanoate (17a) (793 mg, 2.0 mmol) in the presence of 10 wt-% palladium on charcoal (Pd/C) containing ~50 wt-% water (~350 mg) in methanol (MeOH) (20 mL) and under an atmosphere of hydrogen (~15 psi, $H_2$-balloon). The crude material, after filtration over Celite® 545, may be used directly and without further isolation in the next step or may be purified by silica gel chromatography to afford the title compound (17b).

Step C: tert-Butyl(3S)-4-[2-[bis(2-chloroethyl)amino]phenoxy]-3-(tert-butoxycarbonyl-amino)butanoate (17c)

Following the General Procedure of Description 7 (Variant C), tert-butyl(3S)-4-[2-[bis(2-chloroethyl)amino]phenoxy]-3-(tert-butoxycarbonyl-amino)butanoate (17c) is prepared from tert-butyl(3S)-4-(2-aminophenoxy)-3-(tert-butoxycarbonylamino)butanoate (17b) (733 mg, 2.0 mmol), 2-chloroacetaldehyde (~50 wt-% in water, ~7.87 M) (1.27 mL, 10.0 mmol), and sodium cyanoborohydride ($NaBH_3CN$) (529 mg of 95% purity=503 mg, 8.0 mmol) in a mixture of methanol (MeOH) (10 mL) and 85 wt-% phosphoric acid ($H_3PO_4$) (3 mL). Aqueous work-up and purification by silica gel column chromatography furnish the title compound (17c).

Step D: (3S)-3-Amino-4-[2-[bis(2-chloroethyl)amino]phenoxy]butanoic acid (17)

Following the General Procedure of Description 9 (Variant B), (3S)-3-amino-4-[2-[bis(2-chloroethyl)amino]phenoxy]butanoic acid (17) is prepared from tert-butyl(3S)-4-[2-[bis(2-chloroethyl)amino]phenoxy]-3-(tert-butoxycarbonyl-amino)butanoate (17c) (491 mg, 1.0 mmol) in 2.0 N HCl in diethyl ether (2.0 N HCl in $Et_2O$) (10 mL, 20 mmol) to yield the target compound (17) as an solid dihydrochloride salt after evaporation of the solvents and lyophilization from an aqueous solution. The material may be further purified by preparative HPLC followed by lyophilization. Optionally, the lyophilization is conducted in the presence of 1 equivalent of 1.0 M hydrochloric acid (HCl).

Example 18

(3R)-3-Amino-5-[5-[bis(2-chloroethyl)amino]-2-methyl-phenyl]pentanoic acid (18)

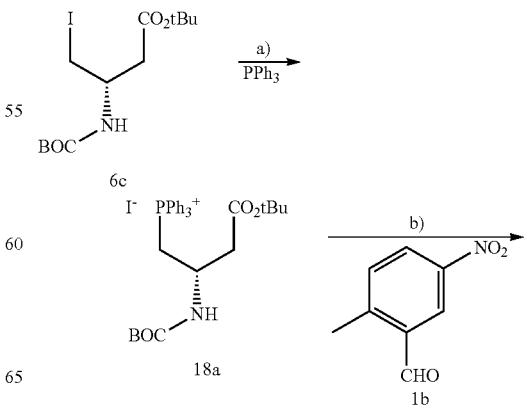

Step A: tert-Butyl(3S)-3-(tert-butoxycarbonylamino)-4-(2-nitrophenoxyl)butanoate (17a)

Adapting literature procedures (Bookster, et al., International Publication No. WO 2010/047982), tert-butyl(3S)-3-(tert-butoxycarbonylamino)-4-(2-nitrophenoxyl)butanoate (17a) is prepared from tert-butyl(3S)-3-(tert-butoxycarbonylamino)-4-iodo-butanoate (6c) (1.16 g, 3.0 mmol) and commercial 2-nitrophenol (558 mg, 4.0 mmol) in the presence of cesium carbonate ($Cs_2CO_3$) (1.63 g, 5.0 mmol) in anhydrous N,N-dimethylformamide (DMF) (10 mL) at 50° C. (oil bath). Aqueous work-up and purification by silica gel chromatography furnish the title compound (17a).

Step B: tert-Butyl(3S)-4-(2-aminophenoxy)-3-(tert-butoxycarbonylamino)butanoate (17b)

Following the General Procedure of Description 6 (Variant B), tert-butyl(3S)-4-(2-aminophenoxy)-3-(tert-butoxycarbo-

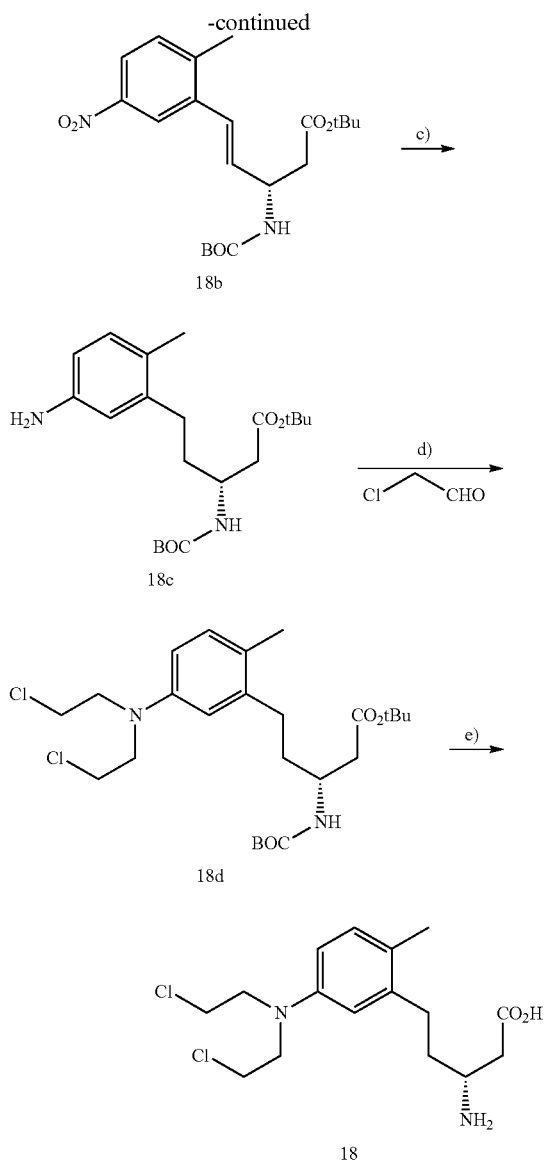

nylamino)-5-(2-methyl-5-nitro-phenyl)pent-4-enoate (18b) is prepared from [(2S)-4-tert-butoxy-2-(tert-butoxycarbonylamino)-4-oxo-butyl]-triphenyl-phosphonium iodide (18a) (1.30 g, 2.0 mmol), 2-methyl-5-nitro-benzaldehyde (1b) (495 mg, 3.0 mmol) (commercial or prepared in two steps from commercial 2-methyl-5-nitro benzoic acid (i) $BH_3.SMe_2$, THF, reflux, ii) $MnO_2$, DCM, room temperature) as described in Example 1) with a commercial ~1.0 M solution of potassium tert-butoxide (KOtBu) (3.0 mL, 3.0 mmol) in anhydrous tetrahydrofuran (THF) (10 mL) at with gradual warming from 0° (ice bath) to room temperature for 24 hours. Aqueous work and purification by silica gel column chromatography furnish the title compound (18b) as a mixture of geometric isomers ((E)/(Z)-isomers).

Step C: tert-Butyl(3R)-5-(5-amino-2-methyl-phenyl)-3-(tert-butoxycarbonylamino)-pentanoate (18c)

Following the General Procedure of Description 6 (Variant B), tert-butyl(3R)-5-(5-amino-2-methyl-phenyl)-3-(tert-butoxycarbonylamino)-pentanoate (18c) is prepared by catalytic reduction of tert-butyl(3S)-3-(tert-butoxycarbonylamino)-5-(2-methyl-5-nitro-phenyl)pent-4-enoate (18b) (813 mg, 2.0 mmol) in the presence of 10 wt-% palladium on charcoal (Pd/C) containing ~50 wt-% water (~40 mg) in methanol (MeOH) (20 mL) and under an atmosphere of hydrogen (~15 psi, $H_2$-balloon). The crude material, after filtration over Celite® 545, may be used directly and without further isolation in the next step or may be purified by silica gel chromatography to afford the title compound (18c).

Step D: tert-Butyl(3R)-5-[5-[bis(2-chloroethyl)amino]-2-methyl-phenyl]-3-(tert-butoxycarbonylamino)pentanoate (18d)

Following the General Procedure of Description 7 (Variant C), tert-butyl(3R)-5-[5-[bis(2-chloroethyl)amino]-2-methyl-phenyl]-3-(tert-butoxycarbonylamino)pentanoate (18d) is prepared from tert-butyl(3R)-5-(5-amino-2-methyl-phenyl)-3-(tert-butoxycarbonylamino)-pentanoate (18c) (757 mg, 2.0 mmol), 2-chloroacetaldehyde (~50 wt-% in water, ~7.87 M) (1.27 mL, 10.0 mmol), and sodium cyanoborohydride ($NaBH_3CN$) (529 mg of 95% purity=503 mg, 8.0 mmol) in a mixture of methanol (MeOH) (10 mL) and 85 wt-% phosphoric acid ($H_3PO_4$) (3 mL). Aqueous work-up and purification by silica gel column chromatography furnish the title compound (18d).

Step D: (3R)-3-Amino-5-[5-[bis(2-chloroethyl)amino]-2-methyl-phenyl]pentanoic acid (18)

Following the General Procedure of Description 9 (Variant B), (3R)-3-amino-5-[5-[bis(2-chloroethyl)amino]-2-methyl-phenyl]pentanoic acid (18) is prepared from tert-butyl(3R)-5-[5-[bis(2-chloroethyl)amino]-2-methyl-phenyl]-3-(tert-butoxycarbonylamino)pentanoate (18d) (504 mg, 1.0 mmol) in 2.0 N HCl in diethyl ether (2.0 N HCl in $Et_2O$) (10 mL, 20 mmol) to yield the target compound (18) as an solid dihydrochloride salt after evaporation of the solvents and lyophilization from an aqueous solution. The material may be further purified by preparative HPLC followed by lyophilization. Optionally, the lyophilization is conducted in the presence of 1 equivalent of 1.0 M hydrochloric acid (HCl).

Step A: [(2S)-4-tert-Butoxy-2-(tert-butoxycarbonylamino)-4-oxo-butyl]-triphenyl-phosphonium iodide (18a)

Adapting a literature procedure (Rémond, et al, J. Org. Chem., J. Org. Chem. 2012, 77, 7579-7587), [(2S)-4-tert-butoxy-2-(tert-butoxycarbonylamino)-4-oxo-butyl]-triphenyl-phosphonium iodide (18a) is prepared from tert-butyl (3S)-3-(tert-butoxycarbonylamino)-4-iodo-butanoate (6c) (1.16 g, 3.0 mmol) and triphenylphosphine ($Ph_3P$) (1.81 g, 6.9 mmol) at 80° C. under a nitrogen atmosphere. After cooling to room temperature and trituration with toluene and diethyl ether ($Et_2O$), the residue is purified by silica gel column chromatography with an acetone and hexane mixture.

Step B: tert-Butyl(3S)-3-(tert-butoxycarbonylamino)-5-(2-methyl-5-nitro-phenyl)pent-4-enoate (18b)

Adapting a literature procedure (Jandeleit et al., U.S. Pat. No. 8,168,617 (2012)), tert-butyl(3S)-3-(tert-butoxycarbo-

Example 19

(3R)-3-Amino-4-[5-(2-chloroethyl(chloromethyl)carbamoyl)oxy-2-methyl-phenyl]butanoic acid (19)

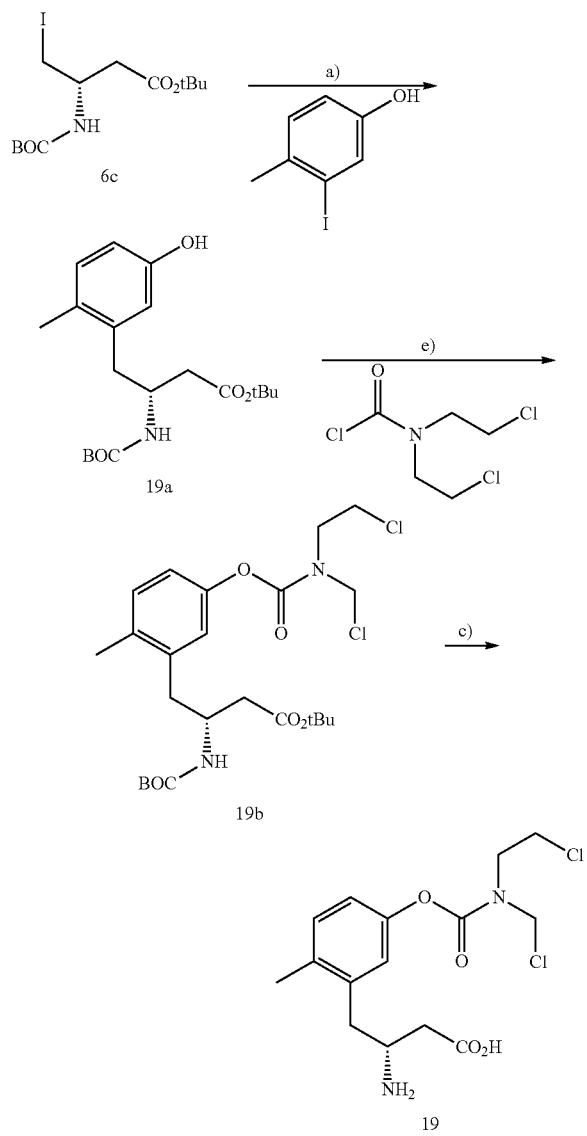

Step A: tert-Butyl(3R)-3-(tert-butoxycarbonylamino)-4-(5-hydroxy-2-methyl-phenyl)-butanoate (19a)

Following the General Procedure of Description 15 (Part A), zinc dust (Zn) (392 mg, 6.0 mmol) is activated with elemental iodine (I$_2$) (38 mg, 0.15 mmol, 15 mol-%) and trimethylsilylchloride (MeSiCl, TMSCl) (19 µL, 16 mg, 0.15 mmol, 15 mol-%) in degassed anhydrous N,N-dimethylformamide (DMF) (3 mL). The zinc insertion product is prepared from tert-butyl(3S)-3-(tert-butoxycarbonylamino)-4-iodo-butanoate (6c) (385 mg, 1.0 mmol) in the presence of additional I$_2$ (38 mg, 0.15 mmol, 15 mol-%) and TMSCl (19 µL, 16 mg, 0.15 mmol, 15 mol-%). Following the General Procedure of Description 15 (Part B), the zinc insertion product of (6c) is used in situ to cross couple with commercial 3-iodo-4-methyl-phenol (234 mg, 1.0 mmol) in the presence of tris(benzylideneacetone)dipalladium (Pd$_2$(dba)$_3$) (23 mg, 0.025 mmol, 2.5 mol-%) and tris(o-tolyl)phosphine (P(o-tol)$_3$) (30 mg, 0.10 mmol, 10 mol-%) in anhydrous degassed DMF (3 mL). Filtration, aqueous work-up, and purification by silica gel column chromatography furnish the title compound (19a).

Step B: tert-Butyl(3R)-3-(tert-butoxycarbonylamino)-4-[5-(2-chloroethyl(chloromethyl)-carbamoyl)oxy-2-methyl-phenyl]butanoate (19b)

Adapting a literature known protocol (Fex, et al., U.S. Pat. No. 3,299,104), tert-butyl(3R)-3-(tert-butoxycarbonylamino)-4-[5-(2-chloroethyl(chloromethyl)-carbamoyl)oxy-2-methyl-phenyl]butanoate (19b) is prepared through carbamoylation of tert-butyl(3S)-3-(tert-butoxycarbonylamino)-4-(5-hydroxy-2-methyl-phenyl)-butanoate (19a) (731 mg, 2.0 mmol) with commercial N,N-bis(2-chloroethyl)carbamoyl chloride (439 µL, 614 mg, 3.0 mmol) in anhydrous pyridine (15 mL) at about 0° C. The reaction mixture is stirred with gradual warming to room temperature. The reaction is monitored by TLC and/or LC/MS to completion. Excess of the carbamoyl chloride is destroyed with crushed ice. Aqueous work-up followed by purification through silica gel column chromatography afford the title compound (19b).

Step C: (3R)-3-Amino-4-[5-(2-chloroethyl(chloromethyl)carbamoyl)oxy-2-methyl-phenyl]butanoic acid (19)

Following the General Procedure of Description 9 (Variant B), (3R)-3-amino-4-[5-(2-chloroethyl(chloromethyl)carbamoyl)oxy-2-methyl-phenyl]butanoic acid (19) is prepared from tert-butyl(3R)-3-(tert-butoxycarbonylamino)-4-[5-(2-chloroethyl(chloromethyl)-carbamoyl)oxy-2-methyl-phenyl]butanoate (19b) (519 mg, 1.0 mmol) in 2.0 N HCl in diethyl ether (2.0 N HCl in Et$_2$O) (10 mL, 20 mmol) to yield the target compound (19) as an solid dihydrochloride salt after evaporation of the solvents and lyophilization from an aqueous solution. The material may be further purified by preparative HPLC followed by lyophilization. Optionally, the lyophilization is conducted in the presence of 1 equivalent of 1.0 M hydrochloric acid (HCl).

Example 20

(3R)-3-Amino-4-[5-[bis(2-chloroethyl)carbamoyloxymethyl]-2-nitro-phenyl]butanoic acid (20)

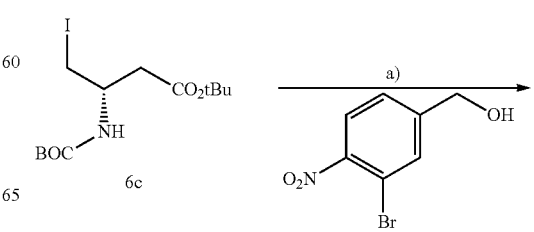

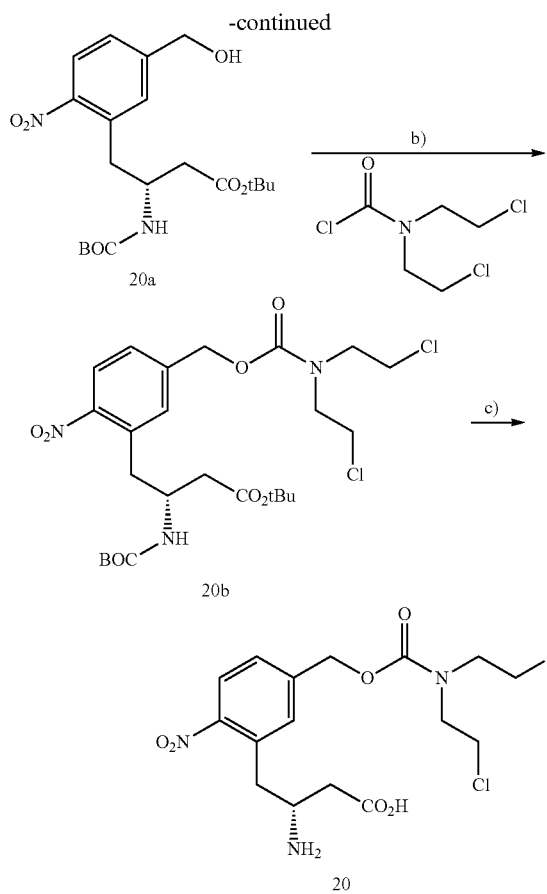

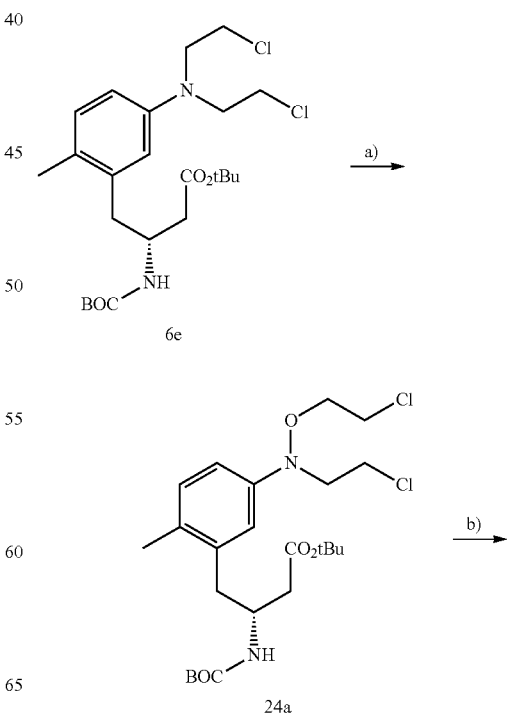

lamino)butanoate (20b) is prepared through carbamoylation of tert-butyl(3R)-3-(tert-butoxycarbonylamino)-4-[5-(hydroxymethyl)-2-nitro-phenyl]butanoate (20a) (731 mg, 2.0 mmol) with commercial N,N-bis(2-chloroethyl)carbamoyl chloride (439 μL, 614 mg, 3.0 mmol) in anhydrous pyridine (15 mL) at about 0° C. The reaction mixture is stirred with gradual warming to room temperature. The reaction is monitored by TLC and/or LC/MS to completion. Excess of the carbamoyl chloride is destroyed with crushed ice. Aqueous work-up followed by purification through silica gel column chromatography afford the title compound (20b).

Step C: (3R)-3-Amino-4-[5-[bis(2-chloroethyl)carbamoyloxymethyl]-2-nitro-phenyl]butanoic acid (20)

Following the General Procedure of Description 9 (Variant B), (3R)-3-amino-4-[5-[bis(2-chloroethyl)carbamoyloxymethyl]-2-nitro-phenyl]butanoic acid (20) is prepared from tert-Butyl(3R)-4-[5-[bis(2-chloroethyl)carbamoyloxymethyl]-2-nitro-phenyl]-3-(tert-butoxycarbonylamino)butanoate (20b) (578 mg, 1.0 mmol) in 2.0 N HCl in diethyl ether (2.0 N HCl in Et$_2$O) (10 mL, 20 mmol) to yield the target compound (20) as an solid dihydrochloride salt after evaporation of the solvents and lyophilization from an aqueous solution. The material may be further purified by preparative HPLC followed by lyophilization. Optionally, the lyophilization is conducted in the presence of 1 equivalent of 1.0 M hydrochloric acid (HCl).

Example 21

(3R)-3-amino-4-[5-(2-chloroethoxy(2-chloroethyl)amino)-2-methyl-phenyl]butanoic acid (21)

Step A: tert-Butyl(3R)-3-(tert-butoxycarbonylamino)-4-[5-(hydroxymethyl)-2-nitro-phenyl]butanoate (20a)

Following the General Procedure of Description 15 (Part A), zinc dust (Zn) (392 mg, 6.0 mmol) is activated with elemental iodine (I$_2$) (38 mg, 0.15 mmol, 15 mol-%) and trimethyl silylchloride (MeSiCl, TMSCl) (19 μL, 16 mg, 0.15 mmol, 15 mol-%) in degassed anhydrous N,N-dimethylformamide (DMF) (3 mL). The zinc insertion product is prepared from tert-butyl(3S)-3-(tert-butoxycarbonylamino)-4-iodo-butanoate (6c) (385 mg, 1.0 mmol) in the presence of additional I$_2$ (38 mg, 0.15 mmol, 15 mol-%) and TMSCl (19 μL, 16 mg, 0.15 mmol, 15 mol-%).

Following the General Procedure of Description 15 (Part A), the zinc insertion product of (6c) is used in situ to cross couple with commercial (3-bromo-4-nitro-phenyl)methanol (232 mg, 1.0 mmol) in the presence of tris(benzylideneacetone)dipalladium (Pd$_2$(dba)$_3$) (23 mg, 0.025 mmol, 2.5 mol-%) and tris(o-tolyl)phosphine (P(o-tol)$_3$) (30 mg, 0.10 mmol, 10 mol-%) in anhydrous degassed DMF (3 mL). Filtration, aqueous work-up, and purification by silica gel column chromatography furnish the title compound (20a).

Step B: tert-Butyl(3R)-4-[5-[bis(2-chloroethyl)carbamoyloxymethyl]-2-nitro-phenyl]-3-(tert-butoxycarbonylamino)butanoate (20b)

Adapting a literature known protocol (Fex, et al., U.S. Pat. No. 3,299,104), tert-butyl(3R)-4-[5-[bis(2-chloroethyl)carbamoyloxymethyl]-2-nitro-phenyl]-3-(tert-butoxycarbony-

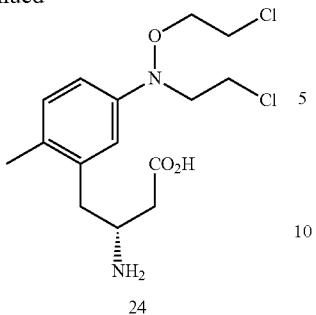

24

Step A: tert-Butyl(3R)-3-(tert-butoxycarbonylamino)-4-[5-(2-chloroethoxy(2-chloroethyl)amino)-2-methyl-phenyl]butanoate (21a)

Adapting literature known protocols (Tercel, et al., J. Med. Chem. 1995, 38, 1247-1252; Kirkpatrick, U.S. Pat. No. 5,602,278; Kirkpatrick, et al., Anti-Cancer Drugs, 1994, 5, 467-472; and Kirkpatrick, et al., U.S. Pat. No. 7,399,785), tert-butyl(3R)-3-(tert-butoxycarbonylamino)-4-[5-(2-chloroethoxy(2-chloroethyl)amino)-2-methyl-phenyl]butanoate (21a) is prepared by adding 3-chloroperoxybenzoic acid (1.42 g, 80 wt-%, 6.6 mmol) to a solution of tert-butyl(3R)-4-[5-[bis(2-chloroethyl)amino]-2-methyl-phenyl]-3-(tert-butoxycarbonylamino)butanoate (6e) (2.43 g, 5.0 mmol) in dichloromethane (DCM) (30 mL) at about room temperature for about 2 h. The reaction is followed by TLC and/or LC/MS to completion. After quenching with a saturated aqueous solution of sodium hydrogencarbonate (NaHCO₃), the reaction mixture is extracted with DCM (3×). Further aqueous work-up and purification by silica gel column chromatography yield the title compound (21a).

Step B: (3R)-3-amino-4-[5-(2-chloroethoxy(2-chloroethyl)amino)-2-methyl-phenyl]butanoic acid (21)

Following the General Procedure of Description 9 (Variant B), (3R)-3-amino-4-[5-(2-chloroethoxy(2-chloroethyl)amino)-2-methyl-phenyl]butanoic acid (21) is prepared from tert-butyl(3R)-3-(tert-butoxycarbonylamino)-4-[5-(2-chloroethoxy(2-chloroethyl)amino)-2-methyl-phenyl]butanoate (21a) (506 mg, 1.0 mmol) in 2 N HCl in diethyl ether (2.0 N HCl in Et₂O) (10 mL, 20 mmol) to yield the target compound (21) as an solid dihydrochloride salt after evaporation of the solvents and lyophilization from an aqueous solution. The material may be further purified by preparative HPLC followed by lyophilization. Optionally, the lyophilization is conducted in the presence of 1 equivalent or an excess of 1.0 M hydrochloric acid (HCl).

Example 22

4-[1-(Aminomethyl)-3-hydroxy-1-methyl-3-oxopropyl]-N,N-bis(2-chloroethyl)-3-methyl-benzeneamine oxide (22)

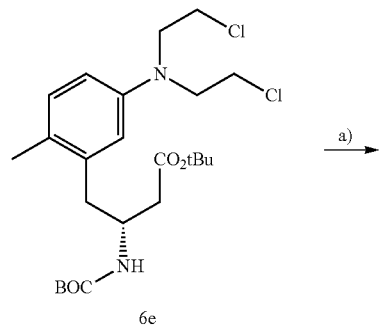

6e

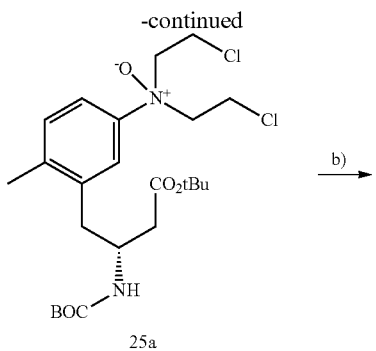

25a

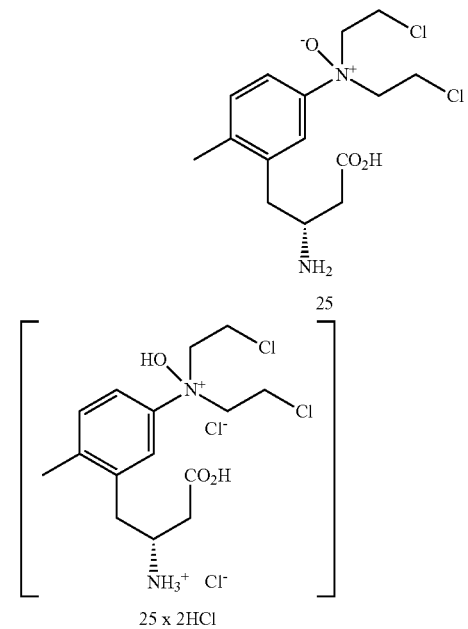

Step A: 3-[(2R)-4-tert-Butoxy-2-(tert-butoxycarbonylamino)-4-oxo-butyl]-N,N-bis(2-chloroethyl)-4-methyl-benzeneamine oxide (22a)

Adapting literature known protocols (Tercel, et al., J. Med. Chem. 1995, 38, 1247-1252; and Kirkpatrick, et al., U.S. Pat. No. 7,399,785), peracetic acid (H₃CCO₃H) is freshly prepared by adding hydrogen peroxide (H₂O₂) (1.5 mL of a 35 wt-% aqueous solution, 14.0 mmol) dropwise to acetic anhydride (Ac₂O) (1.52 mL, 1.65 g, 16.0 mmol). When the reaction mixture is homogeneous, a solution of tert-butyl(3R)-4-[5-[bis(2-chloroethyl)amino]-2-methyl-phenyl]-3-(tert-butoxycarbonylamino)butanoate (6e) (1.61 g, 3.29 mmol) in dichloromethane (DCM) (20 mL) is added with vigorous stirring at about room temperature for about 2 h. The reaction is followed by TLC and/or LC/MS to completion. The reaction is quenched with 2.0 N hydrochloric acid (HCl), and the aqueous layer separated and repeatedly washed with DCM to the organic extracts are colorless. The aqueous phase is evaporated to dryness under reduced pressure, dried over anhydrous sodium sulfate (Na₂SO₄), and partially reduced in volume. Diethyl ether (Et₂O) is added to separate the title compound 3-[(2R)-4-tert-butoxy-2-(tert-butoxycarbonylamino)-4-oxo-butyl]-N,N-bis(2-chloroethyl)-4-methyl-benzeneamine oxide (22a). The material may be purified by silica gel column chromatography.

143

Step B: 3-[(2R)-2-Amino-4-hydroxy-4-oxo-butyl]-N,N-bis(2-chloroethyl)-4-methyl-benzeneamine oxide (22)

Following the General Procedure of Description 9 (Variant B), 3-[(2R)-2-amino-4-hydroxy-4-oxo-butyl]-N,N-bis(2-chloroethyl)-4-methyl-benzeneamine oxide (22) is prepared from 3-[(2R)-4-tert-Butoxy-2-(tert-butoxycarbonylamino)-4-oxo-butyl]-N,N-bis(2-chloroethyl)-4-methyl-benzeneamine oxide (22a) (506 mg, 1.0 mmol) in 2 N HCl in diethyl ether (2 N HCl in Et$_2$O) (10 mL, 20 mmol) to yield the target compound (22) as an solid dihydrochloride salt (22.2HCl) after evaporation of the solvents and lyophilization from an aqueous solution. The material may be further purified by preparative HPLC followed by lyophilization. Optionally, the lyophilization is conducted in the presence of 1 equivalent or an excess of 1.0 M hydrochloric acid (HCl).

Example 23

(3R)-3-Amino-4-[2-[bis(2-chloroethyl)carbamoyl]phenyl]butanoic acid (23)

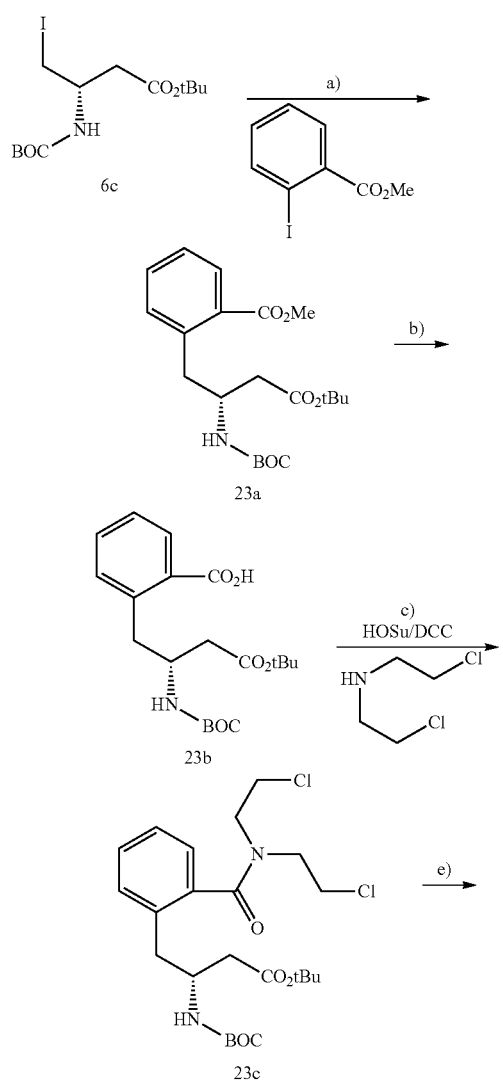

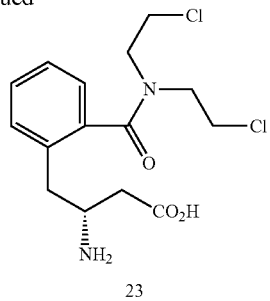

Step A: Methyl 2-[(2R)-4-tert-butoxy-2-(tert-butoxycarbonylamino)-4-oxo-butyl]benzoate (23a)

Following the General Procedure of Description 15 (Part A), zinc dust (Zn) (392 mg, 6.0 mmol) is activated with elemental iodine (I$_2$) (38 mg, 0.15 mmol, 15 mol-%) and trimethylsilylchloride (MeSiCl, TMSCl) (19 μL, 16 mg, 0.15 mmol, 15 mol-%) in degassed anhydrous N,N-dimethylformamide (DMF) (3 mL). The zinc insertion product is prepared from tert-butyl(3S)-3-(tert-butoxycarbonylamino)-4-iodo-butanoate (6c) (385 mg, 1.0 mmol) in the presence of additional I$_2$ (38 mg, 0.15 mmol, 15 mol-%) and TMSCl (19 μL, 16 mg, 0.15 mmol, 15 mol-%).

Following the General Procedure of Description 15 (Part B), the zinc insertion product is used in situ to cross couple with commercial methyl 2-iodobenzoate (262 mg, 1.0 mmol) in the presence of tris(benzylideneacetone)dipalladium (Pd$_2$(dba)$_3$) (23 mg, 0.025 mmol, 2.5 mol-%) and tris(o-tolyl)phosphine (P(o-tol)$_3$) (30 mg, 0.10 mmol, 10 mol-%) in anhydrous degassed DMF (3 mL). Filtration, aqueous work-up, and purification by silica gel column chromatography furnish the title compound (23a).

Step B: 2-[(2R)-4-tert-Butoxy-2-(tert-butoxycarbonylamino)-4-oxo-butyl]benzoic acid (23b)

Adapting a literature known protocol (Dayal, et al., Steroids, 1990, 55(5), 233-237), a reaction mixture of methyl 2-[(2R)-4-tert-butoxy-2-(tert-butoxycarbonylamino)-4-oxo-butyl]benzoate (23a) (1.97 g, 5.0 mmol) and commercial lithium hydroxide monohydrate (LiOH.H$_2$O) (420 mg, 10.0 mmol) in a mixture of water (10 mL) and methanol (MeOH) (3 mL) is stirred at room temperature. The reaction is monitored by TLC and/or LC/MS to completion. The solvent is partially removed under reduced pressure using a rotary evaporator. Acidic aqueous work-up and purification by silica gel column chromatography furnish the title compound 2-[(2R)-4-tert-butoxy-2-(tert-butoxycarbonylamino)-4-oxo-butyl]benzoic acid (23b) which may be used directly in the next step without further isolation and purification.

Step C: tert-Butyl(3R)-4-[2-[bis(2-chloroethyl)carbamoyl]phenyl]-3-(tert-butoxycarbonylamino)butanoate (23c)

Adapting a literature known protocol (Levi and Weed, U.S. Pat. No. 3,235,594), to a reaction mixture of 2-[(2R)-4-tert-butoxy-2-(tert-butoxycarbonylamino)-4-oxo-butyl]benzoic acid (23b) (759 mg, 2.0 mmol), N-hydroxysuccinimide (NHS, HOSu) (235 mg, 2.2 mmol) in anhydrous acetonitrile (MeCN) (10 mL) is added solid dicyclohexylcarbodiimide (DCC) (433 mg, 2.1 mmol) in small portions at about room temperature. The reaction mixture is stirred for about 12 hours and the precipitated dicyclohexylurea side product is filtered off using a Büchner funnel. The filtrate is treated with commercial di-(2-chloroethyl)amine hydrochloride (2-chloro-N-(2-chloroethyl)ethanamine hydrochloride; $HN(CH_2—CH_2—Cl)_2 \cdot HCl$) (393 mg, 2.2 mmol) followed by neat triethylamine ($Et_3N$, TEA) (321 µL, 233 mg, 2.3 mmol). The reaction mixture is stirred for about 12 hours at room temperature. The reaction is followed by TLC and/or LC/MS to completion. Acidic aqueous work-up and purification by silica gel column chromatography furnish the title compound tert-butyl(3R)-4-[2-[bis(2-chloroethyl)carbamoyl]phenyl]-3-(tert-butoxycarbonylamino)butanoate (23c).

Step E: (3R)-3-Amino-4-[2-[bis(2-chloroethyl)carbamoyl]phenyl]butanoic acid (23)

Following the General Procedure of Description 9 (Variant B), (3R)-3-amino-4-[2-[bis(2-chloroethyl)carbamoyl]phenyl]butanoic acid (23) is prepared from tert-butyl(3R)-4-[2-[bis(2-chloroethyl)carbamoyl]phenyl]-3-(tert-butoxycarbonylamino)butanoate (23c) (504 mg, 1.0 mmol) in 2 N HCl in diethyl ether (2 N HCl in $Et_2O$) (10 mL, 20 mmol) to yield the target compound (23) as an solid dihydrochloride salt after evaporation of the solvents and lyophilization from an aqueous solution. The material may be further purified by preparative HPLC followed by lyophilization. Optionally, the lyophilization is conducted in the presence of 1 equivalent or an excess of 1.0 M hydrochloric acid (HCl).

Example 24

LAT1 Uptake Inhibition Assays

The ability of compounds to interact with LAT1 was measured using a radiolabeled competition uptake assay with [$^3$H]-Gabapentin (GP) in 96-well plates with LLCPK cells conditionally expressing hLAT1. $5 \times 10^4$ cells/well were plated in white, clear bottom plates in the presence or absence of tetracycline or doxycycline to induce hLAT1 expression. The next day, cells were treated with butyrate to stimulate additional hLAT1 expression. On the third day, the cells were washed and then incubated with 50,000 cpm of [$^3$H]-GP in PBS in the presence or absence of 1 mM of test compound in at least triplicate for 15 min. At end of the assay time, the incubation solution was removed, and the plates were washed three times with 100 µl of ice-cold PBS. 150 µl of scintillation fluid was added to each well, and the radioactivity retained within the cells was measured on a 96-well scintillation counter. The data are expressed as a percent of specific [$^3$H]-GP uptake. Unlabeled GP and other large amino acids (phenylalanine and leucine) were used as controls.

The ability of various compounds to interact with LAT1 was assessed by measuring the inhibition of [$^3$H]-GP uptake into LAT1-expressing cells in the presence of 1 mM test compound. Unlabeled GP and phenylalanine (Phe) and leucine (Leu) were used as controls. After incubation for 15 min, cells were washed, scintillation fluid added, and cell-bound radioactivity determined in a scintillation counter. Data are expressed as a percent of specific GP uptake.

The specific uptake of radiolabeled gabapentin into LAT1-expressing cells was inhibited by 1 mM of unlabeled gabapentin, phenylalanine, leucine, and the compounds of Examples 1-4. Treatment with gabapentin, phenylalanine, leucine, and the compound of Example 3 resulted in specific uptake of less than 10%. The compounds of Examples 1, 2, and 4 resulted in specific uptake of greater than 20% but less than 50% at this concentration. The specific uptake of radiolabeled gabapentin in the absence of any compound was 100%.

Example 25

LAT1-specific in vitro Cytotoxicity Assays

The LAT1-specific in vitro cytotoxicity of compounds was assessed by using a modified clonigenic assay in 96-well plates with LLCPK cells conditionally expressing hLAT1. 1000 cells/well were plated in clear bottom plates in the presence or absence of tetracycline or doxycycline to induce hLAT1 expression. The next day, cells were treated with butyrate to stimulate additional hLAT1 expression. On the third day, cells were washed and incubated with various concentrations of test compounds in PBS buffer in at least quadruplicate for 30 minutes. At the end of the treatment, test compounds were removed and growth media was added to the cells. Clonal populations were allowed to grow until the control wells (mock treatment) were near confluency (7 to 10 days). Cell growth was quantified by fixing and staining the cells post-wash with crystal violet in glutaraldehye, washing away unadhered dye, solubilizing the stained cells in acetic acid and monitoring absorbance at 530 nm. Data from each test concentration were expressed as the percent of live, mock-treated controls (% surviving cells). LAT1 specificity was determined by the differential toxicity in cells induced (LAT1+) vs. non-induced (no LAT1) to express hLAT1. Melphalan, a N-mustard compound, was used as a control.

The LAT1-specific cytotoxicity of various compounds was assessed by treating cells expressing or not expressing LAT1 with 3 µM of test compound for 30 min. Melphalan was used as a control compound. Following treatment, cells were washed and growth media was added. Surviving cells were allowed to proliferate for 7-10 days, and then stained and quantified. Results were expressed as the percent of untreated cells (% surviving cells).

The percent surviving cells for melphalan and the compound of Example 2 was about the same in cells expressing LAT1 and in cells not expressing LAT1. The percent surviving cells for the compounds of Examples 1, 3, and 4 was significantly reduced by at least 25% in cells expressing LAT1 compared to cells not expressing LAT1.

The in vitro cytotoxicity of the two enatiomers of QBS10072 was assessed by treating LAT1-expressing cells with various concentrations of the S (solid circles) or the R (open circles) isomer for 30 min. Following treatment, cells were washed and growth media was added. Surviving cells were allowed to proliferate for 7-10 days, and then stained and quantified. Results were expressed as the percent of untreated cells (% surviving cells) and graphed vs. test concentration.

The in vitro cytotoxicity of the two single enantiomers of Example 3 was assessed by treating LAT1-expressing cells with various concentrations of the S (solid circles) or the R (open circles) isomer for 30 min. Following treatment, cells were washed and growth media was added. Surviving cells were allowed to proliferate for 7-10 days, and then stained and quantified. Results were expressed as the percent of untreated cells (% surviving cells) and graphed vs. test concentration.

Example 26

In Vivo Tumor Growth Suppression Assays

The ability to suppress the growth of tumors in vivo was measured using a B16 efficacy model (Kato, et al., Cancer Res., 1994, 54, 5143-5147). Briefly, the hind flank of C57BL/6 mice were injected with $5 \times 10^5$ B16 melanoma cells subcutaneously. Once the tumors reached 40 mm$^3$, animals were separated into various treatment arms (n=5) and dosed IP daily with vehicle or test compound (5 and 10 mg/kg) for 12 days. Tumor sizes were monitored every third day for up to three weeks. Melphalan was used as a control compound (2.5 mg/kg). The results are presented in Table 1.

TABLE 1

Tumor Suppression by QBS Compounds in vivo

| Treatment | Tumor Growth (% Control) | |
|---|---|---|
| | End of dosing | 5 days post-dosing |
| Vehicle | 100 | 100 |
| QBS10072 | 11 | 11 |
| Melphalan | 33 | 56 |

Finally it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A compound selected from the group consisting of:
    3-Amino-3-[5-[bis(2-chloroethyl)amino]-2-methyl-phenyl]propanoic acid (1);
    3-Amino-3-[4-[bis(2-chloroethyl)amino]-2-methyl-phenyl]propanoic acid (2);
    3-Amino-4-[5-[bis(2-chloroethyl)amino]-2-methyl-phenyl]butanoic acid (3);
    3-Amino-4-[4-[bis(2-chloroethyl)amino]-2-methyl-phenyl]butanoic acid (4);
    (3S)-3-Amino-4-[5-[bis(2-chloroethyl)amino]-2-methyl-phenyl]butanoic acid (5);
    (3R)-3-Amino-4-[5-[bis(2-chloroethyl)amino]-2-methyl-phenyl]butanoic acid (6);
    (3S)-3-Amino-4-[5-[bis(2-chloroethyl)amino]-2-methoxy-phenyl]butanoic acid (7);
    (3S)-3-Amino-4-[3-[bis(2-chloroethyl)amino]-2,6-dimethyl-phenyl]butanoic acid (8);
    (3S)-3-Amino-4-[5-[bis(2-chloroethyl)amino]-2-methyl-phenyl]-3-methyl-butanoic acid (9);
    [(2R)-2-Amino-3-[5-[bis(2-chloroethyl)amino]-2-methyl-phenyl]propyl]phosphinic acid (10);
    (3R)-3-Amino-4-[5-(bis(2-methylsulfonyloxyethyl)amino)-2-methyl-phenyl]butanoic acid (11);
    (3R)-3-Amino-4-[5-(bis(2-bromoethyl)amino)-2-methyl-phenyl]butanoic acid (12);
    (3R)-3-Amino-4-[5-(2-chloroethyl(2-methylsulfonyloxyethyl)amino)-2-methyl-phenyl]butanoic acid (13);
    (3R)-3-Amino-4-[5-(2-bromoethyl(2-chloroethyl)amino)-2-methyl-phenyl]butanoic acid (14);
    (3R)-3-Amino-4-[5-(2-bromoethyl(2-methylsulfonyloxyethyl)amino)-2-methyl-phenyl]butanoic acid (15);
    (3S)-3-Amino-4-[[5-[bis(2-chloroethyl)amino]-2-methyl-phenyl]amino]-4-oxo-butanoic acid (16);
    (3R)-3-Amino-5-[5-[bis(2-chloroethyl)amino]-2-methyl-phenyl]pentanoic acid (18);
    (3R)-3-Amino-4-[5-(2-chloroethyl(chloromethyl)carbamoyl)oxy-2-methyl-phenyl]butanoic acid (19);
    (3R)-3-Amino-4-[5-[bis(2-chloroethyl)carbamoyloxymethyl]-2-nitro-phenyl]butanoic acid (20);
    (3R)-3-amino-4-[5-(2-chloroethoxy(2-chloroethyl)amino)-2-methyl-phenyl]butanoic acid (21); and
    3-[(2R)-2-Amino-4-hydroxy-4-oxo-butyl]-N,N-bis(2-chloroethyl)-4-methyl-benzeneamine oxide (22);
    or a pharmaceutically acceptable salt of any of the foregoing.

2. The compound of claim 1, which exhibits:
    a LAT1/4F2hc-dependent uptake of at least 10% that of gabapentin measured at an extracellular concentration of 1 mM (1 mmol/L); and
    a system A-, system N-, a system ASC-, and a LAT2/4F2hc-dependent uptake of less than 50% that of L-leucine measured at an extracellular concentration of 1 mM (1 mmol/L).

3. A pharmaceutical composition comprising the compound of claim 1 or a pharmaceutically acceptable salt thereof and a pharmaceutically acceptable vehicle.

4. The compound of claim 1, wherein the compound is 3-amino-3-[5-[bis(2-chloroethyl)amino]-2-methyl-phenyl]propanoic acid (1) or a pharmaceutically acceptable salt thereof.

5. The compound of claim 1, wherein the compound is 3-amino-3-[4-[bis(2-chloroethyl)amino]-2-methyl-phenyl]propanoic acid (2) or a pharmaceutically acceptable salt thereof.

6. The compound of claim 1, wherein the compound is 3-amino-4-[5-[bis(2-chloroethyl)amino]-2-methyl-phenyl]butanoic acid (3) or a pharmaceutically acceptable salt thereof.

7. The compound of claim 1, wherein the compound is 3-amino-4-[4-[bis(2-chloroethyl)amino]-2-methyl-phenyl]butanoic acid (4) or a pharmaceutically acceptable salt thereof.

8. The compound of claim 1, wherein the compound is (3S)-3-amino-4-[5-[bis(2-chloroethyl)amino]-2-methyl-phenyl]butanoic acid (5) or a pharmaceutically acceptable salt thereof.

9. The compound of claim 1, wherein the compound is (3R)-3-amino-4-[5-[bis(2-chloroethyl)amino]-2-methyl-phenyl]butanoic acid (6) or a pharmaceutically acceptable salt thereof.

10. The compound of claim 1, wherein the compound is (3S)-3-amino-4-[5-[bis(2-chloroethyl)amino]-2-methoxy-phenyl]butanoic acid (7) or a pharmaceutically acceptable salt thereof.

11. The compound of claim 1, wherein the compound is (3S)-3-amino-4-[3-[bis(2-chloroethyl)amino]-2,6-dimethyl-phenyl]butanoic acid (8) or a pharmaceutically acceptable salt thereof.

12. The compound of claim 1, wherein the compound is (3S)-3-amino-4-[5-[bis(2-chloroethyl)amino]-2-methyl-phenyl]-3-methyl-butanoic acid (9) or a pharmaceutically acceptable salt thereof.

13. The compound of claim 1, wherein the compound is [(2R)-2-amino-3-[5-[bis(2-chloroethyl)amino]-2-methyl-phenyl]propyl]phosphinic acid (10) or a pharmaceutically acceptable salt thereof.

14. The compound of claim 1, wherein the compound is (3R)-3-amino-4-[5-(bis(2-methylsulfonyloxyethyl)amino)-2-methyl-phenyl]butanoic acid (11) or a pharmaceutically acceptable salt thereof.

15. The compound of claim 1, wherein the compound is (3R)-3-amino-4-[5-(bis(2-bromoethyl)amino)-2-methyl-phenyl]butanoic acid (12) or a pharmaceutically acceptable salt thereof.

16. The compound of claim 1, wherein the compound is (3R)-3-amino-4-[5-(2-chloroethyl(2-methylsulfonyloxyethyl)amino)-2-methyl-phenyl]butanoic acid (13) or a pharmaceutically acceptable salt thereof.

17. The compound of claim 1, wherein the compound is (3R)-3-amino-4-[5-(2-bromoethyl(2-chloroethyl)amino)-2-methyl-phenyl]butanoic acid (14) or a pharmaceutically acceptable salt thereof.

18. The compound of claim 1, wherein the compound is (3R)-3-amino-4-[5-(2-bromoethyl(2-methylsulfonyloxyethyl)amino)-2-methyl-phenyl]butanoic acid (15) or a pharmaceutically acceptable salt thereof.

19. The compound of claim 1, wherein the compound is (3S)-3-amino-4-[[5-[bis(2-chloroethyl)amino]-2-methylphenyl]amino]-4-oxo-butanoic acid (16) or a pharmaceutically acceptable salt thereof.

20. The compound of claim 1, wherein the compound is (3R)-3-amino-5-[5-[bis(2-chloroethyl)amino]-2-methylphenyl]pentanoic acid (18) or a pharmaceutically acceptable salt thereof.

21. The compound of claim 1, wherein the compound is (3R)-3-amino-4-[5-(2-chloroethyl(chloromethyl)carbamoyl)oxy-2-methyl-phenyl]butanoic acid (19) or a pharmaceutically acceptable salt thereof.

22. The compound of claim 1, wherein the compound is (3R)-3-amino-4-[5-[bis(2-chloroethyl)carbamoyloxymethyl]-2-nitro-phenyl]butanoic acid (20) or a pharmaceutically acceptable salt thereof.

23. The compound of claim 1, wherein the compound is (3R)-3-amino-4-[5-(2-chloroethoxy(2-chloroethyl)amino)-2-methyl-phenyl]butanoic acid (21) or a pharmaceutically acceptable salt thereof.

24. The compound of claim 1, wherein the compound is 3-[(2R)-2-amino-4-hydroxy-4-oxo-butyl]-N,N-bis(2-chloroethyl)-4-methyl-benzeneamine oxide (22) or a pharmaceutically acceptable salt thereof.

\* \* \* \* \*